US006214588B1

(12) United States Patent
Young et al.

(10) Patent No.: US 6,214,588 B1
(45) Date of Patent: *Apr. 10, 2001

(54) FACTORS WHICH MODIFY GENE TRANSCRIPTION AND METHODS OF USE THEREFOR

(75) Inventors: Richard A. Young, Weston; Anthony J. Koleske, Braintree, both of MA (US); Craig M. Thompson, New Haven, CT (US); David M. Chao, Cambridge, MA (US)

(73) Assignee: Whitehead Institute Biomedical Research, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/590,399

(22) Filed: Jan. 26, 1996

Related U.S. Application Data

(63) Continuation-in-part of application No. 08/540,804, filed on Oct. 11, 1995, now Pat. No. 5,919,666, which is a continuation-in-part of application No. 08/521,872, filed on Aug. 31, 1995, which is a continuation-in-part of application No. 08/218,265, filed on Mar. 25, 1994, now Pat. No. 5,922,585.

(51) Int. Cl.$^7$ .............................. C12P 19/34; C12N 9/12; C07K 1/00; C07H 21/02

(52) U.S. Cl. ...................... 435/91.3; 435/91.1; 435/91.2; 435/91.21; 435/194; 530/350; 536/23.1

(58) Field of Search ............................ 530/350; 435/194, 435/196, 91.3, 91.1, 91.2, 91.21; 536/23.2, 23.74, 23.7, 23.1

(56) References Cited

PUBLICATIONS

Doignon et al., Yeast, 9:189–199, 1993.*
Sayre et al., Reconstitution of transcription with five purified initation factor and RNA polymerase II from Saccharomyces cerevisiae, The Journal of Biological Chemistry, Nov. 15, 1992, vol. 267, No. 32, pp. 23376–23382, see entire document.*
Kolodziej et al. RNA polymerase II subunit composition, stoichiometry, and phosphorylation. Molecular and Cellular Biology, May 1990, vol. 10, No. 5, pp. 1915–1920, see entire document.*
Koleske et al., A novel transcription factor reveals a functional link between the RNA polymerase II CTD and TFIID. Cell May 29, 1992, vol. 69, pp. 883–894, see entire document.*

Thompson et al., A multisubunit complex associated with the RNA polymerase II CTD and TATA–binding protein in yeast. Cell. Jul. 2, 1993, vol. 73, pp. 1361–1375, see entire document.*
Cisek, L.J., and Corden, J.L., "Phosphorylation of RNA Polymerase by the Murine Homologue of the Cell–Cycle Control Protein cdc2," Nature, 339:679–684 (1989).*
Koleske, A.J. and Young, R.A., "An RNA Polymerase II Holoenzyme Responsive to Activators," Nature, 368:466–469 (1994).*
Koleske, A.J., et al., "A Novel Transcription Factor Reveals a Functional Link Between the RNA Polymerase II CTD and TFIID," Cell, 69:883–894 (1992).*
Oliver, S.G., et al., "The Complete DNA Sequence of Yeast Chromosome III," Nature, 357:38–46 (1992).*
Thompson, C.M., et al., "A Multisubunit Complex Associated with the RNA Polymerase II CTD and TATA–Binding Protein in Yeast," Cell, 73:1361–1375 (1993).*
Nonet, M.L. and Young, R.A., "Intragenic and Extragenic Suppressors of Mutations in the Heptapeptide Repeat Domain of Saccharomyces cerevisiae RNA Polymerase II," Genetics, 123:715–724 (1989).*
Conaway, R.C. and Conaway, J.W., "General Initiation Factors for RNA Polymerase II," Annu. Rev. Biochem., 62:161–190 (1993).*
Dynlacht, B.D., et al., "Isolation of Coactivators Associated with the TATA–Binding Protein That Mediate Transcriptional Activation," Cell, 66:563–576 (1991).*
Taggart, A.K.P., et al., "The TATA–Binding Protein and Associated Factors are Components of Pol III Transcription Factor TFIIIB," Cell, 71:1015–1028 (1992).*
Cormack, B.P. and Struhl, K., "The TATA–Binding Protein is Required for Transcription by All Three Nuclear RNA Polymerases in Yeast Cells," Cell, 69:685–696 (1992).*
Usheva, A., et al., "Specific Interaction Between the Non–phosphorylated Form of RNA Polymerase II and the TATA–Binding Protein," Cell, 69:871–881 (1992).*
Comai, L., et al., "The TATA–Binding Protein and Associated Factors Are Integral Components of the RNA Polymerase I Transcription Factor, SL1," Cell, 68:965–976 (1992).*
Sharp, P.A., "TATA–Binding Protein is a Classless Factor," Cell, 68:819–821 (1992).*
Blum, H., et al., "Improved Silver Staining of Plant Proteins, RNA and DNA in Polyacrylamide Gels," Electrophoresis, 8:93–99 (1987).*

(List continued on next page.)

Primary Examiner—Bradley Sisson
Assistant Examiner—Einar Stole
(74) Attorney, Agent, or Firm—Darby & Darby

(57) ABSTRACT

Eukaryotic RNA polymerase II holoenzymes that contain RNA polymerase II and one or more regulatory proteins are described. These holoenzymes selectively initiate transcription in vitro when supplemented with general transcription factors. The regulatory proteins act positively and negatively to regulate transcription initiation, at least in part, via functional interactions with RNA polymerase II.

5 Claims, 46 Drawing Sheets

OTHER PUBLICATIONS

Leung, D.W., et al., "A Method for Random Mutagenesis of a Defined DNA Segment Using a Modified Polymerase Chain Reaction," *Technique—A Journal of Methods in Cell and Molecular Biology*, 1(1) :11–15 (1989).*

Rothstein, R., "Targeting, Disruption, Replacement, and Allele Rescue: Integrative DNA Transformation in Yeast," *Methods in Enzymology*, 194:281–301 (1991).*

Smith, D.B. and Johnson, K.S., "Single–Step Purification of Polypeptides Expressed in *Escherichia coli* as Fusions with Glutathione S–Transferase," *Gene*, 67:31–40 (1988).*

Nicolet, C.M. and Craig, E.A., "Inducing and Assaying Heat–Shock Response in *Saccharomyces cerevisiae*," *Methods in Enzymology*, 194:710–717 (1991).*

Nonet, M., et al., "Eucaryotic RNA Polymerase Conditional Mutant That Rapidly Ceases mRNA Synthesis," *Mol. and Cell. Biol.*, 7(5) :1602–1611 (1987).*

Elder, R.T., et al., "RNA from the Yeast Transposable Element Ty1 has Both Ends in the Direct Repeats, a Structure Similar to Retrovirus RNA," *Proc. Natl. Acad. Sci. USA*, 80:2432–2436 (1983).*

Kolodziej, P.A., et al., "RNA Polymerase II Subunit Composition, Stoichiometry, and Phosphorylation," *Mol. and Cell. Biol.*, 10(5) :1915–1920 (1990).*

Studier, F.W. and Moffatt, B.A., "Use of Bacteriophage T7 RNA Polymerase to Direct Selective High–Level Expression of Cloned Genes," *J. Mol. Biol.*, 189:113–130 (1986).*

Woontner, M., et al., "Transcriptional Activation in an Improved Whole–Cell Extract from *Saccharomyces cerevisiae*," *Mol. and Cell. Biol.*, 11(9):4555–4560 (1991).*

Schiestl, R.H. and Gietz, R.D., "High Efficiency Transformation of Intact Yeast Cells using Single Stranded Nucleic Acids as a Carrier," *Curr. Genet.*, 16:339–346 (1989).*

Hoffman, C.S. and Winston, F., "A Ten–Minute DNA Preparation from Yeast Efficiently Releases Autonomous Plasmids for Transformation of *Escherichia coli*," *Gene*, 57:267–272 (1987).*

Buchman, A.R., et al., "Connections Between Transcriptional Activators, Silencers, and Telomeres as Revealed by Functional Analysis of a Teast DNA–Binding Protein," *Mol. and Cell. Biol.*, 8(1) :5086–5099 (1988).*

Thompson, N.E., et al., "Inhibition of in Vivo and in Vitro Transcription by Monoclonal Antibodies Prepared against Wheat Germ RNA Polymerase II That React with the Heptapeptide Repeat of Eukaryotic RNA Polymerase II," *J. Biol. Chem.*, 264(19) :11511–11520 (1989).*

Alani, E., et al., "A Method for Gene Disruption That Allows Repeated Use of URA3 Selection in the Construction of Multiply Disrupted Yeast Strains," *Genetics*, 116:541–545 (1987).*

Sawadogo, M. and Sentenac, A., "RNA Polymerase B (II) and General Transcription Factors," *Annu. Rev. Biochem.*, 69:711–754 (1990).*

Pugh, B.F. and Tjian, R., "Transcription from a TATA–Less Promoter Requires a Multisubunit TFIID Complex," *Genes & Dev.*, 5:1935–1945 (1991).*

Young, R.A., "RNA Polymerase II," *Annu. Rev. Biochem.*, 60:689–715 (1991).*

Nonet, M., et al., "Functional Redundancy and Structural Polymorphism in the Large Subunit of RNA Polymerase II," *Cell*, 50:909–915 (1987).*

Liao, S–M., et al., "RNA Polymerase II Carboxy–Terminal Domain Contributes to the Response to Multiple Acidic Activators In Vitro," *Genes & Dev.*, 5:2431–2440 (1991).*

Sayre, M.H., et al., "Purification and Properties of *Saccharomyces cerevisiae* RNA Polymerase II General Initiation Factor a," *J. Biol. Chem.*, 267(32) :23383–23387 (1992).*

Flores, O., et al., "Factors Involved in Specific Transcription by Mammalian RNA Polymerase II," *J. Biol. Chem.*, 263(22):10812–10816 (1988).*

Knapp, G., et al., "Transcription and Processing Intervening Sequences in Yeast tRNA Genes," *Cell*, 14:221–236 (1978).*

Kunkel, T.A., et al., "Rapid and Efficient Site–Specific Mutagenesis Without Phenotypic Selection," *Methods in Enzymology*, 154:367–382 (1987).*

Boeke, J.D., et al., "5–Fluoroorotic Acid as a Selective Agent in Yeast Molecular Genetics," *Methods in Enzymology*, 154:164–175 (1987).*

Gill, G. and Tjian, R., "Eukaryotic Coactivators Associated with the TATA Box Binding Protein," *Current Opinion in Genetics & Dev.*, 2:236–242 (1992).*

Hanahan, D., et al., "Plasmid Transformation of *Escherichia coli* and Other Bacteria," *Methods in Enzymology*, 204:63–113 (1991).*

Tjian, R. and Maniatis, T., "Transcriptional Activation: A Complex Puzzle with Few Easy Pieces," *Cell*, 77:5–8 (1994).*

Liao, S–M., et al., "A Kinase–Cyclin Pair in the RNA Polymerarse II Holoenzyme," *Nature*, 374:193–196 (1995).*

Boguski, M.S., et al., "Gene Discovery in dbEST," *Science*, 265:1993–1994 (1994).*

Gerber, H–P., et al., "RNA Polymerarse II C–Terminal Domain Required for Enhancer–Driven Transcription," *Nature*, 374:660–662 (1995).*

Conaway, J.W. and Conaway, R.C., "Initiation of Eukaryotic Messenger RNA Synthesis," *J. of Biol. Chem.*, 266(27):17721–17724 (1991).*

Kempers–Veenstra, A.E., et al., "3'–End Formation of Transcripts from the Yeast rRNA Operon," *EMBO J.*, 5(10):2703–2710 (1986).*

Thompson, C.M. and Young, R.A., "General Requirement for RNA Polymerase II Holoenzymes in vivo," *Proc. Natl. Acad. Sci. USA*, 92:4587–4590 (1995).*

Thompson, N.E., et al., "Purification of Eukaryotic RNA Polymerase II by Immunoaffinity Chromatography," *J. Biol. Chem.*, 265(12) :7069–7077 (1990).*

Elledge, S.J., et al., "λYES: A Multifunctional cDNA Expression Vector for the Isolation of Genes by Complementation of Yeast and *Escherichia coli* Mutations," *Proc. Natl. Acad. Sci. USA*, 88:1731–1735 (1991).*

Manley, J.L., et al., "DNA–Dependent Transcription of Adenovirus Genes in a Soluble Whole–Cell Extract," *Proc. Natl. Acad. Sci. USA*, 77(7) :3855–3859 (1980).*

Carey, M.F., "A Holistic View of the Complex," *Current Biology*, 5(9) :1003–1005 (1995).*

Emili A. and Ingles, C.J., "The RNA Polymerase II Carboxy–Terminal Domain: Links to a Bigger and Better 'Holoenzyme'?" *Current Opinion and Genetics and Dev.*, 5:204–209 (1995).*

Donovan, R.S., et al., "Detection Enhancement of Computer Images of Bands from Western Blots Using a Grayscale Scanner," *BioTechniques*, 17(4) :660–661 (1994).*

Hengartner, C.J., et al., "Association of an Activator with an RNA Polymerase II Holoenzyme," *Genes & Dev.*, 9:897–910 (1995).*

Barberis, A., et al., "Contact with a Component of the Polymerase II Holoenzyme Suffices for Gene Activation," *Cell*, 81:359–368 (1995).*

Kim, Y–J., et al., "A Multiprotein Mediator of Transcriptional Activation and Its Interaction with the C–Terminal Repeat Domain of RNA Polymerase II," *Cell*, 77:599–608 (1994).*

Koleske, A.J. and Young, R.A., "The RNA Polymerase II Holoenzyme and its Implications for Gene Regulation," *Trends in Biochemical Sciences*, 20::113–116 (1995).*

Fields, S. and Song, Ok–Kyu, "A Novel Genetic System to Detect Protein–Protein Interactions," *Nature*, 340:245–246 (1989).*

Chaseman, D.I., et al., "Activation of Yeast RNA Polymerase II Transcription by Herpes Virus VP16 and GAL 14 Derivatives in vitro," *Mol. Cell. Biol.*, 9:4746–4749 (1989).*

Kuchin S., et al., "Cyclin–Dependent Protein Kinase and Cyclin Homologs SSN3 and SSN8 Contribute to Transcriptional Control in Yeast," *Proc. Natl. Acad. Sci. USA*, 92:4006–4010 (1995).*

Cairns, B.R., et al., "A Mutisubunit Complex Containing the SWI1/ADR6, SWI2/SNF2, SWI3, SNF5, and SNF6 Gene Products Isolated From Yeast," *Proc. Natl. Acad. Sci. USA*, 91:1950–1954 (1994).*

Carlson, M. and Laurent, B.C., "The SNF/SWI Family of Global Transcriptional Activators," *Curr. Opin. in Cell Biol.*, 6:396–402 (1994).*

Hirschhorn, J.N., et al., "Evidence that SNF2/SWI2 and SNF5 Activate Transcription in Yeast by Altering Chromatin Structure," *Genes & Dev.*, 6:2288–2298 (1992).*

Laurent, B.C. and Carlson, M., "Yeast SNF2/SWI2, SNF5, and SNF6 Proteins Function Coordinately with the Gene–Specific Transcriptional Activators, GAL4 and Biocoid," *Genes & Dev.*, 6:1707–1715 (1992).*

Laurent, B.C, et al., "Functional Interdependence of the Yeast SNF2, SNF5, and SNF6 Proteins in Transcriptional Activation," *Proc. Natl. Acad. Sci. USA*, 88:2687–2691 (1991).*

Muchardt, C. and Yaniv, M., "A Human Homologue of *Saccharomyces cerevisiae* SNF2/SWI2 and Drosophila brm Genes Potentiates Transcriptional Activation by the Glucocorticoid Receptor," *EMBO J.*, 12(11):4279–4290 (1993).*

Peterson, C.L., et al., "Five SWI/SNF Gene Products are Components of a Large Multisubunit Complex Required for Transcriptional Enhancement," *Proc. Natl. Acad. Sci. USA*, 91:2905–2908 (1994).*

Treich, I., et al., "SNF11, a New Component of the Yeast SNF–SWI Complex that Interacts with a Conserved Region of SNF2," *Mol. and Cell.Biol.*, 15(8):4240–4248 (1995).*

Winston, F. and Carlson, M., "Yeast SNF/SWI Transcriptional Activators and the SPT/SIN Chromatin Connection," *Trends Genet.*, 8(11):387–391 ((1992).*

Côté, J., et al., "Stimulation of GAL4 Derivative Binding to Nucleosomal DNA by the Yeast SWI/SNF Complex," *Science*, 265:53–60 (1994).*

Yoshinaga, S.K., et al., "Roles of SWI1, SWI2, and SWI3 Proteins for Transcriptional Enhancement by Steroid Receptors," *Science*, 258:1598–1604 (1992).*

Mäkelä, T.P., et al., "A Kinase–Deficient Transcription Factor TFIIH is Functional in Basal and Activated Transcription," *Proc. Natl. Acad. Sci. USA*, 92:5174–5178 (1994).*

Ranish, J.A., et al., "Isolation of Two Genes that Encode Subunits of the Yeast Transcription Factor IIA," *Science*, 255:1127–1129 (1992).*

Buratowski, S., "The Basic of Basal Transcription by RNA Polymerase II," *Cell*, 77:1–3 (1994).*

Hoey, T., et al., "Isolation and Characterization of the Drosophila Gene Encoding the TATA Box Binding Protein, TFIID," *Cell*, 61:1179–1186 (1990).*

Sweetser, D., et al., "Prokaryotic and Eukaryotic RNA Polymerases Have homologous Core Subunits," *Proc. Natl. Acad Sci. USA*, 84:1192–1196 (1987).*

Serizawa, H., et al., "RNA Polymerase II CTD Phosphorylation and Function," (from *Mechanisms of Eukaryotic Transcription*, Cold Spring Harbor Laboratory, p. 206, 1995).*

Chao, D.M., et al., "The RNA Polymerase II Holoenzyme: Kinases and Homologs," (from *Mechanisms of Eukaryotic Transcription*, Cold Spring Harbor Laboratory, p. 42, 1995).*

Chao, D.B., et al., "RNA Polymerase II Holoenzymes and Gene Regulation," (from *Mechanisms of Eukaryotic Transcription*, Cold Spring Harbor Laboratory, p. 12, 1995).*

Peterson, C.L. and Tamkun, J.W., "The SWI–SNF Complex: A Chromatin Remodeling Machine?" *Trends Biochem. Sci.*, 20:143–146 (1995)/.*

Kwon, H., et al., "Nucleosome Disruption and Enhancement of Activator Binding by a Human SWI/SNF Complex," *Nature*, 370:477–481 (1994).*

Tamkun, J.W., et al., "Brahma: A Regulator of Drosophila Homeotic Genes Structurally Related to the Yeast Transcriptional Activator SNF2/SWI2," *Cell*, 68:561–572 (1992).*

Peterson, C.L. and Herskowitz, I., "Characterization of the Yeast SWI1, SWI2, and SWI3 Genes, Which Encode a Global Activator of Transcription," *Cell*, 68:583—583 (1992).*

Khavari, P.A., et al., "BRG1 Contains a Conserved Domain of the SWI2/SNF2 Family Necessary for Normal Mitotic Growth and Transcription," *Nature*, 366:170–174 (1993).*

Kalpana, G.V., et al., "Binding and Stimulation of HIV–1 Integrase by Human Homolog of Yeast Transcription Factor SNF5," *Science*, 266:2002–2006 (1994).*

* cited by examiner

```
GTGTTCAATGGCTCATCTACGGGGCGTTCCTGAGTCCTATAGACACTATTTGTCGTTCCAAGCTGTCCAACATCTGGATGCAGAGGCAGCTCATCAAGGGTG  1100
 V  F  N  G  S  S  T  G  V  P  E  S  I  D  T  I  L  S  S  K  L  S  N  I  W  M  Q  R  Q  L  I  K  G

ATGCCGGTGAGACGTTGATCTTGGACGGGCTCACCGTGCGACTCGTCAACCTCTCTCCTCCACTGGGTTCAAGGGTCTCGATAGAACTGCAGGCGGA  1200
 D  A  G  E  T  L  I  L  D  G  L  T  V  R  L  V  N  L  F  S  S  T  G  F  K  G  L  L  I  E  L  Q  A  D

CGAAGCGGGCGAGTTTGAGACCAAGATTGCAGGCATCGAAGGAGACACCTAGTGAAATCCCGCAAGGAGTACAAAACCTCATCCGACTCGTTGGGGCCG  1300
 E  A  G  E  F  E  T  K  I  A  G  I  E  G  H  L  A  E  I  R  A  K  E  Y  K  T  S  S  D  S  L  G  P

GACACCAGCAACAACGAAATATGTGATTGGGCTACCAGTATGTTCGTCCTCTGGAGCTGTGAGTTCTTACGAATGCTTTTCTTTTTTTTCTGTTTG  1400
 D  T  S  N  E  I  C  D  L  A  Y  Q  Y  V  R  A  L  E  L

TATATTGCGGGTGTATACGTATAGATAGTCTAAATAGTAATCTTCAACTTATGTATCTCGGCTCATGCAGTGAGGAAATCCATGAGATAAGCCCGGA  1500

TTGTAGTCATCGCTGTCGTCGCTGTGCTGGCCTGCGTCTTCCTCGTGACAGGTTCCTCGTGCGGTTGAGAGTCCTCTCCAGGCGTCTTCCT  1600

CCTCCCTTGCATTGTCAATAAACTTGTTCAGTGTACTGGATGCTCAAGTGGGCGGGGTTCCTGGTGTAGCACCTCGTAGCCCTCTGGTAGGTCGGCCTC  1700

TGTCATGGCAACGAATATCGTGGGTTTCTCGATCACTCGTGGTTCTTCAACAATTCTCCGATGCATTTCTCATGTATAGCCAACTCCACCAAGTTTTT  1800

GAATCCATTATGCCGTGCGTGTTGTAAGGGAACGTTTTCGTGTAGAATTTGAGCCCACTCTTCTGTGTCTTTCCTTTCTTTGCTCTTCCGAAC  1900

CGTCTTCGCCCTCTATGCAAGAGCTTGTTCCAGCCAAGCGATAGAATTC  1949
```

FIG. 3A

```
-319  GATCTCGACGATTTGGGATTCTTATAAGGGCGCATAAAAATAAATAACTACCATTCATAACAGAAATTCATTCGT
-243  ATATACATAAAGTTCTCATAAACGTATATATATATATATATATATTGATATCAAAGTGTGTTACTTTCT
-168  ACATTCATAGACGGGGAAGAAAAGTGAGGAAAAAGTGTTTTCTCTGTGCACTGCAGCCCTTGAAAAGTAGAA
 -93  CTGCAGAAAAAATAACTGAACGTAAAGCATTATTTACTTTTCAAAGGCAAAAGAGATAGAGCCAAAAAATTGTA
 -18  AGCAGCTTAAAGCCATAAGCACAATGACAACGAAGATCCAGATTCAAATCACTTAAGTTCCGAAACTGGCATTAAATTG
   1                                  M  T  T  B  D  P  D  S  N  H  L  S  S  B  T  G  I  K  L
  58  GCATTGGACCCGAACTTAATTACATTGCACTAAGTTCTAATCCAAACTCTAGCCTTCATTCACCAACGTCTGAT
  20   A  L  D  P  N  L  I  T  L  A  L  S  S  N  P  N  S  L  H  S  P  T  S  D
 133  GAACCCGTACCTGAATCTGCAGGAAAAGCAGATACTAGTATTCGACTAGAAGGTGATGAGTTAGAGAATAAAACT
  45   E  P  V  P  E  S  A  G  K  A  D  T  S  I  R  L  E  G  D  E  L  E  N  K  T
 208  AAGAAAGACAATGATAAGAACTTAAAATTTTGAAGAATAAAGATTCTCTAGTCAGTAATCCACACGAAATTTAT
  70   K  K  D  N  D  K  N  L  K  F  L  K  N  K  D  S  L  V  S  N  P  H  E  I  Y
 283  GGCTCCATGCCGTTGGAGCAATTGAGCAGCCCAATGATCCCAATGATCATCTTAAGACAGCGTGGTCCAGGCTTTAAATTCGTTGATTTA
  95   G  S  M  P  L  E  Q  L  I  P  I  L  R  Q  R  G  P  G  F  K  F  V  D  L
 358  AATGAAAAAGAATTGCAAAATGAGATTAAGCAGTTGGTAGTGATAGTGACGGTCATAACAGCGAGAAGAAG
 120   N  E  K  E  L  Q  N  E  I  K  Q  L  G  S  D  S  S  D  G  H  N  S  E  K  K
      A──────────────────────────────────────────────────────────────────A
```

FIG. 3B

```
433  GACACTGATGGCGCTGATGAGAATGTACAAATGGAGAATTCATGGAAGTGGATTATGAAGATAAGATAAT
145   D  T  D  G  A  D  E  N  V  Q  I  G  E  D  F  M  E  V  D  Y  E  D  K  D  N

508  CCAGTGGATTCACGAAATGAAACAGACCACAAACGAATGAAAATGGCGAGACCGATGATATATTGAAACGGTA
170   P  V  D  S  R  N  E  T  D  H  K  T  N  E  N  G  E  T  D  D  N  I  E  T  V

583  ATGACACAGGAACAGTTTGTTAAAAGAAGGAGGGATATGCTAGAGCATATAAATCTGGCACATGAACGATCGTCT
195   M  T  Q  E  Q  F  V  K  R  R  R  D  M  L  E  H  I  N  L  A  M  N  E  S  S

658  TTGGCTTTGGAATTCGTTCTTCTTGCTACTGTCGAGTGTTAAAGAGTCTACAGGTATGTCATCAATGTCACCATTT
220   L  A  L  E  F  V  S  L  L  L  S  S  V  K  E  S  T  G  M  S  S  M  S  P  F

733  CTTAGGAAAGTTGTTAAACCTTCTAGTTTAAACAGTGATAAATTCCATATGTTGCACCTACAAAAAAGAATAT
245   L  R  K  V  V  K  P  S  S  L  N  S  D  K  I  P  Y  V  A  P  T  K  K  E  Y

808  ATCGAGTTGGATATATTGAATAAGGGATGGAAGTTAACAAAGTTTAAACGAATCTAAAGATCTCCTACGGCAAGT
270   I  E  L  D  I  L  N  K  G  W  K  L  Q  S  L  N  E  S  K  D  L  L  R  A  S

883  TTTAATAAACTGAGTTCCATATTACAGAACGAACATGACTATTGGAATAAGATAATGCAGAGTATTAGCAACAAG
295   F  N  K  L  S  S  I  L  Q  N  E  H  D  Y  W  N  K  I  M  Q  S  I  S  N  K
```

FIG. 3C

```
 958  GATGTTATTTTTAAGATTAGGGACACAGGACTAGTGGTCAAAAGCTGTTGGCAATTAAGTATGGTTACGAAGACTCT
 320    D  V  I  F  K  I  R  D  R  T  S  G  Q  K  L  L  A  I  K  Y  G  Y  E  D  S

1033  GGATCTACCTATAAGCATGACACAGAGGTTATTGCTAATATATAGAATCACAAAATTTGGATTTGATA
 345    G  S  T  Y  K  H  D  R  G  I  A  N  I  R  N  N  I  E  S  Q  N  L  D  L  I

1108  CCCCACAGTAGTTCAGTGTTCAAAGGCACTGATTTCGTACATTCAGTAAAGAAATTCTTAAGGGTTCGTATCTTC
 370    P  H  S  S  V  F  K  G  T  D  F  V  H  S  V  K  K  F  L  R  V  R  I  F

1183  ACAAAAATCGAATCAGAAGATGATTACATATTGAGTGGCGAAAGTGTGATGGATAGGGATAGTGAAGTGAAGAA
 395    T  K  I  E  S  E  D  D  Y  I  L  S  G  E  S  V  M  D  R  D  S  E  E  E

1258  GCTGAAACGAAAGATATCAGAAAGCAAATCCAACTTTTGAAAAAGATCATTTTTGAAAAAGAACTGATGTACCAA
 420    A  E  T  K  D  I  R  K  Q  I  Q  L  L  K  K  I  I  F  E  K  E  L  M  Y  Q

1333  ATAAAGAAAGAATGCGCTTTGTTGATTTCCTATGGTGTCAGTATTGAAACAAGGTAATAATTGAACTA
 445    I  K  K  E  C  A  L  L  I  S  Y  G  V  S  I  E  N  E  N  K  V  I  I  E  L

1408  CCTAACGAAAAATTTGAAATCGAGTTGTTGTCCCTTGACGATGACTCCATTGTCAATCATGAACAAGACTTACCA
 470    P  N  E  K  F  E  I  E  L  L  S  L  D  D  D  S  I  V  N  H  E  Q  D  L  P
```

FIG. 3D

```
1558  TTACGATCGAGAATAAGCTCACCCCACGGACTGATCAATTTGAATGTTGACGATGATATCTTAATAATACGTCCC
 520   L   R   S   R   I   S   S   P   H   G   L   I   N   L   N   V   D   D   D   I   L   I   I   R   P

1633  ATTCTTGGTAAAGTTCGGTTTGCTAATTACAAACTGTTACTAAAAAATCATAAAGGATTACGTGCTCGATATA
 545   I   L   G   K   V   R   F   A   N   Y   K   L   L   L   K   K   I   I   K   D   Y   V   L   D   I

1708  GTTCCTGGCTCAAGTATAACAGAAACGGAAGTTGAGAGAGAACAACCTCAAGAAAATAAAACATTGATGATGAA
 570   V   P   G   S   S   I   T   E   T   E   V   E   R   E   Q   P   Q   E   N   K   N   I   D   D   E

1783  AATATAACTAAATTAAATAAAGAGATCCGTGCCTTCGATAAAACTATTGAATATACCTAGACGTGAACTCAAATA
 595   N   I   T   K   L   N   K   E   I   R   A   F   D   K   L   N   I   P   R   R   E   L   K   I

1858  AATCTACCATTAACTGAGCACAAAGCCCTAATCTAAGTTTAATGCTCGAAAGTCCTAACTATTGTAACGCACTC
 620   N   L   P   L   T   E   H   K   S   P   N   L   S   L   M   L   E   S   P   N   Y   C   N   A   L
```

FIG. 3E

```
D                                                                                    D
1933  ATTCACATCAAGTTTCAGCTGGTACGGAAGCCAACGCAGTGTCCTTTGACACAACATTTTCTGATTTTAAAGAA
645    I  H  I  K  F  S  A  G  T  E  A  N  A  V  S  F  D  T  T  F  S  D  F  K  E

2008  GTAGAGGACTTCCTACATTTTATTGTCGCTGAGTACATCCAGCAAAAGAAGGTGTAATATCCTGAGTCACTCCTT
670    V  E  D  F  L  H  F  I  V  A  E  Y  I  Q  Q  K  K  V  *

2083  AAACCTACATACATTGCCATAGAATGCCATTTATTACTATATAAAGTCGCATACGTACAAAAGGACAAGATC    2154
```

FIG. 4A

```
-432  GATCTTCAGTATCCTCGCGGAACGCTACAACAATGTAAACGATTAGAACAACATTGGCCATTGCAGCAGCTAAAC
-357  CTCCACTAATTAAGGTATTTGGCGTAAATTGCTGAATAATGAAAAAAGTGAGTACGGCAGTACCACCATGCTG
-282  CAGTAAACAGCATAAGTTTATTAATCACCGCACGAGGAACATCTACAGCCATTATTTGATTCTTTGAAGTCTTG
-207  GTTAGTTTCTACTATTGCTTTCCAGTATTGCGTTCATTTTAGCTTGCAGGTTAGTAATATATAGTGAGAGCTCTT
-132  TTGCCTTCTTTCTTTATTTGAAAAAAATAACCTAGAAAAATTATCAAAGACAAACAACCAAAATAA
-57   AAAAAAGGTAGAAAATTGAATTTTCCAGCCAAGGTATTCCATATATTAAGAAGAAAAGATGGTTCAGCAACTAAGC
                                                             M  V  Q  Q  L  S
 1

19   CTTTTTGGATCTCTATTGGTGATGACGGCTACGATTACTAATTTCAACTTTGACCACAATATCAGTAATCCTCCG
  7   L  F  G  S  I  G  D  D  D  G  Y  D  Y  D  L  L  I  S  T  L  T  T  T  I  S  G  N  P  P

94   CTACTGTATAACAGTTTATGCACTGTCTGAAATCCATCTTACGACGTCGAGAACGTGAACTCTAGAAAC
 32   L  L  Y  N  S  L  C  T  V  W  K  P  N  P  S  Y  D  V  E  N  V  N  S  R  N

169   CAATTGGTTGAACCAAATAGAATAAAACTTTCCAAAGAGGTGCCATTTCTTACCTGATCGATGAAACAATGATG
 57   Q  L  V  E  P  N  R  I  K  L  S  K  E  V  P  F  S  Y  L  I  D  E  T  M  M

244   GATAAGCCATTAAACTTTAGAATCTTTGAAATCTTTTACAAACGATAAATCCCGCTTAACTATGCTATGACACGG
 82   D  K  P  L  N  F  R  I  L  K  S  F  T  N  D  K  I  P  L  N  Y  A  M  T  R

```
319  AATATCTTGCACAACAGTCCGCAAGTCACCAACTTCAACAGCACAAACGAAGATCAAACAACAGTAAGCAT
107   N  I  L  H  N  T  V  P  Q  V  T  N  F  N  S  T  N  E  D  Q  N  N  S  K  H

394  ACAGAAGATACTGTAAATGAAAGTCGAAACAGCGATGACATCATAGATGTCGACATGGATGCAAGTCCCGCCCCT
132   T  E  D  T  V  N  E  S  R  N  S  D  D  I  I  D  V  D  M  D  A  S  P  A  P

469  TCAAACGAGTCATGTTCCCCTTGGTCATTGCAAATTTCAGATATTCCTGCTGCAGGAAACAATAGAAGTGTTTCA
157   S  N  E  S  C  S  P  W  S  L  Q  I  S  D  I  P  A  A  G  N  N  R  S  V  S

544  ATGCAAACGATAGCTGAGACTATCATATTATCTTCAGCTGGCAAAAACTCTTCAGTATCCTCGCTCATGAACGGA
182   M  Q  T  I  A  E  T  I  I  L  S  S  A  G  K  N  S  S  V  S  S  L  M  N  G

619  TTGGGTTATGTATTCGAATTTCAGTATCTTACAATTGGTGTGAAATTTTTTATGAAGCATGGTTAATACTTGAG
207   L  G  Y  V  F  E  F  Q  Y  L  T  I  G  V  K  F  F  M  K  H  G  L  I  L  E

694  TTACAAAAAATTTGGCAAATTCACAAGGCAGGCAATTCACAATAACAAGCGGGAGGTTCCTTTTAAAGCATAC
232   L  Q  K  I  W  Q  I  E  E  A  G  N  S  Q  I  T  S  G  G  F  L  L  K  A  Y

769  ATCAATGTTAGTAGGGGACCGATATCGATCGTATAAACTATACAGAGACTGCCTTGATGAACTTAAAAAGGAA
257   I  N  V  S  R  G  T  D  I  D  R  I  N  Y  T  E  T  A  L  M  N  L  K  K  E
```

FIG. 4C

```
844   CTACAAGGCTATATAGAGTTAAGTGTACCCGATAGACAGTCAATGGACTCGAGGGTAGCACATGGAAATATTCTA
282    L  Q  G  Y  I  E  L  S  V  P  D  R  Q  S  M  D  S  R  V  A  H  G  N  I  L

919   ATATAATCATTGGCACCTGGGGCATATATTTTACAAAATTCACTCATATAGTTATACAGAACAACAGTAACCACTTT
307    I  *

994   TAATGTACAGGTATTTCTATATCTACAAACAAAAATGTGTAGTTATATATCTAATGTTGCTATACCGAGGAATTA
1069  TAAGTAATAAAAGATGTTAAATTAAAAGACAAAATTTTGAGAGGCTATTGGAAAAGAGAAAACTATTTCTT
1144  GGAATCTAGTTTATTCAGTTGTTTGGCAATTGTTTGTTGGCAATTGTTTAGCTTTCTCTTTTTCTTTTTAAGTTCTCAGCTTGTC
1219  CTCCTTTTTAGCATTAGAATACTTCATTTTTGTAAAGTTCTTTTTGTTACTCATCATTATCATTTTCAA
1294  TTTCTTTCTTCTTCTCATCCACCTTCTCTTTTTGTCTTTGACTATTGACATCCTTATCAGCTTCTGA
1369  AGTTTCAGAATATTTGATACCTTGCTTCCAATTCAAGCTCTTTTTGAGCTTGTAGCTCTTGTAGCTCTTCGTCATCGTCATC
1444  ATCTTCTCCAGCAACAACTTCTTGATC   1473
```

FIG. 5A

```
-285  GATCGTTGTGTTGTAGACTCTCTGGAAGAAAGTGCAAGAGGGGCCGGTGTGGCTTTGGTAGCACTGTAACTAACTTAG
-210  TGTATATACTTTGGCACACTTGTATATAATGTATAAATCAGGATAAATCCAGTGTGACCCGGACTGAATTACT
-135  GAAACTTTGAAGTGTTAAGGAAATTGTACTGCCATTAACGCATTACCTAGCATTCACTTAGTAGCATGCATAAGCCA
 -60  TGGGCTAATCATAACAGATTGTGATGATAGGCATCCTGTACTCCTTTTTTTACAAGAAAATGAGCAACCAGGCA
                                                                 M  S  N  Q  A
   1  CTATATGAGAAACTCGAACACAAACCAGGACGATTCTGTCCGTGAAGCTGGCGAATTGATAAATATGACTACGATA
   6   L  Y  E  K  L  E  Q  T  R  T  I  L  S  V  K  L  A  E  L  I  N  M  T  T  I
  91  GCCGATAGAAATGATGATGACGAGGGTTCATTCGCACAAGAAAATTCTGAGCTCGCTGTGGCCACGACCAGTGTG
  31   A  D  R  N  D  D  D  E  G  S  F  A  Q  E  N  S  E  L  A  V  A  T  T  S  V
 166  ATGATGGTGAATAACCAGACCATGCAATTGATTAAAAATGTTCAAGACTTGTTGATCCTGACCAGATCGATAAAA
  56   M  M  V  N  N  Q  T  M  Q  L  I  K  N  V  Q  D  L  L  I  L  T  R  S  I  K

```
241  GAGAAATGGCTACTGAACCAAATTCCTGTAACGGAACACTCAAAAGTGACTCGTTTGACGAGAAGCAGATAGAG
 81   E  K  W  L  L  N  Q  I  P  V  T  E  H  S  K  V  T  R  F  D  E  K  Q  I  E
316  GAATTACTGGATAACTGTATAGAACGTTCGTGGCGGAAAAAACTACGTAAAAAGGCGGTATTTATCTATTATTT
106   E  L  L  D  N  C  I  E  T  F  V  A  E  K  T  T  *
391  GGCCAAAAAAAAAAAAAATACATACTACATATACATATATACGCCATAAAAAATCTCTGCATCTATCTTATTCC
466  CATTATTTGGACAAATGCTTACGTGCTAAATGTCCTTACCCTCGAGTCGAATGCCGGCTCCTAATAGGGTCGTA
541  ATCTTATAAAACGGGTTCATTAGTGTCTTTACGTATAGTTCGTGTACCTCTTGGTAGAATGACCTCATATTATTG
616  TCGTCAATAACTACGCTACGTGTTGGCTGAGTCCCATGGATCATCACGAACTTCATCCCACTATAGCTAATATAA
691  GCCGTTATTGCTAGTCCATAAAAATGATC 719
```

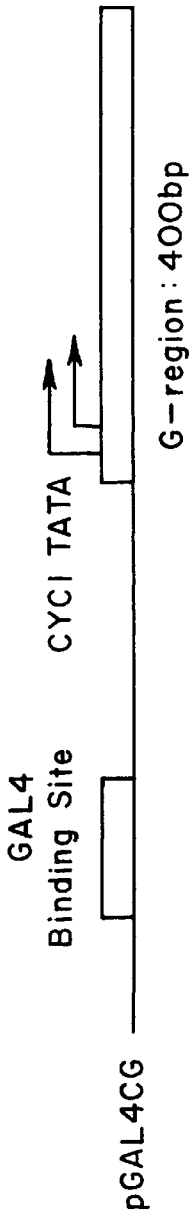

FIG. 6A

GAL4 Binding Site — CYC1 TATA — G-region: 400bp pGAL4CG

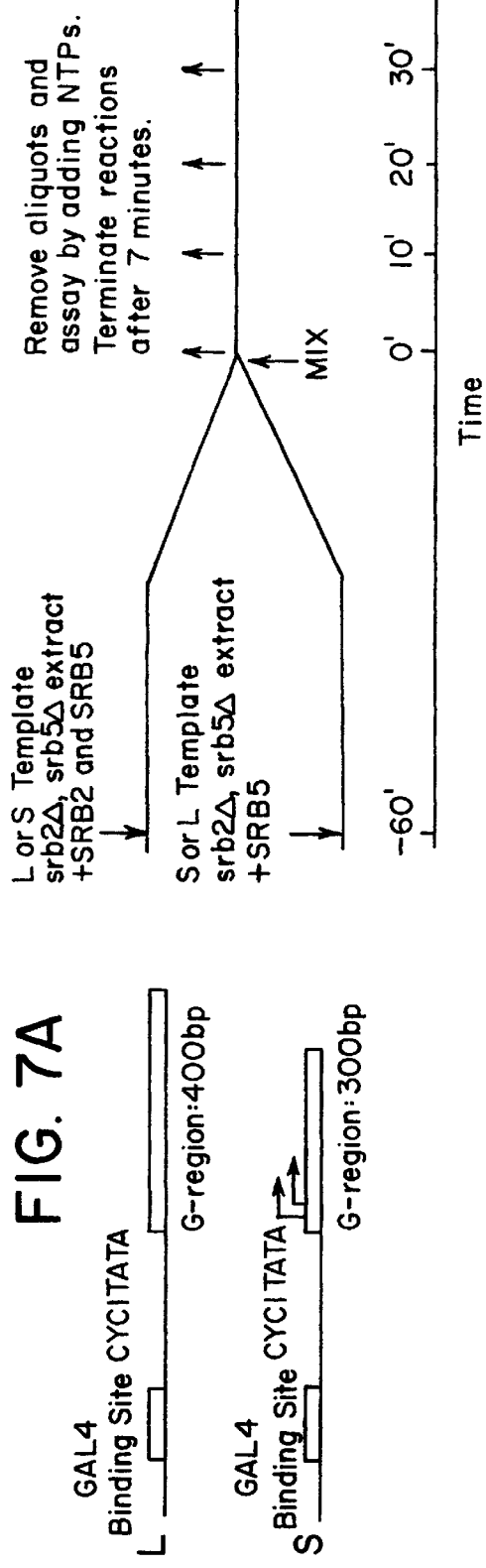
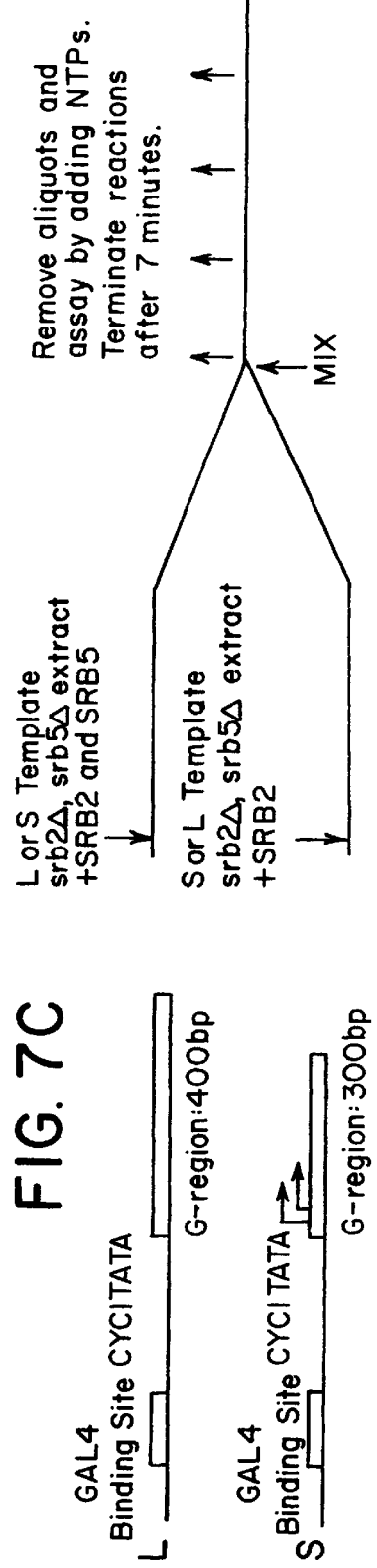
FIG. 7A
FIG. 7C

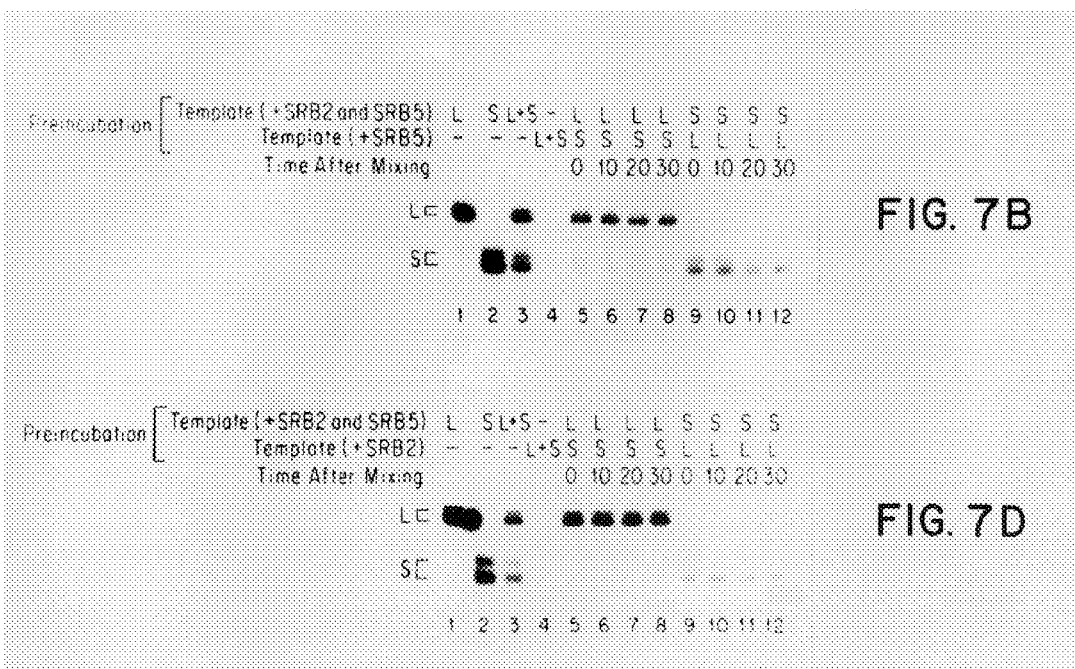

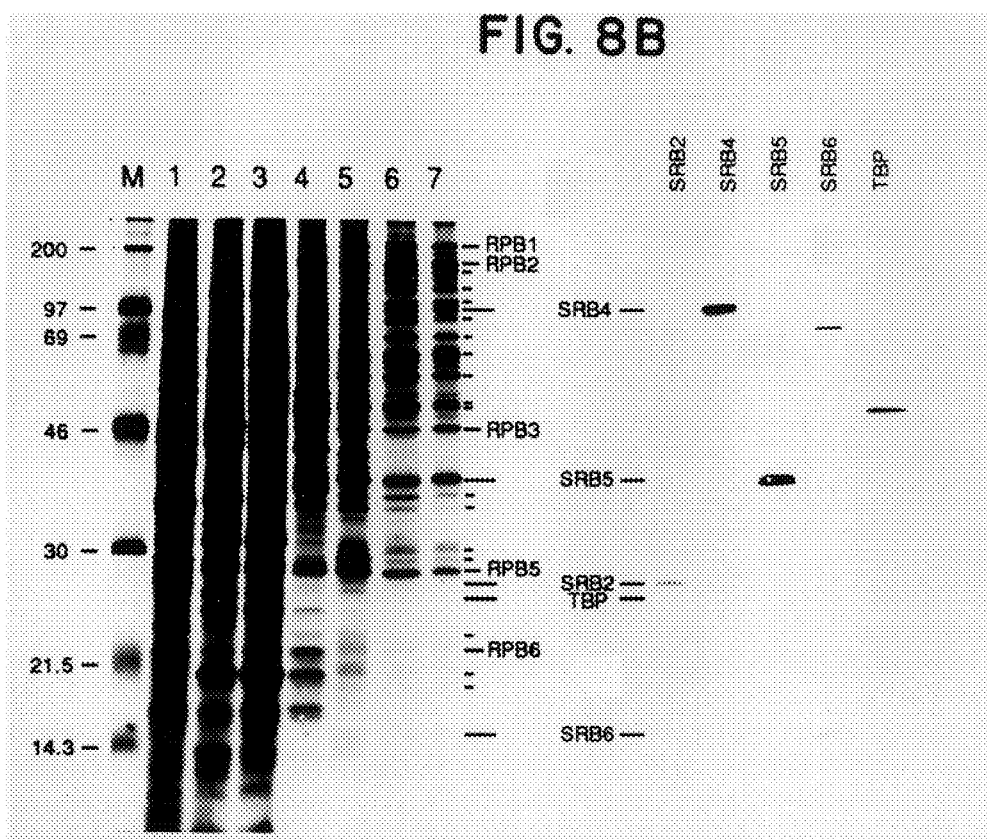

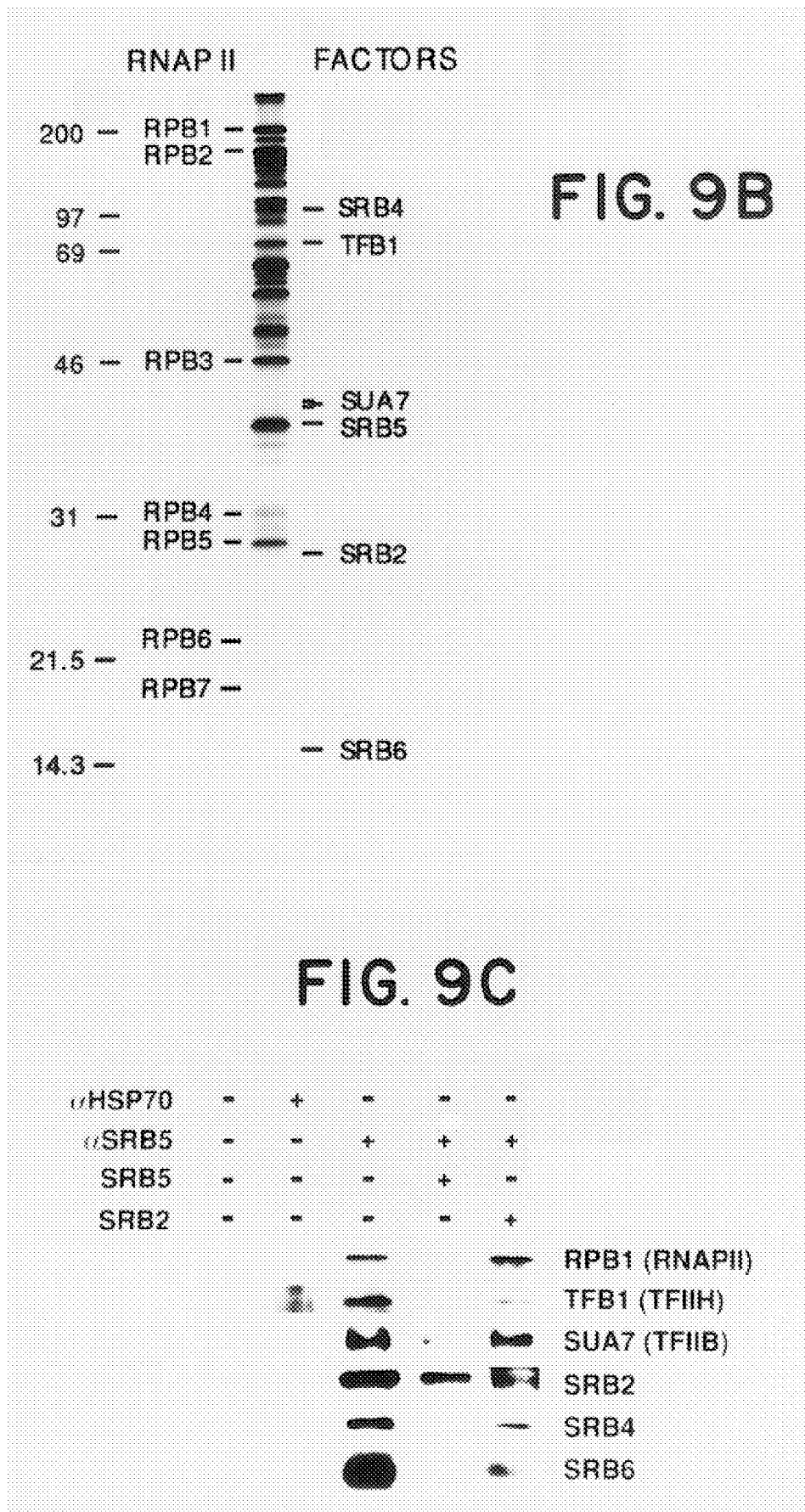

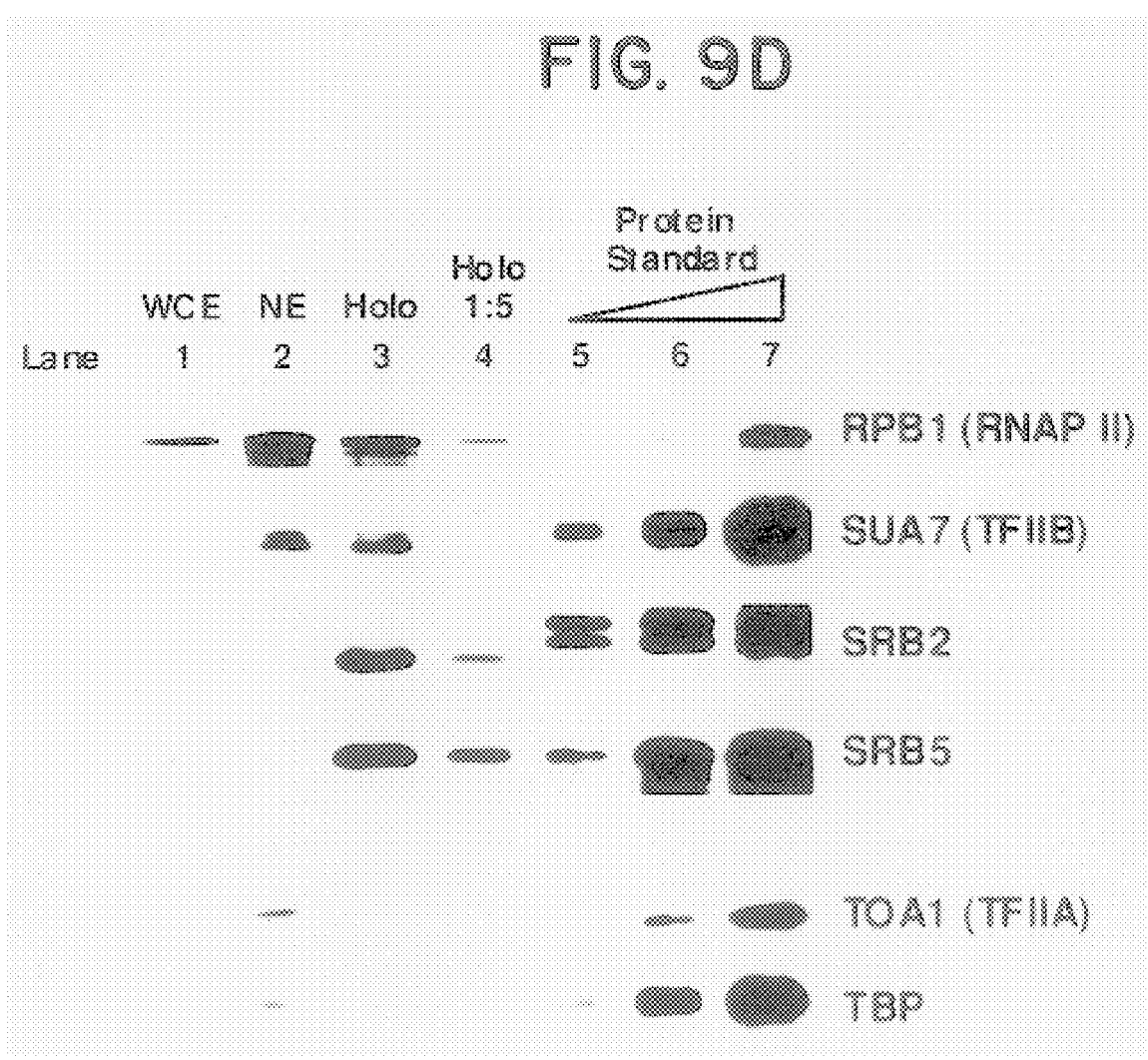

FIG. 10A

| Protein | Amount/ μg holoenzyme | MW (in kD) | Molecules/ RNA polymerase II |
|---|---|---|---|
| RNA polymerase II | 200 ng | 500 | 1.00 |
| factor e (SUA7) | 12 ng | 41 | 0.73 |
| SRB2 | 11 ng | 23 | 1.19 |
| SRB5 | 15 ng | 35 | 1.07 |
| TOA1 | — | 31 | — |
| TBP | — | 27 | — |

FIG. 10B

| Protein | Fold enrichment (holoenzyme vs. NE) | Percent in holoenzyme (approx.) |
|---|---|---|
| RNA polymerase II | 25 | 6 % |
| factor e (SUA7) | 50 | 12 % |
| SRB2 | 600-700 | 65 % |
| SRB5 | 600-700 | 65 % |
| TOA1 | -- | -- |
| TBP | -- | -- |

FIG. 13A

```
-648  TCGATGATGTTCTTTATTCTTTCAACCAGCTCGAGCCCCTGCAAACTTAAGCTAAGGACAGAAAATGAAAAAAA
-573  AAAAAAAAAATCTAAATCAAAGAATCAGCTTATAAACATATTCAAGGACCATCTGAAGTATCATTCATTCGTTTTT
-498  ACTCGTTAATCTCATTCGTTCGTTCCTCATTCTTTGTTCTTTGTTACAAAACAAGGACATTCATTTTTCACTATTAA
-423  AATAACTAGAGCTAACAATATTATTCTCTGCTTTAGTTACACAATTCTTTACAGTTAAACTTTCTGATTATTATATA
-348  CCATACATTCGTTTATTGTTCATATAACAATTCTTTAAACACAATTCTTTACAGTTAAACTTTCTGATTATTATATA
-273  TTACTTAAGATTGTTCATATAACAATTCTCTGTAATCCTTTAAAGCCAACCGTGAAGTGCGCTTTGTAGAACATGGCT
-198  GTTTCTGTAGAAGCCCTTGTCTGTCTTCTTCTCTGTAATCCTTTAAAGGCCAACCGTGAAGTGCGCTTTGTAGAACATGGCT
-123  GCATTGCAAGACATTTCACTAGTTAGAAAAAGTTAGAAAAAATCAATTCTGAAAATATATCTGAAAACGTAAACCATTGGTTAAAA
-48   GAGGGACATAACACATTTCACTAGTTCAAAATCATATATGCTCTTTAACAATGACAGATAGAATTAACACAATTGCAG
                                                          M T D R L T Q L Q
 28   ATATGTTTAGACCAAATGACGGAGCAATTCTGTGCTACTTTAAACTACATAGATAAGAACCATGGTTTTGAACGA
       I C L D Q M T E Q F C A T L N Y I D K N H G F E R
103   TTGACCGTAAATGAACCTCAGATGTCCGATAAGCATGCCACAGTAGTACCTCCTGAGGAATTTTCTAACACGATA
       L T V N E P Q M S D K H A T V V P P E E F S N T I
178   GATGAGCTATCCACGGACATTATACTTAAAACAAGAGATAAACAAGCTTATTGACTCGTTACCTGGTGTTGAC
       D E L S T D I I L K T R Q I N K L I D S L P G V D
                                                          A
```

FIG. 13B

```
253  GTTTCAGCTGAAGAGCAATTAAGGAAGATTGATATGTTGCAGAAAAAGCTAGTTGAAGTTGAAGACGAAAAATT
      V  S  A  E  E  Q  L  R  K  I  D  M  L  Q  K  K  L  V  E  V  E  D  E  K  I

328  GAGGCCATCAAAAAGAAGGAGAAACTTTTAAGGCACGTTGATTCTTTAATTGAAGATTTTGTAGATGGCATTGCA
      E  A  I  K  K  K  E  K  L  L  R  H  V  D  S  L  I  E  D  F  V  D  G  I  A

403  AACTCAAAAAAGAGCACATAAACTTAAGTTTTACAAGAAATTTGCGAACAGAGGACAGAAAATGTACTATAGTT
      N  S  K  K  S  T  *

478  ATATGGCAGAGTTAAGCGTATGTATGTTATTCTTATAAATAATTGTGCTACTCTATTTGTACCGGAGAATTATTG
553  AAGCAATGGGAGAAAAATCATAATGAGAAAATCTTCTACGAGTTACTTTGCAAGGCAATCTAACGATTCTAAA
628  AGACACAATACACTAAAGAAAAACTTTGGAAGTACAGTTTTTCCCAAGTTGAACTGTGGACTCATTGTGAAG
703  ATGTAAAAATGTAAAAACCAACGACACTGCACTCCCAGCCAAATTCATTGTAGACCTCCCATTTGATAGAAAAG
778  GAAGGTTCAGCAGTTGTCCACGGATTCCAAGATATCATTCTTACATTGCACGCACATGAAAATGATC  846
```

```
1111  ACTTTATGGCATCATTAAGGTCCCTACGTAT ATCAGAAAGCTAATCAGTTCCGGCCTACTT TATCTCCAAGATTCCAATGATAAGTTTGTG  400
       T  Y  G  I  I  K  V  P  T  Y    I  R  K  L  I  S  S  G  L  L    Y  L  Q  D  S  N  D  K  F  V
1201  CATGTCCAGCTGTTAATTAACTTGAAAATT TCACCGTTGATGAAAGTCAATACAATATG GTATTGAGGAACGTTATGGAATATGACGTT  430
       H  V  Q  L  L  I  N  L  K  I    S  P  L  M  K  S  Q  Y  N  M    V  L  R  N  V  M  E  Y  D  V
1291  AAATTTATGAAATTTTTAATTTCGACCAA CTCGTGAAATCACAGAACAAATCAAAATG CGAATACTCTCCAATGATAACTAATTTG  460
       K  F  Y  E  I  F  N  F  D  Q    L  V  E  I  T  E  Q  I  K  M    R  I  L  S  N  D  I  T  N  L
1381  CAACTGTCGAAAACTCCTCTGAGCATTAAA ATCATGGTTGCAGAATGGTACTTATCACAT TTATGTTCCGGTATTTTATCTAGTGTTAAC  490
       Q  L  S  K  T  P  L  S  I  K    I  M  V  A  E  W  Y  L  S  H    L  C  S  G  I  L  S  S  V  N
1471  CGCACAGTGTTGCTAAAATATTCAAGATT TTTTGTATCGATCTGGAGGTTTTCCACCAC TTTTTAAGTGGATGATTTATGTCTAC  520
       R  T  V  L  L  K  I  F  K  I    F  C  I  D  L  E  V  F  H  H    F  F  K  W  I  E  F  I  V  Y
1561  CATCAATTGCTAAGTGATATAGAATCTCTG GAGGCATTGATGGACATCTTGCTATGCTAC CAAAAATTGTTCTCACAATTCATTAATGAC  550
       H  Q  L  S  D  I  E  S  L    E  A  L  M  D  I  L  L  C  Y    Q  K  L  F  S  Q  F  I  N  D
1651  CATATTCTTTTTACGAAGACGTTCATATTC ATTTACAAGAAAGTTTGAAAGGAAAAGAC GTGCCTGCTTATAATGTGACTTCATTTATG  580
       H  I  L  F  T  K  T  F  I  F    I  Y  K  K  V  L  K  E  K  D    V  P  A  Y  N  V  T  S  F  M
1741  CCATTCTGGAAATTTTTTATGAAAAACTTC CCTTTTGTTTTAAAGGTGATAACGATTTA AGGATTGAGTTACAATCTGTTTACAATGAT  610
       P  F  W  K  F  F  M  K  N  F    P  F  V  L  K  V  D  N  D  L    R  I  E  L  Q  S  V  Y  N  D
1831  GAGAAATTGAAAACTGAGAAGCTGAAGAAT GATAAATCAGAAGTCTTGAAGGTGTATTCC ATGATCAATAATTCAAACCAAGCTGTTGGA  640
       E  K  L  K  T  E  K  L  K  N    D  K  S  E  V  L  K  V  Y  S    M  I  N  N  S  N  Q  A  V  G
1921  CAGACTTGGAATTTTCCCGAGTTGTTCAA GTAAACATCAGGTTTCTACTACACAACTCC GAGATCATTGATACAAATACAAGCAAACAG  670
       Q  T  W  N  F  P  E  V  F  Q    V  N  I  R  F  L  L  H  N  S    E  I  D  T  N  T  S  K  Q
2011  TTCCAGAAAGCACGAAACAATGTCATGCTT TTGATTGCCACTAACTTGAAGGAGTACAAT AAATTTATGTCCATTTTCTTGAAAAGGAAA  700
       F  Q  K  A  R  N  N  V  M  L    L  I  A  T  N  L  K  E  Y  N    K  F  M  S  I  F  L  K  R  K
2101  GACTTTACTAACAAAAATTTAATTCAATTG ATCTCTCTAAAAACTTCTAACTTTGAAGTG ACGCAGAATGTGTTGGGGCTCGAGTATATT  730
       D  F  T  N  K  N  L  I  Q  L    I  S  L  K  L  L  T  F  E  V    T  Q  N  V  L  G  L  E  Y  I
2191  ATTCGATTATTACCAATAACTTGGAAAAT AATGACGGCTCATATGGTCTGTTTTTGAAG TATCATAAAGAACAATTCATAAAGTCAAAT  760
       I  R  L  L  P  I  N  L  E  N    N  D  G  S  Y  G  L  F  L  K    Y  H  K  E  Q  F  I  K  S  N
2281  TTTGAGAAAATTTTACTTACATGTTATGAA TTAGAAAAGAAAAATATCATGAGATCCAAT GAAATAAATTATTATGAAATCATAAAGAA  790
       F  E  K  I  L  L  T  C  Y  E    L  E  K  K  Y  H  G  N  E  C    E  I  N  Y  Y  E  I  L  L  K
```

FIG. 14C

```
B
2371 ATTTTAATAACTTATGGTCATCTCCCAAA TTACTTGCAACATCTACAAAAATCATTATG TTGTTATTGAATGATAGCGTGAAAACTCA  820
      I  L  I  T  Y  G  S  S  P  K     L  L  A  T  S  T  K  I  I  M     L  L  L  N  D  S  V  E  N  S
2461 TCTAATATTTTGGAGGATATTTGTACTAC TCAACTGTCCGTCGGAAACCGATCTTAAC GATATTCCATGGGTAGTGGACAACCAGAC  850
      S  N  I  L  E  D  I  L  Y  Y     S  T  C  P  S  E  T  D  L  N     D  I  P  L  G  S  G  Q  P  D
2551 AATGACACTGTTGTAACCAACGATGATAAA AGTGACGATGATGATCACACAGTCGACGAA ATTGATCATGTAGAATATTACGTTATGATG  880
      N  D  T  V  V  T  N  D  D  K     S  D  D  D  D  H  T  V  D  E     I  D  H  V  E  Y  Y  V  M  M
2641 GACTTTGCCAATCTTTGGGTTTTCCAAGCG TTTACCTGTTTCTGCATCAAAAAATCATG GAGAATAATGAGCCAGCAATGGCAATGGAA  910
      D  F  A  N  L  W  V  F  Q  A     F  T  C  F  C  I  K  K  I  M     E  N  N  E  P  A  M  A  M  E
2731 GACTGAAGAACTTCATATTCCAAATTATC GAAATAACTAATTCTAATGATTATGTTCA CAAATATTTGACCAACTGAAGGATATGCAG  940
      D  L  K  N  F  I  F  Q  I  I     E  I  T  N  S  N  D  L  C  S     Q  I  F  D  Q  L  K  D  M  Q
2821 ACCATTGAGATGATAACCAAATAGTGGAG AAAGATTTCTGCACTTCTGTTTGCAAAAC ATGATAGTTATTTCCATGGAGAACTATCAT  970
      T  I  E  M  I  T  Q  I  V  E     K  D  F  C  T  S  C  L  Q  N     M  I  V  I  S  M  E  N  Y  H
2911 GTTGTGGTGATCGAGATTATAACGTCATTA TCGATGAGGTTTCAAAGAGAAACTTCTGT GAAATCCAAATAGATGCCGTCTTGAAAATT 1000
      V  V  V  I  E  I  I  T  S  L     S  M  R  F  Q  R  E  T  S  G     E  I  Q  I  D  A  V  L  K  I
3001 TTACTAATAAGATCATAAGACAATTAAGT GAACTGAACGAAGGAAATTTATCTAAGAGA CCCACAAGTCCATTCATTGATAGACATATGC 1030
      L  L  I  K  I  R  Q  L  S     E  L  N  E  G  N  L  S  K  R     P  T  S  P  F  I  D  S  I  C
3091 TTTAGCTTTCATCAGGATTCCATTTTCCAA CGGCATCATCGCTGATTATCAGTCGATAAA TCTTCATTGAAATCATTCGCCATCTATTCA 1060
      F  S  F  H  Q  D  S  I  F  Q     R  I  H  A  D  L  S  A  D  K     S  L  H  E  N  H  S  P  S  I
3181 AAGCTGTTTGATAAAATCATTTAATTTA AGATTGAAGCTGTTCTGTACGAAGAAATTTG CTGAACTTACCACCATTCCAAGTGTCCTCT 1090
      K  L  F  D  K  I  S  F  N  L     R  L  K  L  F  L  Y  E  I  L     S  S  L  K  S  F  A  I  Y  S
3271 TCCACAATTGATGCCCCAGCATTCCACACA AGCGGTAAGGTCAGCAAAGATGCAGACCAA GAAGAATCGTTTAGTTTAAATTTAGGAATC 1120
      S  T  I  D  A  P  F  H  T     S  G  K  V  E  L  P  K  K  L     E  E  S  F  S  L  N  L  G  I
3361 TTCGTTAAGGAAACAAAACTTCATAGTGGC GATGGGGAAGATGCAGACCAG CATAAATGCTCTGCACATTTCCATGGAG 1150
      F  V  K  E  T  K  L  H  S  G     D  Y  G  E  E  D  A  D  Q     E  E  S  F  S  N  L  G  I
3451 GGCATAGTTGAAATAGCGCACGAAACGAA CAGAAATGCTCATTTATGACAAGAAAGAT CATAAATGCTCTGCACATTTCCATGGAG 1180
      G  I  V  E  I  A  H  E  N  E     Q  K  W  L  I  Y  D  K  K  D     H  K  Y  V  C  T  F  S  M  E
3541 CCGTACCACTTCATCTCCAACTATAATACC AAGTACACAGATGACATGGCTACAGGCAGT AATGATACGCGTTAACGATTCCTGT 1210
      P  Y  H  F  I  S  N  Y  N  T     K  Y  T  D  D  M  A  T  G  S     N  D  T  A  F  N  D  S  C
3631 GTAAACCTGAGTCTTTTTGATGCTCGGTTT GAGAGGAAAAATCCACATGATCTCAGAAT ATATCCAAATGATAAATTATAAATTTACC
      V  N  L  S  L  F  D  A  R  F     E  R  K  N  P  H
3721 AATAACAGTAATTATGTCAGTTTTAATA CCCAACCAATTG 3761
```

FIG. 15A

```
-147  GATCAAGTAGTGTAGTATTTATTGTAGTACACTCTTAAGACGAATGGTGTGAAATCGGAAAT
 -72  TACTTTGTGAAGTAAGGTGTAACTATATTTAAGAACGTTTAAGCTGGATATCAAGATCTGAGGAGGTAGTATG
                                                                          M

4  AGTTCTGACGCTTCCACGTACAGACTTGAGGATGTTTTATCCAGCTTCTATAGAGTGGAGAAAATCAAAAGATC
      S  S  D  A  S  T  Y  R  L  E  D  V  L  S  S  F  Y  R  V  E  K  I  K  K  I

79  AACTATCATCAGTACACATTTCTAAAGCCCAAAACGATCAATGGTCTATCCAAATGGAATTCATGCTACGGAAGCAG
      N  Y  H  Q  Y  I  S  K  A  Q  N  D  Q  W  S  I  Q  M  E  F  M  L  R  K  Q

154  GATCCAAAGACTCTAGTGCCGCTGCTTCAAGGGATTATGGTTATGTGTTTCAGTATAAATGATGATCCGGTACCGACA
      D  P  K  T  L  V  A  L  L  S  R  D  L  W  C  F  S  I  N  D  D  P  V  P  T

229  CCTCCTGCGATAGAACATAAACCAGTGAGCCCAGATAAAATCGGAACTTTCACTGCCGATTATTCAAAGCCAAAC
      P  P  A  I  E  H  K  P  V  S  P  D  K  I  G  T  F  T  A  D  Y  S  K  P  N

304  TTACCGCCACACTATGCTCTTTTTTAAAAGCTTTAAGAAGAAAATTTACATTAATTGGCATTAGGTTCACAC
      L  P  P  H  Y  A  L  F  L  K  A  L  R  R  K  I  Y  I  N  L  A  L  G  S  H

379  AATAAGCTAATACAATTTGGGAATGCCTGCATATCATTAAGCGGAGTGCCAAATTATCTCGTACAGCTAGAACCA
      N  K  L  I  Q  F  G  N  A  C  I  S  L  S  G  V  P  N  Y  L  V  Q  L  E  P

454  CACCTTTTTGTAAACGGAGATCTCACAGTGTCGTTATGTGCCAAGAACATGGGATTAGTACCAATGAAGGAGGAA
      H  L  F  V  N  G  D  L  T  V  S  L  C  A  K  N  M  G  L  V  P  M  K  E  E
      └─A
```

FIG. 15B

```
529   AATTGGAAGAATCTTCCTTTCAAAGCATGGCTTTATTTAGCACCATCTGGAATAAGGATGCATTTGGCCCCT
      N L E E S F L S K H A L Y L A P S G I R M H L A P

604   GCTTCCAAGCAAGGATACTTGATAACGCCCAAAACATACAGAACTTCTCTTGACGAGTTAAGTGTATCTCAT
      A S K Q G Y L I T P P K H T E L L L T T L S V S H

679   GGTATAAACTTACAAAATAAAAAAAATTTGAAATGGGTTGCTGTGTTGTTCCTGACTTAGGACATCTCAACGGCCAC
      G I N L Q N K K N L K W V A V V P D L G H L N G H

754   ACACCTACTATAGCTTCGTATTTAACTCCCTTACTTGAAGCAAAGAAGCTAGTATGGCCGCTGCATTTAATCTTC
      T P T I A S Y L T P L L E A K K L V W P L H L I F

829   GCCCAACCAGTAGCTGATATAGAAAATTCTACTTCCGGAGATCCATCAGAATTCACTGTTTGCAAGATGCTCTG
      A Q P V A D I E N S T S G D P S E F H C L Q D A L

904   GATGCCATTGATGATTTCATACAATTAAAGCAAACAGCTGCCTATAGGACTCCAGGAAGTTCCGGCGTATTGAGC
      D A I D D F I Q L K Q T A A Y R T P G S S G V L S

979   AGTAATATTGCTGGTACAAATCCCTTAAGCTCAGATGGAGCATATACAGAACAGTTCAACATTATAAGAACAAC
      S N I A G T N P L S S D G A Y T E Q F Q H Y K N N

1054  TCAATTAGTTCTCAACCCGCTTCTTATCATTCTGTCCAAGAAACTAATAAGATATCCGAAAGATTTCTCCCCT
      S I S S Q P A S Y H S V Q E T N K I S P K D F S P
```

FIG. 15C

```
1129  AATTTCACAGGCATTGATAAATTAATGCTGTCGCCCAGCGATCAATTTGCTCCAGCTTTCTTAAATACCCCTAAT
       N  F  T  G  I  D  K  L  M  L  S  P  S  D  Q  F  A  P  A  F  L  N  T  P  N

1204  AATAACATCAATGAGAGAATGAATTAATTATGATAGGAAACAAACTACAGTATCAAATGACTTAGAGAACAGCCCA
       N  N  I  N  E  N  E  L  F  N  D  R  K  Q  T  T  V  S  N  D  L  E  N  S  P

1279  CTGAAAACGGAACTGGAGGCAAATGGTAGATCACTCGAAAAGGTAAATAATTCCGTGAGCAAGACAGGAAGCGTA
       L  K  T  E  L  E  A  N  G  R  S  L  E  K  V  N  N  S  V  S  K  T  G  S  V

1354  GACACACTTCATAATAAAGAGGGAACACTGGAACAACGAGAACGAAATCTGCCAAGTGATAAAGTGAC
       D  T  L  H  N  K  E  G  T  L  E  Q  R  E  Q  N  E  N  L  P  S  D  K  S  D

1429  TCTATGGTAGACAAGGAATTGTTTGGTGAGGATGAGGATTTATTGGCGATAGCAATAAATCGAATTCT
       S  M  V  D  K  E  L  F  G  E  D  E  D  E  D  L  F  G  D  S  N  K  S  N  S

1504  ACAAACGAATCGAACAAAAGTATATCGGAGGATATGTTCGAAATGTCTGATGAAGAGAAAT
       T  N  E  S  N  K  S  I  S  D  E  I  T  E  D  M  F  E  M  S  D  E  E  E  N

1579  AATAACAATAAAGCATTAATAAAAATAACAAGGAAATGCATACTGATCTTGGTAAAGATATTCCATTTTTCCC
       N  N  N  K  S  I  N  K  N  K  E  M  H  T  D  L  G  K  D  I  P  F  F  P

1654  TCATCTGAAAAACCGAATATCCGTACGATGAGCGGAACTACAAAAAGATTAAATGGAAAGAGGAAATATTGGAT
       S  S  E  K  P  N  I  R  T  M  S  G  T  T  K  R  L  N  G  K  R  K  Y  L  D
```

FIG. 15D

```
1729 ATTCCGATAGATGAAATGACCTTGCCAACGAGTCCATTATATATGGACCCAGGTGCCGCCACTCCCTGTGGAAACA
      I  P  I  D  E  M  T  L  P  T  S  P  L  Y  M  D  P  G  A  P  L  P  V  E  T

1804 CCCCGCGATAGACGCAAAAGTGTGTTCGCTCCACTGAATTTTAACCCCATAATAGAAAACAATGTTGATAACAAA
      P  R  D  R  R  K  S  V  F  A  P  L  N  F  N  P  I  E  N  N  V  D  N  K

1879 TACAAATCTGGAGGGAAATTTCCTTCAGTCCGTTGCAAAAGGAGGAAGCATTAAACTTTGATATTTCTATGGCG
      Y  K  S  G  G  K  F  S  F  S  P  L  Q  K  E  E  A  L  N  F  D  I  S  M  A

1954 GATCTTTCTAGCTCTGAAGAGGAAGAGAAGATGAAGAGAACGGTAGCAGCGATGAGGATCTAAAGTCATTGAAC
      D  L  S  S  S  E  E  E  E  D  E  E  E  N  G  S  S  D  E  D  L  K  S  L  N

2029 GTACGCGACGACACATGAACTTTCTGATAACATCAGTACTAATATTCATGAGCCTCAATACATAAATTAC
      V  R  D  D  M  K  P  S  D  N  I  S  T  N  T  N  I  H  E  P  Q  Y  I  N  Y

2104 TCTTCGATCCCAAGTCTACAAGACTCTATTATATAAAGCAAGAAAATTTCAATTCAGTAAACGATGCTAATATCACT
      S  S  I  P  S  L  Q  D  S  I  I  K  Q  E  N  F  N  S  V  N  D  A  N  I  T

2179 AGCAATAAGGAAGGCTTCAACTCTATTTGGAAAATTCCTCAAAATGATATACCACAGACCGAGTCACCACTGAAG
      S  N  K  E  G  F  N  S  I  W  K  I  P  Q  N  D  I  P  Q  T  E  S  P  L  K
```

FIG. 15E

```
2254  ACCGTTGATTCATCTATTCAACCCATAGAATCCAATATAAAGATGACCTTGGAAGATAATAATGTTACCAGTAAT
       T  V  D  S  S  I  Q  P  I  E  S  N  I  K  M  T  L  E  D  N  N  V  T  S  N

2329  CCGTCCGAATTTACGCCGAATATGGTAAATTCTGAAATTTCTAACCTACCAAGGACAAGAGTGGTATCCCCGAA
       P  S  E  F  T  P  N  M  V  N  S  E  I  S  N  L  P  K  D  K  S  G  I  P  E

2404  TTCACACCGGCGGACCCCAATTTATCTTTTGAATCATCAAGTAGTCTACCGTTTCTATTGAGACACATGCCGCTA
       F  T  P  A  D  P  N  L  S  F  E  S  S  S  L  P  F  L  L  R  H  M  P  L

2479  GCATCTATACCGGACATTTTCATCACGCCTACTCCCCGTTGTTACAATTTCAGAAAAAGAACAAGACATCTTAGAT
       A  S  I  P  D  I  F  I  T  P  T  P  V  V  T  I  S  E  K  E  Q  D  I  L  D

2554  TTAATTGCAGAACAAGTCGTCACTGATTATAATATCTTAGGAAACCTCGGTATTCCAAAGATCGCCTATAGGGGA
       L  I  A  E  Q  V  V  T  D  Y  N  I  L  G  N  L  G  I  P  K  I  A  Y  R  G

2629  GTTAAAGATTGCCAAGAAGGTTTAATAACAACCACAATGTTACAGTTTATTTCCACTTCGGATAGATTAAATGGC
       V  K  D  C  Q  E  G  L  I  T  T  M  L  Q  L  F  S  T  F  D  R  L  N  G

2704  AATGATACGATCTCCAAATTCTATAACATGAAGCAGCCGTACGTTTTTGTAAAGAAACATCGAACTAATCAAA
       N  D  T  I  S  K  F  Y  N  M  K  Q  P  Y  V  F  V  K  K  H  H  E  L  I  K

2779  GTCAAACACGACTCTCAGCCATTTATTAAGTTCCTCAATTTTCGCCCCTCCAAATGGAATAAAAAACTTCAAATCC
       V  K  H  D  S  Q  P  F  I  K  F  L  N  F  R  P  P  N  G  I  K  N  F  K  S
```

FIG. 15F

```
2854  TTATTATTAAGTTCATCTTTCAAAGAAGATTGTCTGTCATTTGCGCCAACTCTCTATCTCAAACATATATTAATCAA
       L  L  S  S  S  F  K  E  D  C  L  S  F  A  P  T  L  S  Q  T  Y  I  N  Q

2929  GAGTTAGGGTTTTGTGAGTTGCTTAAACTAATGAAGACCCGCCGGACTGATGTACTTGAAGGCATTTGAT
       E  L  G  F  C  E  L  L  K  L  T  N  E  D  P  P  G  L  M  Y  L  K  A  F  D

3004  AAAAACAAGTTACTGTTGTTAGCTGCGCAGATTGTTTCATACTGTTCTAATAATAAGAACTCCATCAAAAACGTG
       K  N  K  L  L  L  A  A  Q  I  V  S  Y  C  S  N  N  K  N  S  I  K  N  V

3079  CCACCAATATTAATAATTTACCCTTGGATAATGCAACTCTGACTGAATTAGTAGACAAGGCGAATATTTTTCAG
       P  P  I  L  I  L  P  L  D  N  A  T  L  T  E  L  V  D  K  A  N  I  F  Q

3154  GTGATCAAGAACGAAGTTTGTGCCAAGATGCCTAACATTGAACTATATATTGAAAGTTATTCCTATGGATTTCATT
       V  I  K  N  E  V  C  A  K  M  P  N  I  E  L  Y  L  K  V  I  P  M  D  F  I

3229  AGAAACGTACTGGTGACAGTGGATCAGTGGATCAACGTAGCAATTTCTATATATAACATGCTGCCGCCAAAATCT
       R  N  V  L  V  T  V  D  Q  Y  V  N  V  A  I  S  I  Y  N  M  L  P  P  K  S

3304  GTAAAGTTCACCCACATTGCCATACGCTGCCGGAGAAAGTGAATTTCAGAACCATGCAGCAACAGCAAATGCAA
       V  K  F  T  H  I  A  H  T  L  P  E  K  V  N  F  R  T  M  Q  Q  Q  M  Q

3379  CAGCAACAGCAACAGCAACAGCAGCAGCAATAACAGTACAGGATCATCTTCTATAATATATTATGACTCGTAC
       Q  Q  Q  Q  Q  Q  Q  Q  Q  N  N  S  T  G  S  S  I  I  Y  Y  D  S  Y
```

FIG. 15G

```
3454  ATCCACCTGGCATACTCGCGTAGTGTAGATAAAGAGTGGGTTTTTGCAGCTCTTTCAGATAGCTATGGACAAGGC
       I  H  L  A  Y  S  R  S  V  D  K  E  W  V  F  A  A  L  S  D  S  Y  G  Q  G

3529  AGCATGACGAAAAACGTGGTACGTCGGGAATTCCAGAGGAAATTTGACGACGCATGTAATCAAATATGAATATC
       S  M  T  K  T  W  Y  V  G  N  S  R  G  K  F  D  D  A  C  N  Q  I  W  N  I

3604  GCCCTAAATTTAGCGTCTAAAAAATTCGGAAAAAATATGTCTAATTTTAACTAGATTGAATGGCATACTGCCGAT
       A  L  N  L  A  S  K  K  F  G  K  I  C  L  I  L  T  R  L  N  G  I  L  P  D

3679  GATGAATTGATGAATTGGAGGAGACTTTCTGGTAGGAATATACATCTTGCTGTGGTGTGTGGATGACAACTCT
       D  E  L  M  N  W  R  R  L  S  G  R  N  I  H  L  A  V  V  C  V  D  D  N  S

3754  AAAATCTCCTTCATAGATGAGGACAAATTGTACCCTAGTTTCAAGCCGATCTACAAAGACATCCATGGAGGA
       K  I  S  F  I  D  E  D  K  L  Y  P  S  F  K  P  I  Y  K  D  T  R  F  G  G

3829  CGCATGGATATGACCAGATTATACGACTATGAAATAAGGGATATAGACCAGGACATCCATGGAATAGTATTCAG
       R  M  D  M  T  R  L  Y  D  Y  E  I  R  D  I  D  Q  D  I  H  G  I  V  F  Q

3904  CACCCGTTCCCACTGGCACACTCACAGCATCGCTGTGCTATTAGGAGTGGTGCTTTGATCAAATTCAAAAAATGC
       H  P  F  P  L  A  H  S  Q  H  R  C  A  I  R  S  G  A  L  I  K  F  K  K  C
```

FIG. 15H

```
G                                                                            G
3979  GACGGTGATACGGTTTGGGACAAATTCGCAGTCAACCTTTTAAACTGTCCACATTCTGATAGTACACAATTGCTG
       D  G  D  T  V  W  D  K  F  A  V  N  L  L  N  C  P  H  S  D  S  T  Q  L  L

4054  GAAACCATCTTAGAAGAGTTTCGCAACCTGGCTGCTCTAAACGTGTGGTACGGTCTCTCTGATGGCGAAGATGGC
       E  T  I  L  E  E  F  R  N  L  A  A  L  N  V  W  Y  G  L  S  D  G  E  D  G

4129  CATATTCCATGGCATATCCTAGCCGTGAAAAAAATGATGAACACTCTTGTGCACACCAGAGTAAAAATTGCTAAT
       H  I  P  W  H  I  L  A  V  K  K  M  M  N  T  L  V  H  T  R  V  K  I  A  N

4204  ACTTCCGCCGCTACTGTGCATACCGCTACTTCTTCATCAATTATTCTCTCGGATAAATAAACTTTTTCCGGCAAC
       T  S  A  A  T  V  H  T  A  T  S  S  S  I  L  S  D  K

4279  GTTTTCCTGCTCATCTGTAGCCCTATTTACCAGTTTTGGTTTTTAGTATTATTCCGGGGTGTAAACCCAGAAGTCT
4354  ATTTCTCCAGTCGGATTTATAAAACAAAACCGGAAGCGGTACGGCATTTCACTGGTGATGCACGCCCA
4429  GCGTGTAGTCCGAGACAATTCCACAGAAACGCGAATGAGATTGCGTTAAGGCTGTATTTCAAGGCACACGAAG
4504  CGGCCACGTGGGTCTGCGATGGTGTTGATGATGTCAAGAATGTATCATACTCCGTATAAGGTTATGTAATCG
4579  GAAGTCGCGATTCTTTTTCGTGTTTTTCTTTTATTTTTCCAGTTTTTCGTCTGCGATGGAATGAAAATTGTTG
4654  AAGTTCTCTTGATTAGCAAGTAGTTCTTACATCGCAGGAATCTTATGTT   4702
```

FIG. 16A

```
      5'  AGACGGATTATTGTTTTCAGTTGAAGTTGC  GCACTCGGCATATGATTTATAGATTCCAA
-420  TATATTGTACTTCGTTATATATGTGTTACG      AATATTTTGATTTCGTTTTAGAGAGTTTT      GATTAGAGGAAATTATAGCTTTTTTAACA
-360  GTGAAATAAATATCATTACATCAAAAGTCTT     CAAGAATTACGTGTGTGGCTTAAGTTGCG     TTTCATTTCCCGCTTCAATACTTGAAAGT
-270  TATCCCACAATCACTGCTGACAAAAGGAT       ACAAGAAAGTTTATAGGAGAGAAAAAAAGG    CGGAAGGTATACTGAAGTTAGTAATTTTG
-180  CTTCCCAATTGAATTAAGGCCCGCCTAGTTT     TGACGGAGGAGAAGCTCAATCGTTCGTTGGAAAG  AAGATAGAGACACAAAACTCCTATCAGCCA
 -90  ATGTACCAAAGGCTATGCAGGTACAAGGA       CAACAGCAAGCTCAATCGTTCGTTGGAAAG      AAAAACAATCGGAAGTGTGCATGAAAAA
   1  M  Y  Q  R  P  M  Q  V  Q  G        Q  Q  Q  A  Q  S  F  V  G  K       K  N  T  I  G  S  V  H  G  K       30

91  GCCCCGATGCTAATGGCCAATAATGATGTT      TTTACTATTGGACCTTATAGGCCAAGAAAA    GATAGAATGCGGGTATCTGTCTTAGAAAAG
      A  P  M  L  M  A  N  N  D  V        F  T  I  G  P  Y  R  A  R  K       D  R  M  R  V  S  V  L  E  K       60

181  TACGAAGTTATTGGCTACATTGCTGCGGGC      ACATATGGTAAAGTTTACAAAGCGAAAAGA    CAAATCAACTCCGGTACCAATTCCGCTAAT
      Y  E  V  I  G  Y  I  A  A  G        T  Y  G  K  V  Y  K  A  K  R       Q  I  N  S  G  T  N  S  A  N       90

271  GGTTCTAGTCTGAATGGTACCAATGCGAAA      ATTCCGCAGTTTGACAGCACGCAACCAAAA    TCAAGCTCTTCAATGGACATGCAGGCAAAT
      G  S  S  L  N  G  T  N  A  K        I  P  Q  F  D  S  T  Q  P  K       S  S  S  S  M  D  M  Q  A  N       120

361  ACAAACGCATTAAGAAGAAACTTGTTAAAG      GATGAAGGAGTGACCCCCGGAAGAATACGA    ACTACGAGGAAGATGTATCCCCGCACTAT
      T  N  A  L  R  R  N  L  L  K        D  E  G  V  T  P  G  R  I  R       T  T  R  E  D  V  S  P  H  Y       150

451  AATTCCAAAAACAAACCCTCATTAAAAAA       CCGCTGACGGTATTTTATGCCATTAAAAAG    TTCAAGACAGAGAAGGATGGCGTCGAACAA
      N  S  Q  K  Q  T  L  I  K  K        P  L  T  V  F  Y  A  I  K  K       F  K  T  E  K  D  G  V  E  Q       180

541  TTGCATTATACGGGAATATCTCAGAGTGCC      TGTAGAGAAATGGCATTATGTCGAGAATTG    CACAACAAGCATTAACCACATTAGTGAA
      L  H  Y  T  G  I  S  Q  S  A        C  R  E  M  A  L  C  R  E  L       H  N  K  H  L  T  T  L  V  E       210

631  ATTTTTTGGAAGGAAAATGTGTCCATATG       GTATACGAATATGCGGAGCATGATCTGCTA    CAAATTATCCACTTCCATTCCCATCCGAA
      I  F  L  E  R  K  C  V  H  M        V  Y  E  Y  A  E  H  D  L  L       Q  I  I  H  F  H  S  H  P  E       240

721  AAAAGGATGATACCACCAAGAATGGTTCGG      TCTATTATGTGGCAGTTTTAGACGGCGTA     TCGTATCTTCATCAAAATTGGGTGCTTCAT
      K  R  M  I  P  P  R  M  V  R        S  I  M  W  Q  L  L  D  G  V       S  Y  L  H  Q  N  W  V  L  H       270
```

FIG. 16B

```
     A
 811 CGAGATTTGAAACCCGCAAATATAATGGTG ACCATAGATGATGTGTTAAAATTGGTGAT TTAGGTTTGGCCAGAAAATTTCATAATATG  300
       R D L K P A N I M V   T I D G C V K I G D   L G L A R K F H N M
 901 CTGCAAACCCTCTATACTGGGGATAAAGTG GTTGTCACTATATGGTACCGTGCACCTGAG TTGCTATTGGGAGCACGGCACTATACCCCT  330
       L Q T L Y T G D K V   V V T I W Y R A P E   L L L G A R H Y T P
 991 GCGGGTTGATTATGGTCCGTTGGCTGCATT TTTGCAGAACTGATAGGATTACAGCCCATA TTTAAAGGTGAAGAAGCTAAAACTAGACTCT  360
       A V D L W S V G C I   F A E L I G L Q P I   F K G E E A K L D S
1081 AAAAAGACTGTTCCATTTCAAGTGAATCAA CTACAGAGAATTTGAAGTTCTTGGCACT CCCGATCAAAAAATTTGGCCTTATTGGAG  390
       K K T V P F F Q V N Q   L Q R I L E V L G T   P D D Q K I W P Y L E
1171 AAGTATCCAGAATATGATCAAATTACGAAG TTTCCAAAGTATAGGGATAACCTTGCTACA TGGTATCATTCCGCGGGGAGGAAGGACAAG  420
       K Y P E Y D Q I T K   F P K Y R D N L A T   W Y H S A G G R D K
1261 CATGCTTTAAGCTTACTTTACCACTTGTTA AATTATGATCCAATTAAAAGAATAGATGCA TTTAATGCGTTGGAACATAAGTACTTCACA  450
       H A L S L L Y H L L   N Y D P I K R I D A   F N A L E H K Y F T
1351 GAAAGTGATATTCCTGTTAGTGAAAATGTA TTTGAAGGTCTAACTTACAAATACCCGGCA AGAAGAATTCACACGAACGATAATGACATC  480
       E S D I P V S E N V   F E G L T Y K Y P A   R R I H T N D N D I
           T (srb10-1)
1441 ATGAATCTTGGATCAAGAACGAAAAAACAAT ACACAAGCTTCAGGAATCACCGCAGGTGCC GCTGCAAATGCTTTAGGTGGGCTTGGTGTT  510
       M N L G S R T K N N   T Q . A S G I T A G A   A A N A L G G L G V
1531 AACCGTAGAATTCTGGCCGCGGGCAGCAGCA GCCGCTGCTGCGGTGTCAGGAAACAATGCA TCAGATGAGCCATCTCGAAAGAAAAACAGA  540
       N R R I L A A A A A   A A A A V S G N N A   S D E P S R K K N R
1621 AGATAGGCTTCTATTTTATATATATATTGG AATTTTTCATTCCACAGCACTGTCACTATT ATATTCATTAAACTTTTTTATCTTTATA    541
       R *
1711 GTATTTAAATCGGCATACAGTTTCAATTTT TCGCTTTAGAGGCACTAAGAATGCAAGTCT GCAACATTCAGGTAAAATAATGGGTTGATT
1801 TTAGGTCGAGCTAAAACCCTGTTCTCCGCA GATGTATGCGAATTCGTCATAATTCATCT CAACTAATGGGGCTTTAAAACATATGAATA
1891 TCTCATGCAACCCAAAAAGAAGAAAGAA AAGACTTCAAGTCCCCCCCTTAATTTTAT ATAATGGTAGTAGTAGTTGTTCGTAACT
1981 TATCGGCAATAGTAATATGTTCCCATTATC AACA 3'
```

FIG. 17A

```
GGTACCAGGTCAAGAAGCAGAATACCCAAGGGCATCCTCCTTAATGAGTTGATTTAAACAATTTAAAATTTTAAATCTCATTACGTTTT         90

CCGCATACGAATTGGTGGGAGACTTTCAACCCAAAGCATATTACTGAGTAAAAAAATTTTACTCCATTTGTAAGCTTCGATTTGTGAC        180

GATTCTTTGGTCATGGATTGAAGAACTTTAAACGAGAGAAATTAGAAGACCACTATTAGTTCTTTACCGCAACATAGG                  270

ATAAACAAAGTTATTTCTACTCCTTTATATATTTGAAAAAATATAAAATCCACGGAAAAACATCGAAAATTCATTTTCATGAAGGAA         360

AATTAGGGTTCATACAGGAGTAGAGTTCATTGATGTGGTAGCAACCTTGTTAGCACTCATATTGTTCGAACAAAAAATGCCCTCTCAAAC      450

TTTAGTTGAAGAGGCGATAAGGCATCTCAAAAGTTAGAGCATGTCGGGAGCTTCGAAGTTAGACATGATCATTGGCAAT                540
                                         Met Ser Gly Ser Phe Trp Thr Ser Thr Gln Arg His His Trp Gln

ATACCAAGGCATCATTGGCTAAAGAGAGGCAGAAGTTATGGCTATTGGAGTGCCAGCTGTTTCCTCAAGTTTGAATATTGTAATGGATT       630
Tyr Thr Lys Ala Ser Leu Ala Lys Glu Arg Arg Lys Leu Trp Leu Leu Cys Gln Leu Phe Pro Gln Gly Leu Asn Ile Val Met Asp

CGAAGCAAAACGGGCATCGAACAATCCATCACAGAATACTCACCGAGACTTACACTATGATAAAGATTATAATCTAAGGA               720
Ser Lys Gln Asn Gly Ile Glu Gln Ser Ile Thr Lys Asn Ile Pro Ile Thr His Arg Asp Leu His Tyr Asp Lys Asp Tyr Asn Leu Arg

TCTACTGCTATTTCCTGATAATGAAGCTTGGAAGGAGACTAAATATAAGACAGTATGCACTGGCTACAGCACATATTTATCTATCAAGGT     810
Ile Tyr Cys Tyr Phe Leu Ile Met Lys Leu Gly Arg Arg Leu Asn Ile Arg Gln Tyr Ala Leu Ala His Ile Tyr Leu Ser Arg

TTTTAATAAAGGCTTCAGTTAGAGAAATAAACCTATATATGCTGGTTACTACGTGTATATTTAGCATGCAAAGTTGAAGAATGCCCGC        900
Phe Leu Ile Lys Ala Ser Val Arg Glu Ile Asn Leu Tyr Met Leu Val Thr Thr Cys Val Tyr Leu Ala Cys Lys Val Glu Glu Cys Pro
```

```
AATATATCAGAACTTTGGTAAGTGAAGCCCGTACCTTATGGCCCGAATTTATTCCTCCTGACCCTACTAAAGTTACTGAGTTTGAGTTCT    990
Gln Tyr Ile Arg Thr Leu Val Ser Glu Ala Arg Thr Leu Trp Pro Glu Ile Pro Pro Asp Pro Thr Lys Val Thr Glu Phe Glu Phe

ACTTACTAGAAGAATTGGAAAGTTACTTAATTGTCCACCACCCTTATCAATCCTTAAAGCAAATTGTTCAAGTCTTAAAGCAACCGCCAT    1080
Tyr Leu Leu Glu Glu Leu Glu Ser Tyr Leu Ile Val His Pro Tyr Gln Ser Leu Lys Gln Ile Val Gln Val Leu Lys Gln Pro Pro

TTCAAATAACACTATCGTCAGATGATCTACAAAAACTGTTGGTCCTTAATCAACGACAGTTATATAAATGATGTTCATTTGCTTTACCCTC    1170
Phe Gln Ile Thr Leu Ser Ser Asp Asp Leu Gln Asn Cys Trp Ser Leu Ile Asn Asp Ser Tyr Ile Asn Asp Val His Leu Leu Tyr Pro

CTCATATTATCGCTGTGTTATTCATTACGATTTCATTCCATTCATGGGAAACCAACCAAAGGATCATCGTTAGCATCTGCGGCTTCTG    1260
Pro His Ile Ile Ala Val Ala Cys Leu Phe Ile Thr Ile Ser Ile His Gly Ser Ser Leu Ala Ser Ala Ala Ser

AAGCCATCAGAGATCCTAAAAATTCTAGTTCTCCTGTTCAAATAGCTTTTAATCGTTTTATGGCAGAATCTCTTGTAGATCTTGAGGAGG    1350
Glu Ala Ile Arg Asp Pro Lys Asn Ser Ser Ser Pro Val Gln Ile Ala Phe Asn Arg Phe Met Ala Glu Ser Leu Val Asp Leu Glu Glu

TTATGGATACGATTCAAGAGCAAATTACATTATACGATCATTGGGACAAGTACCACGAACAATGGATAAAGTTTCTGCTACATACTTTGT    1440
Val Met Asp Thr Ile Gln Glu Gln Ile Thr Leu Tyr Asp His Trp Asp Lys Tyr His Glu Gln Trp Ile Lys Phe Leu Leu His Thr Leu

ATCTTAGACCAGCATCTGCAATTAATCATGCGAAGAATAAATTTAAAAACCGTTAAGCCTGTAAATTCAATCATTATGGTGGTGATGAT    1530
Tyr Leu Arg Pro Ala Ser Ala Ile

CCGTTTTGGAAATGTTTCGTCCTTGACTACCTTTGTTTAACATGATATTGGAACGTCAAGACATATTGAGAATAGGTACC    1610
```

FIG. 21A

```
hSRB7
  -9  GGTAGGAACATGGGGATGGCTCAGGCGCTCAGGACGCTTCAGAATTCGCTTCAGATCAGTTTGTAATGCC
                M  A D R L T Q L Q D A V N S L A D Q F C N A
  67  ATTGGAGTATTGCAGCAATGTGGTCCTCCTGCCTCTTTCAATATATTCAGACACAGCCAATTAACAAGACCAGCCA
         I G V L Q Q C G P P A S F N N I Q T A I N K D Q P
 142  GCTAACCCTACAGAAGAGTATGCCCAGTTTTTTGCAGCTCTTATACAGCGTGCTAGCACAAAAGACATTGATGTTTTG
         A N P T E E Y A Q L F A A L I A R T A K D I D V L
 217  ATAGATTCCTTACCCAGTGAAGAATCTACAGCTCTGCTTACAGGCTGCTAGCTTGTATAAGCTAGAAGAAAAC
         I D S L P S E E S T A L Q A A S L Y K L E E N
 292  CATGAAGCTGCTACATGTCTGGAGGATGTGTTATCGAGGAGACATGCTTCTCGAGAAGATACAAAGCGCACTT
         H E A A T C L E D V V Y R G D M L L E K I Q S A L
 367  GCTGATATTGCACAGTCACAGTGCTCACAGTGTACCATGGTACCATAGCAATTCTCATCAGACTTAGATACAAGCCTT
         A D I A Q S Q L K T R S G T H S Q S L P D S *
 442  TGGATACCATGTCGTGAGAAAAGAACTGTTGAGTGCCATTAAGAATTCTGCATCAGACTTAGATGTCTCTATTTCAC
 517  ACCAACATTACAGAAACATTAAACATGACACATTACCTTTTAGCTATTTTAATAGTCTTCTATTTTCAC
 592  TCTTGATAAGCTTATAAATCATGTAATGCAATCAGCTTTAAAGCATCATACCATCATCATTTTTAACTGAGTGAAATT
 667  ATTAAGGCATGTAATACATTAATGAACATAATATAAGGAAACATATGTAAAATTCAAAAAAAAAAAAAAAAAAAAA
 742  AAAAAAAAAAAAAAAAAAAAAAAAA
```

FIG. 21B

```
hSRB7  MADRLTQLQDAVNSLADQFCNAIGVLQ..QCG.PPASFNNIQTAINKDQPANPTEEYA....QLFAALIARTAKDID
       !.!!!!!!   !!: .!!!!(     !!!.! .!:...! !!!:.       ::.! :!  !! :!
ySRB7  MTDRLTQLQICLDQMTEQFCATLNYIDKNHGFERLTVNEPQMS.DKHATVPPEEFSNTIDELSTDIILKT.RQIN hSRB7  VLIDSLPSEESTAA..LQAASLY..KL...EEENHEAATCLEDVVYRGDMLLEKIQSALADIAQSQLKTRSGTHSQSLPDS*
       !!!!!!!!! !. !. :. !! !       ! !:!. ! .!:.:!!!:!:  ::!!!.! ! :!
ySRB7  KLIDSLPGVDVSAEEQLRKIIDMLQKKLVEVEDEKIEALKKEKLLRHVDSLIEDF...VDGIANS..K.KST*
```

FACTORS WHICH MODIFY GENE TRANSCRIPTION AND METHODS OF USE THEREFOR

RELATED APPLICATION

This application is a Continuation-In-Part of Ser. No. 08/540,804, filed Oct. 11, 1995 now U.S. Pat. No. 5,919,666; which is a Continuation-In-Part of U.S. Ser. No. 08/521,872 filed Aug. 31, 1995; which is a Continuation-In-Part of U.S. Ser. No. 08/218,265 filed Mar. 25, 1994, now U.S. Pat. No. 5,922,585, the teachings of which in their entirety are expressly incorporated herein by reference.

BACKGROUND OF THE INVENTION

The regulation of cellular gene expression occurs primarily at the level of transcription initiation by RNA polymerase. Regulated transcription initiation by RNA polymerase II in higher eukaryotes involves the formation of a complex with general transcription factors at promoters (Sawadogo, M. and Sentenac, A., *Ann. Rev. Biochem.* 59:711–754 (1990). One of these factors, transcription factor IID (TFIID), contains the TATA-binding protein (TBP), which is able to bind directly to promoter DNA. The remaining components of the transcription initiation complex include RNA polymerase II and the initiation factors TFIIA, TFIIB, TFIIE, TFIIF, TFIIH, and TFIIJ. These components associate with TFIID-bound promoter DNA to form a transcription initiation complex. Sequence-specific DNA-binding proteins appear to regulate the establishment and activity of transcription initiation complexes, possibly through interactions with TFIIB and TBP and additional factors that make up TFIID.

Several high molecular weight complexes containing TBP have been identified in extracts from human and Drosophila cells (Gill, G, and Tjian, R., *Curr. Opin. Gen. Dev.* 2:236–242 (1992); Sharp, P. A., *Cell* 68:819–821 (1992)). One of these complexes is TFIID, which contains at least eight TBP-associated factors (TAFs) (Pugh B. F., and Tjian, R. J. *Genes Dev.* 5:1935–1945 (1991)). A second complex is the RNA polymerase I promoter selectivity factor, SL1, which contains TBP and three TAFs (Comai, L., et al., *Cell* 68:965–976 (1992)). A third complex is a component of the RNA polymerase III factor TFIIIB, which consists of TBP and two TAFs (Taggart, A. K. P., et al., *Cell* 71:1015–1028 (1992)). Some of the TAFs associated with these complexes appear to function as transcriptional coactivators by providing a functional link between sequence-specific regulators and TBP (Dynlacht, B. D., et al., *Cell* 66:563–576 (1991)).

The RNA polymerase II carboxyl-terminal domain (CTD) is another component of the transcription apparatus that can bind to TBP (Usheva, A., et al., *Cell* 69:871–881 (1992)). The CTD is a highly conserved and apparently unique feature of the largest subunit of RNA polymerase II (Young, R. A., *Ann. Rev. Biochem.* 60:689–715 (1991)). The CTD contains 26–52 repeats, depending on the organism, of the consensus heptapeptide sequence, Tyr-Ser-Pro-Thr-Ser-Pro-Ser. Deletion mutations that remove most or all of the CTD are lethal to cells (Nonet, M., et al., *Cell* 50:909–915 (1987)). CTD partial truncation mutations cause defects in growth and inducible gene expression in vivo and produce substantial defects in transcription initiation in vitro (Liao, S. M., et al., *Genes Dev.* 5:2431–2440 (1991)).

An important feature of RNA polymerase II molecules recruited into the initiation complex is their association with RNA polymerase-associated proteins (RAPs) (Conaway, J. W., et al., *J. Biol. Chem.* 266:17721–17724 (1991)). Two mammalian proteins, RAP30 and RAP74, have been identified as components of the general transcription factor TFIIF (Flores, O., et al., *J. Biol. Chem.* 263:10812–10816 (1988)).

Despite this knowledge of the components of the RNA polymerase II transcription initiation complex, two major questions have not been addressed until now. First, how do RNA polymerase II and the general initiation factors interact with one another in vivo? For example, it is not clear whether RNA polymerase II and general factors assemble in a sequential manner on promoter DNA, or whether a large complex of these components assembles prior to association with DNA. Second, how do transcriptional regulators interact with the transcription initiation complex? Thus, we do not know whether interactions occur only between regulators and the subunit of TFIID, or whether there are additional interactions with other components of the initiation complex.

SUMMARY OF THE INVENTION

The present invention relates to RNA polymerase II holoenzyme complex. An RNA polymerase II holoenzyme complex of the present invention is a multisubunit complex comprising RNA polymerase II and one, or more, regulatory components. The regulatory components include, eukaryotic regulatory proteins, for example, yeast and mammalian SRB (Suppressor of RNA polymerase B) proteins and yeast and mammalian SWI and SNF proteins. The RNA polymerase II holoenzyme is capable of initiating transcription and is responsive to activators. Additional components associated with the RNA polymerase holoenzyme can include one, or more general transcription factors (also referred to herein as GTFs) and other components necessary and sufficient for responding to transcriptional activators. The RNA polymerase II holoenzyme described herein plays a key role in the initiation of transcription in eukaryotic cellular organisms. DNA transcription by the RNA polymerase II holoenzyme is stimulated by activator proteins, a feature not observed with purified RNA polymerase II and general transcription factors alone.

Applicants have identified and characterized eukaryotic RNA polymerase II holoenzyme complexes and their components, including those of mammalian, non-mammalian (including for example, yeasts, fungi, parasites and insects) and human origin. In one embodiment, yeast regulatory proteins, identified herein as SRB2, SRB4, SRB5, SRB6, SRB7, SRB8, SRB9, SRB10 and SRB11, which act as positive and negative regulators of the activity of RNA polymerase II are described. Encompassed by this invention are yeast SRB proteins SRB2, SRB4, SRB5, SRB6, SRB7, SRB8, SRB9, SRB10 and SRB11, the amino acids encoding these SRB proteins, and variants or derivatives (e.g., mutant SRB proteins) thereof, and antibodies reactive with the SRB proteins. The SRB proteins comprise the SRB complex which is tightly associated with the RNA polymerase II carboxy terminal domain, or CTD.

Also described herein is the cloning and sequencing of the first human SRB and the purification and characterization of a mammalian RNA polymerase II holoenzyme. hSRB7 is 35% identical to ySRB7, complements a ySRB7 deletion, and, like its yeast counterpart, binds to the carboxyl terminal domain of RNA polymerase II. hSRB7 is part of a mammalian holoenzyme complex, and results described herein show that this mammalian holoenzyme complex supports activated transcription.

As further described herein, the RNA polymerase II holoenzyme of the present invention includes additional regulatory components, including global gene regulators comprising SWI and SNF gene products. The SWI and SNF gene products are collectively referred to herein as SWI/SNF proteins. The SWI/SNF proteins, or polypeptides, play a key role in the regulation of gene expression. The regulatory function of gene expression of the SWI/SNF proteins includes chromatin remodeling. More specifically, the SWI/SNF proteins provide the RNA polymerase II the holoenzyme capacity to disrupt nucleosomal DNA and, thus, facilitate stable binding of various components of the transcription initiation complex at specific promoters. The SWI/SNF proteins encompassed by the present invention form a multisubunit complex with the SRB proteins, referred to herein as the SRB/SWI/SNF complex. The SRB/SWI/SNF complex associates with the RNA polymerase II CTD. Encompassed by the present invention are the SWI/SNF proteins which comprise the SRB/SWI/SNF complex.

Also encompassed by this invention are the DNA sequences encoding the eukaryotic, e.g., yeast and mammalian, SRB proteins and novel SWI/SNF proteins, the complementary strands of these DNA sequences, and allelic variations thereof, and nucleic acid probes that are sufficiently complementary to a SRB or SWI/SNF DNA sequence that they selectively hybridize to that SRB or SWI/SNF DNA sequence.

This invention further relates to methods of modifying gene transcription by substances that bind to, or interact with, SRB proteins or SWI/SNF proteins; the SRB genes and SWI/SNF genes encoding the proteins, or the SRB or SWI/SNF mRNAs. Such substances can either prevent, or enhance, the formation of the RNA polymerase II holoenzyme, or, if the holoenzyme complex is formed, prevent, or enhance, the function of the holoenzyme as an initiator of transcription. Substances that bind to, or interact with the SRB proteins or SWI/SNF proteins; SRB genes or SWI/SNF genes; or SRB or SWI/SNF mRNAs can also modify the influence that SRB or SWI/SNF proteins have on RNA polymerase II, or on other transcription factors essential to gene transcription. Moreover, differences in SRB and SWI/SNF protein homolog (e.g., differences in the yeast and human SRB7 gene or protein sequences) can be exploited to design therapeutic compounds or drugs, that target pathogenic eukaryotes, e.g., the fungus Candida, and inhibit gene transcription in the pathogen without affecting gene transcription in the mammalian or human host.

This invention also relates to a method of in vitro transcription employing the purified RNA polymerase II holoenzyme and to the use of this method to identify substances, both naturally-occurring, and synthetic, that modify gene transcription.

This invention further relates to methods of detecting SRB genes, or SWI/SNF genes, and gene products in a cell or in biological fluids using nucleic acid probes which hybridize to DNA encoding the SRB protein or SWI/SNF protein, or to SRB or SWI/SNF mRNA, (e.g., antisense nucleotides) or antibodies which bind to the SRB or SWI/SNF gene product.

BRIEF DESCRIPTION OF THE DRAWINGS

FIGS. 2A–2B shows the DNA sequence of the 1.95 kb BstEII-EcoRI DNA fragment containing the SRB2 gene (SEQ ID NO: 1) and the deduced sequence of the SRB2 protein (SEQ ID NO: 2) is shown below the sequence of the gene. The transcription initiation site is indicated by the horizontal arrow. The splice donor and splice acceptor sites are underlined. The TGCTAACA splice branch point site is boxed. The SRB2-1 mutation is a C to A transversion (nt 768) that changes as 14 from Pro to His.

FIGS. 3A–3E, 4A–4C and 5A–5B shows the DNA sequences and predicted amino acid sequences of the SRB4 (SEQ ID NO: 3 and 4), SRB5 (SEQ ID NO: 5 and 6) and SRB6 (SEQ ID NO: 7 and 8) proteins, respectively.

FIGS. 6A–6E shows the results of experiments demonstrating that SRB2 and SRB5 are essential for efficient transcription in vitro.

FIGS. 7A–7D shows the results of experiments demonstrating that SRB2 and SRB5 are essential for efficient preinitiation complex formation.

FIGS. 8A–8C shows the purification scheme of the SRB complex and results of the purification.

FIGS. 9A–9D and 10A–10B shows the results of experiments demonstrating that the RNA polymerase II holoenzyme is a complex of RNA polymerase II and initiation factors.

FIGS. 13A–13B shows the DNA sequence and predicted amino acid sequence of SRB7 (SEQ ID NO: 9 and 10).

FIGS. 14A–14C shows the DNA sequence and predicted amino acid sequence of SRB8 (SEQ ID NO: 11 and 12).

FIGS. 15A–15H shows the DNA sequence and predicted amino acid sequence of SRB9 (SEQ ID NO: 13 and 14).

FIGS. 16A–16B shows the DNA sequence and predicted amino acid sequence of SRB10 (SEQ ID NO: 15 and 16).

FIGS. 17A–17B shows the DNA sequence and predicted amino acid sequence of SRB11 (SEQ ID NO: 17 and 18).

FIG. 21A shows the DNA sequence (SEQ ID NO.: 36) and the predicted amino acid sequence of hSRB7 (SEQ ID NO.: 37).

FIG. 21B compares the predicted amino acid sequence of hsSRB7 and its yeast homolog.

DETAILED DESCRIPTION OF THE INVENTION

Figure 1:
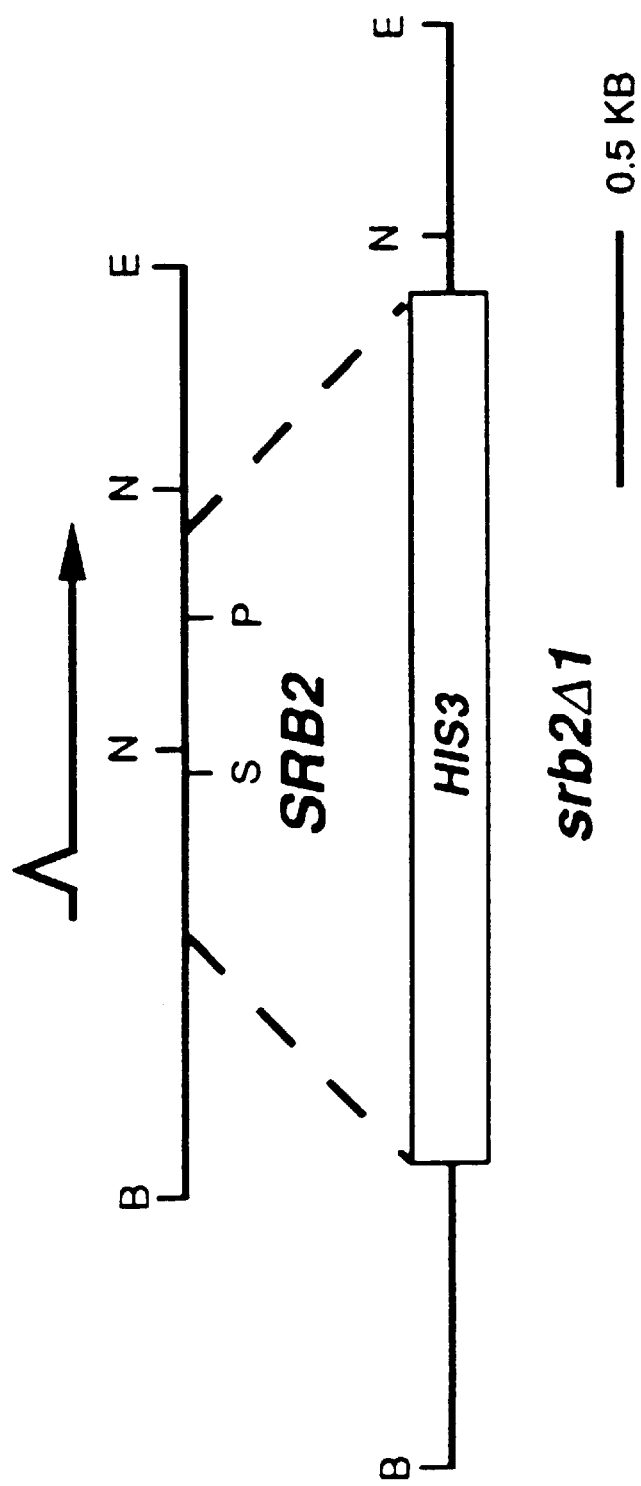
FIG. 1 shows the restriction map of a 1.95 kb BstEII-EcoRI DNA fragment from pCT21 containing the SRB2 gene (B, BstEII; E, EcoRI; N, NcoI; P, PstI; S, SacII). The SRB2 transcript is indicated above the map. The entire coding region of SRB2 was replaced with a 1.75 kb BamHI DNA fragment containing the HIS3 gene to create the deletion allele srb2Δ1.

The present invention relates to the discovery of an RNA polymerase II holoenzyme complex capable of site-specific initiation of gene transcription. RNA polymerase II holoenzymes described in the present invention are multisubunit complexes that contain RNA polymerase II and one, or more, regulatory proteins. Importantly, as described herein, the RNA polymerase II holoenzyme plays a key role in the initiation of transcription in eukaryotic organisms.

Specifically, eukaryotic RNA polymerase II holoenzymes described in the present invention are high molecular weight (1–4 Md), multisubunit complexes that contain RNA polymerase II and one, or more, regulatory proteins. The regulatory proteins as described herein, include SRB proteins, SWI proteins and SNF proteins.

The SRB regulatory proteins, identified herein as SRB2, SRB4, SRB5, SRB6, SRB7, SRB8, SRB9, SRB10 and SRB11, act as positive (enhancing) and negative (suppressing) regulators of the activity of RNA polymerase II. The SRB proteins can have multiple roles in the holoenzyme. The SRBs can act as a regulatory "glue" that stabilizes interactions between RNA polymerase II and transcription factors. They may also confer some degree of responsiveness to transcriptional activators, perhaps serving the holoenzyme in a manner functionally analogous to TAFs in TFIID. Furthermore, the SRBs may regulate events subsequent to initiation complex formation, for example, phosphorylation of the CTD and promoter clearance. The eukaryotic RNA polymerase II holoenzyme, comprising RNA polymerase II and at least one SRB protein, is capable of initiating efficient selective transcription when supplemented with additional proteins involved with gene transcription and is responsive to transcriptional activators.

The SWI and SNF proteins described herein, collectively referred to as SWI/SNF proteins, typically form a complex which associates with the SRB proteins. The SWI/SNF proteins of the SRB/SWI/SNF complex can include, for example, SWI1, SWI2/SNF2, SWI3, SNF5, SNF6 and SNF11. The SRB/SWI/SNF protein complex can also include additional regulatory proteins or components necessary and sufficient to confer gene transcription activity to the holoenzyme.

The SWI and SNF proteins described herein are involved with gene transcription activity and have been implicated in chromatin remodeling. The eukaryotic RNA polymerase II holoenzyme, comprising RNA polymerase II, at least one SRB protein and at least one SWI/SNF protein, is capable of ATP-dependent nucleosome disruption activity.

The proteins involved with gene transcription can be divided into three groups, described as follows: 1) subunits of RNA polymerase needed for some or all of the stages of transcription, but are not specific for individual promoters; 2.) transcription factors that bind RNA polymerase before, during, or after it forms an initiation complex, although they are not part of the free enzyme (these factors are likely to be needed for transcription to initiate at all promoters or, for example, to terminate); and 3.) transcription factors that bind specific sequences in the target promoters. (If the same sequences were present in all promoters, these factors would be part of the general transcription apparatus. If some sequences are present only in certain classes of promoters, factors that recognize them could be needed specifically to initiate at those promoters.) Transcription factors are also referred to herein as initiation factors.

The general transcription factors associated with the RNA polymerase II holoenzymes described herein include, for example, in yeast, the transcription factors b, e, and g and in mammals, including humans, the mammalian transcription factors TFIIH, TFIIB, TFIIE and TFIIF. The association of the holoenzyme with general transcription factors can vary within the cell at different points during the transcription process, or can vary from organism to organism. For example, the RNA polymerase II holoenzyme is capable of initiating gene transcription when interacting with (also referred to herein as associated with, or supplemented with) transcription factor a, in yeast, but with TFIIE and TATA-binding protein in humans. (TATA-binding protein is also referred to herein as TBP, which is a component of a TFIID multisubunit complex containing TBP-associated factors (TAFs) which binds selectively to promoter DNA).

Surprisingly, the RNA polymerase II holoenzymes are responsive to activators, such as the GAL4-VP16 activator protein, a feature not observed with purified yeast GTFs and polymerase II alone. Thus, the eukaryotic RNA polymerase II holoenzymes can be associated with additional components necessary and sufficient for responding to transcriptional activators, such as GAL11/SPT13.

The holoenzymes can also be associated with proteins implicated in transcriptional repression, such as a kinase-cyclin protein pair. (Liao, S. M., et al., *Nature* 374:193–196 (1995); Kuchin, S, et al., *Proc. Natl. Acad. Sci. U.S.A.*, 92:4587–4590 (1995)).

The present invention encompasses the SRB proteins SRB2, SRB4, SRB5, SRB6, SRB7, SRB8, SRB9, SRB10 and SRB11, the SRB amino acid sequences, and variants or derivatives thereof. Also intended to be encompassed by the present invention are proteins described herein with reference to specific SRB amino acid sequences, as well as the SRB proteins which include one, or more "silent changes" in the amino acid sequence. Such silent changes in the amino acid sequence may not reflect the exact SRB amino acid sequence described herein, but nevertheless, do not alter the essential function, or activity of the SRB protein, i.e., as a transcriptional regulator. For example, one, or more, amino acid residue(s) may differ in an amino acid sequence from a SRB amino acid sequence described herein, yet still retain the ability to function as an regulator of gene transcription.

Also encompassed by this invention are the DNA and RNA sequences encoding the SRB proteins, the complementary strands to these DNA/RNA sequences, and nucleic acid sequences (e.g., nucleic acid probes) that are sufficiently complementary to a SRB DNA/RNA sequence to selectively hybridize to that SRB DNA/RNA sequence. Sufficiently complementary is defined herein to mean that the nucleic acid sequence may not reflect the exact sequence described herein, but must be sufficiently complementary to hybridize to the sequence encoding the SRB protein. For example, non-complementary bases can be interspersed in the exact SRB DNA sequence, or a sequence can be longer or shorter than the exact SRB sequence, yet the sequence has sufficient complementarity to hybridize to the exact SRB sequence.

The present invention further encompasses the SRB/SWI/SNF complex which associates with the RNA polymerase II CTD and regulates gene expression. More specifically, encompassed by the present invention is a multi subunit, (e.g., multiprotein) complex comprising one, or more SAB proteins and one, or more SWI/SNF proteins and has the ability to initiate gene transcription, for example, by chromatin remodeling, or nucleosome disruption.

This invention further relates to methods of modifying gene transcription by substances that bind to, or interact with, one or more SRB proteins, SWI/SNF proteins, or the DNA/RNA encoding the SRB or SWI/SNF proteins and, thus, modify the influence of the SRB or SWI/SNF proteins on RNA polymerase II, or on other transcription factors essential to gene transcription. Interact, as used herein, includes inhibiting or promoting post-translational modification of a SRB or SWI/SNF protein. For example, a method of inhibiting gene transcription in a cell by inhibiting the phosphorylation of the CTD of RNA polymerase II via the SRB protein, or inhibiting the phosphorylation/activation of the SRB protein itself, is encompassed by the present invention.

Substances that bind to, or interact with, one, or more SRB or SWI/SNF proteins or the DNA/RNA encoding these regulatory proteins can prevent, or enhance, the formation of the RNA polymerase II holoenzyme complex, thus, inhibiting or enhancing gene transcription. For example, antisense, or nonsense nucleotide sequences that hybridize with the SRB or SWI/SNF DNA or RNA and completely inhibit, or decrease, their translation or transcription can prevent the formation of the holoenzyme complex and inhibit gene transcription. Alternatively, even though the holoenzyme complex is formed, substances that bind to, or interact with the SRB or SWI/SNF proteins, can prevent or enhance the function of the complex in the transcription process. These substances include antibodies that are reactive with, or bind to, the SRB proteins. It is important to note that therapeutic compounds can be identified and/or designed that modify gene transcription by interacting with SRB or SWI/SNF proteins of a eukaryotic pathogen without modifying gene transcription in the host.

This invention also relates to a method of in vitro transcription employing the purified RNA polymerase II holoenzyme and to the use of this method to identify substances, both naturally-occurring, and synthetic, that modify gene transcription. This invention also encompasses methods of identifying additional components, or proteins, that are functional equivalents of the SRB and SWI/SNF proteins described herein, and, therefore, have activity that is equivalent to the SRB and SWI/SNF proteins of the RNA polymerase II holoenzyme. This invention further relates to methods of identifying substances that modify gene transcription, and methods of treating disease conditions resulting from insufficient, or increased, production of, SRB proteins, or production of abnormal SRB or SWI/SNF proteins. These methods include the use of substances that bind to, or interact with, the SRB or SWI/SNF proteins, (naturally occurring and biologically active, also referred to herein as wildtype SRB proteins) genes encoding the SRB or SWI/SNF proteins, SRB or SWI/SNF messenger RNA, or the use of genetically altered SRB or SWI/SNF proteins.

The present invention further encompasses a method of identifying a component that has activity functionally equivalent to the activity of a SRB or SWI/SNF protein by evaluating the activity of the candidate protein to compensate for a deleted SRB or SWI/SNF protein in the RNA polymerase II holoenzyme. More specifically, a method is encompassed to identify a protein that has activity functionally equivalent to the activity of a SRB or SWI/SNF protein comprising inhibiting, either partially or completely, the activity of SRB or SWI/SNF protein in the RNA polymerase II holoenzyme; providing a candidate protein to be tested for SRB or SWI/SNF protein activity; associating the candidate protein with the RNA polymerase II holoenzyme; and determining the activity of the RNA polymerase II holoenzyme associated with the candidate protein, wherein if the candidate protein is functionally equivalent to the inhibited SRB or SWI/SNF protein, the RNA polymerase II holoenzyme retains its ability to initiate gene transcription.

The discovery of novel SRB proteins which modify gene transcription was made possible by a combination of genetic and biochemical selection techniques designed to identify transcription factors involved in RNA polymerase II carboxyl terminal domain (CTD) function. Most, if not all, of these proteins are tightly associated with the RNA polymerase II holoenzyme. Among the SRB proteins are both positive and negative regulators, indicating a dual role for CTD-associated factors in the initiation of transcription.

The CTD is a highly conserved and apparently unique feature of the largest subunit of RNA polymerase II. Depending on the organism, the CTD contains up to about 52 repeats of the consensus heptapeptide sequence Tyr-Ser-Pro-Thr-Ser-Pro-Ser. A subset of the RNA polymerase II molecules in yeast and mammalian cells has highly phosphorylated CTDs, and RNA polymerase II molecules lacking phosphorylation on the CTD are preferentially recruited into the initiation complex. Deletion mutations that remove most, or all, of the CTD are lethal to cells. CTD partial truncation mutations, however, cause defects in growth and gene expression in vivo and produce substantial defects in transcription initiation at multiple promoters in vitro. Thus, suppression analysis of conditional CTD truncation mutations in yeast has been used to identify factors which influence CTD function.

Cloning and Sequence Analysis of SRB2

Figure 2A:
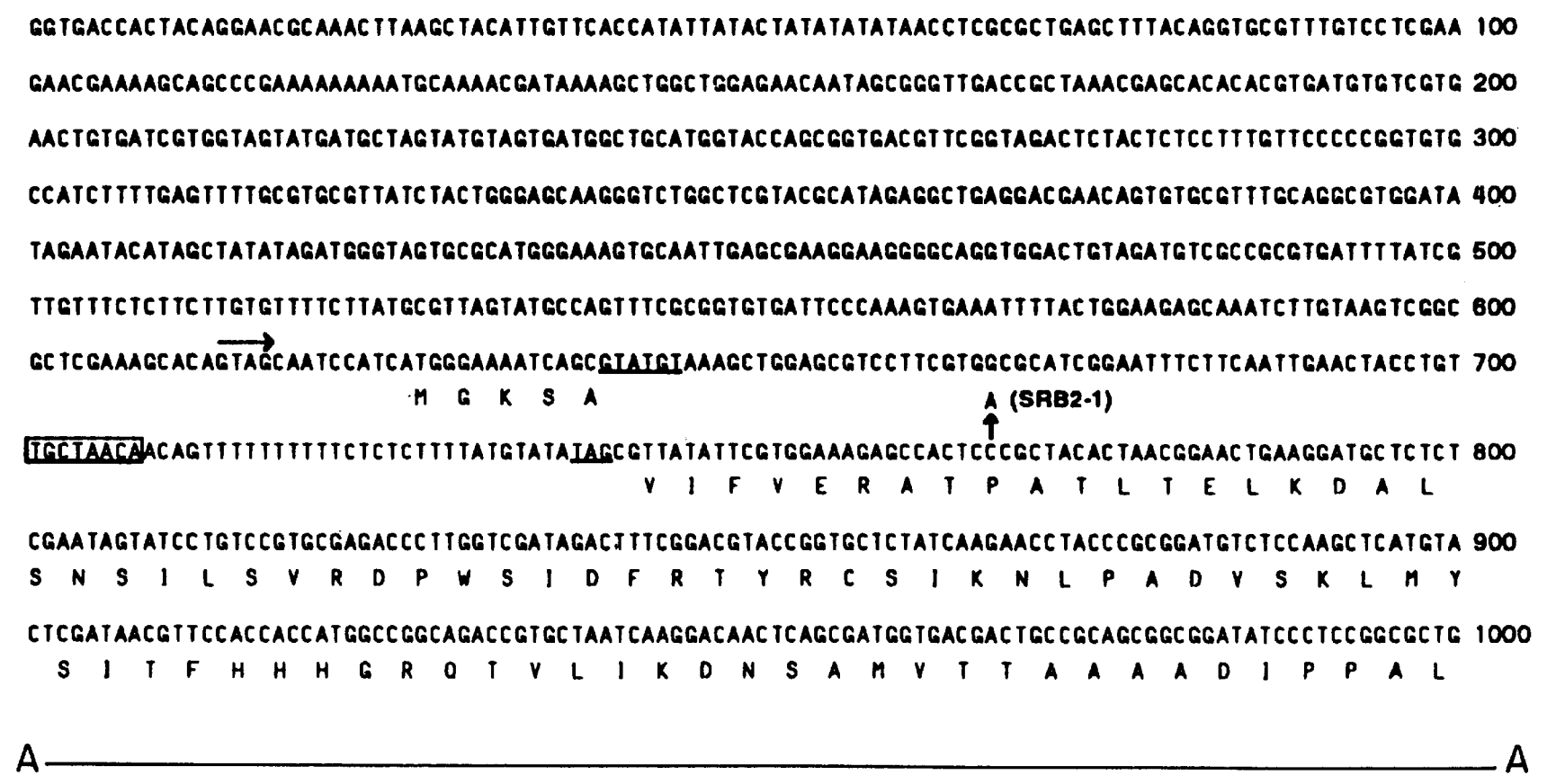

The isolation of suppressors of *Saccharomyces cerevisiae* RNA polymerase II CTD truncation mutations led to the identification of a dominant suppressing allele, SRB2-1, and the isolation of DNA clones containing SRB2-1 and its wild type counterpart, SRB2 (Nonet, M. L. and Young, R. A., *Genetics* 123:715–724 (1989)). The position of SRB2 within a genomic DNA clone is shown in FIG. 1. The sequence was determined for SRB2 and its surrounding DNA, as shown in FIGS. 2A–2B (SEQ ID NO: 1). The SRB2 gene was shown to encode a TBP-binding protein. (Koleske, A. J., et al., *Cell* 69:883–894 (1992)). The predicted SRB2 protein is 210 amino acids long (SEQ ID NO: 2) and has a molecular mass of 23 Kd. It is a hydrophilic protein rich in serine, threonine and tyrosine residues, and it is acidic, with a predicted $pK_a$ of 5.2. (See Example 1).

The SRB2 gene was identified through analysis of extragenic suppressors of CTD truncation mutations, as described in Example 1. The dominant, gain-of-function mutation SRB2-1 specifically suppresses CTD truncation mutations. Cells lacking SRB2 and cells lacking a large portion of the CTD exhibit the same set of conditional growth phenotypes and have the same defects in gene expression. (See Example 1). While the presence of SRB2-1 causes cells with severe CTD truncations to behave as if the CTD was longer, the loss of SRB2 has the opposite effect. The allele specificity of the SRB2 suppressor, the identical behavior of cells with CTD truncations and cells lacking SRB2 all indicate that SRB2 and CTD are involved in the same process during initiation.

To identify additional components of the transcription apparatus that affect CTD function, extragenic suppressors of a *Saccharomyces cerevisiae* RNA polymerase II CTD truncation mutant were isolated, as described in Example 2. The cold-sensitive phenotype of cells containing RNA polymerase II CTDs with only 11 intact heptapeptide repeats (rpb1Δ104) was exploited to obtain 85 independent suppressing isolates, of which approximately one-third were dominant and two-thirds recessive. The dominant suppressing isolates were chosen for further study. Genetic analysis revealed that all of the dominant mutations occurred in four SRB genes: SRB2, SRB4, SRB5, and SRB6. Additional analysis revealed that SRB4, SRB5, and SRB6 were newly identified genes.

Two genetic assays were performed to obtain support for a functional relationship between the new SRB gene products and the CTD. The ability of the suppressing alleles of SRB4, SRB5, and SRB6 to suppress all of the phenotypes associated with the CTD truncation mutation rpb1Δ104 was investigated. These phenotypes include cold-and temperature-sensitive growth, inositol auxotrophy, and the inability to utilize pyruvate as a carbon source. Cells containing either SRB4-1, SRB5-1, or SRB6-1 suppress all of these defective phenotypes, as does SRB2-1.

To assess whether the suppressing activities of SRB4-1, SRB5-1, and SRB6-1 are specific to CTD mutations, the ability of the SRB alleles to suppress the conditional phenotypes associated with mutations elsewhere in RNA polymerase II was investigated. SRB4-1, SRB5-1, and SRB6-1 generally do not suppress the conditional and auxotrophic phenotypes associated with rpbl point mutations. SRB4-1, SRB5-1, and SRB6-1 do suppress the cold-sensitive phenotype of the rpb1-14 mutation. This is the same type of suppression specificity shown by SRB2-1, and this argues that SRB2, SRB4, SRB5, SRB6, and the CTD are involved in the same process in transcription initiation.

Cloning and Sequence Analysis of SRB4, SRB5, and SRB6

Genomic DNA clones containing SRB4-1, SRB5-1, and SRB6-1 were isolated by taking advantage of their ability to suppress dominantly the cold-sensitive phenotype of a cell containing the CTD truncation mutation rpb1Δ104. Genomic DNA was isolated from strains containing the dominant suppressing alleles of SRB4, SRB5, and SRB6. Libraries were constructed in a yeast centromeric plasmid containing the URA3 gene as a selectable marker. These libraries were transformed into yeast cells containing cold-sensitive CTD truncation mutation, and genomic clones were isolated from Ura$^+$ transformants able to grow at 12° C. The mutant genes were further localized by constructing subgenomic libraries with fragments of the SRB4-1, SRB5-1, and SRB6-1 genomic inserts and again selecting for Ura$^+$ transformants able to grow at 12° C. Genomic clones with the smallest inserts were identified and sequenced.

The wild-type allele of SRB4 was cloned from a wild-type genomic DNA library. Wild-type SRB5 and SRB6 alleles were obtained by plasmid gap repair in vivo Plasmids containing the wild-type SRB4, SRB5, and SRB6 genes did not suppress the cold-sensitive phenotype of CTD truncation mutants, confirming that in each case the correct locus was cloned. SRB4, SRB5, and SRB6 were physically mapped using the prime clone grid filters of the yeast genome (provided by L. Riles and M. Olson, Washington University). SRB4 maps to the right arm of chromosome V, approximately 40 kb from the centromere (λ clones 5961 and 6224). SRB5 maps to the right arm of chromosome VII, approximately 30 kb centromere proximal to SPT6 (λ clones 5146 and 4624). SRB6 maps to the right arm of chromosome II, approximately 75 kb centromere distal to CDC28 (λ clone 4796).

DNA fragments containing SRB4 (SEQ ID NO: 3), SRB5 (SEQ ID NO: 5), and SRB6 (SEQ ID NO: 7) were sequenced, and the open reading frames were established by unidirectional deletion analysis and identification of the suppressing mutations. The predicted SRB4 protein is 687 amino acids long (SEQ ID NO: 4) and has a molecular mass of 78 kd (FIGS. 3A–3E). SRB5 is predicted to be 307 amino acids in length (SEQ ID NO: 6) with a molecular mass of 34 kd (FIGS. 4A–4C). The predicted SRB6 protein is 121 amino acids long (SEQ ID NO: 8) and has a molecular mass of 14 kd (FIGS. 5A–5B). A search of sequence data banks revealed that SRB4, SRB5, and SRB6 did not have significant sequence similarity to previously identified proteins. One notable feature of the SRB proteins is their acidic content. The predicted pK values of SRB2, SRB4, SRB5, and SRB6 are 5.2, 5.1, 4.7, and 4.6, respectively.

The suppressing mutations in all three genes were identified by comparing the complete sequences of the cloned wild-type and suppressing alleles of SRB4, SRB5, and SRB6. In each case, the alterations were singlepoint, missense mutations. The mutation in SRB4-1 changes glycine 353 to cysteine. The SRB5-1 mutation changes threonine 22 to isoleucine, and the SRB6-1 mutation changes asparagine 86 to lysine.

To determine whether the SRB genes are essential for cell viability, the entire coding region of each of the SRB genes was deleted to produce srb4Δ2, srb5Δ1, and srb6Δ1. SRB4 and SRB6 are essential. SRB5, like SRB2, is not essential, but cells lacking the gene exhibit the slow-16growth, cold-sensitive, and temperature-sensitive phenotypes characteristic of CTD truncations.

SRB2 and SRB5 Are Required for Efficient Transcription In Vitro

Figure 6B:
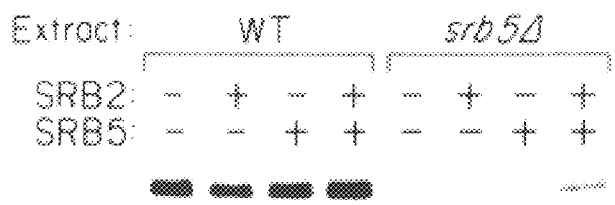
Figure 6C:
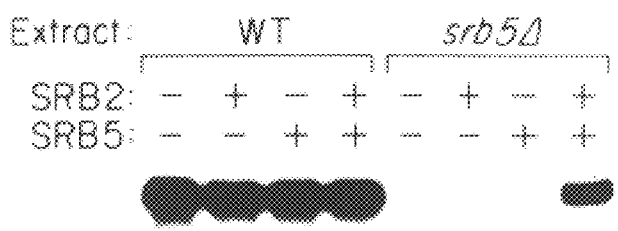

Although yeast cells lacking SRB4 or SRBG are not viable, cells lacking SRB2 or SRB5 are viable despite striking defects in growth, and it is this feature that facilitates investigation of the transcriptional activity of SRB2 and SRB5 proteins using nuclear extracts in vitro. Previous studies had revealed that SRB2 is required for efficient basal and activated transcription initiation in vitro. The role of SRB5 was investigated similarly and was also found to be required for efficient basal and activated transcription initiation in vitro as described in Example 2 (See FIG. 6A). Nuclear extracts were prepared from wild-type and srb5Δ1 cells and tested for their ability to synthesize a specific transcript in the presence and absence of purified recombinant SRB5 and GAL4-VP16 proteins. Extracts from wild-type cells produced two specific transcripts of 375 and 350 nt, and the addition of GAL4-VP16 produced a 35-fold increase in the levels of these transcripts. Extracts from srb5Δ1 cells required additional factors in order to synthesize significant levels of specific transcripts, in both the presence and the absence of GAL4-VP16 (FIGS. 6B–6C). Complementation of the srb5Δ1 extract required both purified recombinant SRB2 and SRB5; the addition of SRB5 alone failed to complement. Western blot analysis revealed that the level of SRB2 protein is greatly reduced in extracts prepared from srb5Δ1 cells.

Figure 6D:
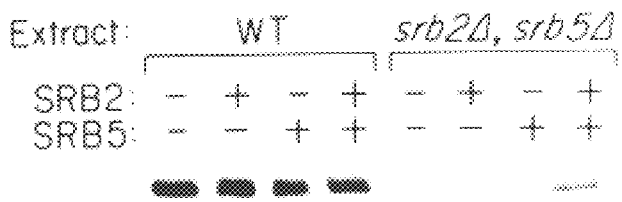
Figure 6E:
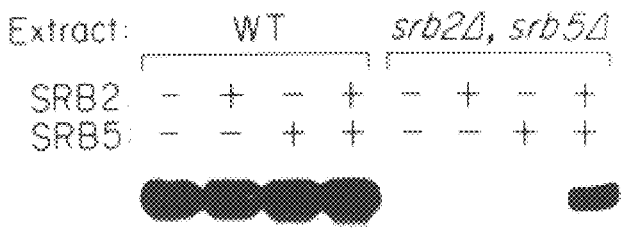

To confirm and extend these results additional transcription assays were performed using nuclear extracts prepared from cells lacking SRB2 and SRB5 (FIGS. 6D–6E). The results obtained using extracts from cells lacking both SRB proteins were identical to those obtained with extracts from srb5Δ1 cells. These extracts exhibited no defects in promoter-independent transcription elongation assays. These results indicate that both SRB2 and SRB5 are required for efficient basal and activated transcription initiation in vitro.

Formation of a Stable Preinitiation Complex Involves SRB2 and SRB5

A template commitment assay was used to investigate whether both SRB2 and SRB5 participate in the formation of a transcription initiation complex (FIGS. 7A–7D). Extracts prepared from cells lacking SRB2 and SRB5 were used for performing this assay. Two templates were employed that contained identical promoters but differed in G-less cassette length. Specific transcripts of 375 and 350 nt were produced from the long template, while transcripts of 275 and 250 nt were produced from the short template.

An experiment was first performed to confirm that SRB2 is required for efficient formation of a stable preinitiation complex (FIGS. 7–7B), as described above. The two templates were incubated separately with nuclear extract and SRB5, and a limiting amount of SRB2 protein was added to 1 of the 2 reaction mixtures. After a 60 min preincubation, the 2 reactions were mixed together. Immediately after mixing and every 10 min thereafter, aliquots were removed and nucleotide triphosphates were added to permit RNA synthesis. The reaction was stopped after 7 min to minimize multiple rounds of transcription. Control experiments are shown in lanes 1–4. When srb2Δ1, srb5Δ1 extracts were preincubated with SRB2 and SRB5 along with either the long template (FIGS. 7A–7B, lane 1) or short template (FIGS. 7A–7B, lane 2), transcripts of the predicted size were produced. When both long and short templates were present in the preincubation mixture, similar levels of long and short transcripts were obtained (FIGS. 7A–7B, lane 3). Virtually no transcript was detected when both templates were preincubated with the extract in the presence of SRB5 alone (FIGS. 7A–7B, lane 4). When SRB2 was added to the long template mixture, long transcripts were predominant after the two extracts were mixed (FIGS. 7A–7B, lanes 5–8). There was no appreciable increase in signal from the short template after 30 min of mixing with the long template. Similarly, when SRB2 was added to the short template mixture, transcripts were produced predominantly from the short template with no appreciable increase in signal from the long template after 30 min of mixing (FIGS. 7A–7B, lanes 9–12).

To determine whether SRB5 is required for efficient preinitiation complex formation, a similar experiment was performed (FIGS. 7C–7D). This time, the two templates were incubated separately with extract and SRB2, and a limiting amount of SRB5 was added to 1 of the 2 reaction mixtures. The remaining steps were performed as described above. The results of the controls (FIGS. 7C–7D, lanes 1–4) were identical to those in FIGS. 7A–7B. Lanes 5–12 in FIGS. 7C–7D show that transcripts were predominantly obtained from the template that was preincubated in the presence of SRB5 and that there was no significant increase in signal, even after 30 min, from the template incubated in the absence of SRB5.

The template commitment assay results indicate that both SRB2 and SRB5 are required for formation of a stable preinitiation complex and that SRB2 and SRB5 act stoichiometrically in the initiation reaction. These conclusions are based upon two observations. First, the template preincubated in the presence of all necessary factors was preferentially transcribed, upon mixing, relative to the other template, which was incubated in the absence of either SRB2 or SRB5. Second, following mixing, there was no appreciable increase in signal from the template incubated in the absence of either SRB2 or SRB5. If SRB2 or SRB5 acted subsequent to initiation, the templates would be transcribed equally well; since up to 30 min of incubation was allowed after template mixing, there was ample time for any catalytic activity to be carried out on the second template. The observation of little to no increase in second template transcription, even after 30 min, indicates that SRB2 and SRB5 became stably associated with the first template during preincubation.

When the experiment in FIGS. 7A–7B was performed using excess SRB2 in the preinitiation step, transcription increased with time from the template that was preincubated in the absence of SRB2. Similarly, when the experiment in FIGS. 7C–7D was performed using excess SRB5 in the preincubation step, transcription increased with time from the template that was preincubated in the absence of SRB5. This indicates that much of the template that was preincubated in the absence of SRB2 or SRB5 was still available for transcription and that SRB2 and SRB5 continued to be active for an extended period in the reaction mixture. These data suggest that SRB2 and SRB5 are integral components of the, preinitiation complex.

SRB Proteins, TBP, and RNA Polymerase Are Components of a 1.2 Md Complex

The ability of mutations in SRB2, SRB4, SRB5, and SRB6 to specifically suppress the growth phenotypes of cells with CTD truncations indicates that the products of these genes are involved in the same functional process as the CTD. Template commitment assays suggest that SRB2 and SRB5 are components of the transcription initiation complex. These functional studies led to the investigation of whether the SRB proteins interact physically with one another. Cells were constructed that produce functional, epitope-tagged SRB4, SRB5, or SRB6 proteins, and transcriptionally competent nuclear extracts were prepared from these cells. When SRB4, SRB5, or SRB6 were immunoprecipitated, SRB2 and 5%–10% of the TBP in the extract were coprecipitated, as revealed by immunoblotting. This observation suggested that the four SRB proteins and TBP are components of a multisubunit complex which led to an attempt of purification of the SRB proteins from wild-type cells by conventional chromatography.

Figure 8A:
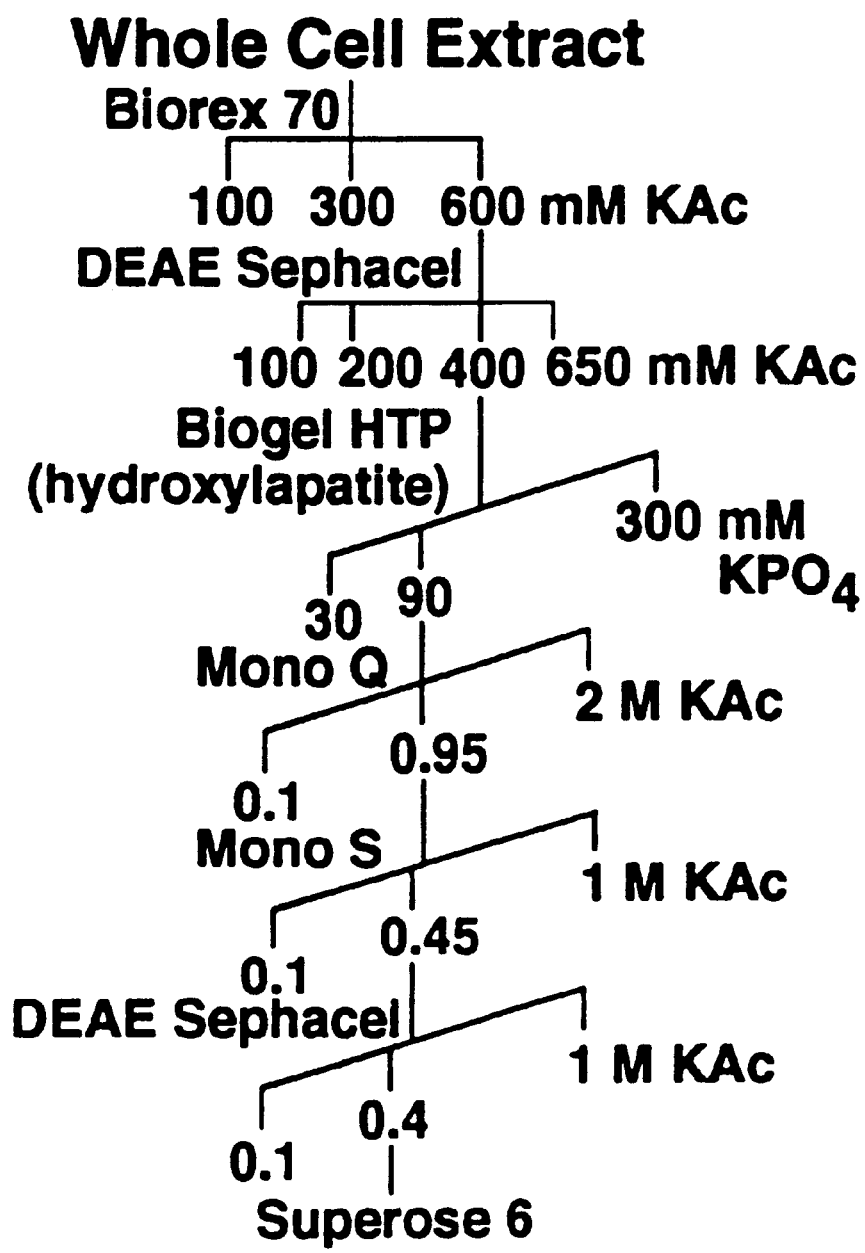

Whole-cell extracts from wild-type cells were fractionated through a series of seven chromatography columns, and rabbit polyclonal antibodies generated against recombinant SRB2, SRB4, SRB5, and SRB6 and against recombinant TBP were used to monitor these proteins during purification (FIG. 8A). Essentially all of the SRB2, SRB4, SRB5, and SRB6 in the whole-cell extract cofractionated through the seven purification steps. Approximately 20 additional polypeptides, including a portion of the TBP in the extract, cofractionated with the four SRB proteins. A subset of these additional polypeptides was identified as RNA polymerase II subunits by Western blot analysis.

Figure 8C:
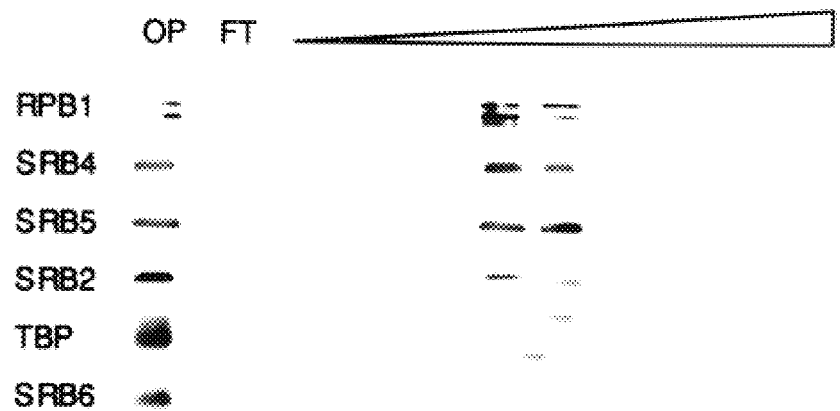

The high molecular weight complex containing TBP, SRB proteins and RNA polymerase II appeared to be quite stable. The proteins in this complex remained tightly associated in fractions exposed to a variety of strong ion exchangers at salt concentrations up to 1.1 M potassium acetate and upon gel filtration in buffers containing 400 mM potassium acetate. FIG. 8C shows, for example, the elution profile of TBP, SRB proteins, and RNA polymerase II from the Mono S column. It is estimated that the complex was purified approximately 10,000-fold by quantitative Western blot analysis. The complex appeared to be purified to near homogeneity, since the composition of the complex did not change on chromatography subsequent to the Mono S column.

Gel filtration on Superose 6 revealed that these approximately two dozen polypeptides comigrate as a complex at a position corresponding to a native molecular mass of about 1.2 Md. The sum of the apparent molecular weights of the polypeptide bands that appear to be components of the complex is 1.4 Md, consistent with the size predicted by gel filtration. Since RNA polymerase II accounts for approximately 0.5 Md, the remaining complex has a mass of 0.7–0.9 Md.

The components of the 1.2 Md complex have both SRB and RNA polymerase activities in vitro. The 1.2 Md complex can complement a nuclear extract lacking SRB2 and SRB5. The specific activity of native SRB2 and SRB5 in the complex was 100-fold that of recombinant SRB2 and SRB5 proteins In this assay. The RNA polymerase activity of the complex is comparable to that obtained with similar amounts of the purified enzyme in nonspecific transcription assays.

A CTD Column Specifically Retains a TBP-Containing Multisubunit Complex

The presence of RNA polymerase II and SRB proteins in a TBP-containing multisubunit complex, together with evidence that the CTD interacts with TBP suggested that the SRB-TBP complex may physically interact with RNA polymerase II via the CTD. To investigate this possibility, yeast whole-cell extract was loaded onto columns containing recombinant glutathione S-transferase (GST)-CTD fusion protein or GST alone. The columns were washed extensively, and bound protein was eluted with low concentrations of guanidine hydrochloride. Guanidine hydrochloride (0.3 M) was used for elution because proteins specifically bound to the GST-CTD column could not be eluted with buffers containing high salt concentrations (2 M potassium acetate). The proteins that specifically bound the GST-CTD affinity column include the four SRB polypeptides, TBP, and at least a dozen additional polypeptides. Many of these proteins appear to be components of the TBP-containing multisubunit complex purified by conventional chromatography.

The RNA Polymerase II Holoenzyme is Responsive to Activators

The SRB proteins, which play essential roles in transcription initiation in vivo and in vitro, copurify with RNA polymerase II and additional unidentified polypeptides in a high molecular weight complex. To further investigate the role of the RNA polymerase II-containing complex in transcription initiation, a search was made for additional components needed for selective transcription in vitro. The RNA polymerase II holoenzyme and factor a were purified as described in Example 2, and as described in Sayre, M. H., et al., *J. Biol. Chem.* 267:23383–23387 (1992). Because the complex contains similar amounts of RNA polymerase II and SRB protein molecules, but substoichiometric amounts of TBP, TBP levels needed to be supplemented to support in vitro transcription. (See Example 3). Specific transcription of promoter-containing DNA was obtained following the addition of recombinant TBP and a fraction from a yeast whole cell extract to the RNA polymerase II-containing complex. Purification of this activity revealed that it is composed of two polypeptides whose chromatographic behavior and size (66 kD and 43 kD) are identical to that described for factor a, the yeast homologue of TFIIE. Thus, the RNA polymerase II-containing complex represents a novel form of the enzyme that is capable of site-specific initiation when supplemented with yeast TBP and transcription factor a. Since purified RNA polymerase II requires the assistance of multiple general transcription factors for selective transcription initiation, these results suggested that the high molecular weight RNA polymerase II complex might contain some of these general factors preassembled into the complex, producing an RNA polymerase II holoenzyme.

Figure 9A:
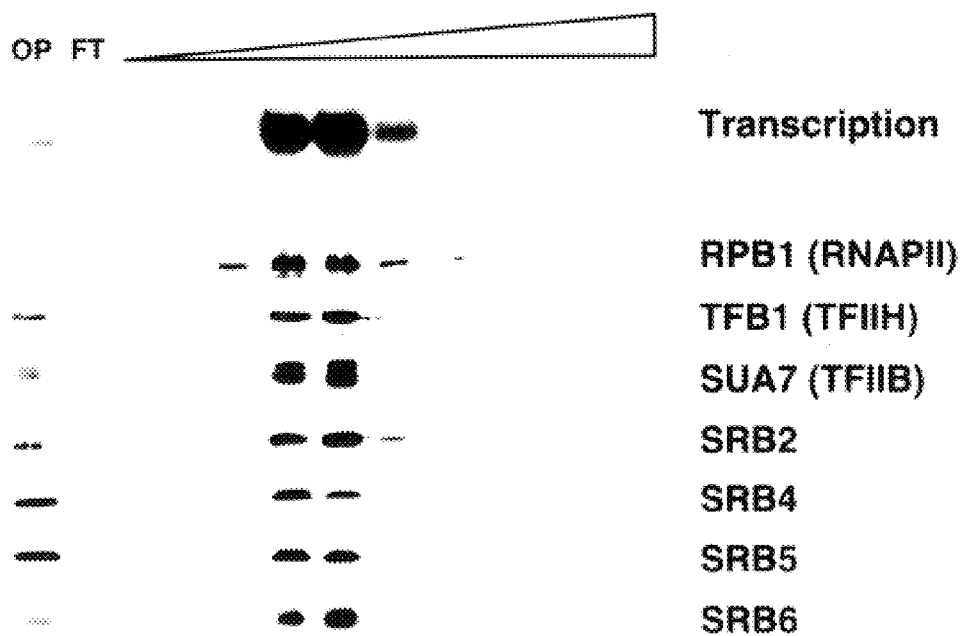

It was further investigated whether a subset of the general transcription factors are associated with RNA polymerase II and SRB proteins in the high molecular weight complex. The general transcription factors bind to common promoter elements such as TATA or initiation motifs. These protein factors include, but are not limited to, TFIIA, TFIIB, TFIID, TFIIE, TFIIF, TFIIG and TFIIH. Five general factors (a, b, d, e, and g) are sufficient to allow yeast RNA polymerase II to accurately initiate transcription in vitro. Column fractions from the final purification step of the RNA polymerase II holoenzyme were tested in reconstituted transcription reactions and subjected to western blot analysis with antisera specific to yeast initiation factors (FIG. 9A). Transcription activity coeluted with RNA polymerase II and the SRB2, SRB4, SRB5, and SRB6 proteins. The activity also coeluted with the 41 Kd yeast factor e (TFIIB) protein and the 73 kD TFB1 subunit of yeast factor b (TFIIH). Although specific antisera are not yet available for factor g (TFIIF), the purified complex (FIG. 9B) contains 3 polypeptides whose sizes coincide with those reported for subunits of purified factor g (105, 55, and 30 Kd). Furthermore, TFIIF and TFIIH are essential for the transcription of linear templates by human RNA polymerase II, and it was found that the RNA polymerase II holoenzyme can transcribe linear templates, supporting the inference that the holoenzyme contains activities homologous to TFIIF and TFIIH. Taken together, these results indicate that the purified complex represents a form of RNA polymerase II that is tightly associated with multiple SRB proteins and with factors b, e, and g (TFIIH, TFIIB, and TFIIF), and that this form of RNA polymerase II holoenzyme can accurately initiate transcription when supplemented with factor a (TFIIE) and TBP.

The RNA polymerase II holoenzyme is a highly stable complex; it remains intact upon chromatography through six ion exchange columns and migrates as a single 1.2 Md complex upon gel filtration. To confirm that the holoenzyme consists of a single multisubunit complex, immunoprecipitation experiments were performed. The four SRB proteins, factor e (TFIIB), the TFB1 subunit of factor b (TFIIH), and RNA polymerase II were all found to specifically coimmunoprecipitate from purified preparations of the RNA polymerase II holoenzyme using anti-SRB5 antibodies (FIG. 9C). Similar results were obtained when the complex was immunoprecipitated with antibodies against other holoenzyme components.

The holoenzyme preparation contains approximately equimolar amounts of SRB2, SRB5, factor e (TFIIB) and RNA polymerase II (FIGS. 9D and 10A–10B). The highly purified holoenzyme does not contain significant amounts of TBP or the TOA1 subunit of yeast TFIIA (FIG. 9D). Although previously shown that some TBP is associated with the multisubunit complex, the highly purified holoenzyme contains less than one molecule of TBP per fifty molecules of RNA polymerase II, consistent with the observation that transcription by the holoenzyme is absolutely dependent on the addition of purified recombinant TBP. At each step in the purification of the holoenzyme, a portion of TBP coelutes from the column with the holoenzyme, while a portion of the TBP elutes as free TBP. This behavior may reflect a weak interaction of TBP with the holoenzyme complex in the absence of DNA, as the purified holoenzyme contains no detectable DNA. TBP can bind to SRB2, SRB5, and the RNA polymerase II CTD on affinity columns, suggesting that TBP may interact physically with these components of the holoenzyme.

Figure 11A:
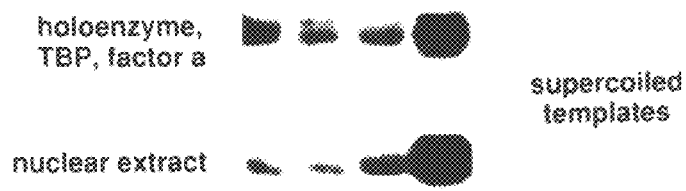
FIGS. 11A–11B shows the results of experiments demonstrating that transcription by the RNA polymerase II holoenzyme is stimulated by GAL4-VP16.
Figure 11B:

The ability of the RNA polymerase II holoenzyme to respond to transcriptional activators was also investigated. Purified yeast RNA polymerase II and general transcription factors alone are unable to respond to transcriptional activators. Transcription of supercoiled templates could be stimulated 5-fold by the transcriptional activator GAL4-VP16 in reactions reconstituted with the RNA polymerase holoenzyme, TBP, and factor a (FIG. 11A). Similar results were obtained when linearized templates were used for in vitro transcription (FIG. 11B). For comparison, GAL4-VP16 stimulated transcription of a supercoiled template in crude yeast nuclear extracts 10-fold under the same conditions (FIG. 11A). These data indicate that one or more components of the holoenzyme are able to respond to activation signals from GAL4-VP16.

The presence of an RNA polymerase II holoenzyme probably escaped earlier detection because of its low abundance relative to free RNA polymerase II. While most of the SRB protein in whole cell extracts is complexed with RNA polymerase II, only 6% of RNA polymerase II and 12% of TFIIB is found in the holoenzyme. The nuclear RNA polymerases were originally purified using nonspecific transcription assays, and the general factors that are necessary to direct selective initiation by the purified enzymes were subsequently identified. In contrast, the discovery of a holoenzyme began with a genetic search for factors involved in RNA polymerase 11 transcription in vivo. The genetic experiments demonstrated a physiological role for the SRB proteins in transcription by RNA polymerase in vivo. The biochemical analysis revealed that the SRB proteins are essential transcription initiation factors, and that most of the SRB protein in cells is contained within the holoenzyme.

It is estimated that yeast haploid cells contain approximately 1000 molecules of the holoenzyme, adequate amounts to initiate transcription at active promoters. However, the proportion of active promoters that are transcribed by the holoenzyme is not yet known. It is possible that the holoenzyme is preferentially utilized at some promoters, while free RNA polymerase II and general factors are recruited in a stepwise fashion to others. A significant fraction of cellular RNA polymerase II is involved in elongation of nascent transcripts, and accounts for at least a portion of the enzyme that is not complexed with SRB proteins.

The existence of an RNA polymerase II holoenzyme preassembled with a subset of general initiation factors has implications for the mechanisms involved in the regulation of transcription. Activators appear to function, at least in part, through interactions with multisubunit TFIID. The holoenzyme may be efficiently recruited to promoters through interactions with gene activators and promoter-bound TFIID. The level of activation in crude extracts is more than two-fold greater than the level of activation obtained with the purified holoenzyme. This difference may reflect the absence of TAFs in the reactions reconstituted with the holoenzyme.

Suppressors of RNA Polymerase II CTD Truncation Mutations

Figure 12:
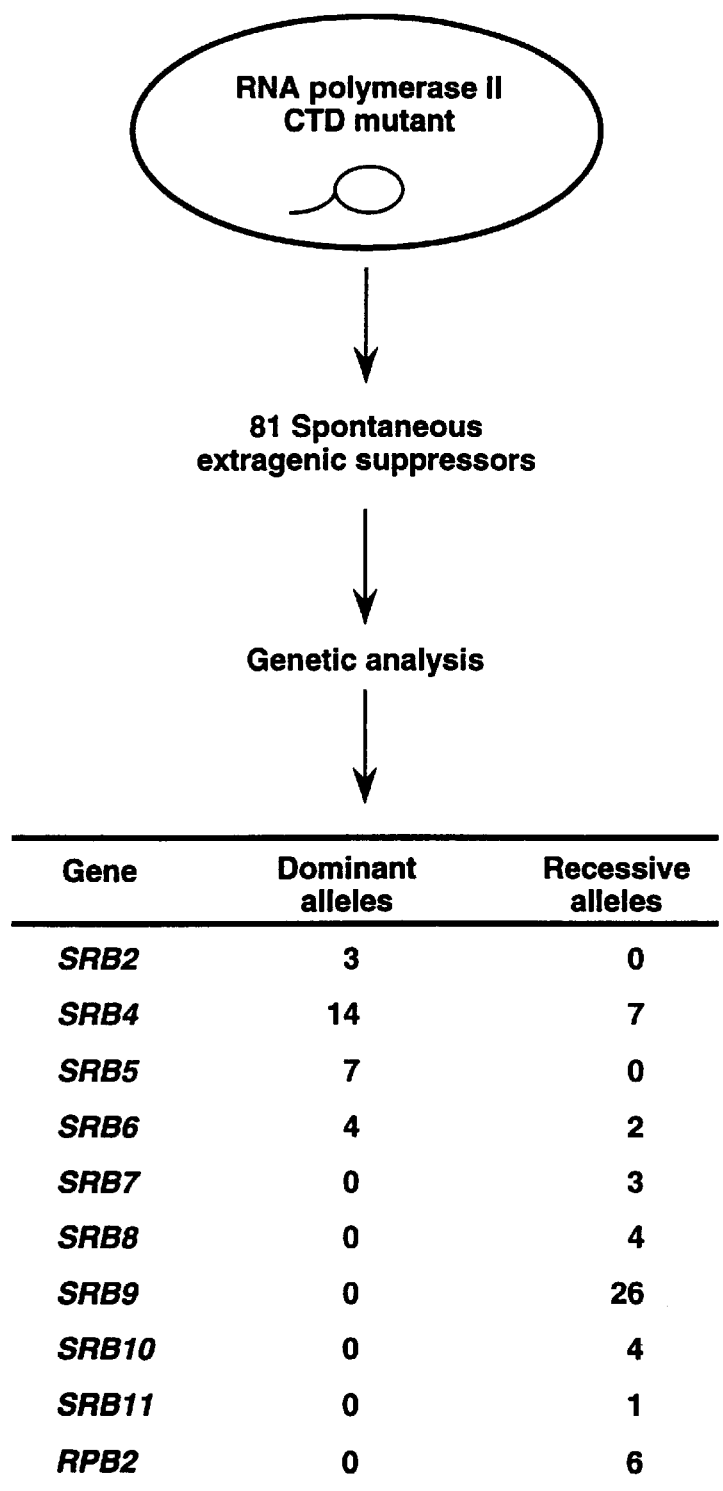
FIG. 12 summarizes extragenic suppressors of CTD truncation mutants.
Figure 18:
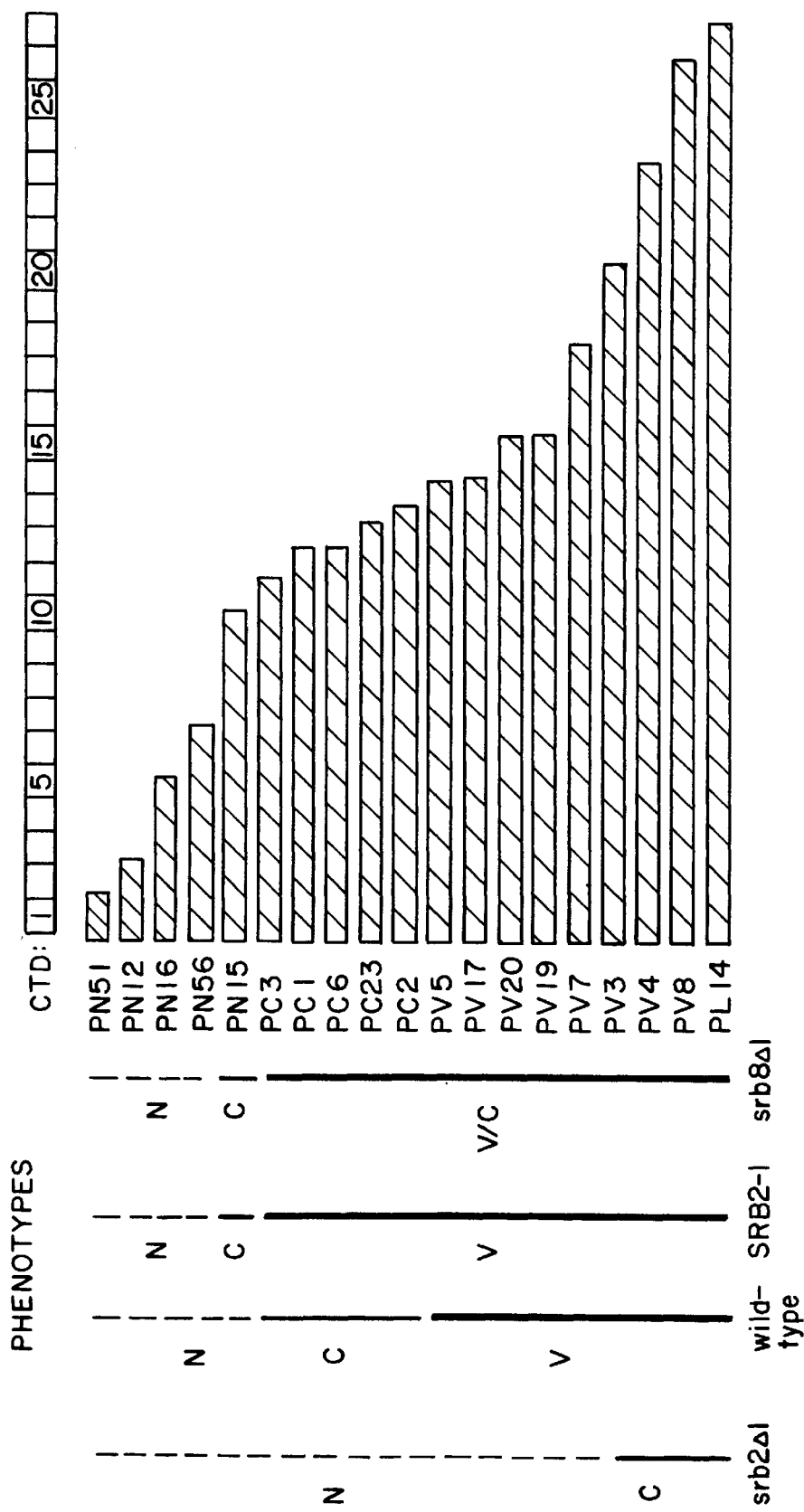
FIG. 18 shows the influence of SRB2 and SRB8 alleles on growth phenotypes of RNA polymerase II CTD truncation mutants.

Extragenic suppressors of a *Saccharomyces cerevisiae* RNA polymerase II CTD truncation mutant were isolated to identify additional components of the transcription apparatus that affect CTD function. (FIG. 12). The cold-sensitive phenotype of cells containing RNA polymerase II CTDs with only 11 intact heptapeptide repeats (rpb1Δ104) was exploited to obtain 81 independent suppressing isolates, of which approximately one third were dominant and two-thirds recessive. Genetic analysis has revealed that mutations in at least ten genes will suppress growth defects of cells containing a truncated CTD. As described above, dominant mutations have been found in four genes, designated SRB2, SRB4, SRB5, and SRB6. Using genetic and molecular complementation analysis, recessive suppressing mutations in six additional genes: SRB7, SRB8, SRB9, SRB10, SRB11, and RPB2 have been identified. Recessive suppressing alleles of SRB4 and SRB6 were also identified.

This selection appears to be nearly saturated since, with the exception of SRB11, more than one independent isolate of each of the ten genes has been identified. The characterization and cloning of the genes containing recessive suppressing mutations is presented in Example 4. SRB7, SRB8, SRB9, SRB10 and SRB11 are newly identified genes, whereas RPB2 is the gene encoding the second largest subunit of RNA polymerase II.

Genetic Analysis of SRB7, SRB8, SRB9, and RPB2

The ability of suppressing alleles of SRB7, SRB8 SRB9, and RPB2 (srb7-1, srb8-1, srb9-1 and rpb2-551, respectively) to suppress conditional phenotypes associated with the CTD truncation mutation rpb1Δ104 was further investigated. These phenotypes include cold- and temperature-sensitive growth and the inability to utilize pyruvate as a carbon source. Growth phenotypes of cells containing an RPB1 CTD truncation mutation and srb7-1, srb8-1, srb9-1, or rpb2-551. Cells were spotted on YEPD medium and incubated at 12° C., 30° C. and 38° C. and on SC medium containing pyruvate as a sole carbon source. Isogenic wild-type, srb7-1, srb8-1, srb9-1, and rpb2-551 backgrounds contained either wild-type RPB1 (27 repeat CTD) or rpb1Δ104 (11 repeat CTD).

The srb7-1, srb8-1, srb9-1, or rpb2-551 alleles permit growth of rpb1Δ104 cells at 12° C. and on media containing pyruvate as a sole carbon source. Cells containing these suppressing alleles, however, do not suppress the temperature-sensitivity associated with the CTD truncation mutation.

These srb and rpb2 alleles do not suppress the conditional phenotypes of other mutations in RPB1 that have been tested. This specificity of suppression argues that SRB7, SRB8, SRB9, RPB2, and the CTD are involved in the same process in transcription initiation.

Cloning and Sequence Analysis of SRB7, SRB8, SRB9, and RPB2

Genomic DNA clones containing SRB7, SRB8, SRB9, and RPB2 were isolated by exploiting their ability to reverse the suppressing phenotype of the recessive srb or rpb2 alleles. A wild-type genomic DNA library constructed in a yeast URA3 centromeric plasmid was transformed into yeast cells containing the CTD truncation mutation rpb1Δ104 and srb7-1, srb8-1, srb9-1, or rpb2-551. Ura$^+$ transformants were then screened for lack of growth at 12° C. and on pyruvate media. When necessary, the wild-type genes were further localized by subcloning fragments of the genomic inserts and again screening Ura$^+$ transformants unable to grow at 12° C. and on pyruvate media. The clones with the smallest inserts were sequenced.

Figure 14A:
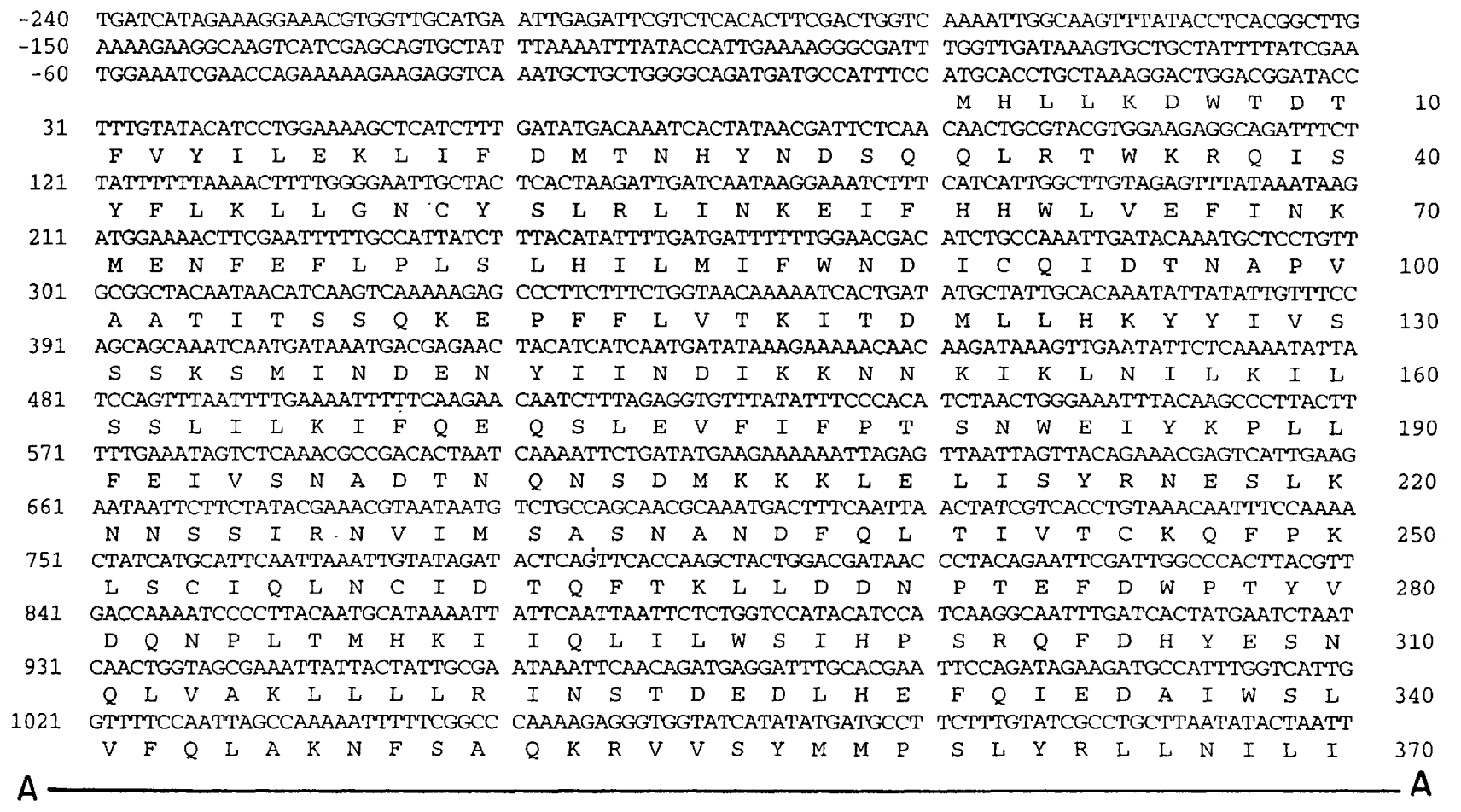

The predicted SRB7 protein is 140 amino acids long (SEQ ID NO: 10) and has a molecular mass of 16 Kd (FIGS. 13A–13B). SRB8 is predicted to be 1226 amino acids in length (SEQ ID NO: 12) with a molecular mass of 144 Kd (FIGS. 14A–14C). Partial sequence analysis of SRB8 revealed that it is ORF YCR81W (Oliver, S. G., et al., *Nature* 357:38–46 (1992)). The predicted SRB9 protein is 1420 amino acids long (SEQ ID NO: 11) and has a molecular mass of 160 Kd (FIGS. 15A–15I). Partial sequence analysis of the fourth clone identified RPB2 as a suppressor of CTD truncations. A search of the sequence data banks revealed that SRB7, SRB8, and SRB9 do not have significant sequence similarity to previously identified proteins. SRB9 does, however, contain a single polyglutamine stretch of 16 residues from amino acids 1121 to 1136. The DNA sequences and predicted amino acid sequences for SRB10 (SEQ ID NO: 15 and 16) and SRB11 (SEQ ID NO: 17 and 18) are shown in FIGS. 16A–16B and FIGS. 17–17B, respectively.

SRB7 and SRB9 were physically mapped using the prime λ, clone grid filters of the yeast genome (provided by L. Riles and M. Olson, Washington University). SRB7 maps to the right arm of chromosome IV, approximately 45 kb centromere distal to GCN2 (λ clone 6118). SRB9 also maps to the right arm of chromosome IV, approximately 35 kb centromere distal to ADE8 (λ clone 5513). SRB8 maps to the right arm of chromosome III, approximately 5 kb centromere proximal to TUP1.

The srb7-1 and rpb2-551 mutant alleles were obtained by plasmid gap repair in vivo. Plasmids containing these mutant alleles did not prevent growth at 12° C., unlike their wild-type counterparts, when transformed into yeast cells containing the CTD truncation mutation rpb1Δ104 and srb7-1 or rpb2-551, respectively. This confirms that in each case the correct locus was cloned. The identification of the correct open reading frame is further supported by identification of the suppressing mutations of srb7-1 and rpb2-551, identified by comparing the complete sequences of the cloned wild-type and suppressing alleles. In each case, the alterations were single-point, missense mutations. The mutation in srb7-1 changes alanine 21 to threonine. The rpb2-551 mutation changes alanine 1200 to valine.

SRB8 and SRB9 are Negative Regulators of CTD Function

To determine whether the SRB genes are essential for cell viability, most, if not the entire coding region of each of the SRB genes was deleted to produce srb7Δ1, srb8Δ1, and srb9Δ1. SRB7, like RPB2, is essential. SRB8 and SRB9 are not essential, but cells lacking either one of these genes flocculate and exhibit mild cold- and temperature-sensitive phenotypes. Significantly, null alleles of SRB8 and SRB9 partially suppress the conditional phenotypes associated with CTD truncations. Phenotypes exhibited by deletions of SRB8 or SRB9 are very similar to those phenotypes exhibited by the suppressing mutant alleles of these genes, indicating that we have cloned and identified the correct gene.

The influence of srb8Δ1 and srb9Δ1 on RNA polymerase II CTD function was further investigated by examining the effect of these deletion alleles on the growth phenotypes of cells containing a spectrum of CTD truncation mutations. Yeast cells lacking SRB8 partially suppressed the conditional phenotypes associated with CTD truncations containing 10–12 complete heptapeptide repeats. Moreover, the lack of SRB8 allowed cells with only nine heptapeptide repeats to survive; thus, loss of SRB8 counters the defects associated with CTD truncation. This pattern of suppression is opposite to that observed with SRB2 alleles. The dominant, gain-of-function SRB2-1 allele produces the same suppression phenotype as the recessive, loss-of-function srb8Δ1 allele. In contrast, the recessive, loss-of-function srb2Δ1 allele, increases the severity of the defects associated with CTD truncation. The influence of srb9Δ1 on the phenotypes of cells containing CTD truncations is similar to that of srb8Δ1. SRB8 and SRB9, therefore, behave as negative regulators of CTD function, while SRB2 behaves as a positive regulator of CTD function.

SRB7, SRB8, and SRB9 are Components of an RNA Polymerase II Holoenzyme

Figure 19:
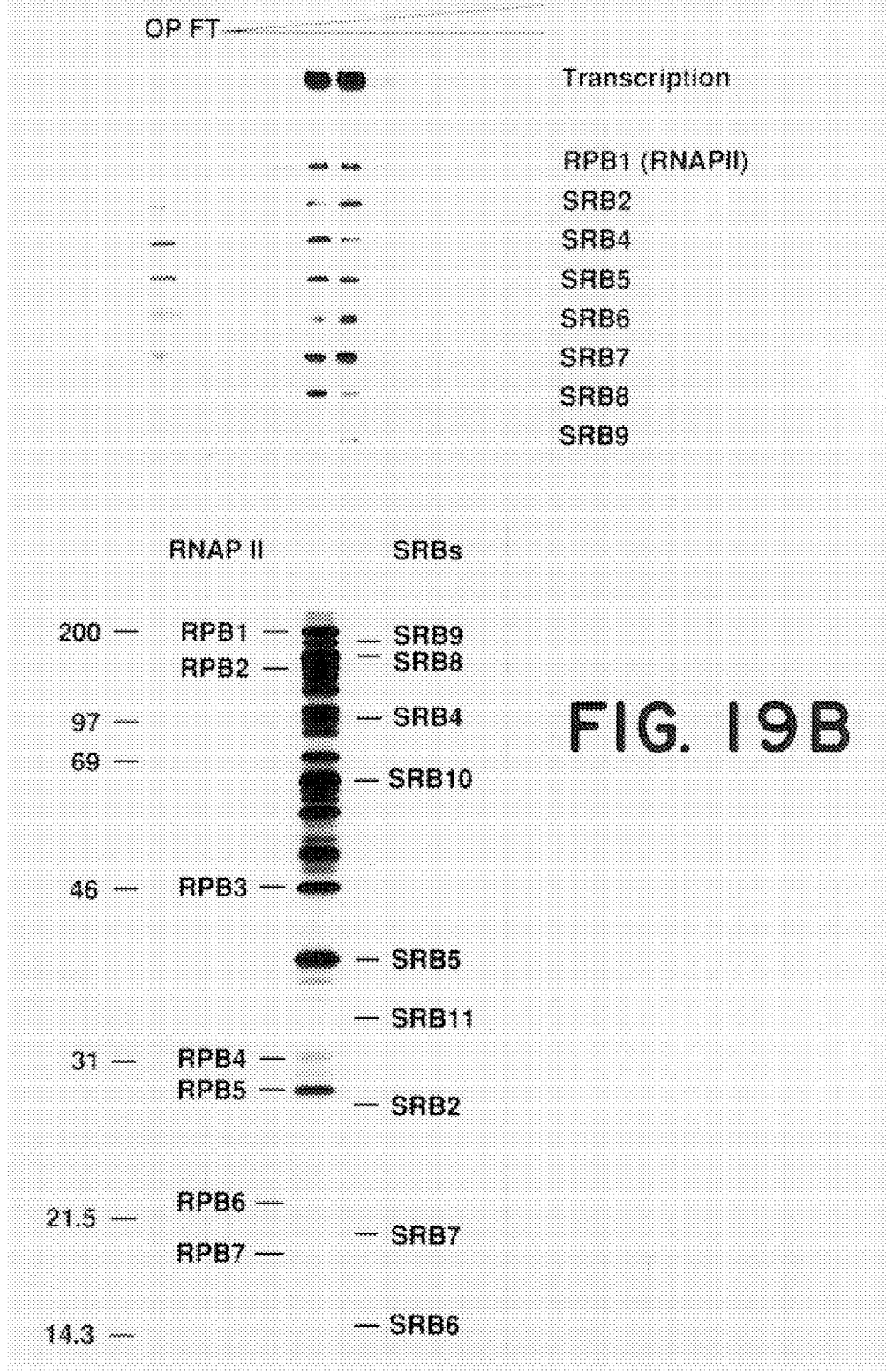
FIGS. 19A–19B shows that SRB2 and SRB4–SRB9 are components of an RNA polymerase II holoenzyme.

It was investigated whether SRB7, SRB8, and SRB9 are also components of a RNA Polymerase II holoenzyme. Rabbit polyclonal antibodies were generated against recombinant SRB7, SRB8, and SRB9. Column fractions from the final purification step of the RNA polymerase II holoenzyme were tested in reconstituted transcription reactions and subject to Western blot analysis with antisera specific to RNA polymerase II and SRB proteins (FIGS. 19A–19B). Transcription activity coeluted with RNA polymerase II and the SRB2, SRB4, SRB5, SRB6, SRB7, SRB8, and SRB9 proteins.

Multiple Factors Influence CTD Activity

In order to better define the role of the CTD of RNA polymerase II in transcription initiation, extragenic suppressors of a CTD truncation mutant have been isolated Ten genes, SRB2, SRB4–SRB11, and RPB2, have now been identified in this selection. The observation that the suppressing mutations in these genes suppress the conditional and auxotrophic phenotypes associated with CTD truncations, but not similar phenotypes associated with point mutations outside of the CTD, argues that these gene products and the CTD are involved in the same process in transcription initiation. Genomic DNA for the genes identified in this selection has been cloned and sequenced. These SRB factors are necessary for yeast cells to grow at wild-type rates and for survival throughout the normal temperature range for cell growth (See Table 1).

TABLE I

| | SRB genes | | | | | |
|---|---|---|---|---|---|---|
| Gene | SDS-PAGE mobility (kDa) | Protein mass (kDa) | pI | Chromosomal Location[a] | Deletion viability | References[c] |
| SRB2 | 27 | 23 | 5.2 | VIII | conditional | 1, 2, 3, 4 |
| SRB4 | 98 | 78 | 5.1 | V | inviable | 3, 4 |
| SRB5 | 38 | 34 | 4.7 | VII | conditional | 3, 4 |
| SRB6 | 15 | 15 | 4.5 | II | inviable | 3, 4 |
| SRB7 | 19 | 16 | 4.8 | IV | inviable | |
| SRB8 | 160 | 144 | 5.7 | III | conditional[b] | |
| SRB9 | 180 | 160 | 5.5 | IV | conditional[b] | |
| RPB2 | 145 | 139 | 6.9 | XV | inviable | 5 |

[a] precise map locations have been determined
[b] null alleles partially suppress conditional phenotypes associated with CTD truncations
[c] 1 Nonet and Young 1989, 2 Koleske et al. 1992, 3 Thompson et al. 1993, 4 Koleske and Young 1994, 5 Sweetser et al. 1987

SRB genes encode positive and negative regulators of CTD function. Dominant, gain-of-function mutations in SRB2 and SRB5 suppress CTD truncation mutations. Furthermore, cells lacking SRB2 can survive only if the CTD is nearly wild-type in length. In contrast, it is the absence of SRB8 or SRB9 which suppress CTD truncation mutations. SRB8 and SRB9 proteins, therefore, appear to repress CTD activity while SRB2 and SRB5 proteins enhance CTD activity.

Figure 20:
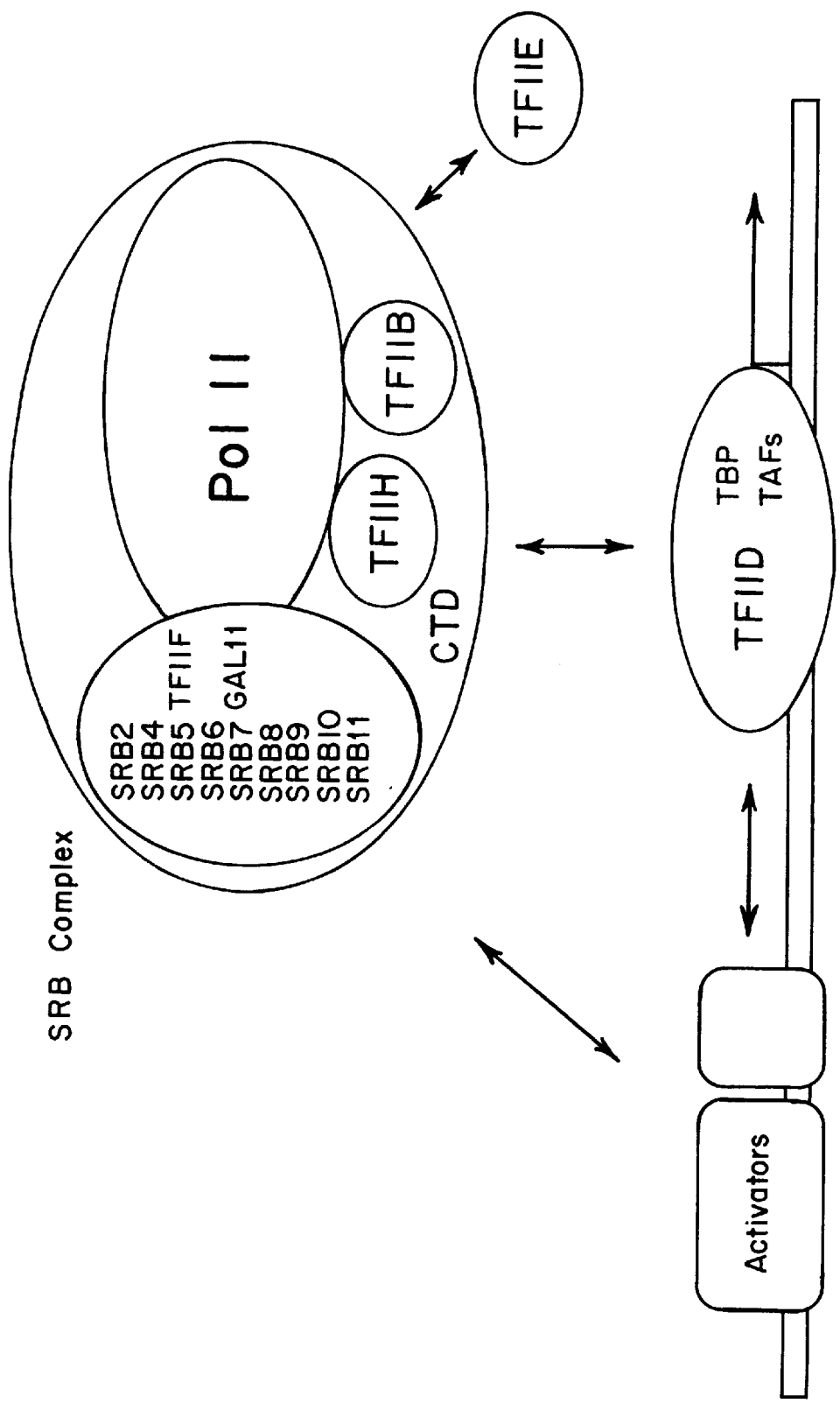
FIG. 20 depicts the RNA Polymerase II holoenzyme model.

FIG. 20 depicts the RNA Polymerase II holoenzyme model for assembly into an initiation complex. Multiple interactions between components of the holoenzyme, activator proteins and transcription factor TFIID facilitate stable initiation-complex formation. The SRBs may influence the stability of the holoenzyme or the recruitment of the holoenzyme into a preinitiation complex, possibly in response to regulatory factors.

The RNA Polymerase II Holoenzyme is the Predominant Form of the Enzyme in the Cell Recruited to Promoters A set of experiments were performed to demonstrate a general requirement for the SRBs in RNA polymerase II s transcription in vivo. These data suggest that the RNA polymerase II holoenzyme is the predominant form of the enzyme recruited to promoters in the cell.

A PCR-based mutagenesis strategy was used to construct a mutagenized library of the SRB4 gene and plasmid shuffle techniques were then used to identify a recessive ts allele, srb4-138. The effect of the srb4-138 mutation on cell growth was investigated. Mutant cells grew normally at the permissive temperature of 30° C. but failed to grow at the restrictive temperature of 37° C. Upon shifting a growing culture of srb4-138 cells to the restrictive temperature, growth rapidly decreased, failing to double before growth ceased altogether. Sequence analysis of srb4-138 revealed multiple point mutations in the open reading frame. The mutation causing the ts phenotype was not determined.

The effect of the srb4-138 mutation on mRNA synthesis was investigated by growing wild-type and mutant cells at the permissive temperature, then shifting the cultures to the restrictive temperature. Aliquots were taken immediately before and at various times after the shift and total RNA was prepared. The amount of poly(A)$^+$ mRNA for each sample was determined by slot blot analysis. Equal amounts of total RNA were blotted and probed with labeled poly(T). Following the shift to the restrictive temperature there is a dramatic and rapid decline in mRNA in mutant cells while wild-type cells are largely unaffected, indicating a general defect in RNA polymerase II transcription at the restrictive temperature in srb4-138 cells.

To investigate the defect in RNA polymerase II transcription in more detail, synthesis of specific mRNAs was investigated. Equal amounts of total RNA prepared from each sample were hybridized with an excess of labeled complementary oligonucleotide to the ACT1, CDC7, DED1, HIS3, MET19, RAD23, STE2, TCM1, and TRP3 transcripts, and the resulting products were treated with S1 nuclease and subjected to denaturing polyacrylamide gel electrophoresis. These nine messages represent a broad spectrum of genes affecting diverse cellular processes.

Since this approach measures steady-state levels of mRNAs, in the absence of new mRNA synthesis, the rate of reduction is a function of mRNA decay rate. All nine of these messages are sensitive to loss of SRB4 activity. Wild-type cells, on the other hand, continue to synthesize these transcripts throughout the entire 4-hour period at 37° C. The transient decrease in the levels of some of the transcripts from wild-type cells is due to a mild heat shock response (Nicolet, C. M. and Craig, E. A., *Meth. Enzymol.* 194:710 (1991)).

The influence of the srb4-138 mutation on tRNA synthesis by RNA polymerase III was also investigated. tRNAs are extremely stable, but their transcripts contain introns which are rapidly processed with half-lives of less than 3 minutes (Cormack B. P., and Struhl, K. *Cell* 69:685 (1992); Knapp, G. et al., *Cell* 14:221 (1978)). S1 nuclease analysis with an oligonucleotide complementary to the 51' intron-exon junction of the tryptophan family of tRNA transcripts was used to measure RNA polymerase III activity. There is no appreciable effect on the RNA polymerase III synthesis of tRNA by the srb4-138 mutant.

rRNA synthesis by RNA polymerase I was similarly investigated using S1 nuclease analysis with an oligonucleotide complimentary to the 3' processing junction of the short lived ribosomal precursor RNA (Cormack B. P., and Struhl, K. *Cell* 69:685 (1992); Kempers-Veenstra, A. E. et al., *EMBO J.* 5:2703 (1986)). There is a substantial decrease in synthesis of the precursor rRNA transcript in the srb4-138 mutant. This decrease in RNA polymerase I activity is similar to that observed in cells containing the ts rpb1-1 allele of RPB1, the gene encoding the largest subunit of RNA polymerase II. (Cormack B. P., and Struhl, K. *Cell* 69:685 (1992); (Nonet, M. et al., *Mol. Cell. Biol.* 7:1602 (1987)). RNA polymerases II and III activities in srb4-138 and rpb1-1 cells are also nearly identical. At the restrictive temperature the synthesis of MET19 and RAD23 transcripts is dramatically reduced while the synthesis of tRNA is largely unaffected. The shutdown of rRNA synthesis in rpb1-1 and srb4-138 cells may be a consequence of a stringent response that shuts off rRNA synthesis under conditions when gene expression is affected (Nonet, M. et al., *Mol. Cell. Biol.* 7:1602 (1987)).

The general cessation of mRNA synthesis in srb4-138 cells is unlikely due to indirect effects of metabolic mayhem at 37° C. or loss of a highly unstable protein that is encoded by an unstable RNA whose synthesis is dependent on SRB4. Similar temperature-shift experiments conducted by Cormack, B. P. and Struhl, K. (*Cell* 69:685 (1992)) using a strain containing a ts mutation in CDC28, the gene encoding the cyclin-associated protein kinase that mediates entry into the cell cycle, showed no appreciable effects on RNA polymerase II transcription. In the same study these investigators examined the effects of cycloheximide, a potent inhibitor of cellular translation, on transcription of a subset of messages in wild-type cells and found no effect on the synthesis of these transcripts.

It was previously estimated that approximately 6% of the RNA polymerase II in the cell was in the holoenzyme, adequate amounts to initiate transcription at active promoters. It was unclear, however, if the holoenzyme was preferentially recruited to some promoters, while free RNA polymerase II and general factors were recruited in a step-wise fashion to others. It appears now that the holoenzyme is the form of RNA polymerase II utilized at most promoters. This conclusion is based upon the above demonstration that SRB4 plays a general role in RNA polymerase II transcription and that the majority of SRB4 in the cell is tightly associated with RNA polymerase II in the holoenzyme.

These results have important implications for the regulation of transcription initiation. A fraction of RNA polymerase II is involved in elongation of nascent transcripts, accounting for at least some of the enzyme not complexed with SRB proteins. Thus, remaining RNA polymerase II and general factors would be competing for limited amounts of SRBs. The SRBs, therefore, can play a key regulatory role in RNA polymerase holoenzyme formation leading to initiation complex assembly.

Mammalian RNA Polymerase II Holoenzyme Complex

The XREFdb service was used to identify three overlapping expressed sequence tags homologous to yeast SRB7 as described in Example 6. hSRB7, a human homolog of yeast SRB7, was cloned and sequenced using sequence information derived from the expressed sequence tags. hSRB7 encodes a 144 amino acid protein with a predicted molecular weight of 15.7 kD (SEQ ID NOs: 36 and 37 as shown in FIG. 21A). It is 35% identical and 58% similar to its yeast counterpart. Homology searches indicate that yeast and human SRB7 are more similar to each other than to any other sequenced gene (FIG. 21B).

There is a restriction length polymorphism at position 627 (numbering from the beginning of the DNA sequence) of the hSRB7 cDNA. In some individuals, the sequence is GAT<u>C</u>; in other individuals the sequence is GAT<u>T</u>. GATC is the restriction site for the enzyme Sau3A. This polymorphism is useful for determining the linkage of locii to the hSRB7 gene. For instance, one could use the polymorphism to determining if a genetic disease is caused by mutation in hSRB7.

Because of the high degree of conservation between the yeast and human genes, it was decided to test whether hSRB7 could functionally complement (e.g., was functionally equivalent to) a yeast SRB7 deletion mutant. Initial results indicated that full length hSRB7 was unable to complement the yeast deletion. Because the most conserved regions of SRB7 are found on its N-terminal end, it was hypothesized that chimeras containing the N-terminus from the human gene and the C-terminus of the yeast gene would be functional. A panel of chimeras was constructed and tested for their ability to complement the yeast SRB7 deletion as described in Example 7. It was found that several hSRB7-ySRB7 chimeras fully complemented the ySRB7 deletion. The chimera containing the largest amount of hSRB7 contains 117 amino acids from the N-terminus of the human gene and only 12 from the C-terminus of the yeast gene. This data presents additional support that hSRB7 is the human counterpart of ySRB7, not only by sequence homology, but also by a functional test.

Corroborating biochemical evidence was obtained to supplement the genetic evidence that hSRB7 is a genuine homolog of ySRB7. A distinctive biochemical property of the yeast SRBs is their ability to bind specifically to the CTD. Several yeast SRBs form a complex that can be isolated by CTD affinity chromatography, therefore it was suspected that yeast SRB7 would also bind to the CTD. Analysis of eluates from control and CTD affinity columns confirmed this hypothesis. Like other SRBs, ySRB7 was specifically retained by a CTD column.

A similar experiment was performed with hSRB7. First, antisera directed against hSRB7 was prepared and characterized, as described in Example 8. This antisera recognizes 16 kD bands in HeLa and calf thymus extracts which represent human and bovine SRB7, respectively. This antisera was then used to probe Western blots of eluates from CTD-affinity and control columns. Mammalian SRB7 derived from both HeLa cells and calf thymus binds specifically to the CTD indicating that hSRB7 and yeast SRB7 not only have similar amino acid sequences and functions in vivo, but also share the ability to bind specifically the CTD. Based on the criteria of sequence similarity, functional complementation and CTD-binding, it is reasonable to conclude that hSRB7 is a bona fide human homolog of ySRB7.

In yeast, SRB proteins are the hallmarks of the RNA polymerase II holoenzyme. Given the homology between ySRB7 and hSRB7, is was hypothesized that hSRB7 would be part of a similar holoenzyme complex in mammalian cells. To test this hypothesis, it was determined whether hSRB7 is associated with RNA polymerase II or other basal transcription factors.

hSRB7 and its associated proteins were precipitated with an anti-hSRB7 peptide antibody and analyzed as described in Example 9. Western blots indicate that the anti-hSRB7 immunoprecipitates contain pol II and hSRB7. This interaction is specific because a control immunoprecipitate with peptide blocked antibody does not contain detectable pol II or hSRB7. Because of interference from the antibody heavy and light chains, it was not possible to use Western blots to assay for the presence of other general factors. As an alternative, in vitro transcription assays were used. These transcriptional assays indicate that the anti-hSRB7 immunoprecipitates contain not only RNA polymerase II activity but also TFIIE and TFIIH activities. It is reasonable to conclude from these results that hSRB7 specifically associates with RNA polymerase II, TFIIE and TFIIH.

The mammalian RNA polymerase II holoenzyme was purified from calf thymus by assaying for the presence of SRB proteins. The progress of the purification procedure with monitored by Western blot analysis with anti-hSRB7 antibody. SRB7 and associated proteins were purified from calf thymus over six ion exchange columns. Mammalian SRB7 coelutes precisely with the RNA polymerase II largest subunit throughout the purification procedure. Silver-staining of the most highly purified fraction suggests that the complex containing SRB7 and RNA polymerase II contains approximately thirty polypeptides. To confirm these results the holoenzyme was purified using a different procedure. Mammalian SRB7 and RNA polymerase II coelute precisely throughout the purification procedure and, again, the same coeluting polypeptides are evident.

It is estimated that SRB7 is associated with at least 20% of the RNA polymerase II that is extracted from calf thymus cells. The purification procedure removed approximately 80% of the RNA polymerase II present in the crude extract before SRB7 could be assayed reliably. Once SRB7 could be reliably detected, the remaining 20% of RNA polymerase II was always observed to cofractionate with SRB7.

The transcriptional activity of the purified holoenzyme was analyzed in vitro as described in Example 10. The template for the reactions contains the adenovirus major late promoter which stringently requires RNA polymerase II, TBP, TFIIB, TFIIF, TFIIE, and TFIIH when in a linear form. In reactions containing column-purified holoenzyme as the source of RNA polymerase II and the other five basal factors, specific transcription from the major late promoter was observed. When the holoenzyme was omitted but the other five factors were included, no RNA product was detected, consistent with the requirement for RNA polymerase. Longer exposure of autoradiograms indicates that omission of TBP, TFIIB, TFIIE or TFIIH resulted in low but significant levels of transcription. These results demonstrate that the holoenzyme is capable of transcription in vitro when supplemented with basal transcription factors and suggest that trace amounts of other basal factors are presented in the purified holoenzyme preparation.

A feature of the yeast holoenzyme is its responsiveness to stimulation by an acidic activating protein in vitro. The response of the purified mammalian holoenzyme to an activator was investigated using two templates containing either the adenovirus major late promoter or the same promoter with upstream binding sites for Gal4. With highly purified transcription factors and core RNA polymerase II, inclusion of Gal4-VP16 had no effect unless the coactivators HMG-2 and PC4 were present, in which case only two-fold activation was observed. In contrast, when the holoenzyme was included in place of core RNA polymerase II, coactivators were still required for activation, but the specific activation by Gal4-VP16 increased to approximately five-fold.

All of the RNA polymerase II holoenzymes that have been described so far contain RNA polymerase II and SRBs. However, different forms of holoenzyme contain different subsets of the general transcription factors. The mammalian holoenzyme described herein contains RNA polymerase II, hSRB7 and is associated with TFIIE, TFIIH. One form of yeast holoenzyme contains RNA polymerase II, SRBs, and is associated with TFIIB, TFIIF, and TFIIH. Other forms of the yeast holoenzyme have the same factors except for TFIIB, TFIIH or both. One explanation for the observed differences is that multiple forms of holoenzyme complex exist in vivo. It is possible that the RNA polymerase II holoenzyme may associate with different subunits during the transcription cycle. For instance, during the transcription cycle, there may be a form of the holoenzyme involved in transcription initiation which is then converted to a form involved in elongation. It is also possible that the RNA polymerase II holoenzyme takes different forms during development and differentiation to allow it to respond to different regulatory environments. A second explanation for the diversity of holoenzymes is that the purified holoenzymes represent subcomplexes of larger entities have been artifactually disrupted. It is likely that holoenzymes and probably all multisubunit complexes larger than a megadalton are particularly sensitive to the extreme conditions of ionic strength and hydrodynamic shear that are consequences of conventional protein purification procedures. It is reasonable to believe that there are multiple forms of RNA polymerase II holoenzyme in vivo.

As described herein, the cloning and sequencing of a human SRB gene and the isolation and characterization of a mammalian RNA polymerase II holoenzyme complex has now been reported. Based on these results, it is reasonable to believe that the mammalian holoenzyme is associated with general transcription factors and additional SRB proteins as in the yeast holoenzyme. Using the techniques described herein, for elucidating the components of the yeast holoenzyme, these specific components associated with the mammalian holoenzyme can be identified. For example, antibodies against hSRB7 can be used to immunoaffinity purify the mammalian holoenzyme as described in Thompson, N. E., et al., *J Biol Chem*, 265:7069–77 (1990). Individual subunits of purified holoenzyme can then be isolated and microsequenced. Oligonucleotide primers for cloning can be designed by reverse translation of these sequences. The primers used for gene isolation of hSRB7 can be used in a two-hybrid system to isolate additional components of the holoenzyme as described in, e.g., Ausubel, F. M., et al. *Current Protocols in Molecular Biology* (Current Protocols, 1994); Fields, S. & Song, O., *Nature*, 340:245–6 (1989). hSRB7 can also be used as a probe to isolate additional proteins in the holoenzyme by screening an expression library with labeled hSRB7 protein (Ausubel, F. M., et al. *Current Protocols in Molecular Biology* (Current Protocols, 1994). hSRB7 can also be used in an affinity column to purify additional proteins in the holoenzyme. (Thompson, C. M. et al., *Cell*, 73:1361–75 (1993); Ausubel, F. M., et al. *Current Protocols in Molecular Biology* (Current Protocols, 1994)).

The hSRB7 gene sequence (SEQ ID NO: 36), or a fragment thereof, can be used as a probe to isolate additional SRB7 homologs. For example, a recombinant library from the appropriate organism can be screened with labeled hSRB7 DNA to identify homologous genes as described in, e.g., Ausubel, F. M., et al., *Current Protocols in Molecular Biology*, (Current Protocols, 1994). Recombinant DNA libraries of chimeras between random DNA from an organism and the C-terminal coding region of ySRB7 can be screened for SRB7 homologs that complement a yeast SRB7 deletion mutation.

Highly conserved SRB7 amino acid sequences have been identified which will allow cloning of SRB7 sequences from other organisms. These amino acid sequences are MXDRLTLQ (SEQ ID NO: 38) and LIDSLP (SEQ ID NO: 39). Degenerate oligonucleotides based on the reverse translation of these amino acid sequences can be used to isolate other SRB7 homologs. In addition, antibodies raised against these peptides, or against hSRB7, or fragments thereof, can be used to screen expression libraries for homologs, again as described in, e.g., Ausubel, F. M., et al., *Current Protocols in Molecular Biology*, (Current Protocols, 1994).

RNA Polymerase II Holoenzyme Contains SWI/SNF Regulatory Proteins

Regulation of class II genes involves a complex interplay among gene-specific activators and cofactors, the general transcription apparatus, and chromatin. Gene specific activities bind to promote and stimulate transcription, at least in part, by binding and recruiting the general transcription apparatus. Chromatin structure can affect the transcriptional activity of genes by blocking access of the transcription apparatus to promoters. The SWI and SNF regulatory proteins are global regulators that function by antagonizing repression mediated by nucleosomes, altering chromatin structure to facilitate binding of the transcription apparatus.

The yeast SWI genes were first identified as positive regulators of HO transcription and SWI1, SWI2, and SWI3 were later shown to be required for the activation of a broad spectrum of inducible genes in vivo. Similarly, the SNF genes were originally identified as positive regulators of SUC2 and SNF2, SNF5, and SNF6 were subsequently found to be essential for activation of a diverse set of inducible genes. Further study revealed that SWI2 and SNF2 are the same gene, referred to herein as SWI2/SNF2. Genetic evidence indicated that the SWI and SNF genes are involved in similar processes in gene activation. More specifically, genetic and biochemical evidence implicated the SWI/SNF proteins in chromatin remodeling via nucleosome disruption.

As described herein, the yeast RNA polymerase II holoenzyme contains SWI2/SNF2, SWI3, SNF5 and SNF11. The SWI/SNF proteins are components of the SRB complex, also known as the mediator, which is tightly associated with the RNA polymerase II CTD. Both the holoenzyme and the SRB/SWI/SNF complex, as well as the SWI/SNF proteins have ATP-dependent nucleosome disruption activities previously ascribed to the SWI/SNF complex. In addition, the holoenzyme facilitates the binding of TBP to nucleosomal DNA in an ATP-enhanced manner.

The data described herein strongly suggests that recruitment of the holoenzyme to a specific promoter in vivo provides a means to facilitate TBP binding, regardless of the nucleosome structure at that promoter. The holoenzyme can enhance binding of TBP and TFIIA to a mononucleosome in vitro in the absence of ATP, a result compatible with evidence that the polymerase and general transcription factor components of the holoenzyme provide additional protein-protein and protein-DNA interactions that should stabilize TBP binding. Holoenzyme-facilitated TBP binding to a mononucleosome is greater in the presence of ATP, which presumably reflects the ATP dependent nucleosome disruption activity of the SWI/SNF proteins.

The SRB/SWI/SNF complex is tightly associated with the RNA polymerase II CTD. Independent attempts to purify various SRB proteins by column chromatography have resulted in purification of the same multiprotein complex: the RNA polymerase II holoenzyme. Only very small amounts of SRB protein can be detected that are not associated with the holoenzyme. Two different methods have been described which permit partial purification of an SRB subcomplex. An SRB complex can be isolated using a CTD affinity column, or by releasing it from a holoenzyme preparation by using monoclonal anti-CTD antibodies. As described herein, preparations of the SRB complex obtained by CTD-affinity chromatography were further purified. The SRB and SWI/SNF proteins coelute in the final step of the purification. Also described herein, the SRB complex isolated by anti-CTD antibody release contains SWI and SNF proteins.

More specifically, the RNA polymerase II holoenzyme, and its SRB/SWI/SNF subcomplex, contains SWI2/SNF2, SWI3, SNF5, and SNF11. Additional genetic and biochemical data indicate that it is highly likely that SWI1 and SNF6 are also subunits of this complex, along with additional components.

Since SWI2/SNF2 and SNF5 are stoichiometric components of the holoenzyme, and yeast cells contain 2000–4000 molecules of RNA polymerase II holoenzyme, there are at least 2000 molecules of SWI2/SNF2 and SNF5 molecules per cell. It has been estimated that there are between 50 and 150 copies of a SWI/SNF complex in yeast cells (Cote, J. et al., *Science*, 256:53–60 (1994)). One interpretation of these results is that most SWI/SNF protein resides in the RNA polymerase II holoenzyme, and the form of SWI/SNF complex purified is the small amount of SWI/SNF protein that is in the process of assembly into holoenzyme or, alternatively, it represents a subcomplex that can be dissociated from the holoenzyme.

The ability to immunoprecipitate very similar holoenzyme complexes from crude yeast fractions using anti-SRB and anti-SWI antibodies suggests that most of the SWI/SNF proteins in these fractions are associated with the holoenzyme. If the SRB and SWI/SNF proteins were in separate complexes, then the relative ratios of SRB and SWI/SNF proteins would differ in the anti-SRB and anti-SWI immunoprecipitates. However, the similar relative ratios of SRB and SWI/SNF proteins found in immunoprecipitates obtained with anti-SRB and anti-SWI antibodies indicates that the SRB and SWI/SNF proteins are components of the same complex in the crude extract.

SWI/SNF proteins and their functions appear to be highly conserved in eukaryotes. Putative homologues of SNF2/SWI2 include Drosophila brahma, human hbrm and hBRG1, and a mammalian homologue of SNF5, called INI1. Recently, a human SWI/SNF complex has been partially purified which has nucleosome disruption activities similar to those of the yeast SWI/SNF complex (Kwon, H. et al., *Nature*, 370:477–481 (1994)). The human SWI/SNF complex contains both hBRG1 and INI1 proteins. Like the yeast SWI/SNF complex, the human SWI/SNF complex facilitates the binding of activators to nucleosomal DNA.

The presence of the SRB/SWI/SNF complex in the RNA polymerase II holoenzyme has implications for the mechanisms involved in transcription activation in vivo. Dynamic competition between chromatin proteins and an activator for a specific DNA site could be resolved in favor of the activator once the SWI/SNF-containing holoenzyme was recruited to the promoter. In this model, the activator and the holoenzyme both contribute to stable transcription initiation complex formation; the activator recruits the holoenzyme by binding to a subset of its components and the SWI/SNF components of the holoenzyme enhance the stability of the activator-DNA interaction by destabilizing nucleosomes.

Methods of Modifying Gene Transcription

As described herein, Applicants have identified genes encoding yeast and human SRB proteins which act as positive and negative regulators of gene transcription via interaction with RNA polymerase II. In particular, Applicants have demonstrated that SRB2 and SRB5 positively regulate CTD function and that SRB8 and SRB9 negatively regulate CTD function. In addition, Applicants have shown that the SRB proteins are an integral part of a multisubunit holoenzyme complex comprising SRB proteins, SWI/SNF proteins, and RNA polymerase II, and is associated with general transcription factors and other components necessary for transcription activation. This RNA polymerase II holoenzyme is preassembled and readily recruited to a DNA promoter, and, when supplemented with factor a (TFIIE) and TATA-binding protein, is capable of site-specific gene transcription. Importantly, the RNA polymerase II holoenzyme described herein is responsive to transcriptional activators, such as GAL4-VP16, unlike purified RNA polymerase II combined with previously known transcription factors. Thus, the regulatory proteins contained in the RNA polymerase II holoenzyme act as signal processors which confer responsiveness to both positive and negative activators, most likely through interaction with RNA polymerase II.

Because of the critical role the SRB and SWI/SNF proteins play in the regulation of gene transcription, it is apparent that modification, or alteration, of one, or more, of the SRB or SWI/SNF proteins results in the modification, or alteration, of the RNA polymerase II holoenzyme and thus, modify, or alter, gene transcription. Based on this model of an RNA polymerase II holoenzyme, it is reasonable to propose methods of modifying gene transcription in a cell by modifying the initiation of transcription by the RNA polymerase II holoenzyme.

Modification of the RNA polymerase II holoenzyme can be accomplished in a number of ways. One, or more, SRB or SWI/SNF proteins can be prevented from associating with other SRB or SWI/SNF proteins, thus, preventing the formation of the holoenzyme complex. One, or more, SRB or SWI/SNF proteins can be modified such that, even though the holoenzyme complex is formed, the holoenzyme is not functional, e.g., it no longer has the ability to initiate gene transcription). Modification of the RNA polymerase holoenzyme can also be accomplished by modifying the SRB or SWI/SNF regulatory proteins such that the signals sent to the RNA polymerase II holoenzyme are altered, leading to either a stimulation or suppression of transcription. This can be accomplished by the use of a substance that specifically interacts with a component of the RNA polymerase II holoenzyme. Substances used in the methods described herein can be proteinaceous in nature, such as peptides (comprised of natural and non-natural amino acids) and peptide analogs (comprised of peptide and non-peptide components), or can be non-proteinaceous in nature, such as small organic molecules. The substance can also be a genetically engineered SRB or SWI/SNF protein with an altered amino acid sequence. These substances would be designed to bind to, or interact with the SRB or SWI/SNF protein based on the DNA or amino acid sequences of the SRB or SWI/SNF proteins described herein, or the antibodies reactive with the SRB or SWI/SNF proteins described herein.

For example, a substance can be identified, or designed, that specifically interferes with the interaction of one, or more SRB or SWI/SNF proteins in the holoenzyme complex. These substances would mimic a site on at least one SRB or SWI/SNF protein (e.g., a binding site on the SRB or SWI/SNF protein) that interacts with another SRB or SWI/SNF protein, thus preventing, or inhibiting, the association of at least one SRB or SWI/SNF protein as part of the holoenzyme complex. Thus, formation of the RNA polymerase II holoenzyme is prevented. By preventing the holoenzyme from forming, transcription would be inhibited. Alternatively, these substances would mimic a site on the RNA polymerase II which interacts with, or binds to, at least one SRB or SWI/SNF protein, again preventing, or inhibiting an SRB or SWI/SNF protein from interacting with the RNA polymerase II CTD. Thus, the RNA polymerase II holoenzyme complex would be formed, but it would not be a functional holoenzyme complex, capable of initiating transcription. Monoclonal or polyclonal antibodies (e.g, the polyclonal antibodies described herein) specific for one, or more, of the SRB or SWI/SNF proteins can also be used to prevent, or inhibit, the SRB or SWI/SNF proteins from participating in the initiation of gene transcription. The antibody would react with, or bind to, the SRB or SWI/SNF protein and, for example, prevent the SRB or SWI/SNF protein from associating with other SRB or SWI/SNF proteins and forming the holoenzyme complex. Thus, gene transcription is inhibited.

The RNA polymerase II holoenzyme is unusual in that it can respond to transcriptional activators, whereas RNA polymerase II or transcriptional factors alone cannot. Thus, the SRB proteins act as sort of a "regulatory glue" to hold the transcriptional complex together and confer responsiveness to the activator on the holoenzyme. Because of the presence of the SRB proteins, gene transcription can be up-regulated or down-regulated. Thus, substances, including antibodies, that bind to one or more SRB proteins in the holoenzyme complex, would result in up-regulation or down-regulation of gene transcription. For example, SRB2 and SRB5 have been shown to positively regulate gene transcription. Thus, a substance which interacts with either the SRB2 or SRB5 proteins, or both proteins, can decrease, or reduce, the activation of gene transcription. In contrast, substance that interacts with SRB8 or SRB9, which have been shown to negatively regulate gene transcription, can stimulate gene transcription. Alternatively, a mutant SRB protein can be introduced into the cell which is incapable of processing regulatory signals, thus preventing gene transcription.

Certain of the SRB proteins also contain amino acid sequences characteristic of protein kinase domains, thus, indicating that they have kinase activity. It is reasonable to predict that these SRB proteins play a role in the phosphorylation of SRB proteins, or other proteins or factors involved with the transcription machinery. Thus, modifying, or altering the kinase activity of one, or more, SRB proteins can also modify, or alter, gene transcription by e.g., preventing the phosphorylation of another transcription factor.

Both the RNA polymerase II holoenzyme of the present invention and the SRB/SWI/SNF complex have ATP-dependent nucleosome disruption activities. In addition, the holoenzyme facilitates the binding to TBP to nucleosomal DNA in an ATP-enhanced manner. As described herein, data indicate that the SRB/SWI/SNF complex contributes chromatin remodeling activity to the RNA polymerase II holoenzyme. Thus, gene transcription can be up-regulated or down-regulated via the SWI/SNF proteins. For example, substances, including antibodies, that bind to one, or more SWI/SNF proteins in the holoenzyme complex, would result in up-regulating or down-regulating of gene transcription. Alternatively, a mutant SWI/SNF protein can be introduced into the cell. The mutant protein is incapable of participating in the formation of, or functional activity of the SWI/SNF protein complex, thus, preventing the formation of a functional SWI/SNF complex, thus preventing gene transcription.

Transcription of DNA sequences, or translation of mRNA sequences, encoding the SRB or SWI/SNF proteins can also be inhibited or decreased, resulting in decreased production of, or complete absence of one, or more critical SRB or SWI/SNF proteins. Gene transcription can be modified by introducing an effective amount of a substance into a cell that inhibits transcription of one or more of the SRB or SWI/SNF genes, or that inhibits translation of mRNA encoding one or more of the SRB or SWI/SNF gene products. For example, antisense nucleotide sequences can be introduced into the cell that will hybridize with the gene encoding one of the SRB proteins and inhibit transcription of the gene. Alternatively, an antisense sequence can be introduced into the cell that will interfere with translation of the mRNA encoding a SRB or SWI/SNF protein.

The substances described in the present invention can be identified and tested for their ability to modify gene transcription using an in vitro transcription assay. For example, DNA of interest (i.e., DNA to be transcribed) can be admixed with purified RNA polymerase II, the SRB and/or SWI/SNF proteins, transcription factors b, e, g or a (or homologies thereof), TBP and the substance to be tested and maintained under conditions sufficient for DNA transcription to occur. The resulting combination is referred to as a test mixture. DNA transcription can be assessed by determining the quantity of mRNA produced. DNA transcription is determined in the presence of the substance being tested and compared to DNA transcription in the absence of the test substance taking place under identical conditions (e.g., a control mixture). If DNA transcription occurs to a lesser extent in the test mixture (i.e., in the presence of the substance being evaluated) than in the control mixture, the substance has interacted with one, or more SRB proteins in such a manner as to inhibit DNA transcription. If DNA transcription occurs to a greater extent in the test mixture than in the control mixture, the substance has interacted with one, or more, SRB or SWI/SNF proteins in such a manner as to stimulate DNA transcription.

The SRB or SWI/SNF proteins can also be genetically altered, such as by site directed mutagenesis, resulting in a SRB or SWI/SNF protein with altered activity. Genetically altered SRB or SWI/SNF proteins would affect gene transcription. For example, one, or more genetically altered SRB or SWI/SNF proteins may be introduced into a cell via a liposome, or linked to a carrier protein known to cross the cell membrane. Alternatively, DNA encoding such a protein may be introduced into the cell using for example, a vector containing the DNA sequence via standard laboratory procedures. These genetically altered SRB proteins would be impaired in their ability to interact with naturally occurring (i.e., unmodified) SRB or SWI/SNF proteins, thus inhibiting the formation of the RNA polymerase II holoenzyme, or inhibiting the formation of a functional holoenzyme, thus inhibiting gene transcription. In addition, DNA encoding a wild-type SRB or SWI/SNF proteins with biological activity (i.e., being capable of participating in gene transcription) may be introduced into the cell to supplement a diminished supply of endogenous SRB or SWI/SNF protein. The wild-type SRB or SWI/SNF protein would be expressed in the cell, thus increasing the level of SRB or SWI/SNF protein in the cell, resulting in an increased amount of RNA polymerase II holoenzyme being formed, and, thus, increasing gene transcription.

The ability to modify gene transcription is useful in three categories of human disease: 1) inherited, or genetic, disease; 2) acquired disease, not of infectious origin; and 3) acquired disease, of infectious origin. Changes in gene transcription in these three situations will contribute to changes in the manifestation of the disease.

For example, in an inherited disease, the level of expression of a critical gene is altered relative to the expression of the gene in an individual who does not manifest the disease. If the amount of gene product produced is inadequate, the introduction of a substance into a cell which interacts with at least one SRB protein, resulting, for example, in stimulating gene transcription will result in increased gene product, thus, improving the condition of the individual.

In the example of an acquired disease that is not of infectious origin, such as cancer, modifying gene transcription will also modify the disease state. Typically a cancer is the result of the loss of growth control concomitant with increased transcriptional activity, in a particular cell type. In this case, a substance that interacts with one, or more SRB proteins, thus decreasing gene transcription, will improve the condition of the individual. Because cancer cells have an extraordinarily high rate of gene transcription, the substances will significantly affect the rate of gene transcription in cancer cells, (i.e., rapidly growing cells) but insignificantly affect the rate of gene transcription in normal cells (analogous to the use of anti-metabolites in the treatment of cancer).

In the case of acquired disease where the disease is the result of an infectious agent, such as a bacteria or a virus, an increase in the transcription of genes encoding proteins involved in the immune response would result in the improvement of the condition of the individual. For example, in HIV infection, a substance which interacts with SRB8 or SRB9, which negatively regulate gene transcription, could be targeted for delivery to lymphocytic cells, resulting in the increase of transcription of important lymphocytic proteins. Also, in the case of some virus infections, such as vaccinia virus, host cell gene transcription is completely shut down by the virus. A substance as described above, targeted to the virally infected cells, would turn on the host cell's transcription machinery. Alternatively, for some viruses, i.e., adenovirus, it may be advantageous to turn down the host cell's transcription machinery (as described above for cancer).

As described herein, the RNA polymerase II holoenzyme plays a critical role in gene transcription in eukaryotes. Homologs of the SRB and SWI/SNF proteins can exhibit differences in sequence identity and these differences can be exploited in designing substances (e.g., drugs) that target eukaryotic pathogens without the interfering with the hosts' gene transcription machinery. For example, a drug can be identified, or designed, e.g., an antisense DNA sequence that hybridizes to a fungal SRB DNA sequence and thus this inhibits gene transcription in the fungus. The antisense nucleotide will specifically hybridize to fungal SRB DNA, but will not hybridize with human SRB DNA, thus, gene transcription in the human host is not compromised. Eukaryotic pathogens can include, e.g., fungi such as Candida or Pneumocystis; parasites such as Plasmodium and Schistosoma; pathogenic worms; and insects that affect animals or agricultural crops.

It is important to note that only the modification, or alteration, of gene transcription is necessary to see an effect. The inhibition or stimulation of gene transcription may be partial inhibition or partial stimulation. Complete inhibition, or complete stimulation of gene transcription is not necessary. All that is needed is to diminish or enhance gene transcription relative to the rate of gene transcription in a cell that does not have the substance introduced in to it. Thus, as defined herein, an effective amount of a substance to modify gene transcription is that amount of the substance necessary to diminish or enhance gene transcription relative to the rate of gene transcription in a cell that does not have the substance introduced into it.

Introduction of a substance into the cell may be by any conventional means, such as the use of a carrier protein which will interact with the cell membrane; attachment to an antibody which reacts with a cell surface antigen; or encapsulation in a liposome. If the substance is proteinaceous in nature, e.g., a peptide, DNA encoding the substance can be introduced into the cell, and the substance can be genetically expressed in the cell. Alternatively, the DNA can be directly introduced into a cell, e.g., an epidermal cell, via a "gene gun", or other electroporation technique. Other methods of cell targeting known to those of skill in the art may also be used.

According to this invention, the substances can be formulated into pharmaceutical compositions containing a pharmaceutically acceptable carrier and/or other excipients using conventional materials and means. They can be administered using conventional routes such as parenteral, oral, inhalation and the like, using appropriate formulations. Other methods of passive or active transport of small molecules known to those of skill in the art can also be employed.

Suitable pharmaceutically acceptable carriers include, but are not limited to, water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, perfume oil, fatty acid esters, hydroxymethycellulose, polyvinyl pyrrolidone, etc. For parenteral application, particularly suitable are injectable, sterile solutions, preferably oily or aqueous solutions, as well as suspensions, emulsions, or implants, including suppositories.

It will be appreciated that the actual preferred effective amounts of substance in a specific case will vary according to the specific substance being utilized, the particular compositions formulated, the mode of application, the particular situs of application, and the organism being treated. If administered to an individual, dosages for a given recipient will be determined on the basis of individual characteristics, such as body size, weight, age and the type and severity of the condition being treated.

Also encompassed by the present invention are methods of diagnosing disease conditions in humans resulting from abnormalities in the production of, or in the SRB, or SWI/SNF proteins themselves. These methods are based on the detection, and/or quantification, of e.g., SRB proteins, DNA or RNA in the cell, or in a biological sample. A biological sample includes biological fluids such as blood, urine, feces, tissue samples or cells isolated from these sources.

For example, a method of detecting SRB DNA in a biological sample can be accomplished by obtaining a sample and isolating the DNA by known laboratory procedures resulting in DNA available for hybridization with a DNA probe. The DNA probe would be a nucleic acid probe having a nucleic acid sequence of sufficient complementarity to a SRB DNA sequence such that it is capable of selectively hybridizing with SRB DNA under standard hybridization conditions. These conditions may be conditions of high stringency as determined by one of skill in the art. Detection and quantification of SRB DNA can be determined using standard techniques of detection, such as fluorescence detection, if fluorescent-tagged probes are used.

An immunoassay can also be used to detect, or quantify, the amount of SRB, or SWI/SNF protein present in a cell. Alternatively, an immunoassay can also be used to determine the biological activity of a SRB or SWI/SNF protein. For example, a biological sample can be obtained and reacted with an antibody under conditions suitable for binding of the antibody to a SRB protein. If the sample contains SRB protein, the antibody will bind to the protein, forming an antibody/SRB protein complex. This antibody/SRB complex can be detected using, for example, a second antibody which is detectably-tagged and which would bind to this complex as is known to those of skill in the art.

The present invention is illustrated by the following examples, which are not intended to be limited in any way.

EXAMPLES

Example 1

The SRB2 Gene and Encoded Protein Molecular Analysis of SRB2 pCT21 contains the SRB2 gene within a 6.2 kb Sacl-BamHI DNA fragment from pCT19 (Nonet, M. L, and Young, R. A., *Genetics* 123: 715–724 (1989), inserted into the Sacl-BamHI sites of the pUC18 poly-linker. A set of nested deletions of pCT21 was created as described previously (Nonet, M. L., et al., *Mol. Cell Biol.* 7:1602–1611 (1987), and SRB2 and surrounding DNA sequenced from double-stranded plasmid DNAs. pCT20 is a pUC18 plasmid that contains the 6.2 kb Sacl-BamHI DNA fragment from pCT1 inserted into the Sacl-BamHI sites of the poly-linker. The SRB2-1 mutation was deduced by sequencing double-stranded pCT20 DNA using a set of six 20 bp oligonucleotide primers:

CT100=ACTACAATCCGGGCTTATCC (SEQ ID NO: 19);
CT101=TCTTGGTCTCAAACTCGCCC (SEQ ID NO: 20);
CT102=GTTGTCCTTGATTAGCACGG (SEQ ID NO: 21);
CT200=CCAAAGTGAAATTTTACTGG (SEQ ID NO: 22);
CT201=TAGACTTTCGGACGTACCGG (SEQ ID NO: 23);
CT202=CGGTGAGACGTTGATCTTGG (SEQ ID NO: 24);

Total RNA was isolated from wild-type and from rna2 yeast cells, and poly(A)+ RNA was purified from these preparations, utilizing procedures described in Elder et al., *Proc. Natl. Acad. Sci. USA* 80:2432–2436 (1993). Northern analysis were performed as described in Nonet, M. et al., *Cell*, 50:909–15 (1987). The 550 bp NcoI DNA fragment from pCT21 was nick-translated and used as a probe. In addition, strand-specific probes were generated and used to identify the orientation of the SRB2 transcript. Oligonucleotides were synthesized complementary to sequences 932–952 and 1206–1226 and used for primer extension analysis with poly(A)+ RNA to locate the 5' end of the SRB2 transcript.

DNA Constructs

All DNA manipulations were performed according to Sambrook et al., *Molecular Cloning: A Laboratory Manual* (Cold Spring Harbor Laboratory 1989). Site-directed mutagenesis was performed as described in Kunkel, T. A., et al., *Meth. Enzymol.* 154:367–382 (1987). The entire coding region of SRB2 was deleted from pCT29 using the primer GAAGGAAGGGGCAGGTGGTTACGCGGTG-TATACGTATAG (SEQ ID NO: 25). This replaced the coding sequence of SRB2 with an HpaI site, creating pCM28-2. To introduce HIS3 into the HpaI site, the 1.75 kb BamHI DNA fragment from pRB328 was blunt-ended by treatment with Klenow and ligated into pCM28-2 to produce pTK33 (containing the deletion allele srb2Δ1::HIS3).

The 12CA5 epitope coding sequence (Kolodziej, P. A., et al., *Mol. Cell. Biol.* 10:1915–1929 (1990)) was introduced contiguous to the carboxyl terminus of the SRB2 protein coding sequence of pCT29 using the primer AGCATTCG-TAAGAACTCAAGCGTAGTCTGG-GACGTCGTATGGGTACAGCTCCAGAGCA CGAAC (SEQ ID NO: 26), producing pTK2. The epitope-tagged SRB2 is fully able to complement the deletion allele srb2Δ1.

The intron of SRB2 was removed from the gene on pTK2, using the oligomer TCCACGAATATAACAGCT-GATTTTCCCATG (SEQ ID NO: 27), to generate pTK21. Two primers, TCGGCATATGGGAAAATCAGCTGTTAT (SEQ ID NO: 28) and CCGTGGATCCTCACAGCTCCA-GAGCACGAA (SEQ ID NO: 29), were used to PCR amplify the coding region of the epitope-tagged SRB2 gene of pTK21 for insertion into the NdeI-BamHI sites of the bacterial expression vector pET3a (Studier, F. W. and Moffatt, B. A., *J. Mol. Biol.* 189:113–130, (1986)), forming pTK27.

To construct isogeneic strains for analyzing the growth phenotypes of strains containing various SRB2 alleles, pTK44 and pTK45 were constructed by inserting the 2.5 kb XbaI-SalI fragment from pCT25 (SRB2-1) or pCT27 (SRB2) into YCp405, pCT25 is identical to pCT27 except that it contains the SRB2-1 mutation.

Several plasmid DNAs were used as templates for in vitro transcription. pSL187, a gift of Sha-Mei Liao (Whitehead Institute), is identical to pGAL4CG-(Chasman, D. I., et al., *Nature* 339:679–684 (1989)) except that the GAL4 binding site has been removed. pJJ460 was a kind gift of Michael Woontner and Judith Jaehning (Wootner, M., et al. *Mol. Cell. Biol.* 11:4555–4560 (1991)).

Genetic Analysis

Analysis of the growth phenotypes of cells containing CTD truncation mutations in SRB2 wild-type cells has described previously (Nonet, M. et al., (1987); Nonet and Young, (1989)), and the experiments described here were performed similarly. To create strains for analysis of CTD length requirements in an srb2Δ1 back-ground, strain Z426 was transformed with the 3.3 kb EcoRI fragment containing srb2Δ1::HIS3 from pTK33. Z426 has a genomic deletion of RPB1 covered by a wild-type copy of RPB1 on a URA3 CEN plasmid (Table 2). A His+ colony confirmed to have SRB2 replaced by srb2Δ1::His by Southern analysis was designated Z404. The viability of cells containing CTD truncations in combination with the srb2Δ1 allele was assayed by plasmid shuffle with strain Z404 (Boeke, J., et al. *Meth. Enzymol.* 154:164–175 (1987)). Plasmids containing the various CTD truncations have been described (Nonet et al., (1987)). Surviving strains were tested for temperature sensitivity at 38° C., cold sensitivity at 12° C., and inositol auxotrophy was previously described (Nonet and Young, (1989)). Strains were previously constructed for analysis of CTD length requirements in an SRB2-1 background (Nonet and Young, (1989)).

TABLE 2

Strain List

| Strain | Common Name | Genotype |
|---|---|---|
| Z494 | YTK54 | Mat α ura-352 his3Δ200 leu2-77 ade2-101 lys2-801 trpl-901 tyr1-501 gal4-542 gal80-538 rpb1Δ182 srb2Δ1::HIS3 [pRP112 (URA3 RPB1)] |
| Z405 | RY1 | |
| Z406 | YTK35 | Mat α rna2-1 ura1 ade1 his 7 lys2 tyr1 gal Mat α ura3-52 his3Δ200 leu2-77 ade2-101 lys2-801 trp1901 tyr1-501 gal4-542 gal80-538 rpb1Δ182 srb2Δ1::HIS3 [pC6(rpb1-104 LEU2) pTK44 (SRB2 LYS2)] |
| Z407 | YTK34 | Mat α ura3-52 his3Δ200 leu2-77 ade2-101 lys2-801 trp1901 tyr1-501 gal4-542 gal80-538 rpb1Δ182 srb2Δ1::HIS3 [pC6(rpb1-104 LEU2) pTK45 (SRB2 LYS2)] |
| Z408 | YTK36 | Mat α ura3-52 his3Δ200 leu2-77 ade2-101 lys2-801 trp1901 tyr1-501 gal4-542 gal80-538 rpb1Δ182 srb2Δ1::HIS3 [pRP114(RPB1 LEU2) YCP405(LYS2)] |
| Z409 | YTK38 | Mat α ura3-52 his3Δ200 leu2-77 ade2-101 lys2-801 trp1901 tyr1-501 gal4-542 gal80-538 rpb1Δ182 srb2Δ1::HIS3 [pRP114(RPB1 |

TABLE 2-continued

Strain List

| Strain | Common Name | Genotype |
|---|---|---|
| Z410 | YTK37 | LEU2) pTK44(SRB2-1 LYS2)] |
| | | Mat α ura3-52 his3Δ200 leu2-77 ade2-101 lys2-801 trp1901 tyr1-501 gal4-542 gal80-538 rpb1Δ182 srb2Δ1::HIS3 [pRP114(RPB1 |
| Z411 | YTK13 | LEU2) [pRP114(RPB1 LEU2) pTK45(SRB2 LYS2)] |
| Z412 | YTK14 | YTK54 [pV17 (LEU2 rpb1-115)] |
| Z413 | YTK15 | YTK54 [pV8 (LEU2 rpb1-112)] |
| Z414 | YTK16 | YTK54 [pV4 (LEU2 rpb1-109)] |
| Z415 | YTK17 | YTK54 [pC23 (LEU2 rpb1-105)] |
| Z416 | YTK18 | YTK54 [pC3 (LEU2 rpb1-103)] |
| Z417 | YTK19 | YTK54 [pVS (LEU2 rpb1-110)] |
| Z418 | YTK20 | YTK54 [pV3 (LEU2 rpb1-108)] |
| Z419 | YTK21 | YTK54 [pV7 (LEU2 rpb1-111)] |
| Z420 | YTK22 | YTK54 [pV19 (LEU2 rpb1-117)] |
| Z421 | YTK23 | YTK54 [pC1 (LEU2 rpb1-101)] |
| Z422 | YTK24 | YTK54 [pC2 (LEU2 rpb1-102)] |
| Z423 | YTK25 | YTK54 [pC6 (LEU2 rpb1-104)] |
| Z424 | YTK72 | YTK54 [pV20 (LEU2 rpb1-118)] |
| Z425 | YTK73 | Mat α his3Δ200 leu2-3 leu2-112 ura3-52 trp1Δ1 ade2-101 |
| Z426 | N402 | Mat α his3Δ200 leu2-3 leu2-112 yra3-52 trp1Δ1 lys2-801 srb2Δ1::HIS3 |
| Z427 | CM94 | Mat α ura3-52 his3Δ200 leu2-77 ade2-101 lys 2-801 trpl-901 tyr1-501 gal4-542 gal80-583 rpb1Δ182 [pRP112(URA3 RPB1)] |
| | | Mat a/Mat α his3Δ200/his3Δ200 leu 2-3/leu2-112/leu2-112 ura3-52/ura3-52 trp1Δ1/trp1Δ1 ADE2/ade2 LYS2/lys2-801 |

Strains containing combinations of SRB2 alleles and CTD truncation alleles were assayed for growth at 38° C., 25° C., and 12° C. and for their ability to grow on minimal medium lacking inositol.

Example 2

The SRB4, SRB5, SRB6 Genes and Encoded Proteins

Yeast strains and plasmids are listed in Tables 3 and 4, respectively. Yeast medium was prepared as described (Nonet, M. L. and Young, R. A., *Genetics* 123:715–724 (1989)), except pyruvate medium, which consists of synthetic complete (SC) medium with 2% pyruvic acid (Sigma) as a carbon source. Yeast transformations were done using a lithium acetate procedure (Schiestl, R. H. and Gietz, R. D., *Curr. Genet.* 16:339–346 (1989)). Plasmid shuffle techniques were performed as described by Boeke, J., et al. *Meth. Enzymol.* 154:164–175 (1987)), using 5-fluoroorotic acid (5-FOA) as a selective agent against URA3 plasmids.

TABLE 3

Yeast Strains

| Strain | Alias | Genotype |
|---|---|---|
| BJ926 | | Mat a/Mat α trp1/TRP1 prc1-126/prc1-126 pep4-3/pep4-3 prp1-1122/prb1-1122 can1/can1 |
| Z22 | N114 | Mat α ura3-52 his3Δ200 leu2-3, 112 |
| Z26 | N247 | Mat α ura3-52 his3Δ200 leu2-3, 112 rpb1Δ187::HIS3 (pRP112[URA3 RPB1]) |
| Z28 | RY4 | Mat a/MAT α mal-/mal- gal2/gal2 |
| Z425 | YTK73 | Mat a his3Δ200 leu2-3, 112 ura3-52 trp1Δ1 lys2-801 srb2Δ1::HIS3 |
| Z551 | N400 | Mat a ura3-52 his3Δ200 leu2-3, 112 rpb1Δ187::HIS3 (pC6[LEU2 rpb1Δ104]) |
| Z552 | CTY3 | Mat a ura3-52 his3Δ200 leu2-3, 112 rpb1Δ187::HIS3 SRB4-1 (pC6[LEU2 rpb1Δ104]) |
| Z553 | CTY8 | Mat a ura3-52 his3Δ200 leu2-3, 112 rpb1Δ187::HIS3 SRB5-1 (pC6[LEU2 rpb1Δ104]) |
| Z554 | CTY9 | Mat a ura3-52 his3Δ200 leu2-3, 112 rpb1Δ187::HIS3 SRB6-1 (pC6[LEU2 rpb1Δ104]) |
| Z555 | CTY15 | Mat a ura3-52 his3Δ200 leu2-3, 112 rpb1Δ187::HIS3 SRB4-1 (pRP112[URA3 RPB1]) |
| Z556 | CTY20 | Mat a ura3-52 his3Δ200 leu2-3, 112 rpb1Δ187::HIS3 SRB5-1 (pRP112[URA3 RPB1]) |
| Z557 | CTY21 | Mat a ura3-52 his3Δ200 leu2-3, 112 rpb1Δ187::HIS3 SRB6-1 (pRP112[URA3 RPB1]) |
| Z558 | CTY143 | Mat a/MAT α ura3-52/ura3-52 his3Δ200/his3Δ200 leu2-3, 112/leu2-3, 112 |
| Z559 | CTY144 | Mat a/MAT α ura3-52/ura3-52 his3Δ200/his3Δ200 leu2-3, 112/leu2-3, 112 srb5Δ1::URA3hisG/SRB5 |
| Z560 | CTY148 | MAT α ura3-52 his3Δ200 leu2-3, 112 srb5Δ1::URA3hisG |
| Z561 | CTY151 | MAT a ura3-52 his3Δ200 leu2-3, 112 lys2-801 |

TABLE 3-continued

Yeast Strains

| Strain | Alias | Genotype |
|---|---|---|
| Z562 | CTY153 | Mat a ura3-52 his3Δ200 leu2-3, 112 lys2-801 srb5Δ1::URA3hisG |
| Z563 | CTY154 | Mat a ura3-52 his3Δ200 leu2-3, 112 lys2-801 srb2Δ1::HIS3 srb5Δ1::URA3 hisG |
| Z564 | CTY158 | Mat a/Mat α ura3-52/ura3-52 his3Δ200/his3Δ200 leu2-3, 112/leu2-3, 112 srb6Δ1::URA3hisG/SRB6 |
| Z565 | CTY176 | Mat a/Mat α ura3-52/ura3-52 his3Δ200/his3Δ200 leu2-3, 112/leu2-3, 112 srb4Δ2::HIS3/SRB4 |
| Z566 | CTY184 | Mat a ura3-52 his3Δ200 leu2-3, 112 srb6Δ1::hisG (pCT66[LEU2 SRB6]) |

TABLE 4

Plasmids

| Plasmid | Description |
| --- | --- |
| pCT3 | URA3 CEN plasmid. pUN55 (Elledge and Davis, 1988) with HpaI-NaeI fragment removed, XhoI site in polylinker SalI-SalI destroyed by digestion and blunting, and XhoI linker (CCGCTCGAGCGG) inserted into SmaI site of polylinker |
| pCT108 | pGAL4CG⁻ (Leu et al., 1989) with 300 bp G-less cassette created by ligating SmaI G-less cassette from pJJ460 (Woontner et al., 1991) with SmaI vector fragment of pGAL4CG⁻. |
| pDC127 | pQE9 (Qiagen) with 6xHIS-GST-12CA5 fusion. An oligonucleotide encoding the 12CA5 epitope flanked by a BglII and a BamHI site was cloned into same of pSP72 (Promega), followed by insertion into BamHI of pGEX-2T (Pharmacia). GST-12CA5 fusion was amplified by PCR and inserted into BamHI-SalI-digested pSP72. GST-12CA5 fusion was then cloned into pQE9; |
| pDC130 | pQE9 (Qiagen) with 6xHIS-GST-12CA5-CTD fusion. A KpnI RPB1 containing fragment from pV14 (Nonet et a1., 1987b) was inserted into same of pSP72 (Promega), followed by insertion of the BamHI fragment encoding the CTD and 98 N-terminal adjoining amino acids of RPB1 into PDC127. |
| SRB4 | |
| pCT4 | pCT3 with 9 kb genomic (Z28) Sau3a fragment containing SRB4 inserted at XhoI site. |
| pCT8 | pcT3 with 8 kb genomic (Z552) Sau3A fragment containing SRB4-1 inserted at XhoI site. |
| pCT15 | pCT3 with 2.5 kb subgenomic (pCT4) Sau3A fragment containing SRB4 inserted at XhoI site. |
| pCT16 | pCT3 with 2.8 kb subgenomic (PCT4) Sau3A fragment containing SRB4 inserted at XhoI site. |
| pCT48 | pCT15 with BstXI-SnaBI 5RB4-1 C-terminus fragment from pCT8 replacing some SRB4 fragment. |
| pCT54 | srb4Δ2::HIS3, created by ligation of SRB4 SalI-BamHI from pCT16 with SalI-BamHI of pSP72 (Promega), followed by PCR with the oligonucleotides TAATATCCTGAGTCACTCCT and TATGGCTTTTAAGCTGCTTA and ligation of PCR product with SmaI HIS3 kan fragment from B2179 (G.R. Fink, Whitehead). |
| pCT107 | pGEX-2T (Smith and Johnson, 1988) with GST-SRB4 fusion. NdeI site at ATG of SRB4 created by ligation of SRB4 SalI-XbaI from pCT15 with SalI-XbaI of pBSIISK(-) (Stratagene), followed by site-directed mutagenesis. NdeI (partial/blunt)- SnaBI SRB4 containing fragment was then ligated with BamHI (blunt)-digested pGEX-2T. |
| SRB5 | |
| pcT14 | pCT3 with 9 kb genomic (Z553) Sau3A fragment containing SRB5-1 inserted at XhoI site. |
| pCT20 | PCT3 with 1.9 kb subgenomic (pCT14) Sau3A fragment containing SRB-1 inserted at XhoI site. |
| pCT32 | pcT20 with unique SacI site in insert, created by removal of NarI (blunt)-SacII (blunt) fragment from vector. |
| pCT37 | srb5Δ1::URA3hisG, created by ligation of SRB5-1 EcoRI-BamHI from pCT20 with EcoRI-BamHI of pSP72 (Promega), followed by PCR with the oligonucleotides TAATCATTGGCACCCTGGGCA and CTTTTCTTCTTAATATGGAA and ligation of PCR product with BglIII (blunt)-BamHI (blunt) URA3 kan hisG cassette from B2178 (G.R. Fink). |
| pCT39 | pcT32 containing SRB5, obtained by gap repair of vector containing fragment of PCT32 SacI-XhoI digest. |
| PCT98 | pET-3a (Studier and Moffat, 1986) with SRB5. NdeI site at ATG of SRB5 created by ligation of SRB5 EcoRI-BamHI from PCT39 with EcoRI-BamHI of pBSIISK(-) (Stratagene), followed by site-directed mutagenesis. NdeI-EcoRI (blunt) SRB5-containing fragment was then ligated with NdeI-BamHI (blunt)-digested pET-3a. |
| SRB6 | |
| pCT26 | pCT3 with 3 kb genomic (Z554) Sau3A fragment containing SRB6-1 inserted at XhoI site. |
| PCT29 | pCT3 with 1.0 kb subgenomic (pCT26) Sau3A fragment containing SRB6-1 inserted at XhoI site. |
| pCT38 | srb6Δ1::URA3hisG, created by ligation of SRB6-1 EcoRI-BamHI from pCT29 with EcoRI-BamHI of pSP72 (Promega), followed by PRC with oligonucleotides TAAAAAGGCGGTATTTATCT and CATATAGTGCCTGGTTGCTC and ligation of PRC product with BglIII (blunt)-BamHI (blunt) URA3 kan hisG cassette from B2178 (G.R. Fink). |
| pCT40 | pCT29 with SRB6, obtained by gap repair of vector containing fragment of pCT29 BalI-SphI digest. |
| pCT66 | LEU2 CEN pUN105 (Elledge and Davis, 1988) with SRB6, created by ligation of SRB6 BamHI (blunt)-SalI (blunt) from pCT40 with SmaI-digested pUN105. |
| pCT116 | pGEX-2T (Smith and Johnson, 1988) with GST-SRB6 fusion. NdeI site at ATG of SRB6 created by ligation of SRB6 SalI-XbaI from pCT40 |

TABLE 4-continued

Plasmids

| Plasmid | Description |
| --- | --- |
| | with SalI-XbaI of pBSIISK(+) (Stratagene), followed by site-directed mutagenesis. NdeI (blunt)-XhaI SRB6-containing fragment was then ligated with BamHI (blunt)-digested pGEX-2T. |

Extragenic suppressors of the cold-sensitive phenotype of Z551 were isolated as previously described (Nonet, M. and Young, R. A., Genetics 123:715–724 (1989)). Dominant suppressors were identified by mating to Z26, selecting against the presence of pRP112 using 5-FOA and assaying growth at 12° C. on YEPD. Diploids able to grow at 12° C. contained a dominant suppressor. Isogeneic wild-type, SRB4-1, SRB5 1, and SRB6-1 strains containing various RPB1 alleles (rpb1-4, rpb1-5, rpb1-6, rpb1-10, rpb1-12, rpb1-13, rpb1-14, rpb1-15, and rpb1-18) on LEU2 CEN plasmids were constructed using Z26, Z555, Z556, and Z557 and plasmid shuffle techniques. Isogeneic wildtype, SRB4-1, SRB5-1, and SRB6-1 strains containing rpb1-1 on a URA3 CEN plasmid, pRP1-1 [U] were constructed by transforming Z551, Z552, Z553, and Z554 with pRP1-1 [U], followed by growth in SC-Ura medium to permit loss of pC6. Growth assays were performed by suspending similar numbers of cells in water and transferring equal volumes to agar plates with a 48 prong apparatus.

Deletions of SRB4, SRB5, and SRB6 were created by a single step disruption method (Rothstein, R., Meth. Enzymol. 194:281–301 (1991)). Z558 was transformed with the desired DNA fragment and plated on the proper selective medium. Southern analysis was used 10 confirm that a single copy of the desired SRB gene had been deleted. The diploid was sporulated and tetrads (more than 20) were dissected on YEPD plates and scored for nutritional auxotrophies and growth at a variety of temperatures. Z565 was created by transformation with the EcoRl-Xbal fragment of pCT54 containing the srb4Δ2::HIS3 fragment and plating on SC-His medium. Two spores or fewer from each tetrad were viable, and these were all histidine auxotrophs, indicating that SRB4 is essential. To confirm that SRB4 is essential, Z565 was transformed with pCT15 (URA3 SRB4), tetrads were dissected, and His$^+$ Ura$^+$ segregants were streaked to 5-FOA plates. They were unable to grow on 5-FOA-containing medium, confirming that SRB4 is essential. Z559 was created by transformation with the EcoRI-Sphl fragment of pCT37 containing the srb5Δ1::URA3-hisG fragment and plating on SC-Ura medium. Segregants scored 2:2 for uracil prototropy and air uracil prototrophs exhibited cold-sensitive, temperature-sensitive, and slow growth phenotypes, indicating that SRB5 deletion strains are conditionally viable. Z564 was created by transformation with the BglII-BamHl fragment of pCT38 containing the srb6Δ1::URA3-hisG fragment and plating on SC-Ura medium. Two spores of fewer from each tetrad were viable, and these spores were all uracil auxotrophs, indicating that SRB6 is essential. To confirm that SRB6 is essential, Z564 was transformed with pCT66 (LEU2 SRB6) tetrads were dissected and Z566 was created by placing a Ura$^+$ Leu$^+$ segregant onto 5-FOA to select for the excision of the URA3 gene. Z566 was transformed with pCT40 (URA3 SRB6), grown in SC-Ura medium to permit loss of pCT66, and then tested for growth on 5-FOA plates. No growth was observed on 5-FOA. Confirming that SRB6 is essential.

Several strains were constructed for producing yeast nuclear extracts for in vitro transcription assays. Z425 was mated to Z560, and tetrads were dissected to produce the wild-type Z561, srb5Δ1::URA3-hisG strain Z562, and srb2Δ1::HIS3, srb5Δ1:URA3-hisG strain Z563, Z562 and Z563 displayed identical temperature-sensitive, cold-sensitive and slow growth phenotypes.

DNA Methods

DNA manipulations were performed according to Sambrook et al., Molecular Cloning: A Laboratory Manual (Cold Spring Harbor Laboratory 1989). Site directed mutagenesis was performed as described in Kunkel, T. A., et al., Meth. Enzymol. 154:367–382 (1987). Polymerase chain reaction (PCR) amplifications to produce pCT54 (srb4Δ2), pCT37 (srb5Δ1) and pCT38 (srb6Δ1) were performed with Taq DNA polymerase (Perkin Elmer) in 100 μl of buffer (provided by the manufacturer) supplemented with 1.0 mM MgCl$_2$ and 200 μM dNTP for a total of 25 cycles. Primer concentrations were 0.5 μM with 50 ng of DNA and cycling was at 94° C. (1.0 min), 50° C. (1.0 min), and 72° C. (2.5 min).

Library Construction and Cloning

Yeast genomic DNA libraries were prepared from strains Z28 (wild type), Z552 (SRB4-1), Z553 (SRB5-1), and Z554 (SRB6-1). Genomic DNA was isolated partially digested with Sau3A and separated on a 0.7% agarose gel, 6–12 kb fragments were purified by electroelution, and the ends were partially filled in with d(AG)TP using Klenow. The URA3 centromeric plasmid pCT3 was digested with Xhol, and the ends were partially filled in with d(CT)TP to make them compatible with the ends of the Sau3A digested genomic DNA. Following ligation, DH5α cells made competent by the method of Hanahan (Hanahan, D., et al., Meth. Enzymol. 204:63–113 (1991)) were transformed. Libraries contained approximately 150,000 individual recombinants with an average insert size of approximately 10 kb. Subgenomic DNA libraries were prepared from pCT4 (SRB4), pCT14 (SRB5-1), and pCT26 (SRB6-1) in a manner similar to that described above for the genomic DNA libraries. Plasmid insert DNA was partially digested with Sau3A and separated on a 1.5% agarose gel, and 1–3 kb fragments were purified by gene clean (BIO 101), and the ends were partially filled in with d(AG)TP using Klenow. Fragments were ligated with pCT3 prepared as described above and transformed into DH5α cells. Subgenomic libraries contained approximately 20,000 individual recombinants with an average insert size of 2 kb.

Genomic clones of SRB4-1 (pCT8). SRB5-1 (pCT14), and SRB6-1 (pCT26) were isolated by transformation of the respective genomic library into Z551, plating to SC-Ura medium and placing plates at 12° C. following a 12 hr recovery period at 30° C. Approximately 1 in 2000 primary transformants was able to grow at 12° C. For each library transformed, the genomic clone was isolated by the method of Hoffman, C. S. and Winston, F., Gene 57:267–272 (1987), from over 12 Ura colonies able to grow at 12° C., and was retested for the ability to suppress the cold-sensitive phenotype of Z551. A genomic clone of SRB4 (pCT4) was isolated from the wild-type Z28 library using a recessive SRB4 allele, which has a tight temperature-sensitive phenotype in combination with a CTD truncation allele of 11 repeats. The presence of pCT4 restores a leaky temperature-sensitive phenotype to this strain at 38° C. Subgenomic clones made from pCT4 (SRB4), pCT14 (SRB5-1), and pCT26 (SRB6-1) were selected as described above in order to isolate pCT15 and pCT16 (SRB4), pCT20 (SRB5-1), and pCT29 (SRB6-1), respectively. pCT15 and pCT16 differ only in the amount of DNA downstream of SRB4. pCT39 was created from pCT32 in vivo by transforming Z22 with SacI-XhoI-digested pCT32 DNA and isolating the plasmid from a Ura$^+$ transformant that had repaired the plasmid with wild-type SRB5 sequences from the chromosome (Rothstein. 1991). Similarly, SRB6 was isolated using BalI-SphI-digested pCT29 DNA to create pCT40.

Sequence Analysis

Insert DNAs from pCT15, pCT20, and pCT29 (containing SRB4. SRB5-1, and SRB6-1, respectively) were completely sequenced on each strand. Unidirectional deletions were constructed using the Erase-a-Base system (Promega), and double-stranded sequencing with dideoxynucleotides and Sequenase (US Biochemical) was carried out as described by the manufacturer, using T3 and T7 promoter primers. The suppressing mutations in SRB4, SRB5, and SRB6 were deduced by sequencing using oligonucleotide primers that spanned the entire open reading frames. Positive numbering of the DNA begins with the predicted start site of translation. pCT15 (SRB4) and pCT48 (SRB4-1) were sequenced, and the SRB4-1 mutation was identified as a G to T transversion (nucleotide 1057) that changed amino acid 353 from Gly to Cys.pCT39 (SRB5) and pCT32 (SRB5-1) were sequenced, and the SRB5-1 mutation was identified as a C to T transition (nucleotide 65) that changed amino acid 22 from Thr to Ile.pCT40 (SRB6) and pCT29 (SRB6-1) were sequenced, and the SRB6-1 mutation was identified as a C to G transversion (nucleotide 258) that changed amino acid 86 from Asn to Lys. Sequence comparison analysis was performed at the National Center for Biotechnology Information using the BLAST network service.

Purification of Recombinant Proteins

Purification of SRB2 has been previously described. SRB5 protein was purified from the bacterial strain BL21 (DE3) pLysS carrying the plasmid pCT98 in the same manner in which SRB2 was purified. SRB4 and SRB6 were purified as fusions to GST from DH5α carrying pCT107 and pCT116, respectively, according to the method of Smith, D. B. and Johnson K. S., *Gene*. 67:31–40 (1988). GAL4(1-147)-VP16 protein was purified as described by Chasman, D. I., et al., *Nature* 339:679–684 (1989) from XA90 carrying pJL2. GST-fusion proteins for CTD affinity purification were purified from DH5α, carrying pDC127 or pDC130 by affinity chromatography on glutathione-agarose (Sigma) and Ni-NTA agarose (Qiagen), and then by ion exchange chromatography on SP Sepharose (Pharmacia) to an approximate purity of 95%.

In Vitro Transcription

Promoter-dependent in vitro transcription was carried out as described by Liao, S. M. et al., *Genes. Dev*. 5:2431–2440 (1991). Three hundred nanograms of template were used for promoter-dependent in vitro transcription reactions, except the template commitment assays, in which 600 ng of template was used per reaction. Optimal activity was obtained using 100 μg of Z561 protein, 150 μg of Z562 protein, and 150 μg of Z563 protein. Transcripts were quantified using a Fuji Bio-image analyzer, promoter-independent transcription assays were performed according to (Nonet, M., et al., *Cell* 50:909–915 (1987). Purified SRB complex used in in vitro transcription assays was purified as described below. Eluate from the second Biorex 70 column was dialyzed in buffer A(50) (buffer A containing 50 MM potassium acetate) and concentrated 4-fold by centrifugation through Centricon 10 filter units (Amicon).

FIG. 6A shows the template pGAL4CG$^-$ contains a CYC1 TATA element downstream of a single GAL4 binding site that directs expression of a G-less transcript.

FIGS. 6B–6C shows nuclear extracts made from wild-type cells (Z561) or srb5Δ mutant cells (Z562) were tested for their ability to synthesize specific transcripts from the pGAL4CG$^-$ template in the presence or absence of recombinant SRB2 (250 ng) and/or SRB5 (250 ng). Transcription reactions were carried out in the absence (B) or presence (C) of recombinant GAL4-VP16 (150 ng). The film shown in (B) was exposed five times longer than that in (C). Quantitation of the results indicates that the level of specific transcripts produced by srb5Δ extracts is 50-fold less than that produced by wild-type extracts in the absence of added SRB proteins. Addition of both SRB2 and SRB5 to srb5Δ extracts restored transcript levels to approximately 40% of those observed in wild-type extracts.

FIGS. 6D–6E shows nuclear extracts made from wild-type cells (Z561) or srb2Δ1, srb5Δ1 mutant cells (Z563) were tested for their ability to synthesize specific transcripts from the pGAL4CG$^-$ template in the presence or absence of recombinant SRB2 (250 ng) and/or SRB5 (250 ng). Transcription reactions were carried out in the absence (D) or presence (E) of recombinant GAL4-VP16 (150 ng). The film shown in (D) was exposed five times longer than that in (E). Quantitation of the results indicates that the level of specific transcripts produced by srb2Δ, srb5Δ extracts is 50-fold less than that produced by wild-type extracts in the absence of added SRB proteins. Addition of both SRB2 and SRB5 to srb2Δ, srb5Δ extracts restored transcript levels to approximately 40% of those observed in wild-type extracts.

Template Commitment Assay

As shown in FIGS. 7A–7D, are essential for efficient preinitiation complex formation. (A) SRB2 is necessary for formation of stable preinitiation complex. The templates used in the template commitment assay each contained in a CYC1 TATA element downstream of a single GAL4-binding site that directs expression of a G-less transcript. The long (L) template (pGAL4CG) contained in a G-less cassette of 400 nt, and the short (S) template (pCT108) contained a G-less cassette of 300 nt. The two templates were incubated separately with nuclear extracts from srb2Δ1, srb5Δ1 cells (Z563), SRB5 (250 ng) and GAL4-VP16 (150 ng). A limiting amount of SRB2 protein (25 ng) was added to 1 of the 2 reaction mixtures. After a 60 min preincubation, the 2 reactions were mixed together, and aliquots were removed at 10 min intervals and transcriptionally competent complexes were assayed by the addition of nucleoside triphosphates. The reactions were terminated after 7 min to minimize reinitiation. Control experiments are shown in lanes 1–4. Extracts from srb2Δ1, srb5Δ1 cells were preincubated with SRB2, SRB5 and GAL4-VP16 along with short and long template, individually (lanes 1–2) or in combination (lane 3). In lane 4, both templates were incubated in the presence of SRB5 and GAL4-VP16 but in the absence of SRB2. After mixing of preincubation reactions, aliquots were removed and nucleoside triphosphates were added at the indicated times (lanes 5–12).

(B) SRB5 is necessary for formation of a stable preinitiation complex. The template commitment assay was performed as in (A), except that preincubations were performed in the presence or absence of limiting amounts of SRB5 (75 ng) and excess of SRB2 (250 ng).

Purification of SRB Complex

An outline of the purification scheme is shown in FIG. 8A. Yeast strain BJ926 (Buchman, A. R. et al., *Mol. Cell. Biol.* 8:5086–5099 (1988)) was grown at 30° C. to $OD_{600}$ of 4.0–4.5 in 1×YNB medium (0.15% Difco yeast nitrogen base, 0.5% ammonium sulfate, 200 µM inositol, 2% glucose). The level of the SRB complex appeared to be elevated in cells grown in minimal medium, and this observation was exploited to facilitate purification of the TBP containing SRB complex. Cells were collected by centrifugation and washed in ice cold buffer (20 mM HEPES KOH (pH 7.5), 10% glycerol, 50 mM potassium acetate, 1 mM dithiothreitol (DTT), and 1 mM EDTA). Whole-cell extract was prepared from 480 g of cell paste as described by Sayre, M. H. et al. *J. Biol. Chem.* 267:23376–23382 (1992). Protease inhibitors used where indicated were: 1 mM phenylmethylsufonyl fluoride, 2 mM benzamidine, 2 µM pepstatin A, 0.6 µM leupeptin, 2 µg/ml chymostatin. 5 µg/ml antipain HCl (Sigma).

During purification, the SRB complex was monitored by Western blot using antibodies to SRB2, SRB4, SRB5, and SRB6. Silver staining of gels was performed as per Blum, H. et al. *Electrophoresis* 8:93–99 (1987), with minor modifications. The gels were fixed for a minimum of 4 hr, and the impregnation with silver nitrate was performed for 40 min.

Whole-cell extract (8 g of protein in 390 ml) was diluted 1:5 in buffer A (20% glycerol, 20 mM HEPES KOH (pH 7.5), 1 mM DTT, 1 mM EDTA. and protease inhibitors). The extract was loaded onto a 5 cm×17 cm Biorex 70 (Bio Rad Laboratories) column at a flow rate of 5 ml/min. The column was washed with buffer A (100) until no further protein could be eluted from the column. The column was then eluted with step washes of buffer A (300) and buffer A (600). The SRB complex eluted in the 600 mM potassium acetate step.

The Biorex 70 (600) fraction (250 mg in 120 ml) was diluted 1:6 with buffer B (20% glycerol, 20 mM Tris-acetate (pH 7.9), 1 mM DTT, 1 mM EDTA. 0.01% Nonidet P-40, and protease inhibitors and was loaded onto a 2.5 cm×8.5 cm diethylaminoethyl (DEAE)-Sephacel column (Pharmacia) at a flow rate of 4 ml/min. The column was washed extensively with buffer B (100) and then eluted with step washes of buffer B (400) and buffer 6 (650). The SRB complex eluted from this column in the 400 mM potassium acetate step.

The DEAE-Sephacel (400) fraction (48 ml) was dialyzed into buffer C (20% glycerol, 10 mM potassium phosphate (pH 7.7), 100 mM potassium acetate, 1 mM DTT, 0.25 mM EDTA, 0.01% Nonidet P-40, and protease inhibitors). The dialysate was spun in a Sorvall SS34 rotor at 10,000 rpm for 20 min and the supernatant (50 mg of protein in 50 ml) was loaded onto a 1.5 cm×6.5 cm Bio-Gel HTP Hydroxylapatite at a flow rate of 1 ml/min. The column was washed with 20 ml of loading buffer and eluted with a 120 ml linear gradient of buffer C to buffer D (buffer D is identical to buffer C except that it contains 300 mM potassium phosphate (pH 7.71). The SRB complex eluted from this column in a peak corresponding to 68–112 mM potassium phosphate.

The 20 ml of eluate from the Bio-Gel HTP (Bio-Rad Laboratories) was dialyzed against buffer E (same as buffer B except 0.25 mM EDTA) containing 100 mM potassium acetate. The dialyzed material was spun in a Sorvall SS34 rotor at 10,000 rpm for 20 min. and the supernatant (11 mg protein in 20 ml) was loaded onto a Mono Q HR 5/5 fast protein liquid chromatography column (Pharmacia) and eluted with a 15 ml linear gradient from buffer E (100) to buffer E (2000) at a flow rate of 0.5 ml/min. The SRB complex eluted from this column at 0.95 M potassium acetate.

Peak fractions containing SRB activity were diluted 1:6 with buffer F (same as buffer A except 0.25 mM EDTA). This material (1.1 mg of protein in 10 ml) was loaded onto a Mono S HR 0.5/5 FPLC column (Pharmacia) and eluted with a 10 ml gradient from buffer F (100) to buffer F (1000) at a flow rate of 0.5 ml/min. The SRB complex eluted from this column at 450 mM potassium acetate. This material (0.6 mg of protein in 8 ml) was diluted 1:4 in buffer E (0) and loaded onto a 1.5 um×1.5 cm DEAE-Sephacel column and eluted with a 20 ml gradient from buffer E (100) to buffer E (1000) at a flow rate of 0.3 ml/min. The SRB complex eluted from this column at 400 mM potassium acetate. (Further chromatography revealed that this material was approximately 90% pure.) This material (0.5 mg of protein in 2 ml) was diluted 1:4 in buffer F (0) and loaded onto a 1.5 cm×1 cm Biorex 70 column and was eluted with a 10 ml gradient from buffer F (100) to buffer F (1000). The SRB complex eluted from this column at 600 mM potassium acetate and was approximately 95% pure. The total yield of the SRB complex was 0.5 mg, and purification was estimated to be 10,000-fold.

The SRB complex was subjected to gel filtration chromatography in buffer F (400) on a Superose 6 HR 10/30 FPLC column (Pharmacia). The estimated molecular size of the SRB complex was determined by extrapolation of a calibration curve performed with thyroglobulin (669 kd), apoferritin (443 kd), bovine serum albumin (132 kd, 66 kd) and carbonic anhydrase.

CTD Affinity Purification

Whole-cell extracts were prepared by adding 1.61 of 4% glucose to 800 g of Red Star dry yeast, incubating the mixture at room temperature for 45 min, and adding 800 ml of disruption buffer (1.2 M ammonium sulfate, 0.16M K-HEPES (pH 7.3), 4 mM DTT, and protease inhibitors [as in the conventional purification above]). Aliquots (200 ml) were frozen dropwise in liquid nitrogen and blended for 5–10 min in a Waring blender. After thawing at 55° C., viscosity was reduced by brief blending. Disrupted cells were centrifuged for 30 min at 12,000 rpm in a Sorvall GSA rotor, and the clarified supernatant was filtered through cheesecloth. One-twentieth volume of a 10% solution of Polymin P was added, the extract was incubated on ice for 30 min. and the solution was centrifuged for 30 min at 12,000 rpm in a Sorvall GSA rotor. The supernatant was collected and brought to 70% saturation with solid ammonium sulfate and stored at 4° C.

An aliquot of the suspension was removed from storage and centrifuged at 12,000 rpm in a Sorvall GSA rotor for 30 min. The pellet was resuspended in 1.5 vol of 1×transcription buffer (Liao, S. M., et al., *Genes Dev.* 5:2431–2440 (1991)), 1991) plus protease inhibitors and centrifuged at 17,000 rpm in a Sorvall SS34 rotor for 20 min. The supernatant was then diluted 1:6 in 1×transcription buffer plus protease inhibitors and centrifuged at 12,000 rpm in a Sorvall GSA rotor for 30 min. The supernatant was incubated with 10 g/100 milliliters of cell debris remover (Whatman Labsales) for 15 min. The cell debris remover was removed by centrifugation and filtration. The cleared supernatant was then centrifuged at 40,000 rpm in a Beckman 50.2Ti rotor for 1–2 hr.

GST fusion proteins were coupled to Pharmacia activated CH Sepharose according to the manufacturers directions at a concentration of 5 milligrams of protein per milliliter of matrix. The affinity matrices were washed with 6 M guanidine hydrochloride followed by 1×transcription buffer before use. Twenty milliliters of yeast whole-cell extract were mixed with 1/10 vol of 1×transcription buffer plus 10%. Triton X-100 and applied to 100 μl of either GST-Sepharose or GST-CTD Sepharose. The columns were washed with 20 ml of 1×transcription buffer plus 1% Triton X-100, followed by 5 ml of 1×transcription buffer without Triton X-100. Bound proteins were eluted with 1×transcription buffer containing various concentrations of guanidine hydrochloride.

Western Blot Analysis

Western blotting of fractions was performed with polyclonal rabbit antisera raised against whole TBP, SRB2, and SRB5 proteins. A GST-SRB4 fusion protein, or a GST-SRB6 fusion protein, by standard methods. RPB1 was detected via the CTD with 8WG16 monoclonal antibody ascites fluid (Thompson, N. E. et al., *J. Biol. Chem.* 164:11511–11520 (1989)). Polyclonal anti-TBP, anti-SRB2, anti-GST-SRB4, and anti-SRB5 antisera were diluted 1:1000. Anti-GST-SRB6 antiserum was diluted 1:200. A 1:1000 dilution of 8WG16 monoclonal antibody ascites fluid was used. In all cases, bands were visualized by secondary probing with alkaline phosphatase conjugate secondary antibodies (Promega).

FIG. 8B, left panel, shows a liver-stained SDS-polyacrylamide (15w) gel containing approximately 1 μg of protein from each fraction of the SRB complex purification. Lane 1, whole-cell extract; lane 2, biorex 70; lane 3, DEAE-Sephacel; lane 4, hydroxylapatite; lane 5, Mono Q; lane 6, Mono S; lane 7, DEAE-Sephacel. The positions of RNA polymerase II subunits, SRB proteins, TBP, and additional polypeptides that are candidate subunits of the complex are indicated, M, markers.

FIG. 8B, right panel, shows Western blot analysis of 1 μg of SRB complex protein from the DEAE-Sephacel fraction loaded onto a SDS-polyacrylamide (15%) gel and probed with antibodies against SRB and TBP proteins. The antibody probes were: lane 1, polyclonal anti-SRB2; lane 2, polyclonal anti-SRB4; lane 3, polyclonal anti-SRBS; lane 4, polyclonal anti-SRB6; and lane 5, polyclonal anti-TBP.

FIG. 8C shows that Western blot analysis reveals that SRB proteins, RNA polymerase II and TBP coelute from a Mono S column, Semipurified SRB complex (0.8 mg of total protein) from the Mono Q column was loaded onto a Mono S column and eluted with a 0.1–1.0 M gradient of potassium acetate as described in Experimental Procedures. The onput and flow-through material (1/25) and every other eluate fraction (1/50) were analyzed by Western blot for the presence of RPB1, SRB4, SRB5, SRB2, TBP, and SRB6. The SRB complex eluted in a peak corresponding to approximately 0.4 M potassium acetate.

Example 3

RNA Polymerase II Holoenzyme Activity

In Vitro Transcription Activity of the RNA Polymerase II Holoenzyme

The RNA polymerase II holoenzyme was purified as described in Example 2.

Factor a is required in addition to TBP and the RNA polymerase II complex for in vitro transcription Sayre, M. H. et al., *J. Biol. Chem.* 267:23383–23387 (1992). Semipurified factor a (300 μg protein in 2 ml) eluted from the Heparin-CL6B column was loaded onto a DEAE-Sephacel column and eluted with a 0.15–1.0 M gradient of potassium acetate. The onput and flow-through and a portion of every other fraction eluting from this column between 0.32 and 1.0 M potassium acetate were analyzed for transcriptional activity and for the presence of polypeptides by SDS-PAGE. Assays were performed using pGAL4G-template (300 ng), RNA polymerase II complex (1 μg), recombinant TBP (40 ng), and 1 μl of the OP, FT, and every other fraction from the column, 2.5 μl of the OP, FT, and every other column fraction was subjected to electrophoresis on a 12% SDS-PAGE gel. Gel was stained with silver using standard protocols.

The holoenzyme, factor a, and TBP are sufficient for in vitro transcription. Transcription reactions were performed using the pGAL4G- template (300 ng) and standard conditions, 30 The holoenzyme (1 μg), factor a (40 ng), and recombinant TBP (40 ng) were added to reactions as indicated. This and other figures in this application were prepared from digital replicas of primary data scanned using a UMax UC80 Max Vision digital scanner.

The Holoenzyme is a Complex of RNA Polymerase II and Initiation Factors

Semipurified holoenzyme that eluted from the Q-Sepharose column (FIG. 9A) was loaded onto a Mono S column and eluted with a 0.1–1.0 M gradient of potassium acetate. The onput (OP) and flow-through (FT) and a portion of every other fraction eluting between 0.1 and 0.9 M potassium acetate were analyzed for holoenzyme activity (top panel). These samples were also analyzed by western blot for the presence of RNA polymerase II and transcription factors (bottom panels). Top panel, Transcription assays were performed using the pGAL4G- template (300 ng), Factor a (40 ng), recombinant TBP (40 ng), and 1 μl of the OP, FT, and every other fraction from the Mono S column. Bottom panels, one μl of the same fractions were also separated on an SDS-polyacrylamide gel and blotted to nitrocellulose. The blots were probed with polyclonal antibodies specific to the 73 kD subunit of factor b (TFB1), factor e (SUA7), SRB2, SRB4, SRB5, and SRB6 and monoclonal specific to the largest subunit of RNA polymerase II (RPBI).

FIG. 9B shows the polypeptide composition of RNA polymerase holoenzyme. One microgram of purified holoenzyme was subjected to SDS-PAGE and stained with silver. Western blots of purified holoenzyme were performed on samples run on adjacent lanes of the gel with antiserum used in FIG. 9A to identify subunits of the SRB complex. Proteins in the holoenzyme preparation that correspond in size to subunits of RNA polymerase II SRB proteins, or subunits of initiation factors are indicated. The sizes of protein molecular weight standards are indicated in kD.

FIG. 9C shows coimmunoprecipitation of holoenzyme components with SRB5. Fifteen micrograms of the purified RNA polymerase II were diluted in 0.5 ml of transcription buffer containing potassium acetate instead of potassium glutamate, 0.01% NP40, and 0.1 mg/ml BSA. One microgram of affinity purified anti-HSP70 or anti-SRB5 antibodies, and five micrograms of recombinant SRB2 or SRB5 protein were added as indicated. Immunoprecipitated material was analyzed by western blot as indicated in (B) for the presence of transcription factor subunits and RNA polymerase II.

FIG. 9D shows quantitation of holoenzyme components. Samples of whole cell extract, nuclear extract, and purified holoenzyme together with standard amounts of purified RNA polymerase II and recombinant transcription factor subunits were quantitated by western blotting. Each gel contained the following: 25 μg yeast whole cell extract (lane 1), 25 μg yeast nuclear extract (lane 2), 1 μg purified holoenzyme (lane 3), and 0.2 μg purified holoenzyme (lane 4). The gels also contained purified standard proteins in lanes 5–7 in following amounts: 8, 40, and 200 ng RNA polymerase II; 4, 20, and 100 ng 6His-tagged factor e (SUA7); 3.2, 16, and 80 ng SRB2; 4, 20, and 100 ng SRB5; 3.2, 16, and 80 ng TOA1; 3.2, 16, and 80 ng TBP. Epitope-tagged SRB2 and 6His-tagged factor e (SUA7) used in this analysis exhibit slightly lower mobility on gels than their untagged counterparts. The RNA polymerase II CTD in the holoenzyme is the hypophosphorylated form (IIA).

FIGS. 10A–10B shows a summary of holoenzyme components. The amount of each holoenzyme component in 1 µg of the holoenzyme was determined by comparison with standard amounts in (D). Taking the molecular weight of each component into account, the stoichiometry of each factor per RNA polymerase II molecule is presented.

Transcription by the Holoenzyme is Stimulated by GAL4-VP16

As shown in FIG. 11A, transcription reactions were performed using either a template containing a CYCI TATA element that directs transcription of a G-less cassette (−GAL4 Site template) or a template that contained in addition a single consensus DNA binding site for the GAL4 protein upstream of the TATA element (+GAL4 Site template). GAL4-VP16 (150 ng) was added to reactions as indicated. Top panel, reactions were performed with the holoenzyme (1 µg), factor a (40 ng), recombinant TBP (40 ng), and each template (100 ng) as indicated. Bottom panel, reactions were performed with yeast nuclear extract protein (150 µg). Transcription in reactions containing nuclear extract is stimulated 10-fold by GAL4-VP16. Transcription by the holoenzyme is stimulated 5-fold by GAL4-VP16. The +GAL4 site template is pGAL4G-. The GAL4 site template is pSL187. The exposure in the top panel was 5 times longer than the exposure in the bottom panel. Levels of transcript were quantitated using a Fuji Bio-image Analyzer.

As shown in FIG. 11B, reactions were performed with the holoenzyme as detailed above except 225 ng of template, linearized by digestion with PvuII restriction lo endonuclease, was used. This exposure was 3 times longer than the holoenzyme panel in (A).

Example 4

SRB7, SRB8, SRB9, SRB10, SRB11 Genes and Their Encoded Proteins

Yeast strains and plasmids are listed in Table 5 and 6, respectively.

TABLE 5

Yeast Strains

| Strain | Alias | Genotype |
|---|---|---|
| Z26 | N247 | Mat α ura3-52 his3Δ200 leu2-3, 112 rpb1Δ187::HIS3[pRP112(URA3 RPB1)] |
| Z551 | N400 | MAT a ura3-52 his3Δ200 leu2-3, 112 rpb1Δ187::HIS3[pC6(LEU2 rpb1Δ104)] |
| Z558 | CTY143 | Mat a/Mat α ura3-52/ura3-52 his3Δ200 leu2-3, 112/leu2-3, 112 |
| Z567 | S242 | Mat a ura3-52 his3Δ200 leu2-3, 112 rpb1Δ187::HIS3 srb7-1[pC6(LEU2 rpb1Δ104)] |
| Z568 | S358 | Mat a ura3-52 his3Δ200 leu2-3, 112 rpb1Δ187::HIS3 srb8-1[pC6(LEU2 rpb1Δ104)] |
| Z569 | 5363 | Mat a ura3-52 his3Δ200 leu2-3, 112 rpb1Δ187::HIS3 srb9-1[pC6(LEU2 rpbiΔ104)] |
| Z570 | S456 | Mat a ura3-52 his3Δ200 leu2-3, 112 rpb1Δ187::HIS3 rpb2-551 [pC6(LEU2 rpb1Δ104)] |
| Z571 | CHY1 | Mat a ura3-52 his3Δ200 leu2-3, 112 rpb1Δ187::HIS3 srb7-1[pRP112(URA3 RPB1)] |
| Z572 | SLY63 | Mat a ura3-52 his3Δ200 leu2-3, 112 rpb1Δ187::HIS3 srb8-1[pRP114(LEU2 RPB1)] |
| Z573 | CHY3 | Mat a ura3-52 his3Δ200 leu2-3, 112 rpb1Δ187::HIS3 srb9-1[pRP112(URA3 RPB1)] |
| Z574 | SLY64 | Mat a ura3-52 his3Δ200 leu2-3, 112 rpb1Δ187::HIS3 rpb2-551[pRP114(LEU2 RPB1)] |
| Z575 | CHY102 | Mat a/Mat α ura3-52/ura3-52 his3Δ200/his3Δ200 leu2-3, 112/leu2-3, 112 srb7Δ1::URA3hisG/SRB7 |
| Z576 | SLY35 | Mat a/Mat α ura3-52/ura3-52 his3Δ200/his3Δ200 leu2-3, 112/leu2-3, 112 srb8Δ1::URA3hisG/SRB8 |
| Z577 | CHY105 | Mat a/Mat α ura3-52/ura3-52 his3Δ200/his3Δ200 leu2-3, 112/leu2-3, 112 srb9Δ1::URA3hisG/SRB9 |
| Z578 | SLY61 | MAT α ura3-52 his3Δ200 leu2-3, 112 rpb1Δ187::HIS3 srb8Δ1::hisG[pRP114(LUE2 RPB1)] |
| Z579 | SLY76 | MAT α ura3-52 his3Δ200 leu2-3, 112 rpb1Δ187::HIS3 srb8Δ1::hisG[pC6(LUE2 rpb1Δ104)] |
| Z580 | CHY113 | MAT α ura3-52 his3Δ200 leu2-3, 112 rpb1Δ187::HIS3 srb9Δ1::hisG[pRP114(LUE2 RPBI)] |
| Z581 | CHY116 | MAT α ura3-52 his3Δ200 leu2-3, 112 rpb1Δ187::HIS3 srb9Δ1::hisG[pC6U(URA3 rpb1Δ104)] |

TABLE 6

Plasmids

| Plasmid | Description |
|---|---|
| SRB7 | |
| pCH2 | SRB7 (6.7 kb) URA3 CEN. |
| PCH7 | SRB7 (2.0 kb) URA3 CEN. |
| PCH36 | srb7-1 URA3 CEN. |
| pCH34 | SRB7 in pET-3a (Studier and Moffat, 1986). |
| pCH46 | srb7Δl::URA3hisG in pSP72 (Promega). |
| SRB8 | |
| pSL301 | SRB8 (9.0 kb) URA3 CEN. |
| pSL311 | SRB8 (6.0 kb) URA3 CEN. |
| pSL307 | SRB8 (encoding aa 868 to 1226) in pET-3a (Studier and Moffat, 1986). |
| pSL315 | srb8Δ1::URA3hisG in pBSIISK (+) (Stratagene). |
| SRB9 | |
| pCH47 | SRB9 (7.3 kb) URA3 CEN. |
| pCH64 | SRB9 (encoding aa 45 to 501) in pGEX-1 (Smith and Johnson, 1988). |
| pCH66 | SRB9Δ1::URA3hisG in pSP72 (Promega). |
| RPB2 | |
| pSL401 | RPB2 (10 kb) URA3 CEN. |
| pSL411 | rpb2-551 URA3 CEN. |

Yeast media was prepared as described (Thompson, C. M., et al., *Cell* 73:1361–1375 (1993). Yeast transformations were done using a lithium acetate procedure (Schiestl and Gietz, 1989). Plasmid shuffle techniques were performed as described by Boeke, J., et al. *Meth. Enzymol.* 154:164–175 (1987) using 5-fluoroorotic acid (5-FOA) as a selective agent against URA3 plasmids. Plasmids were recovered from yeast as described by Hoffman, C. S. and Winston, F., *Gene* 57:267–272 (1987). Growth assays were performed by suspending similar numbers of cells in water and transferring equal volumes to agar plates with a 48-prong apparatus. To reduce flocculation of some strains, cells were first washed in 100 mM EGTA, 10 mM Tris-HCl 7.5.

Extragenic suppressors of the cold sensitive phenotype of Z551 were isolated as previously described. Dominant and recessive suppressors were identified by mating to Z26, selecting against the presence of pRP112 using 5-FOA and assaying growth at 12° C. on YEPD. Diploids able to grow at 12° C. contained a dominant suppressor. Diploids unable to grow at 12° C. contained a recessive suppressor.

Yeast strains of the opposite mating type of approximately half of the dominant suppressors and half of the recessive suppressors were generated by inducing a mating type switch by expression of the HO gene placed on a plasmid under the control of a galactose inducible promoter. Random spore analysis of the dominantly suppressing mutations was used to determine if two independent isolates were likely to contain mutations in the same gene. Haploids were mated to each other, each containing the CTD truncation mutation rpb1Δ104 and an independently isolated SRB mutation, to form diploids. These diploids were sporulated on plates and a small quantity of spores scraped off and shaken overnight at 30° C. in 0.5 ml 30 mM β-mercaptoethanol and 100 ng/ml Zymolase 100 T (ICN). 0.5 ml of 1.5% NP-40 and 0.4 g glass beads were added and the mixture held on ice for 15 min. The suspension was then vortexed 3 min, held on ice 5 min, vortexed 2 min, and the glass beads allowed to settle for 10 min at room temperature. The supernatant was removed, spun 2 min, the pellet washed once in water, then resuspended in water and a portion plated onto YEPD. Approximately fifty of the haploid offspring were assayed for their ability to grow at 12° C. If all haploids were able to grow at 12° C. then the two SRB isolates were assumed to contain mutations in the same gone. Genetic complementation of the recessive alleles involved mating haploids to each other, each containing the CTD truncation mutation rpb1Δ104 and an independently isolated srb mutation, to form diploids and assessing the ability of these diploids to grow at 12° C. Diploids able to grow at 12° C. were assumed to contain srb mutations in the same gene. Genomic clones of each complementation group were used to confirm the identity of each member of the complementation group and to identify additional members. Cells containing the CTD truncation mutation rpb1Δ104 and a recessive srb allele were unable to grow at 12° C. and on pyruvate media when transformed with the corresponding wild-type SRB allele.

Deletions of SRB7, SRB8 and SRB9 were created by a single step disruption method. Z558 was transformed with the desired DNA fragment and plated on SC-Ura media. Southern analysis was used to confirm that a single copy of the desired SRB gene had been deleted. The diploid was sporulated and tetrads dissected (>20) on YEPD plates and scored for nutritional auxotrophies and growth at a variety of temperatures. Z575 was created by transformation with the srb7Δ1::URA3hisG fragment from pCH46. Two or less spores from each tetrad were viable and these spores were uracil auxotrophs, indicating that SRB7 is essential. Z576 was created by transformation with the srb8Δ1::URA3hisG fragment from pSL315 and Z577 was created by transformation with the srb9Δ1::URA3hisG fragment from pCH66. In each case segregants scored 2:2 for uracil prototrophy and all uracil prototrophs exhibited mild cold-sensitive, temperature-sensitive, and slow growth phenotypes, indicating that SRB8 and SRB9 deletion strains are conditionally viable. srb8Δ1 and srb9Δ1 strains are also flocculent as are the suppressing isolates of SRB8 and SRB9. Strains containing unmarked deletions of SRB8 and SRB9 were created by selecting for excision of the URA3 gene by growth on 5-FOA (Alani, E. et al., *Genetics* 116:541–545 (1987)).

The influence of SRB2 and SRB8 alleles on growth phenotypes of RNA polymerase II CTD truncation mutants was tested as follows. Strains containing combinations of SRB2 or SRB8 alleles and CTD truncation alleles were assayed for growth on YEPD medium at 12° C., 30° C., and 38° C. and on SC medium containing pyruvate as a sole carbon source. The degree of CTD truncation is shown for each mutant on the horizontal axis, and the plasmid carrying each CTD truncation allele is indicated (i.e., pN51). The phenotypes exhibited by each of the CTD truncation mutants in a wild-type, srb2Δ1, SRB2-1, or srb8Δ1 background are shown on left. Nonviable strains (N) are indicated by a dashed line, conditional strains (C) that were extremely sensitive to high (38° C.) and low (12° C.) temperatures and failed to grow on pyruvate media are indicated by a thin solid line, and viable (V) strains that exhibit nearly wild-type growth characteristics under all conditions tested are indicated by a heavy solid line. Viable/conditional srb8Δ1 strains (V/C) were able to grow at low temperatures and on pyruvate medium but were sensitive to high temperatures and are indicted by a solid line. Not every CTD truncation allele was tested in every background, but for each background the phenotypic boundaries are well established.

DNA methods

DNA manipulations were performed according to Sambrook et al., *Molecular Cloning: A Laboratory Manual* (Cold Spring Harbor Laboratory 1989). Site-directed mutagenesis was performed as described in Kunkel, T. A., et al., *Meth. Enzymol.* 154:367–382 (1987). PCR amplifications to produce pCH45 (srb766 1), pSL315 (srb8Δ1), and pSL307 (SRB8 in pET-3a) were performed with Taq DNA polymerase (Perkin Elmer) in 100λ of buffer (provided by the manufacturer) supplemented with 200 μM dNTP for a total of 25 cycles. Primer concentrations were 0.5 μM with 50 ng of DNA and cycling was at 94° C. (1.0 min), 50° C. (1.0 min) and 72° C. (2.5 min).

Cloning and Sequence analysis

Genomic clones of SRB7 (pCH2), SRB8 (pSL301), SRB9 (pCH47), and RPB2 (pSL401) were isolated by transformation and complementation of Z567, Z568, Z569, and Z570, respectively. pCH36 was created from pCH7 in vivo by transforming Z567 with linearized pCH7 lacking SRB7 coding DNA and isolating the plasmid from a Ura+ transformant which had repaired the plasmid with the mutant srb7-1 sequences from the chromosome. Similarly, rpb2-551 (pSL411) was isolated from Z570 using pRP212. SRB7 and SRB9 were completely sequenced on each strand using genomic DNA from pCH7 and pCH47, respectively. Unidirectional deletions were constructed using the Erase-a-Base system (Promega) and double stranded sequencing with dideoxynucleotides and Sequenase (US Biochemical) was carried out as described by the manufacturer using T3 and T7 promoter primers. Gaps in the sequence were filled in by sequencing with internal oligonucleotide primers. The suppressing mutations in SRB7 and RPB2 were deduced by sequencing using oligonucleotide primers that spanned the entire open reading frames. Sequence comparison analysis was performed at the National Center for Biotechnology Information using the BLAST network service.

A restriction map of a 2.0 kb DNA fragment from pCH7 containing the SRB7 gene was determined. The entire coding region of SRB7 was replaced with a 5.5 kb DNA fragment containing the URA3 and kanamycin genes flanked by direct repeats of Salmonella hisG DNA to create the deletion allele srb7Δ1::URA3hisG. The predicted 140 aa sequence of the SRB7 protein is shown in FIGS. 13A–13B. Positive numbering of the DNA begins with the predicted start site of translation. The srb7-1 mutation is a G to A transition (nt 61) that changes aa 21 from Ala to Thr.

A restriction map of a 6.0 kb DNA fragment from pSL311 containing the SRB8 gene was also determined. Approximately 500 bp upstream of SRB8 there is an inversion, relative to the genomic DNA used to sequence that region of chromosome III, encompassing greater than 2 kb. The entire coding region of SRB8 was replaced with a 5.5 kb DNA fragment containing the URA3 and kanamycin genes flanked by direct repeats of Salmonella hisG DNA to create the deletion allele srb8Δ1::URA3hisG. The DNA sequence SRB8, with its predicted amino acid sequence is shown in FIGS. 14A–14C.

A restriction map of a 7.3 kb DNA fragment from pCH47 containing the SRB9 gene was also determined. Most of the coding region of SRB9 was replaced with a 5.5 kb DNA fragment containing the URA3 and kanamycin genes flanked by direct repeats of Salmonella hisG DNA to create the deletion allele srb9Δ1::URA3hisG. FIGS. 15A–15I shows the sequence of the 7.3 kb DNA fragment containing the SRB9 gene. The predicted 1420 aa sequence of the SRB9 protein is shown below the sequence of the gene. The DNA sequences and their predicted amino acid sequences for SRB10 and SRB11 are shown in FIGS. 16A–16B and 17A–17B respectively.

Purification of Recombinant Proteins

Recombinant proteins were purified for generating polyclonal antibodies in rabbits. SRB7 and a portion of SRB8 (amino acids 868 to 1226) were purified from the bacterial strain BL21 (DE3) pLysS (Studier and Moffatt, 1986) carrying the plasmids pCH34 and pSL307, respectively, in the same manner SRB2 was purified. A portion of SRB9 (amino acids 45 to 501) was purified as a fusion to glutathione-S-transferase from DH5α carrying pCH64 according to the method of Smith, D. B. and Johnson K. S., *Gene*. 67:31–40 (1988).

In Vitro Transcription and Western Blot Analysis

In vitro transcription assay for holoenzyme activity was performed as described above. Western blotting was performed by standard methods. RPB1 was detected via the CTD with 8WG16 monoclonal antibody ascites fluid (Promega). Polyclonal rabbit anti-SRB2, anti-GST-SRB4, anti-SRB5, anti-GST-SRB6, anti-SRB7, anti-SRB8 (aa 868 to 1226), and anti-GST-SRB9 (aa 45 to 501) antiserum were used to detect the SRBs. In all cases, bands were visualized by secondary probing with alkaline phosphatase conjugate secondary antibodies (Promega).

FIGS. 19A–19B shows that SRB2 and SRB4-SRB9 are components of an RNA polymerase II holoenzyme. (A) Semipurified holoenzyme that eluted from the Q-sepharose column as described in Example 3 was loaded onto a Mono S column and eluted with a 0.1–1.0 M gradient of potassium acetate. The onput (OP) and flow-through (FT) and a portion of every other fraction eluting between 0.1 and 0.9 M potassium acetate were analyzed for holoenzyme activity (top panel). These samples were also analyzed by Western blot for the presence of RNA polymerase II and SRB proteins. This figure was prepared from digital replicas of primary data scanned using a UMAX UC840 Max Vision digital scanner. (B) Polypeptide composition of RNA polymerase II holoenzyme. One microgram of purified holoenzyme was subjected to SDS-PAGE and stained with silver. Proteins in the holoenzyme preparation that correspond in size to subunits of RNA polymerase and SRB proteins are indicated. The sizes of protein molecular weight standards are indicated in kd.

Example 5

General Requirement for RNA Polymerase II Holoenzyme In Vivo

PCR mutagenesis was performed as described by D. W. Leung, E. Chen, D. V. Goeddel, *Technique*. 1:11 (1989). The plasmid pCT127 (SRB4 LEU2 CEN) contains a unique NdeI site at the SRB4 ATG and a unique XbaI site following the SRB4 stop codon, both created by site-specific mutagenesis (T. A. Kunkel, J. D. Roberts, R. A. Zakour, *Meth. Enzymol*. 154:367 (1987)). PCR of SRB4 from pCT127 with oligonucleotides flanking the ORF was performed in buffer containing 0.1 mM, 0.2 mM, and 0.4 mM $Mn^{2+}$. Reactions were pooled, DNA digested with NdeI-XbaI, ligated with NdeI-XbaI digested pCT127 vector fragment, and transformed into DH5α. Approximately 30,000 transformants were obtained.

Plasmid shuffle techniques were performed as described by J. Boeke, J. Truehart, B. Natsoulis, G. R. Fink, *Meth. Enzymol*. 154:164 (1987), using 5-flouroorotic acid (5-FOA) as a selective agent against URA3 plasmids. Genetic manipulations of yeast were performed as previously described. DNA molecules containing LEU2 and mutagenized SRB4 genes were transformed into a yeast strain (CTY182) deleted for the chromosomal copy of SRB4, but carrying a URA3 centromeric plasmid encoding a wild-type copy of the gene. Approximately 20% of the transformants were unable to grow in the presence of 5-FOA, indicating a lethal mutation in the LEU2 plasmid-borne SRB4 gene. Approximately 0.5% of the transformants were able to grow on 5-FOA plates at 30° C. but not at 37° C., indicating a ts allele in the LEU2 plasmid-borne SRB4 gene. The LEU2 plasmids from these transformants were recovered and reintroduced in CTY182 to verify the ts phenotype. The plasmid pCT181 contains the srb4-138 mutant allele.

Total RNA from cells was isolated using hot acidic phenol extraction (F. M. Ausubel et al., Ed., *Current Protocols in Molecular Biology* (John Wiley and Sons, New York, (1993)). RNA was quantified by absorbance at 260 nm and the integrity of the RNA confirmed by ethidium bromide straining of RNA in agarose gels.

S1 nuclease protection assays were carried out with 5–30 ug of RNA and DED1, HIS3, TRP3, rRNA and $tRNA^w$ oligonucleotide probes as previously described (Cormack & Struhl). The sequences for the other oligonucleotide probes are: ACT1 (GGAAGAGTACAAGGACAAAACGGCTTGGATGG AAA CGTAGAAGGCATTCCA) (SEQ ID NO: 30), CDC7 (GGGGCTACTCTC GAAGATCCCGTCATTATGTA-CAGCAGGTTGAGCAT GCCT) (SEQ ID NO: 31), MET 19 (GCCTTACCGGCACGCATCATGATGGGGACGCCCT CCCAACGCTCGAC ACTT) (SEQ ID NO: 32), RAD23

(GCAGTGGCTGCAGGAGCTGCAG AAGCATCGGTACTGGGGGATGCAATCCA) (SEQ ID NO: 33), STE2 (GTCGACGGGTTCAACTTCTCCCTCTTTGTAACTT GCATCAGCAAACGGATGACA) (SEQ ID NO: 34), AND TCM1 (GGAGTGTCAACAACGGTGACAGCTTCGAC AACTTCACGCTTGTGGTGAGCT) (SEQ ID NO: 35). Oligonucleotides are written in the 5' 3' direction and contain 6 residues at their 3' ends that are not complementary to the RNA, permitting distinction between bands due to appropriate RNA-DNA hybrids and undigested probe.

Example 6

Cloning and Sequencing of hSRB7

XREF db was used to screen the dbEST for expressed sequence tags similar to ySRB7 (Boguski, M. S. et al., Jr. Science, 265:1993–1994 (1994)). Overlapping sequences (Genbank accession numbers H08048, R19473, and F13227) were identified as encoding a potential ySRB7 homolog. Sequences derived from the tags were used to design primers for amplifying the hSRB7 gene. Vent DNA polymerase (New England Biolabs) was used according to the manufacturer's directions to amplify a hSRB7 probe from a human peripheral blood lymphocyte cDNA library constructed in IYES (Elledge, S. J. et al., Proc. Natl. Acad. Sci. USA, 88:1731–1735 (1991)). The probe was used to isolate a full length clone of hSRB7 from the same library by standard techniques. (Ausubel, F. M., current Protocols in Molecular Biology (Current Protocols, 1994)). The DNA sequence of hSRB7 was determined with Sequenase (US Biochemical) according to the manufacturer's directions. The initiating ATG was assigned based on homology to ySRB7.

ySRB7 and hSRB7 are 35% identical and 58% similar. ySRB7 and hSRB7 are more similar to each other than to any other sequenced genes. ySRB7 and hSRB7 were aligned using the program BESTFIT (Genetics Computer Group, Inc.). A gap weight of 1.0 and a length weight of 0.1 were used. Using the hSRB7 sequence as a query, a BLAST search of the National Center for Biotechnology Information non-redundant protein database retrieved ySRB7 with a smallest sum probability of $6.4 \times 10^{-6}$ (Altschul, S. F. et al., J. Mol. Biol., 215:402–410 (1990)). No other significant matches were reported. A BLAST search with ySRB7 did not retrieve any significant matches other than ySRB7 itself.

Example 7

Complementation of a ySRB7 deletion with ySRB7-hSRBy Chimeras

The appropriate regions of ySRB7 were amplified by PCR with Vent DNA polymerase (New England Biolabs) according to the manufacturer's directions. The appropriate regions of hSRB7 were similarly amplified except that an 18 bp region of homology to the appropriate segment of ySRB7 was appended to the 3' primer used to amplify each fragment. The PCR fragments were gel purified, combined and amplified again with primers hybridizing to the N-terminus of hSRB7 and the C-terminus of ySRB7. The appropriate PCR fragments were gel purified, amplified again and cloned into the BglII site of the yeast expression vector DB20LBgl2 (a gift of L. Guarente) The chimeras are full length ySRB7 (residues 1–140); hSRB7(1–20)-ySRB7 (21–140); hSRB7(1–77)-ySRB7(82–140); hSRB7(1–117)-ySRB7(129–140); and full length hSRB7(1–144). Plasmids expressing the chimeras were shuffled into the strain EGY112 (MATa ura3-52, his3D200, leu2-3,112, SRB7D1 (pCH7: SRB7 URA3 CEN) by LiOAc transformation and selection on 5-fluoroorotic acid (Boeke, J. D. et al., Methods Enzymol, 154:164–175 (1987); Schiestl, R. H. and Gietz, R. D., Curr. Genet, 16:339–346 (1989)). Three independent clones were tested for each chimera, and the sequence of at least one clone for each chimera was confirmed by DNA sequencing.

Example 8 hSRB Binding to the CTD

A BioRex 70 fraction containing SRBs prepared from a wild-type S288C strain was mixed with an equal volume of Buffer A(20 mM K-HEPES pH 7.6, 1 mM EDTA, 20% glycerol, 1 mM DTT, 0.5 mM PMSF, 1 mM benzamidine, 0.5 uM pepstatin, 0.15 uM leupeptin, and 1 ug/ml chymostatin)+2% Triton X-100 and applied to a preclearing column. The precleared extract was applied to a GST or GST-CTD column (Hengartner, C. J. et al., Genes and Development, 9:897–910 (1995); Thompson, C. M. et al., Cell, 73:1361–1375 (1993)). Columns were washed sequentially with Buffer A+300 mM KOAc+1% Triton X-100 and Buffer A+300 mM KOAc and then eluted with Buffer A+300 mM KOAc+4 M Urea. Eluates were precipitated with TCA and separated by SDS-polyacrylamide gel electrophoresis on 4–20% gradient gels (BioRad). Western blotting was performed with as described Hengartner, C. J. et al., Genes and Development, 9:897–910 (1995).

Example 9 hSRB7 Association with RNA Polymerase II pEG121 was constructed by amplifying amino acids 65 to 92 of hSRB7 by PCR with Vent DNA polymerase (New England Biolabs) according to manufacturer's directions and inserting the PCR product into the BamHI and SalI sites of pGEX-4T-3 (Pharmacia Biotech). The resulting GST-hSRB7 C-terminal fragment fusion was purified as described [Smith, 1988 #1936] and used to immunize female New Zealand white rabbits with RIBI adjuvant (RIBI ImmunoChem Research, Inc.) according to manufacturer's directions.

In HeLa and COS cell extracts, antibody raised against hSRB7 recognizes a protein with a relative mobility of 16 kD. This relative mobility is consistent with hSRB7's predicted molecular weight of 15.7 kD. Additional evidence that the antibody specifically recognizes hSRB7 comes from experiments with COS cells transiently transfected with an hSRB7 expression construct. When probed with antibody raised against hSRB7, Western blots of extracts from these cells contain a 16 kD band whose signal is twenty-fold greater than in extracts from control cells (data not shown). We conclude from these experiments that the anti-hSRB7 antibody specifically recognizes hSRB7 in Western blots. The antibody directed against human SRB7 recognizes a comigrating 16 kD band in calf thymus extracts. Because of the high degree of conservation among mammalian transcription factors, it is reasonable to believe this 16 kD protein represents bovine SRB7.

A HeLa whole cell extract (Manley, J. L. et al., Proc. Natl. Acad. Sci. USA, 77:3855–3859 (1980)) was applied to a CTD column as above. The blot was probed with a 1:250 dilution of an antisera raised against the C-terminal fragment of hSRB7.

Aliquots of frozen calf thymus (1 kg) were placed in a nylon bag (The North Face) and broken with a hammer. The frozen pieces were added to 2 l of 50 mM Tris-OAc pH 7.8, 10 mM EDTA, 10 mM EGTA, 5% glycerol, 0.2 mM DTT and protease inhibitors as in Buffer A. Aliquots of the calf thymus were mixed in a Waring blender for 2 minutes each. The mixed calf thymus was pooled and aliquots were blended for an additional 2 minutes. The blended thymus was spun at 5,000 r.p.m. for 30 min. in a Sorvall RC3B centrifuge. The supernatant was decanted through Miracloth (CalBiochem), centrifuged and decanted through Miracloth again. After the addition of 29.1 g of ammonium sulfate/100 ml of supernatant, the suspension was stirred for 15 minutes at 4° C. and centrifuged at 6,000 r.p.m. for 30 minutes in an RC3B. The supernatant was decanted, and the pellet was resuspended in Buffer D (50 mM Tris-OAc pH 7.8, 0.1 mM EDTA, 5 % glycerol ) such that the conductivity was equal to that of Buffer D+300 mM ammonium sulfate. 5.5 ml of 10% polyethylenimine was added per liter of extract and the extract was stirred for 10 minutes at 4° C. The extract was centrifuged at 8,000 RPM for 30 minutes in a Sorvall GS3 rotor. The supernatant was decanted and Buffer D was added so that the conductivity was equal to that of Buffer D+150 mM ammonium sulfate. 200 ml of DEAE Sepharose CL6B (Pharmacia) was added, and the slurry was stirred for 1 hour at 4° C. The resin was collected in a Buchner funnel and packed into a 5 cm diameter column. Bound proteins were eluted with Buffer D+400 mM ammonium sulfate. The DEAE eluate was flash frozen in liquid nitrogen and stored at −70° C. until use. The DEAE eluate was applied to the CTD column and analyzed as for HeLa extracts.

All primary data were scanned and electronically processed as described (Koleske, A. J. and Young, R. A., Nature, 368:466–469 (1994)). Western blots were scanned as described (Donovan, R. S. et al., Biotechniques, 17:660–661.

A peptide corresponding to amino acids to amino acids 39–58 of hSRB7 was synthesized using the MAP system and used to prepare polyclonal antisera (Research Genetics). The hSRB7 peptide was used to prepare affinity purified anti-hSRB7 antibody according to the manufacturer's directions, except that 1 volume of 1 M Na-Borate pH 8.5 was used to neutralize the eluate. The eluate was concentrated in a Centriprep 30 ultrafiltration unit (Amicon).

Aliquots of frozen calf thymus (1 kg) were placed in a nylon bag (The North Face) and broken with a hammer. The frozen pieces were added to 2 l of 50 mM Tris-SO4 pH 7.6, 10 mM EDTA, 10 mM EGTA, 5% glycerol, 0.1 mM DTT and protease inhibitors as in Buffer A. Aliquots of the calf thymus were mixed in a Waring blender for 2 minutes each. The mixed calf thymus was pooled and aliquots were blended for an additional 2 minutes. The blended thymus was spun at 5,000 r.p.m. for 30 min. in a Sorvall RC3B centrifuge. The supernatant was decanted through Miracloth (CalBiochem), centrifuged again and decanted through Miracloth again. Ammonium sulfate was added to 30% saturation. After 15 minutes of stirring at 4° C., the suspension was centrifuged at 5,000 r.p.m. for 1 hour in a Sorvall RC3B centrifuge. The supernatant was decanted and the pellet was resuspended in Buffer B (20 mM K-HEPES pH 7.6, 0.1 mM EDTA, 10% glycerol, 0.1 mM DTT, protease inhibitors as above) so that the conductivity equaled that of Buffer B+75 mM ammonium sulfate. The suspension was centrifuged for 10 min. at 5,000 r.p.m. in a Sorvall RC3B. The supernatant was decanted and incubated with 500 g of damp phosphocellulose P11 (Whatman) precycled according to the manufacturer's directions and equilibrated in Buffer B+75 mM ammonium sulfate. The slurry was stirred for 1 hour, filtered through a Buchner funnel, washed with Buffer B+75 mM ammonium sulfate, and packed into a 5 cm diameter column. Bound proteins were eluted with Buffer B+250 mM ammonium sulfate, frozen in liquid nitrogen, and stored at −70° C. until use.

100 ul of the phosphocellulose fraction was mixed with 200 ul Buffer B+0.1% NP-40 and incubated with 5 ul of protein A-Sepharose (Pharmacia) for 1 hour. The fraction was centrifuged for 5 minutes in a microcentrifuge. The supernatant was incubated with 5 ul of protein A-Sepharose and 1.5 ug of affinity purified anti-SRB7 peptide antibody for 2 hours. The immune complexes were pelleted by a brief spin in a microcentrifuge and washed 4 times with 0.5 ml of 60 mM KCl, 50 mM Tris-Cl pH 7.9, 5 mM MgCl2, 2.5 mM MnCl2. Control immunoprecipitations were performed in the same manner except that 20 ug of hSRB7 peptide was used to block antigen-binding sites.

Western blotting was performed as described above and probed with antibody directed against the C-terminus of hSRB7.

In the control immunoprecipitation, pol II was added to all assays. In the anti-hSRB7 immunoprecipitation, exogenous pol II was omitted because pol II was known to be present in the immunoprecipitates.

A phosphocellulose fraction was prepared as above. The 250 mM elute was flash frozen in liquid nitrogen and stored at −70° C. The extract was thawed and Buffer B was added so that the conductivity equaled that of Buffer B+150 mM ammonium sulfate. The extract was then spun at 5,000 r.p.m. for 10 minutes in an RC3B centrifuge (Sorvall). The supernatant was decanted and applied to an 80 ml column of Heparin-Sepharose CL-6B at 3 ml/min. The column was washed with Buffer B+200 mM ammonium sulfate and eluted with Buffer B+500 mM ammonium sulfate. Eluted proteins were pooled, and ammonium sulfate was added to 60% saturation. After stirring for thirty minutes at 4° C., the suspension was centrifuged for 10 minutes at 10,000 r.p.m. in an SS-343 rotor (Sorvall). The supernatant was decanted and the pellet was stored at −70° C. until use. The pellet was resuspended in 1.5 ml of Buffer B and dialyzed against 1 l of Buffer B +100 mM ammonium sulfate for 4 hours. The dialyzed sample was centrifuged for 10 minutes in a microcentrifuge and loaded onto a Sephacryl S-400 16/60 column (Pharmacia) at a flow rate of 0.5 ml/min. 1.5 ml fractions were collected. The column was calibrated with gel filtration standards (BioRad) run under similar conditions. Antibodies raised against TFIIH p89. TFIIE p56 and p34 (gifts of J. Kim, B. Shykind, and P. Sharp) and against MO15 (gift of T. Makela and R. Weinberg) were used for Western Blotting.

Example 10

Purification and Characterization of the Mammalian Holoenzyme

Chromatography of calf thymus on P11 was as described for immunoprecipitations. Ammonium sulfate was added to the 250 mM eluate to achieve 35% saturation. After stirring at 4° C. for 15 minutes, the suspension was spun at 17,000 r.p.m. for 10 minutes in an SS-34 rotor (Sorvall). The supernatant was decanted and the pellet was stored at −70° C. The pellet was suspended in Buffer B such that the conductivity was equal to that of Buffer B+150 mM ammonium sulfate. The resuspended pellet was centrifuged at 8,000 r.p.m. for 10 minutes in an SS-34 rotor (Sorvall). The supernatant was decanted and loaded onto a 40 ml column of Heparin Sepharose CL6B. 1/25 volume of 1 M Tris-SO4 pH 7.6 was added to the flow through. The fraction was then centrifuged at 8,000 r.p.m. for 10 minutes in an SS-34 rotor (Sorvall) and applied to a 5 ml HiTrap Q cartridge (Pharmacia). Bound proteins were eluted with a 24 ml gradient of Buffer C (20 mM Tris-SO4 pH 7.6, 0.1 mM EDTA, 10% glycerol, 0.1 mM DTT, protease inhibitors as for Buffer A)+75 mM ammonium sulfate to Buffer C+1000 mM ammonium sulfate. Fractions containing SRB7 were pooled and stored at −70° C. until use. Buffer B was added to the pooled fractions such that the conductivity was equal to that of Buffer B+75 mM ammonium sulfate. The pooled fractions were centrifuged at 8,000 r.p.m. for 10 minutes in an SS-34 rotor (Sorvall). The supernatant was decanted and loaded onto a 5 ml Heparin HiTrap cartridge (Pharmacia). Bound proteins were eluted with 30 ml gradient from Buffer B+75 mM ammonium sulfate to buffer B+1000 mM ammonium sulfate. Fractions containing SRB7 were pooled and stored at −70° C. until use. Buffer C was added to one third of the pooled fractions such that the conductivity was equal to that of Buffer C+75 mM ammonium sulfate. The pooled fractions were centrifuged at 8,000 r.p.m. for 10 minutes in an SS-34 rotor (Sorvall). The supernatant was decanted and loaded onto a Mono Q HR 5/5 column (Pharmacia). Bound proteins were eluted with a 20 ml gradient from Buffer C+75 mM ammonium sulfate to buffer C+1000 mM ammonium sulfate. Fractions containing SRB7 were pooled, flash frozen in liquid nitrogen, and sorted at −70° C. until use. Pooled fractions were dialyzed against 1 1 of buffer B+25 mM ammonium sulfate for 2 hours. Buffer B was added so that the conductivity was equal to that of Buffer B+25 mM ammonium sulfate. The pooled fractions were filtered through a 0.2 um filter and loaded onto a Mono S, PC 1.6/5 (Pharmacia). Bound proteins were eluted in 100 ul fractions with a 2 ml gradient from Buffer B+25 mM ammonium sulfate to Buffer B+1000 mM ammonium sulfate.

In the second purification procedure, 4 volumes of Buffer C were added to one third of the pooled material from the Haparin HiTrap column. The pooled fractions were centrifuged at 8,000 r.p.m. for 10 minutes in an SS-34 rotor (Sorvall. The supernatant was decanted and loaded onto a 7.5×75 mm DEAE 5PW column (Toso-Haas) at a flow rate of 0.5 ml/min. Bound proteins were eluted with a 30 ml gradient from Buffer C+75 mM ammonium sulfate to Buffer B+750 mM ammonium sulfate. Fractions containing SRB7 were pooled, flash frozen in liquid nitrogen, and stored at −70° C. until use. Pooled fractions were thawed and dialyzed against 1 1 of Buffer C for 2 hours. The dialyzed material was filtered through a 0.2 um filter and loaded onto a Mono Q, PC 1.6/5 (Pharmacia) at 0.1 ml/min. Bound proteins were eluted in 100 ul fractions with a 2 ml gradient from Buffer C+75 mM ammonium sulfate to Buffer C+1000 mM ammonium sulfate. Silver staining and Western blotting were performed.

Transcription reactions were performed as described (Makela, T. P. et al., Proc. Natl. Acad. Sci. U.S.A., 92:5174–5178 (1995)). Holoenzyme was the peak fraction from the Mono S column. Protein preparations for all of the basal factors used here have been shown to be free of cross-contamination.

In vitro transcription assays were used to test column purified holoenzyme (Mono S) for the ability to support specific transcription and for the presence of general transcription factors. The template was the adenovirus major late promoter with a linear topology. Products were obtained from a reaction containing all of the indicated factors, and with a single different factor omitted. Purified holoenzyme supports basal transcription when supplemented with general factors.

Core RNA polymerase II or column purified holoenzyme were tested for their response to Gal4-VP16 in the presence or absence of the coactivators HMG-2 or PC4. The upper transcript is derived from a template containing the adenovirus major late promoter and 3 Gal4 binding sites. The lower transcript is derived from a control template containing the adenovirus major late promoter but no Gal4 binding sites. In the presence of coactivators, the holoenzyme supports five-fold levels of activation while core RNA polymerase II shows a two-fold level of activation.

Example 11

Anti-SRB and Anti-SWI Antibodies Coprecipitate Holoenzyme

All immunoprecipitations were done as described (Hengartner, C. J. et al., Genes and Development, 9:897–910 (1995)). Briefly, 50 μl of the DEAE(400) fraction was diluted 1:4 with modified transcription buffer (MTB) (50 mM HEPES KOH pH 7.3, 100 mM potassium acetate, 25 mM MgAc, 5 mM EGTA, 1 μM DTT, 10% glycerol, 0.01% NP-40, 1 mM PMSF, 2 mM benzamidine, 2 μM pepstatin A, 0.6 μM leupeptin, and 2 μg/ml chymostatin) minus the potassium acetate. 4 μg of ovalbumin, 4 μg HA-GST, and 2 μg BSA were added to each reaction prior to the addition of antibody. 0.4 μg of affinity purified α-SRBS, -0.15 μg of affinity purified α-SWI3, or 1.5 μg of affinity purified α-TGFβ were added to the respective reactions and allowed to incubate 2 hours at 4° C. 15 μl of goat anti-rabbit covalently linked to magnetic beads (Dynal) were then added and incubated for 1 hour at 4° C. with constant agitation. Beads were precipitated with a magnet and washed three times in 200 μd MTB buffer. The final wash contained no NP-40. Proteins were eluted of the magnetic beads by boiling in 20 μl of sample buffer.

All Western blots were performed as described (Koleske, A. J., and Young, R. A., Nature, 368:466–9 (1994)). Proteins were detected with the following antibodies: SRB2, 4, 5, 6 (Thompson, C. M. et al., Cell, 73:1361–1375 (1993)), SRB8, 9 (Hengartner, C. J. et al., Genes and Development, 9:897–910 (1995)), SRB10, 11 (Liao, S. M. et al., Nature, 374:193–196 (1995)), SWI2/SNF2, SNF5 (gift of B. Laurent), SWI3 (gift of C. Peterson), SNF11 (gift of I. Treich and M. Carlson), TFIIEα and TFIIEβ. The production of antibodies, polyclonal and monoclonal are well-known to those of skill in the art and antibodies to additional components of the RNA polymerase II holoenzyme can be produced accordingly. Quantitative Western blots were performed as described in Koleske A. J. and Young R. A., Nature, 368:466–469 (1994). Recombinant standards were SRB5 Thompson, C. M. and Young, R. A., Proc. Natl. Acad. Sci. USA, (1995), GST-SNF2/SWI2$_{1256-1703}$ and GSTSNF5$_{1-193}$ (gifts of B. Laurent). GST proteins were purified as described (Smith, D. B. and Johnson, K. S., Gene, 67:31–40 (1988)). Concentrations of recombinant proteins were determined using a calorimetric assay (BioRad) with bovine serum albumin as a standard.

SRB regulatory proteins are found tightly and exclusively associated with other components of the RNA polymerase II holoenzyme in cell extracts. If SWI and SNF proteins are subunits of the RNA polymerase II holoenzyme, then antibodies against SRB5 should precipitate both the holoenzyme and SWI/SNF proteins from crude extracts. The results in demonstrate that this is indeed the case. SWI2/SNF2, SWI3 and SNF5 proteins coprecipitate with holoenzyme obtained through SRB5 immunoprecipitation. The fraction of SWI and SNF proteins immunoprecipitated from the crude extract appears to be the same as that of the SRB proteins. Control proteins introduced into the crude lysate did not coprecipitate, indicating that the immunoprecipitate was specific for the holoenzyme. When the immunoprecipitation experiment was carried out with antibody against SWI3, essentially identical results were obtained. The SWI/SNF and SRB proteins were immunoprecipitated from the crude extract with similar efficiency whether the immunoprecipitating antibody used was directed against SRB5 or SWI3. A control experiment with antibody against TGFβ failed to precipitate SWI/SNF or SRB proteins. These results indicate that SRB and SWI/SNF proteins are tightly associated with one another, and form as SRB/SWI/SNF complex.

Example 12

Purified Holoenzyme Contains SWI/SNF Proteins

Holoenzyme was purified and transcription assays for holoenzyme were done as described in Koleske and Young, 1994. Mediator was purified as described in Hengartner, C. J. et al., *Genes and Development*, 9:897–910 (1995).

Antibodies against selected SWI and SNF proteins were used to determine whether these proteins coelute with the RNA polymerase II holoenzyme in the final purification step of the holoenzyme. The data demonstrate that SN2/SWI2, SNF5, SWI3 and SNF11 proteins coelute with other known components of the holoenzyme and with transcription activity.

The holoenzyme contains stoichiometric amounts of RNA polymerase II, SRB proteins, and general transcription factors. To ascertain whether the SWI/SNF proteins are stoichiometric components of the holoenzyme, the amounts of SNF2 and SNF5 were estimated by Western blot analysis with various amounts of recombinant proteins as standards. These data indicate that the purified RNA polymerase II holoenzyme contains approximately equimolar amounts of SNF2, SNF5 and SRB5, the latter being a standard against which other holoenzyme components have previously been compared. Since yeast cells contain between 2000 and 4000 molecules of RNA polymerase II holoenzyme, it appears that there are at least this number of SWI2/SNF2 and SNF5 molecules per cell.

Example 13

SWI/SNF Proteins Are Components of CTD-Binding SRB Complexes

SRB/SWI/SNF Complex Purification

Whole cell extract was prepared from Red Star Yeast as described in Thompson, C. M. et al., *Cell*, 73:1367–1375 (1993) 1.2 L of the ammonium sulfate pellet was centrifuged for 30 minutes at 5,000 RPM. in an RC3B centrifuge (Sorvall). The pellet was resuspended in 900 ml of Buffer A (20 mM K-Hepes pH 7.61 mM EDTA 1 mM DTT 20% glycerol, and protease inhibitors (Thompson, C. M. et al., *Cell*, 73:1367–1375 (1993)). The suspension was centrifuged again for 30 minutes at 5,000 RPM. in an RC3B centrifuge (Sorvall). The supernatant was mixed with 200 g (dry) of BioRex 70 and stirred for 20 minutes. The suspension was packed into a column with a 5 cm diameter and washed with 1.51 of Buffer A+100 mM KOAc. Bound proteins were eluted with Buffer A+600 mM KOAc. Fractions containing protein were pooled, frozen in liquid nitrogen and stored at −70° C. until use. Eluates from 2 BioRex columns (320 ml, 1.0 g protein) were thawed and pooled. 320 ml of Buffer A+2% Triton X-100 were added and the mixture was centrifuged for 30 minutes at 12,000 RPM. in a GSA rotor (Sorvall). The supernatant was loaded onto a 15 ml CTD affinity column prepared as described in Thompson, C. M. et al., *Cell*, 73:1367–1375 (1993) at a flow rate of 200 ml/hr. The column was washed with 100 ml of Buffer A+300 mM KOAc+1 Triton X-100, 100 ml or Buffer A+300 mM KOAc. Bound proteins were eluted with Buffer A+300 mM KOAc+1 M Urea at a flow rate of 25 ml/hr. Fractions containing protein (3.7 mg) were pooled, frozen in liquid nitrogen, and stored at −70° C. The CTD column was equilibrated with Buffer A+300 mM KOAc+1 Triton X-100 and the flow through was loaded again. The column was washed and eluted as before. Fractions containing protein (1.8 mg) were pooled, frozen in liquid nitrogen, and stored at −70° C. The CTD eluates were pooled, diluted with 1.5 volumes of Buffer A+0.01% NP-40, and centrifuged for 10 minutes at 17,000 RPM. in an SS-34 rotor (Sorvall). The supernatant was loaded onto a Mono S HR 5/5 (Pharmacia) at a flow rate of 0.3 ml/min. The column was washed with 3 ml of Buffer A+120 mM KOAc+0.01% NP-40. Bound proteins were eluted with a 20 ml gradient of Buffer A+0.01% NP-40 from 120 mM to 1000 mM KOAc. Fractions were frozen in liquid nitrogen and stored at −70° C. until use. Fractions containing SRB4 and SRB5 as assayed by Western blotting were pooled and diluted with 2 volumes of Buffer B (20 mM Tris OAc pH 7.6+20% glycerol+1 mM DTT+0.01% NP-40+protease inhibitors). The mixture was centrifuged for 5 minutes in a microcentrifuge. The supernatant was loaded onto a Mono Q HRR 5/5 column (Pharmacia) at a flow rate of 0.3 ml/min. The column was washed with 1 ml of Buffer B+200 mM KOAc. Bound proteins were eluted with a 40 ml gradient of Buffer B from 200 mM to 2000 mM KOAc. The yield of SRB complex was approximately 100 μg. 1 μl of each fraction was analyzed by silver staining. 7.5 μl–10 μl of each fraction were analyzed by Western blotting.

Genetic evidence indicates the SRB regulatory proteins and the RNA polymerase II C-terminal domain (CTD) have related functions in transcription initiation, and that these involve the response to transcriptional regulators. Since the SWI and SNF proteins are also involved in activation of a wide variety of genes, and mutations in SWI and SNF genes can produce phenotypes similar to those observed with mutations in SRB genes, it was investigated whether SWI and SNF proteins are associated with the SRB complex. The SRB protein complex can be released from the holoenzyme when the latter is treated with monoclonal antibodies against the CTD, and this preparation has been called mediator (Kim, Y. J. et al. *Cell*, 77:599–608 (1994)). A mediator complex was prepared according to Kim et al. This mediator complex was confirmed to have the coactivator activity previously described and further, it was demonstrated that the mediator contains all of the SRB proteins (Hengartner, C. J. et al. *Genes and Development*, 9:897–910 (1995)). When this mediator preparation was assayed for the presence of SNF2/SWI2, SNF5 and SWI3 proteins by Western blot, all three SWI/SNF proteins were found.

The SRB complex can also be isolated from crude extracts using a recombinant CTD column (Thompson, C. M. et al. *Cell*, 73:1361–1374 (1993)). An SRB complex was purified extensively by using a recombinant GST-CTD column, followed by chromatography with mono S and mono Q columns. The SRB, SWI, and SNF proteins bind to a GST-CTD column, but not to a control GST column, indicating that they bind specifically to the CTD. Sliver stain and Western blot analysis confirm that a multiprotein complex containing SRB proteins and each of the three SWI/

SNF proteins assayed comigrate from the mono Q column. There are approximately 25 polypeptides in this complex and several correspond in size to previously identified SRB, SWI, and SNF proteins. No signals were obtained when Western Blots containing the SRB/SWI/SNF complex were probed with antibodies against RNA polymerase II, TBP, TFIIB, or the TFB1 subunit of TFIIH. These results indicate that the SRB complex is in fact an SRB/SWI/SNF complex and furthermore, that the SWI and SNF proteins interact with the holoenzyme, at least in part through their association with RNA polymerase II CTD.

Example 14

Nucleosome Disruption Activity in Holoenzyme and SRB/SWI/SNF Complex

The PH MLT or PH MLT(+3) restriction fragments were assembled into rotationally phased mononucleosome particles, purified by glycerol gradient centrifugation, and assayed as described by Imbalzano, A. M. et al., Nature, 370:481–485 (1994). At the nucleosome concentrations and reaction conditions employed in this and previous studies, nucleosomes were determined to be stable on the basis of resistance to micrococcal nuclease, the appearance of a 10 bp repeat pattern upon DNAse I digestion, and exhibition of reduced mobility upon electrophoresis in native polyacrylamide gels. The appearance of free DNA due to nucleosome dissociation was not observed in any of these experiments.

Holoenzyme fractions were the same as those used in Example 11. 0.3 µl of each fraction was assayed in the presence of 4 mM ATP. For the titration of holoenzyme, 0 µl, 0.015 µl, 0.05 µl, 0.15 µl, 0.5 µl of fraction 60 was used respectively with and without 4 mM ATP as indicated. SRB/SWI/SNF-fractions were as those used above. 1.7 µl of each fraction was assayed in the presence of 4 mM ATP. For the titration in 0 µl, 0.07 µl, 0.2 µl, 0.7 µl, and 2.0 µl of fraction 24 was used respectively with and without 4 mM ATP.

Binding of yTBP and yTHIIA to nucleosomes containing the PH MLT(+3) restriction fragment was performed as previously described in Imbalzano, A. N. et al., Nature, 370:481–485 (1994). All reactions contained 4 mM ATP. Following a 30 minute incubation at 30° C. in the presence or absence of holoenzyme, increasing amounts of yTBP in the presence of yTFIIA were added. TBP concentrations were 0, 0.04 micromolar, 0.4 micromolar and 4 micromolar. 1.5 micromolar yTFIIA was also added to all reactions. Reactions were treated with holoenzyme, alone, in the presence of 4 mM ATP or in the presence of 4 mM ATPYS for 30 minutes at 30° C., followed by addition of 4 micromolar yTBP in the presence of 1.5 micromolar yTHIIA.

Recombinant yTBP was purified as described (Hoey, T. et al., Cell, 61:1179–1186 (1990)), except that the heparin peak was further purified on a Mono S HR5/5 FPLC column (Pharmacia). Recombinant YTFIIA was purified as described (Ranish, A. A. et al., Science, 255:1127–1129 (1992)).

Previous evidence that SWI1, SWI2, SWI3, SNFS, SNF6, and SNF11 gene products can be isolated as a large multisubunit complex capable of altering nucleosome structure led us to investigate whether the purified RNA polymerase II holoenzyme and the SRB/SWI/SNF complex were able to alter nucleosome structure. Mononucleosome particles were reconstituted from purified histone octamers and a DNA fragment containing two copies of an artificial phasing sequence (Shrader, T. E., and Crothers, D. M., Proc Natl Acad Sci USA, 86, 7418–22 (1989)). Digestion of the mononucleosomes with DNAse I showed a 10 bp cleavage ladder typical of a rotationally phased nucleosome. Fractions in the last chromatographic step in the purification of the holoenzyme were mixed with mononucleosomes and assayed for the ability to alter nucleosome structure, which can be visualized by changes in the accessibility of the nucleosome to DNAse I cleavage. The results show that nucleosome disruption activity coeluted with the RNA polymerase holoenzyme. The ability of the SRB/SWI/SNF complex to alter nucleosome structure was assayed in a similar experiment using fractions from the last step in the SRB/SWI/SNF purification. The results show that nucleosome disruption activity coeluted with the SRB/SWI/SNF complex. Further analysis of the RNA polymerase II holoenzyme and SRB/SWI/SNF complex showed that the nucleosome disruption activity was ATP dependent. In addition, purified core RNA polymerase II showed no nucleosome alteration capability. These data indicate that the SRB/SWI/SNF complex contributes chromatin remodeling activity to the RNA polymerase II holoenzyme.

Example 15

Purified Holoenzyme And The SRB/SWI/SNF Complex Disrupts Plasmid Chromatin Supercoiling Reduction Assay Plasmid chromatin was assembled and purified as described (Kwon, H. et al., Nature, 370:477–481 (1994)). Reactions, total volume 12.5 Δ1, contained chromatin (2 ng DNA), 1 U Topoisomerase I (Promega), 2.5 µl ~30% Glycerol Gradient Buffer, 7 µl Buffer A minus KCl, 7 mM $MgCl_2$, 50–100 mM KOAc (final), 4 mM ATP where indicated, and 2 µl holoenzyme mono S fractions or 1 µl SRB/SWI/SNF complex mono Q fractions. Reactions were stopped after 90 minutes at 30° C. by addition of 6 µl stop buffer (3% SDS, 100 mM EDTA, 50 mM Tris HCl pH 8.0, 25% Glycerol, 2 mg/ml proteinase K). Reactions were incubated for 90 minutes at 37° and resolved on a 2% agarose gel (50 mM Tris-Phosphate pH 7.3, 1 mM EDTA) for 40 hrs, at 40 V. Gels were dried and exposed to film.

To further characterize the nucleosome-disruption capabilities of the holoenzyme and the SRB/SWI/SNF complex, a supercoiling reduction assay was used. In this assay chromatin is assembled onto a relaxed closed-circular plasmid which is subsequently purified by glycerol gradient centrifugation. Each assembled nucleosome introduces approximately one negative supercoil to the plasmid, which can be resolved by agarose gel electrophoresis after the removal of histones. When no protein is added to the nucleosome-assembled plasmid, it is highly supercoiled. Fractions from the last column of the holoenzyme purification were tested for their ability to disrupt nucleosome structure and thereby reduce supercoiling in the presence of added Topoisomerase I. This activity coelutes with holoenzyme transcription activity, with the SRB and SWI/SNF proteins, and with nucleosome-core disruption activity. The supercoiling-reduction activity was dependent on ATP, as has been shown for the human SWI/SNF complex (Kwon, H. et al. Nature, 370:477–481 (1994)). Repeating the experiment using fractions from the last column of the SRB/SWI/SNF complex shows that this complex also has an ATP-dependent supercoiling-reduction activity.

Example 16

Holoenzyme Facilitates the Binding of TBP to Nucleosomes

Previous work has shown that both yeast and human SWI/SNF complexes can facilitate transcription factor binding to nucleosomal DNA containing the relevant factor binding site The holoenzyme described herein was tested as to whether it could increase the binding of TBP to a mononucleosome containing a TBP binding site. With holoenzyme and ATP present, TBP and TFIIA bound to the mononucleosome at TBP concentrations of $4\times10^{-6}$M, while no TBP/TFIIA binding was observed in the absence of holoenzyme.

This holoenzyme-facilitated TBP binding might be caused by the stabilizing effects of the additional protein-protein and protein-DNA interactions that occur in the presence of RNA polymerase and general transcription factors, by the ATP dependent nucleosome disruption effects of SWI/SNF, or by a combination of both effects. To address this issue, whether facilitated TBP binding was ATP dependent was tested and partial protection of the TATA region on the mononucleosome when ATP is withheld or when ATPγS is used instead of ATP was observed. However, addition of ATP enhanced the TBP binding as indicated by the increased protection from DNAse I cleavage over the TATA box, the extension of the footprint in the 5' direction, and the appearance of a hypersensitive band in the 3' direction. Thus, it appears that the holoenzyme can partially stabilize binding of TBP and TFIIA to a mononucleosome in the absence of ATP. However, the full effect of holoenzyme-facilitated TBP binding requires ATP, presumably because it involves the ATP-dependent nucleosome disruption activity of the SWI/SNF proteins.

Equivalents

Those skilled in the art will recognize, or be able to ascertain, using no more than routine experimentation, many equivalents to the specific embodiments of the invention described herein. Such equivalents are intended to be encompassed by the following claims:

What is claimed is:

1. A purified multisubunit RNA polymerase II holoenzyme wherein the holoenzyme comprises at least eight SRB polypeptides, wherein the polypeptides are selected from the group consisting of SRB2, SRB4, SRB5, SRB6, SRB7, SRB8, SRB9, SRB10, and SRB11, wherein at least one of the SRB polypeptides binds specifically to a polyclonal antibody raised against *S. cerevisiae* SRB2, SRB4, SRB5, SRB6, SRB7, SRB8, SRB9, or human SRB7, general transcription factors b, e and g, RNA polymerase II, and at least one SWI/SNF protein, the holoenzyme having a molecular weight of approximately 1–4 Md.

2. The purified RNA polymerase II holoenzyme of claim 1 wherein the SWI/SNF protein is a component of a complex which comprises SRB proteins.

3. The purified RNA polymerase II holoenzyme of claim 1 wherein the SWI/SNF protein is a member selected from the group consisting of SWI1, SWI2/SFN2, SWI3, SNF5, SNF6 and SNF11.

4. A method of increasing gene transcription in a cell, comprising introducing into the cell DNA encoding a peptide which is expressed in the cell, the peptide being selected from the group consisting of a SRB protein and a SWI/SNF protein, wherein the SRB protein or SWI/SNF protein is capable of functioning as a component of an RNA polymerase II holoenzyme, thereby increasing the formation of an RNA polymerase II holoenzyme in the cell.

5. A method of in vitro transcription of a DNA sequence, comprising the steps of:

a) providing DNA to be transcribed, transcription factor a and TATA-binding protein;

b) admixing the DNA, transcription factor a and TATA binding protein of step a) with purified RNA polymerase II holoenzyme which comprises at least eight SRB polypeptides, wherein the SRB polypeptides are selected from the group consisting of SRB2, SRB4, SRB5, SRB6, SRB7, SRB8, SRB9, SRB10, and SRB11, wherein at least one of the SRB polypeptides binds specifically to a polyclonal antibody raised against *S. cerevisiae* SRB2, SRB4, SRB5, SRB6, SRB7, SRB8, SRB9, or human SRB7, general transcription factors b, e and g, and at least one SWI/SNF protein; and c) maintaining said admixture of step b) under conditions sufficient for transcription of the DNA.

* * * * *

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
      (A) LENGTH: 1949 base pairs
      (B) TYPE: nucleic acid
      (C) STRANDEDNESS: double
      (D) TOPOLOGY: linear (ii) MOLECULE TYPE: DNA (genomic)

(ix) FEATURE:
      (A) NAME/KEY: CDS
      (B) LOCATION: 743..1358

(xi) SEQUENCE DESCRIPTION: SEQ ID NO:1:

```
GGTGACCACT ACAGGAACGC AAACTTAAGC TACATTGTTC ACCATATTAT ACTATATATA      60

TAACCTCGCG CTGAGCTTTA CAGGTGCGTT TGTCCTCGAA GAACGAAAAG CAGCCCGAAA     120

AAAAAATGCA AAACGATAAA AGCTGGCTGG AGAACAATAG CGGGTTGACC GCTAAACGAG     180

CACACACGTG ATGTGTCGTG AACTGTGATC GTGGTAGTAT GATGCTAGTA TGTAGTGATG     240

GCTGCATGGT ACCAGCGGTG ACGTTCGGTA GACTCTACTC TCCTTTGTTC CCCCGGTGTG     300

CCATCTTTTG AGTTTTGCGT GCGTTATCTA CTGGGAGCAA GGGTCTGGCT CGTACGCATA     360

GAGGCTGAGG ACGAACAGTG TGCGTTTGCA GGCGTGGATA TAGAATACAT AGCTATATAG     420

ATGGGTAGTG CGCATGGGAA AGTGCAATTG AGCGAAGGAA GGGGCAGGTG GACTGTAGAT     480

GTCGCCGCGT GATTTTATCG TTGTTTCTCT TCTTGTGTTT TCTTATGCGT TAGTATGCCA     540

GTTTCGCGGT GTGATTCCCA AAGTGAAATT TTACTGGAAG AGCAAATCTT GTAAGTCGGC     600

GCTCGAAAGC ACAGTAGCAA TCCATCATGG GAAAATCAGC GTATGTAAAG CTGGAGCGTC     660

CTTCGTGGCG CATCGGAATT TCTTCAATTG AACTACCTGT TGCTAACAAC AGTTTTTTTT     720

TTCTCTCTTT TATGTATATA GC GTT ATA TTC GTG GAA AGA GCC ACT CCC GCT     772
                        Val Ile Phe Val Glu Arg Ala Thr Pro Ala
                         1               5                  10

ACA CTA ACG GAA CTG AAG GAT GCT CTC TCG AAT AGT ATC CTG TCC GTG     820
Thr Leu Thr Glu Leu Lys Asp Ala Leu Ser Asn Ser Ile Leu Ser Val
          15                  20                  25
```

```
CGA GAC CCT TGG TCG ATA GAC TTT CGG ACG TAC CGG TGC TCT ATC AAG      868
Arg Asp Pro Trp Ser Ile Asp Phe Arg Thr Tyr Arg Cys Ser Ile Lys
            30                  35                  40

AAC CTA CCC GCG GAT GTC TCC AAG CTC ATG TAC TCG ATA ACG TTC CAC      916
Asn Leu Pro Ala Asp Val Ser Lys Leu Met Tyr Ser Ile Thr Phe His
            45                  50                  55

CAC CAT GGC CGG CAG ACC GTG CTA ATC AAG GAC AAC TCA GCG ATG GTG      964
His His Gly Arg Gln Thr Val Leu Ile Lys Asp Asn Ser Ala Met Val
 60                  65                  70

ACG ACT GCC GCA GCG GCG GAT ATC CCT CCG GCG CTG GTG TTC AAT GGC     1012
Thr Thr Ala Ala Ala Ala Asp Ile Pro Pro Ala Leu Val Phe Asn Gly
 75                  80                  85                  90

TCA TCT ACG GGC GTT CCT GAG TCC ATA GAC ACT ATT TTG TCG TCC AAG     1060
Ser Ser Thr Gly Val Pro Glu Ser Ile Asp Thr Ile Leu Ser Ser Lys
                 95                 100                 105

CTG TCC AAC ATC TGG ATG CAG AGG CAG CTC ATC AAG GGT GAT GCC GGT     1108
Leu Ser Asn Ile Trp Met Gln Arg Gln Leu Ile Lys Gly Asp Ala Gly
            110                 115                 120

GAG ACG TTG ATC TTG GAC GGG CTC ACC GTG CGA CTC GTC AAC CTC TTC     1156
Glu Thr Leu Ile Leu Asp Gly Leu Thr Val Arg Leu Val Asn Leu Phe
            125                 130                 135

TCC TCC ACT GGG TTC AAG GGT CTC CTG ATA GAA CTG CAG GCG GAC GAA     1204
Ser Ser Thr Gly Phe Lys Gly Leu Leu Ile Glu Leu Gln Ala Asp Glu
140                 145                 150

GCG GGC GAG TTT GAG ACC AAG ATT GCA GGC ATC GAA GGA CAC CTA GCT     1252
Ala Gly Glu Phe Glu Thr Lys Ile Ala Gly Ile Glu Gly His Leu Ala
155                 160                 165                 170

GAA ATC CGG GCC AAG GAG TAC AAA ACC TCA TCC GAC TCG TTG GGG CCG     1300
Glu Ile Arg Ala Lys Glu Tyr Lys Thr Ser Ser Asp Ser Leu Gly Pro
                175                 180                 185

GAC ACC AGC AAC GAA ATA TGT GAT TTG GCG TAC CAG TAT GTT CGT GCT     1348
Asp Thr Ser Asn Glu Ile Cys Asp Leu Ala Tyr Gln Tyr Val Arg Ala
            190                 195                 200

CTG GAG CTG T GAGTTCTTAC GAATGCTTTT TCTTTTTTTT TTTTTCTGTT           1398
Leu Glu Leu
        205

TGTATATTGC GGTGTATACG TATAGATAGA TAGTCTAAAT AGTAATCTTC AACCTTATGT   1458

ATCTCGGCTC ATGCAGTGAG GAAATCCATG GATAAGCCCG GATTGTAGTC ATCGTCGCTG   1518

TCGCTGTCGC TGTCGCTGGC GTCCTGTGTT TCCTTCTGTA CAGGTTCTTC TGTCGGTTGA   1578

GAGTCCTCTT CAGCGTCTTC CTCCTCCCTT GCATTGTCAA TAAACTTGTT CAGTGTACTC   1638

GTATGCTCAA GTGGGCGGGG TTCCTGGTGT AGCACCTCGT AGCCCTCTGG TAGGTCGGCC   1698

TCTGTCATGG CAACGAATAT CGTGGGTTTC TCGATCACTG TGGTGTTCTT CAACAATTCT   1758

CCGATGCATT TCTCATGTAT AGCCAACTCC ACCAAGTTTT TTGAATCCAT TATATGCGTG   1818

GTGTTGTAAG GGAACGTTTT CGTGTAGAAT TTGAGCCCAC TCTTCTGTAG GATCTGTGTT   1878

CTTTCCTCTT TGGTCTCCGA ACCGTCTTCG CCCTCTATGC AAGAGCTTGT TCCAGCCAAG   1938

CGATAGAATT C                                                       1949

(2) INFORMATION FOR SEQ ID NO:2:

(i) SEQUENCE CHARACTERISTICS:
        (A) LENGTH: 205 amino acids
        (B) TYPE: amino acid
        (D) TOPOLOGY: linear (ii) MOLECULE TYPE: protein (xi) SEQUENCE DESCRIPTION: SEQ ID NO:2:
```

```
Val Ile Phe Val Glu Arg Ala Thr Pro Ala Thr Leu Thr Glu Leu Lys
  1               5                  10                  15

Asp Ala Leu Ser Asn Ser Ile Leu Ser Val Arg Asp Pro Trp Ser Ile
             20                  25                  30

Asp Phe Arg Thr Tyr Arg Cys Ser Ile Lys Asn Leu Pro Ala Asp Val
         35                  40                  45

Ser Lys Leu Met Tyr Ser Ile Thr Phe His His Gly Arg Gln Thr
     50                  55                  60

Val Leu Ile Lys Asp Asn Ser Ala Met Val Thr Thr Ala Ala Ala Ala
 65              70                  75                   80

Asp Ile Pro Pro Ala Leu Val Phe Asn Gly Ser Ser Thr Gly Val Pro
             85                  90                  95

Glu Ser Ile Asp Thr Ile Leu Ser Ser Lys Leu Ser Asn Ile Trp Met
            100                 105                 110

Gln Arg Gln Leu Ile Lys Gly Asp Ala Gly Glu Thr Leu Ile Leu Asp
            115                 120                 125

Gly Leu Thr Val Arg Leu Val Asn Leu Phe Ser Ser Thr Gly Phe Lys
130                 135                 140

Gly Leu Leu Ile Glu Leu Gln Ala Asp Glu Ala Gly Glu Phe Glu Thr
145                 150                 155                 160

Lys Ile Ala Gly Ile Glu Gly His Leu Ala Glu Ile Arg Ala Lys Glu
                165                 170                 175

Tyr Lys Thr Ser Ser Asp Ser Leu Gly Pro Thr Ser Asn Glu Ile
            180                 185                 190

Cys Asp Leu Ala Tyr Gln Tyr Val Arg Ala Leu Glu Leu
            195                 200                 205

(2) INFORMATION FOR SEQ ID NO:3:

(i) SEQUENCE CHARACTERISTICS:
        (A) LENGTH: 2473 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 320..2380

(xi) SEQUENCE DESCRIPTION: SEQ ID NO:3:

GATCTCGACG ATTTGGGATT CTTATAAGGG CGCATAAAAA ATAAATAACT ACCATTCATA    60

ACAGAAATTC ATTCGTATAT ACATAAAGTT CTCATAAACG TATATATATA TATATATATA   120

TACTTATTGA TATCAAAGTG TGTTACTTTC TACATTCATA GACGGGGAAG AAAAGTGAGG   180

AAAAGTTGTT TTCTCTTGTG CACTGCAGCC CTTTGAAAAA GTAGAACTGC AGAAAAAATA   240

ACTGAACGTA AAGCATTATT TACTTTTCAA AGGCAAAAGA GATAGAGCCA AAAAAATTGT   300

AAGCAGCTTA AAAGCCATA ATG ACA ACG GAA GAT CCA GAT TCA AAT CAC TTA   352
                    Met Thr Thr Glu Asp Pro Asp Ser Asn His Leu
                      1               5                  10

AGT TCC GAA ACT GGC ATT AAA TTG GCA TTG GAC CCG AAC TTA ATT ACA   400
Ser Ser Glu Thr Gly Ile Lys Leu Ala Leu Asp Pro Asn Leu Ile Thr
         15                  20                  25

TTG GCA CTA AGT TCT AAT CCA AAC TCT AGC CTT CAT TCA CCA ACG TCT   448
Leu Ala Leu Ser Ser Asn Pro Asn Ser Ser Leu His Ser Pro Thr Ser
        30                   35                  40
```

```
GAT GAA CCC GTA CCT GAA TCT GCA GGA AAA GCA GAT ACT AGT ATT CGA         496
Asp Glu Pro Val Pro Glu Ser Ala Gly Lys Ala Asp Thr Ser Ile Arg
    45                  50                  55

CTA GAA GGT GAT GAG TTA GAG AAT AAA ACT AAG AAA GAC AAT GAT AAG         544
Leu Glu Gly Asp Glu Leu Glu Asn Lys Thr Lys Lys Asp Asn Asp Lys
60                  65                  70                  75

AAC TTA AAA TTT TTG AAG AAT AAA GAT TCT CTA GTC AGT AAT CCA CAC         592
Asn Leu Lys Phe Leu Lys Asn Lys Asp Ser Leu Val Ser Asn Pro His
                80                  85                  90

GAA ATT TAT GGC TCC ATG CCG TTG GAG CAA TTG ATC CCA ATC ATC TTA         640
Glu Ile Tyr Gly Ser Met Pro Leu Glu Gln Leu Ile Pro Ile Ile Leu
                    95                  100                 105

AGA CAG CGT GGT CCA GGC TTT AAA TTC GTT GAT TTA AAT GAA AAA GAA         688
Arg Gln Arg Gly Pro Gly Phe Lys Phe Val Asp Leu Asn Glu Lys Glu
            110                 115                 120

TTG CAA AAT GAG ATT AAG CAG CTT GGT AGT GAT AGT AGT GAC GGT CAT         736
Leu Gln Asn Glu Ile Lys Gln Leu Gly Ser Asp Ser Ser Asp Gly His
        125                 130                 135

AAC AGC GAG AAG AAG GAC ACT GAT GGC GCT GAT GAG AAT GTA CAA ATT         784
Asn Ser Glu Lys Lys Asp Thr Asp Gly Ala Asp Glu Asn Val Gln Ile
140                 145                 150                 155

GGA GAA GAT TTC ATG GAA GTG GAT TAT GAA GAT AAA GAT AAT CCA GTG         832
Gly Glu Asp Phe Met Glu Val Asp Tyr Glu Asp Lys Asp Asn Pro Val
                160                 165                 170

GAT TCA CGA AAT GAA ACA GAC CAC AAA ACG AAT GAA AAT GGC GAG ACC         880
Asp Ser Arg Asn Glu Thr Asp His Lys Thr Asn Glu Asn Gly Glu Thr
            175                 180                 185

GAT GAT AAT ATT GAA ACG GTA ATG ACA CAG GAA CAG TTT GTT AAA AGA         928
Asp Asp Asn Ile Glu Thr Val Met Thr Gln Glu Gln Phe Val Lys Arg
        190                 195                 200

AGG AGG GAT ATG CTA GAG CAT ATA AAT CTG GCC ATG AAC GAA TCG TCT         976
Arg Arg Asp Met Leu Glu His Ile Asn Leu Ala Met Asn Glu Ser Ser
205                 210                 215

TTG GCT TTG GAA TTC GTT TCT TTG CTA CTG TCG AGT GTT AAA GAG TCT        1024
Leu Ala Leu Glu Phe Val Ser Leu Leu Leu Ser Ser Val Lys Glu Ser
220                 225                 230                 235

ACA GGT ATG TCA TCA ATG TCA CCA TTT CTT AGG AAA GTT GTT AAA CCT        1072
Thr Gly Met Ser Ser Met Ser Pro Phe Leu Arg Lys Val Val Lys Pro
                240                 245                 250

TCT AGT TTA AAC AGT GAT AAA ATT CCA TAT GTT GCA CCT ACA AAA AAA        1120
Ser Ser Leu Asn Ser Asp Lys Ile Pro Tyr Val Ala Pro Thr Lys Lys
            255                 260                 265

GAA TAT ATC GAG TTG GAT ATA TTG AAT AAG GGA TGG AAG TTA CAA AGT        1168
Glu Tyr Ile Glu Leu Asp Ile Leu Asn Lys Gly Trp Lys Leu Gln Ser
        270                 275                 280

TTA AAC GAA TCT AAA GAT CTC CTA CGC GCA AGT TTT AAT AAA CTG AGT        1216
Leu Asn Glu Ser Lys Asp Leu Leu Arg Ala Ser Phe Asn Lys Leu Ser
285                 290                 295

TCC ATA TTA CAG AAC GAA CAT GAC TAT TGG AAT AAG ATA ATG CAG AGT        1264
Ser Ile Leu Gln Asn Glu His Asp Tyr Trp Asn Lys Ile Met Gln Ser
300                 305                 310                 315

ATT AGC AAC AAG GAT GTT ATT TTT AAG ATT AGG GAC AGG ACT AGT GGT        1312
Ile Ser Asn Lys Asp Val Ile Phe Lys Ile Arg Asp Arg Thr Ser Gly
                320                 325                 330

CAA AAG CTG TTG GCA ATT AAG TAT GGT TAC GAA GAC TCT GGA TCT ACC        1360
Gln Lys Leu Leu Ala Ile Lys Tyr Gly Tyr Glu Asp Ser Gly Ser Thr
            335                 340                 345

TAT AAG CAT GAC AGA GGT ATT GCT AAT ATA AGG AAT AAT ATA GAA TCA        1408
Tyr Lys His Asp Arg Gly Ile Ala Asn Ile Arg Asn Asn Ile Glu Ser
        350                 355                 360
```

```
CAA AAT TTG GAT TTG ATA CCC CAC AGT AGT TCA GTG TTC AAA GGC ACT    1456
Gln Asn Leu Asp Leu Ile Pro His Ser Ser Ser Val Phe Lys Gly Thr
365                 370                 375

GAT TTC GTA CAT TCA GTA AAG AAA TTC TTA AGG GTT CGT ATC TTC ACA    1504
Asp Phe Val His Ser Val Lys Lys Phe Leu Arg Val Arg Ile Phe Thr
380                 385                 390                 395

AAA ATC GAA TCA GAA GAT GAT TAC ATA TTG AGT GGC GAA AGT GTG ATG    1552
Lys Ile Glu Ser Glu Asp Asp Tyr Ile Leu Ser Gly Glu Ser Val Met
                400                 405                 410

GAT AGG GAT AGT GAA AGT GAA GAA GCT GAA ACG AAA GAT ATC AGA AAG    1600
Asp Arg Asp Ser Glu Ser Glu Glu Ala Glu Thr Lys Asp Ile Arg Lys
                415                 420                 425

CAA ATC CAA CTT TTG AAA AAG ATC ATT TTT GAA AAA GAA CTG ATG TAC    1648
Gln Ile Gln Leu Leu Lys Lys Ile Ile Phe Glu Lys Glu Leu Met Tyr
        430                 435                 440

CAA ATA AAG AAA GAA TGC GCT TTG TTG ATT TCC TAT GGT GTC AGT ATT    1696
Gln Ile Lys Lys Glu Cys Ala Leu Leu Ile Ser Tyr Gly Val Ser Ile
445                 450                 455

GAA AAC GAA AAC AAG GTA ATA ATT GAA CTA CCT AAC GAA AAA TTT GAA    1744
Glu Asn Glu Asn Lys Val Ile Ile Glu Leu Pro Asn Glu Lys Phe Glu
460                 465                 470                 475

ATC GAG TTG TTG TCC CTT GAC GAT GAC TCC ATT GTC AAT CAT GAA CAA    1792
Ile Glu Leu Leu Ser Leu Asp Asp Asp Ser Ile Val Asn His Glu Gln
                480                 485                 490

GAC TTA CCA AAA ATC AAC GAC AAG AGA GCA AAT TTA ATG CTT GTT ATG    1840
Asp Leu Pro Lys Ile Asn Asp Lys Arg Ala Asn Leu Met Leu Val Met
                495                 500                 505

TTG AGA CTA TTA TTA GTC GTT ATA TTC AAG AAA ACA TTA CGA TCG AGA    1888
Leu Arg Leu Leu Leu Val Val Ile Phe Lys Lys Thr Leu Arg Ser Arg
        510                 515                 520

ATA AGC TCA CCC CAC GGA CTG ATC AAT TTG AAT GTT GAC GAT GAT ATC    1936
Ile Ser Ser Pro His Gly Leu Ile Asn Leu Asn Val Asp Asp Asp Ile
525                 530                 535

TTA ATA ATA CGT CCC ATT CTT GGT AAA GTT CGG TTT GCT AAT TAC AAA    1984
Leu Ile Ile Arg Pro Ile Leu Gly Lys Val Arg Phe Ala Asn Tyr Lys
540                 545                 550                 555

CTG TTA CTA AAA AAA ATC ATA AAG GAT TAC GTG CTC GAT ATA GTT CCT    2032
Leu Leu Leu Lys Lys Ile Ile Lys Asp Tyr Val Leu Asp Ile Val Pro
                560                 565                 570

GGC TCA AGT ATA ACA GAA ACG GAA GTT GAG AGA GAA CAA CCT CAA GAA    2080
Gly Ser Ser Ile Thr Glu Thr Glu Val Glu Arg Glu Gln Pro Gln Glu
                575                 580                 585

AAT AAA AAC ATT GAT GAT GAA AAT ATA ACT AAA TTA AAT AAA GAG ATC    2128
Asn Lys Asn Ile Asp Asp Glu Asn Ile Thr Lys Leu Asn Lys Glu Ile
590                 595                 600

CGT GCC TTC GAT AAA CTA TTG AAT ATA CCT AGA CGT GAA CTC AAA ATA    2176
Arg Ala Phe Asp Lys Leu Leu Asn Ile Pro Arg Arg Glu Leu Lys Ile
605                 610                 615

AAT CTA CCA TTA ACT GAG CAC AAA AGC CCT AAT CTA AGT TTA ATG CTC    2224
Asn Leu Pro Leu Thr Glu His Lys Ser Pro Asn Leu Ser Leu Met Leu
620                 625                 630                 635

GAA AGT CCT AAC TAT TGT AAC GCA CTC ATT CAC ATC AAG TTT TCA GCT    2272
Glu Ser Pro Asn Tyr Cys Asn Ala Leu Ile His Ile Lys Phe Ser Ala
                640                 645                 650

GGT ACG GAA GCC AAC GCA GTG TCC TTT GAC ACA ACA TTT TCT GAT TTT    2320
Gly Thr Glu Ala Asn Ala Val Ser Phe Asp Thr Thr Phe Ser Asp Phe
                655                 660                 665

AAA GAA GTA GAG GAC TTC CTA CAT TTT ATT GTC GCT GAG TAC ATC CAG    2368
Lys Glu Val Glu Asp Phe Leu His Phe Ile Val Ala Glu Tyr Ile Gln
```

-continued

```
              670              675              680
CAA AAG AAG GTG TAATATCCTG AGTCACTCCT TAAACCTACA TACATTGCCA       2420
Gln Lys Lys Val
        685

TAGAATGCCA TTTATTACTA TATAAAGTCG CATACGTACA AAAGGACAAG ATC       2473
```

(2) INFORMATION FOR SEQ ID NO:4:

(i) SEQUENCE CHARACTERISTICS:
        (A) LENGTH: 687 amino acids
        (B) TYPE: amino acid
        (D) TOPOLOGY: linear (ii) MOLECULE TYPE: protein (xi) SEQUENCE DESCRIPTION: SEQ ID NO:4:

```
Met Thr Thr Glu Asp Pro Asp Ser Asn His Leu Ser Ser Glu Thr Gly
 1               5                  10                  15

Ile Lys Leu Ala Leu Asp Pro Asn Leu Ile Thr Leu Ala Leu Ser Ser
                20                  25                  30

Asn Pro Asn Ser Ser Leu His Ser Pro Thr Ser Asp Glu Pro Val Pro
            35                  40                  45

Glu Ser Ala Gly Lys Ala Asp Thr Ser Ile Arg Leu Glu Gly Asp Glu
        50                  55                  60

Leu Glu Asn Lys Thr Lys Asp Asn Asp Lys Asn Leu Lys Phe Leu
65                  70                  75                  80

Lys Asn Lys Asp Ser Leu Val Ser Asn Pro His Glu Ile Tyr Gly Ser
                85                  90                  95

Met Pro Leu Glu Gln Leu Ile Pro Ile Ile Leu Arg Gln Arg Gly Pro
            100                 105                 110

Gly Phe Lys Phe Val Asp Leu Asn Glu Lys Glu Leu Gln Asn Glu Ile
        115                 120                 125

Lys Gln Leu Gly Ser Asp Ser Ser Asp Gly His Asn Ser Glu Lys Lys
    130                 135                 140

Asp Thr Asp Gly Ala Asp Glu Asn Val Gln Ile Gly Glu Asp Phe Met
145                 150                 155                 160

Glu Val Asp Tyr Glu Asp Lys Asp Asn Pro Val Asp Ser Arg Asn Glu
                165                 170                 175

Thr Asp His Lys Thr Asn Glu Asn Gly Glu Thr Asp Asp Asn Ile Glu
            180                 185                 190

Thr Val Met Thr Gln Glu Gln Phe Val Lys Arg Arg Arg Asp Met Leu
        195                 200                 205

Glu His Ile Asn Leu Ala Met Asn Glu Ser Ser Leu Ala Leu Glu Phe
    210                 215                 220

Val Ser Leu Leu Leu Ser Ser Val Lys Glu Ser Thr Gly Met Ser Ser
225                 230                 235                 240

Met Ser Pro Phe Leu Arg Lys Val Lys Pro Ser Ser Leu Asn Ser
                245                 250                 255

Asp Lys Ile Pro Tyr Val Ala Pro Thr Lys Lys Glu Tyr Ile Glu Leu
            260                 265                 270

Asp Ile Leu Asn Lys Gly Trp Lys Leu Gln Ser Leu Asn Glu Ser Lys
        275                 280                 285

Asp Leu Leu Arg Ala Ser Phe Asn Lys Leu Ser Ser Ile Leu Gln Asn
    290                 295                 300

Glu His Asp Tyr Trp Asn Lys Ile Met Gln Ser Ile Ser Asn Lys Asp
305                 310                 315                 320
```

```
Val Ile Phe Lys Ile Arg Asp Arg Thr Ser Gly Gln Lys Leu Leu Ala
            325                 330                 335

Ile Lys Tyr Gly Tyr Glu Asp Ser Gly Ser Thr Tyr Lys His Asp Arg
            340                 345                 350

Gly Ile Ala Asn Ile Arg Asn Asn Ile Glu Ser Gln Asn Leu Asp Leu
            355                 360                 365

Ile Pro His Ser Ser Ser Val Phe Lys Gly Thr Asp Phe Val His Ser
            370                 375             380

Val Lys Lys Phe Leu Arg Val Arg Ile Phe Thr Lys Ile Glu Ser Glu
385                 390                 395                 400

Asp Asp Tyr Ile Leu Ser Gly Glu Ser Val Met Asp Arg Asp Ser Glu
            405                 410                 415

Ser Glu Glu Ala Glu Thr Lys Asp Ile Arg Lys Gln Ile Gln Leu Leu
            420                 425                 430

Lys Lys Ile Ile Phe Glu Lys Glu Leu Met Tyr Gln Ile Lys Lys Glu
            435                 440                 445

Cys Ala Leu Leu Ile Ser Tyr Gly Val Ser Ile Glu Asn Gly Asn Lys
            450                 455                 460

Val Ile Ile Glu Leu Pro Asn Glu Lys Phe Glu Ile Glu Leu Leu Ser
465                 470                 475                 480

Leu Asp Asp Asp Ser Ile Val Asn His Glu Gln Asp Leu Pro Lys Ile
            485                 490                 495

Asn Asp Lys Arg Ala Asn Leu Met Leu Val Met Leu Arg Leu Leu Leu
            500                 505                 510

Val Val Ile Phe Lys Lys Thr Leu Arg Ser Arg Ile Ser Ser Pro His
            515                 520                 525

Gly Leu Ile Asn Leu Asn Val Asp Asp Asp Ile Leu Ile Ile Arg Pro
            530                 535                 540

Ile Leu Gly Lys Val Arg Phe Ala Asn Tyr Lys Leu Leu Leu Lys Lys
545                 550                 555                 560

Ile Ile Lys Asp Tyr Val Leu Asp Ile Val Pro Gly Ser Ser Ile Thr
            565                 570                 575

Glu Thr Glu Val Glu Arg Glu Gln Pro Gln Glu Asn Lys Asn Ile Asp
            580                 585                 590

Asp Glu Asn Ile Thr Lys Leu Asn Lys Glu Ile Arg Ala Phe Asp Lys
            595                 600                 605

Leu Leu Asn Ile Pro Arg Arg Glu Leu Lys Ile Asn Leu Pro Leu Thr
            610                 615                 620

Glu His Lys Ser Pro Asn Leu Ser Leu Met Leu Glu Ser Pro Asn Tyr
625                 630                 635                 640

Cys Asn Ala Leu Ile His Ile Lys Phe Ser Ala Gly Thr Glu Ala Asn
            645                 650                 655

Ala Val Ser Phe Asp Thr Thr Phe Ser Asp Phe Lys Glu Val Glu Asp
            660                 665                 670

Phe Leu His Phe Ile Val Ala Glu Tyr Ile Gln Gln Lys Lys Val
            675                 680                 685

(2) INFORMATION FOR SEQ ID NO:5:

(i) SEQUENCE CHARACTERISTICS:
        (A) LENGTH: 1905 base pairs
        (B) TYPE: nucleic acid
        (C) STRANDEDNESS: double
        (D) TOPOLOGY: linear
```

-continued (ii) MOLECULE TYPE: DNA (genomic)

(ix) FEATURE:
    (A) NAME/KEY: CDS
    (B) LOCATION: 433..1353

(xi) SEQUENCE DESCRIPTION: SEQ ID NO:5:

| | |
|---|---|
| GATCTTCAGT ATCCTCGCGG AACGCTACAA CAATGTAAAC GATTAGAACA ACATTGGCCA | 60 |
| TTGCAGCAGC TAAACCTCCA CTAATTAAGG TATTTGGCGT AAATTGCTGA ATAATGAAAA | 120 |
| AAGTGAGTAC GGGCAGTACC ACCATCGCTG CAGTAAACAG CATAAGTTTA TTAATCACCG | 180 |
| CACGAGGAAC ATCTACAGCC ATTATTTGAT TCTTTTGAAG TCTTGGTTAG TTTCTACTAT | 240 |
| TGCTTTCCAG TATTGCGTTC ATTTTAGCTT GCAGGTTAGT AATATATAGT GAGAGCTCTT | 300 |
| TTGCCTTTCT TTTATTTGAA AAAAATAAAA TAACCTAGAA AATTATCAAA TATCGAAGAC | 360 |
| AAACAACCAA ATAAAAAAAA AAGGTAGAAA ATTGAATTTT CCAGCCAAGG TATTCCATAT | 420 |

```
TAAGAAGAAA AG ATG GTT CAG CAA CTA AGC CTT TTT GGA TCT ATT GGT          468
              Met Val Gln Gln Leu Ser Leu Phe Gly Ser Ile Gly
                1               5                  10

GAT GAC GGC TAC GAT TTA CTA ATT TCA ACT TTG ACC ACA ATA TCA GGT        516
Asp Asp Gly Tyr Asp Leu Leu Ile Ser Thr Leu Thr Thr Ile Ser Gly
            15                  20                  25

AAT CCT CCG CTA CTG TAT AAC AGT TTA TGC ACT GTC TGG AAA CCA AAT        564
Asn Pro Pro Leu Leu Tyr Asn Ser Leu Cys Thr Val Trp Lys Pro Asn
        30                  35                  40

CCA TCT TAC GAC GTC GAG AAC GTG AAC TCT AGA AAC CAA TTG GTT GAA        612
Pro Ser Tyr Asp Val Glu Asn Val Asn Ser Arg Asn Gln Leu Val Glu
 45                  50                  55                  60

CCA AAT AGA ATA AAA CTT TCC AAA GAG GTG CCA TTT TCT TAC CTG ATC        660
Pro Asn Arg Ile Lys Leu Ser Lys Glu Val Pro Phe Ser Tyr Leu Ile
                65                  70                  75

GAT GAA ACA ATG ATG GAT AAG CCA TTA AAC TTT AGA ATC TTG AAA TCT        708
Asp Glu Thr Met Met Asp Lys Pro Leu Asn Phe Arg Ile Leu Lys Ser
            80                  85                  90

TTT ACA AAC GAT AAA ATC CCG CTT AAC TAT GCT ATG ACA CGG AAT ATC        756
Phe Thr Asn Asp Lys Ile Pro Leu Asn Tyr Ala Met Thr Arg Asn Ile
        95                  100                 105

TTG CAC AAC ACA GTT CCG CAA GTC ACC AAC TTC AAC AGC ACA AAC GAA        804
Leu His Asn Thr Val Pro Gln Val Thr Asn Phe Asn Ser Thr Asn Glu
    110                 115                 120

GAT CAA AAC AAC AGT AAG CAT ACA GAA GAT ACT GTA AAT GAA AGT CGA        852
Asp Gln Asn Asn Ser Lys His Thr Glu Asp Thr Val Asn Glu Ser Arg
125                 130                 135                 140

AAC AGC GAT GAC ATC ATA GAT GTC GAC ATG GAT GCA AGT CCC GCC CCT        900
Asn Ser Asp Asp Ile Ile Asp Val Asp Met Asp Ala Ser Pro Ala Pro
                145                 150                 155

TCA AAC GAG TCA TGT TCC CCT TGG TCA TTG CAA ATT TCA GAT ATT CCT        948
Ser Asn Glu Ser Cys Ser Pro Trp Ser Leu Gln Ile Ser Asp Ile Pro
            160                 165                 170

GCT GCA GGA AAC AAT AGA AGT GTT TCA ATG CAA ACG ATA GCT GAG ACT        996
Ala Ala Gly Asn Asn Arg Ser Val Ser Met Gln Thr Ile Ala Glu Thr
        175                 180                 185

ATC ATA TTA TCT TCA GCT GGC AAA AAC TCT TCA GTA TCC TCG CTC ATG       1044
Ile Ile Leu Ser Ser Ala Gly Lys Asn Ser Ser Val Ser Ser Leu Met
    190                 195                 200

AAC GGA TTG GGT TAT GTA TTC GAA TTT CAG TAT CTT ACA ATT GGT GTG       1092
Asn Gly Leu Gly Tyr Val Phe Glu Phe Gln Tyr Leu Thr Ile Gly Val
205                 210                 215                 220

AAA TTT TTT ATG AAG CAT GGT TTA ATA CTT GAG TTA CAA AAA ATT TGG       1140
```

```
Lys Phe Phe Met Lys His Gly Leu Ile Leu Glu Leu Gln Lys Ile Trp
                225                 230                 235

CAA ATA GAA GAA GCA GGC AAT TCA CAA ATA ACA AGC GGA GGG TTC CTT     1188
Gln Ile Glu Glu Ala Gly Asn Ser Gln Ile Thr Ser Gly Gly Phe Leu
            240                 245                 250

TTA AAA GCA TAC ATC AAT GTT AGT AGG GGG ACC GAT ATC GAT CGT ATA     1236
Leu Lys Ala Tyr Ile Asn Val Ser Arg Gly Thr Asp Ile Asp Arg Ile
        255                 260                 265

AAC TAT ACA GAG ACT GCC TTG ATG AAC TTA AAA AAG GAA CTA CAA GGC     1284
Asn Tyr Thr Glu Thr Ala Leu Met Asn Leu Lys Lys Glu Leu Gln Gly
    270                 275                 280

TAT ATA GAG TTA AGT GTA CCC GAT AGA CAG TCA ATG GAC TCG AGG GTA     1332
Tyr Ile Glu Leu Ser Val Pro Asp Arg Gln Ser Met Asp Ser Arg Val
285                 290                 295                 300

GCA CAT GGA AAT ATT CTA ATA TAATCATTGG CACCTGGGCA TATTTTACA         1383
Ala His Gly Asn Ile Leu Ile
                305

AAATTCACTC ATATAGTTAT ACAGAACAAC AGTAACCACT TTTAATGTAC AGGTATTTCT   1443

ATATCTACAA ACAAAAATGT GTAGTTATAT ATCTAATGTT GCTATACCGA GGAATTATAA   1503

AGTAATAAAG ATGTTAAATT AAAAGACAAA ATTTTTGAGA GGCTATTGGA AAAGAAGAGA   1563

AAACTATTTC TTGGAATCTA GTTTATTCAG TTTAGCTTTT TGTTTGGCAA TTTGCTTCTT   1623

TTTCTTTTTT AAGTTCTCAG CTTGTTCCTC CTTTTTAGCA TTAGAATACT TCATTTTTTT   1683

GTAAAGTTTC TTTTGTTTGT TACTCATCAT TATCATTTTC AATTTCTTTT CTTCTTCTTC   1743

TTCATCCACC TTTCTCTTTT TGTTCTTTGA CTTATTGACA TCCTTATCAG CTTCTGAAGT   1803

TTCAGAATAT TTGATACCTT GTGCTTCCAA TTCAAGCTCT TTTTGAGCTT GTAGCTCTTC   1863

GTCATCGTCA TCATCTTCTT CTCCAGCAAC AACTTCTTGA TC                     1905

(2) INFORMATION FOR SEQ ID NO:6:

(i) SEQUENCE CHARACTERISTICS:
            (A) LENGTH: 307 amino acids
            (B) TYPE: amino acid
            (D) TOPOLOGY: linear (ii) MOLECULE TYPE: protein (xi) SEQUENCE DESCRIPTION: SEQ ID NO:6:

Met Val Gln Gln Leu Ser Leu Phe Gly Ser Ile Gly Asp Asp Gly Tyr
1               5                   10                  15

Asp Leu Leu Ile Ser Thr Leu Thr Thr Ile Ser Gly Asn Pro Pro Leu
            20                  25                  30

Leu Tyr Asn Ser Leu Cys Thr Val Trp Lys Pro Asn Pro Ser Tyr Asp
        35                  40                  45

Val Glu Asn Val Asn Ser Arg Asn Gln Leu Val Glu Pro Asn Arg Ile
    50                  55                  60

Lys Leu Ser Lys Glu Val Pro Phe Ser Tyr Leu Ile Asp Glu Thr Met
65                  70                  75                  80

Met Asp Lys Pro Leu Asn Phe Arg Ile Leu Lys Ser Phe Thr Asn Asp
            85                  90                  95

Lys Ile Pro Leu Asn Tyr Ala Met Thr Arg Asn Ile Leu His Asn Thr
            100                 105                 110

Val Pro Gln Val Thr Asn Phe Asn Ser Thr Asn Glu Asp Gln Asn Asn
        115                 120                 125

Ser Lys His Thr Glu Asp Thr Val Asn Glu Ser Arg Asn Ser Asp Asp
    130                 135                 140
```

```
Ile Ile Asp Val Asp Met Asp Ala Ser Pro Ala Pro Ser Asn Glu Ser
145                 150                 155                 160

Cys Ser Pro Trp Ser Leu Gln Ile Ser Asp Ile Pro Ala Ala Gly Asn
                165                 170                 175

Asn Arg Ser Val Ser Met Gln Thr Ile Ala Glu Thr Ile Ile Leu Ser
            180                 185                 190

Ser Ala Gly Lys Asn Ser Ser Val Ser Ser Leu Met Asn Gly Leu Gly
        195                 200                 205

Tyr Val Phe Glu Phe Gln Tyr Leu Thr Ile Gly Val Lys Phe Phe Met
    210                 215                 220

Lys His Gly Leu Ile Leu Glu Leu Gln Lys Ile Trp Gln Ile Glu Glu
225                 230                 235                 240

Ala Gly Asn Ser Gln Ile Thr Ser Gly Gly Phe Leu Leu Lys Ala Tyr
                245                 250                 255

Ile Asn Val Ser Arg Gly Thr Asp Ile Asp Arg Ile Asn Tyr Thr Glu
            260                 265                 270

Thr Ala Leu Met Asn Leu Lys Lys Glu Leu Gln Gly Tyr Ile Glu Leu
        275                 280                 285

Ser Val Pro Asp Arg Gln Ser Met Asp Ser Arg Val Ala His Gly Asn
    290                 295                 300

Ile Leu Ile
305

(2) INFORMATION FOR SEQ ID NO:7:

(i) SEQUENCE CHARACTERISTICS:
        (A) LENGTH: 1004 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 286..648

(xi) SEQUENCE DESCRIPTION: SEQ ID NO:7:

GATCGTTGTT GTAGACTCTC TGGAAGAAAG TGCAAGAGGG GCCGGTGGCT TTGGTAGCAC    60

TGGTAACTAA CTTAGTGTAT ATACTTTGGC ACACTTGTAT AATGTATAAT AAAATCAGGA   120

TAAATCCAGT GTGACCCGGA CTGAATTACT GAAACTTTGA AGTGTTAAGG AAATTGTACT   180

GCCATTTAAC GCATTTACCT ATCACTTAGT AGCATGCATA AGCCATGGGC TAATCATAAC   240

AGATTGTGAT GATAGGCATC CTGTACTCCT TTTTTTTACA AGAAA ATG AGC AAC       294
                                                 Met Ser Asn
                                                 1

CAG GCA CTA TAT GAG AAA CTC GAA CAA ACC AGG ACG ATT CTG TCC GTG    342
Gln Ala Leu Tyr Glu Lys Leu Glu Gln Thr Arg Thr Ile Leu Ser Val
    5                   10                  15

AAG CTG GCG GAA TTG ATA AAT ATG ACT ACG ATA GCC GAT AGA AAT GAT    390
Lys Leu Ala Glu Leu Ile Asn Met Thr Thr Ile Ala Asp Arg Asn Asp
 20                  25                  30                  35

GAT GAC GAG GGT TCA TTC GCA CAA GAA AAT TCT GAG CTC GCT GTG GCC    438
Asp Asp Glu Gly Ser Phe Ala Gln Glu Asn Ser Glu Leu Ala Val Ala
            40                  45                  50

ACG ACC AGT GTG ATG ATG GTG AAT AAC CAG ACC ATG CAA TTG ATT AAA    486
Thr Thr Ser Val Met Met Val Asn Asn Gln Thr Met Gln Leu Ile Lys
        55                  60                  65
```

-continued

```
AAT GTT CAA GAC TTG TTG ATC CTG ACC AGA TCG ATA AAA GAG AAA TGG      534
Asn Val Gln Asp Leu Leu Ile Leu Thr Arg Ser Ile Lys Glu Lys Trp
         70                  75                  80

CTA CTG AAC CAA ATT CCT GTA ACG GAA CAC TCA AAA GTG ACT CGT TTT      582
Leu Leu Asn Gln Ile Pro Val Thr Glu His Ser Lys Val Thr Arg Phe
     85                  90                  95

GAC GAG AAG CAG ATA GAG GAA TTA CTG GAT AAC TGT ATA GAA ACG TTC      630
Asp Glu Lys Gln Ile Glu Glu Leu Leu Asp Asn Cys Ile Glu Thr Phe
100                 105                 110                 115

GTG GCG GAA AAA ACT ACG TAAAAAGGCG GTATTTATCT ATTATTTGGC              678
Val Ala Glu Lys Thr Thr
                120

CAAAAAAAAA AAAAAAATAC ATACTACATA TACATATACG CCATAAAAAA TCTCTGCATC    738

TATCTTATTT CCCATTATTT GGACAAATGC TTACGTGCTA ATGTCCTTAC CCTCGAGTCG    798

AATGCCGGGC TCCTAATAGG GTCTGTAATC TTATAAAACG GGTTCATTAG TGTCTTTACG    858

TATAGTTCGT GTACCTCTTG GTAGAATGAC CTCATATTAT TGTCGTCAAT AACTACGCTA    918

CTGTTGGCTG AGTTCCCATG GATCATCACG AACTTCATCC CACTATAGCT AATATAAGCC    978

GTTATTGCTA GTCCATAAAA ATGATC                                        1004
```

(2) INFORMATION FOR SEQ ID NO:8:

(i) SEQUENCE CHARACTERISTICS:
        (A) LENGTH: 121 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ser Asn Gln Ala Leu Tyr Glu Lys Leu Glu Gln Thr Arg Thr Ile
 1               5                  10                  15

Leu Ser Val Lys Leu Ala Glu Leu Ile Asn Met Thr Thr Ile Ala Asp
             20                  25                  30

Arg Asn Asp Asp Glu Gly Ser Phe Ala Gln Glu Asn Ser Glu Leu
         35                  40                  45

Ala Val Ala Thr Thr Ser Val Met Met Val Asn Asn Gln Thr Met Gln
     50                  55                  60

Leu Ile Lys Asn Val Gln Asp Leu Leu Ile Leu Thr Arg Ser Ile Lys
 65                  70                  75                  80

Glu Lys Trp Leu Leu Asn Gln Ile Pro Val Thr Glu His Ser Lys Val
                 85                  90                  95

Thr Arg Phe Asp Glu Lys Gln Ile Glu Glu Leu Leu Asp Asn Cys Ile
            100                 105                 110

Glu Thr Phe Val Ala Glu Lys Thr Thr
            115                 120
```

(2) INFORMATION FOR SEQ ID NO:9:

(i) SEQUENCE CHARACTERISTICS:
        (A) LENGTH: 423 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..420

(xi) SEQUENCE DESCRIPTION: SEQ ID NO:9:

```
ATG ACA GAT AGA TTA ACA CAA TTG CAG ATA TGT TTA GAC CAA ATG ACG         48
Met Thr Asp Arg Leu Thr Gln Leu Gln Ile Cys Leu Asp Gln Met Thr
  1               5                  10                  15

GAG CAA TTC TGT GCT ACT TTA AAC TAC ATA GAT AAG AAC CAT GGT TTT         96
Glu Gln Phe Cys Ala Thr Leu Asn Tyr Ile Asp Lys Asn His Gly Phe
                 20                  25                  30

GAA CGA TTG ACC GTA AAT GAA CCT CAG ATG TCC GAT AAG CAT GCC ACA        144
Glu Arg Leu Thr Val Asn Glu Pro Gln Met Ser Asp Lys His Ala Thr
             35                  40                  45

GTA GTA CCT CCT GAG GAA TTT TCT AAC ACG ATA GAT GAG CTA TCC ACG        192
Val Val Pro Pro Glu Glu Phe Ser Asn Thr Ile Asp Glu Leu Ser Thr
         50                  55                  60

GAC ATT ATA CTT AAA ACA AGA CAG ATA AAC AAG CTT ATT GAC TCG TTA        240
Asp Ile Ile Leu Lys Thr Arg Gln Ile Asn Lys Leu Ile Asp Ser Leu
 65                  70                  75                  80

CCT GGT GTT GAC GTT TCA GCT GAA GAG CAA TTA AGG AAG ATT GAT ATG        288
Pro Gly Val Asp Val Ser Ala Glu Glu Gln Leu Arg Lys Ile Asp Met
                 85                  90                  95

TTG CAG AAA AAG CTA GTT GAA GTG GAA GAC GAA AAA ATT GAG GCC ATC        336
Leu Gln Lys Lys Leu Val Glu Val Glu Asp Glu Lys Ile Glu Ala Ile
                100                 105                 110

AAA AAG AAG GAG AAA CTT TTA AGG CAC GTT GAT TCT TTA ATT GAA GAT        384
Lys Lys Lys Glu Lys Leu Leu Arg His Val Asp Ser Leu Ile Glu Asp
            115                 120                 125

TTT GTA GAT GGC ATT GCA AAC TCA AAA AAG AGC ACA TAA                    423
Phe Val Asp Gly Ile Ala Asn Ser Lys Lys Ser Thr
        130                 135                 140
```

(2) INFORMATION FOR SEQ ID NO:10:

(i) SEQUENCE CHARACTERISTICS:
        (A) LENGTH: 140 amino acids
        (B) TYPE: amino acid
        (D) TOPOLOGY: linear (ii) MOLECULE TYPE: protein (xi) SEQUENCE DESCRIPTION: SEQ ID NO:10:

```
Met Thr Asp Arg Leu Thr Gln Leu Gln Ile Cys Leu Asp Gln Met Thr
  1               5                  10                  15

Glu Gln Phe Cys Ala Thr Leu Asn Tyr Ile Asp Lys Asn His Gly Phe
                 20                  25                  30

Glu Arg Leu Thr Val Asn Glu Pro Gln Met Ser Asp Lys His Ala Thr
             35                  40                  45

Val Val Pro Pro Glu Glu Phe Ser Asn Thr Ile Asp Glu Leu Ser Thr
         50                  55                  60

Asp Ile Ile Leu Lys Thr Arg Gln Ile Asn Lys Leu Ile Asp Ser Leu
 65                  70                  75                  80

Pro Gly Val Asp Val Ser Ala Glu Glu Gln Leu Arg Lys Ile Asp Met
                 85                  90                  95

Leu Gln Lys Lys Leu Val Glu Val Glu Asp Glu Lys Ile Glu Ala Ile
                100                 105                 110

Lys Lys Lys Glu Lys Leu Leu Arg His Val Asp Ser Leu Ile Glu Asp
            115                 120                 125

Phe Val Asp Gly Ile Ala Asn Ser Lys Lys Ser Thr
        130                 135                 140
```

(2) INFORMATION FOR SEQ ID NO:11:

(i) SEQUENCE CHARACTERISTICS:
    (A) LENGTH: 4002 base pairs
    (B) TYPE: nucleic acid
    (C) STRANDEDNESS: double
    (D) TOPOLOGY: linear (ii) MOLECULE TYPE: DNA (genomic)

(ix) FEATURE:
    (A) NAME/KEY: CDS
    (B) LOCATION: 241..3918

(xi) SEQUENCE DESCRIPTION: SEQ ID NO:11:

```
TGATCATAGA AAGGAAACGT GGTTGCATGA ATTGAGATTC GTCTCACACT TCGACTGGTC        60

AAAATTGGCA AGTTTATACC TCACGGCTTG AAAAGAAGGC AAGTCATCGA GCAGTGCTAT       120

TTAAAATTTA TACCATTGAA AAGGGCGATT TGGTTGATAA AGTGCTGCTA TTTTATCGAA       180

TGGAAATCGA ACCAGAAAAA GAAGAGGTCA ATGCTGCTG GGGCAGATGA TGCCATTTCC        240

ATG CAC CTG CTA AAG GAC TGG ACG GAT ACC TTT GTA TAC ATC CTG GAA         288
Met His Leu Leu Lys Asp Trp Thr Asp Thr Phe Val Tyr Ile Leu Glu
  1               5                  10                  15

AAG CTC ATC TTT GAT ATG ACA AAT CAC TAT AAC GAT TCT CAA CAA CTG         336
Lys Leu Ile Phe Asp Met Thr Asn His Tyr Asn Asp Ser Gln Gln Leu
             20                  25                  30

CGT ACG TGG AAG AGG CAG ATT TCT TAT TTT TTA AAA CTT TTG GGG AAT         384
Arg Thr Trp Lys Arg Gln Ile Ser Tyr Phe Leu Lys Leu Leu Gly Asn
         35                  40                  45

TGC TAC TCA CTA AGA TTG ATC AAT AAG GAA ATC TTT CAT CAT TGG CTT         432
Cys Tyr Ser Leu Arg Leu Ile Asn Lys Glu Ile Phe His His Trp Leu
     50                  55                  60

GTA GAG TTT ATA AAT AAG ATG GAA AAC TTC GAA TTT TTG CCA TTA TCT         480
Val Glu Phe Ile Asn Lys Met Glu Asn Phe Glu Phe Leu Pro Leu Ser
 65                  70                  75                  80

TTA CAT ATT TTG ATG ATT TTT TGG AAC GAC ATC TGC CAA ATT GAT ACA         528
Leu His Ile Leu Met Ile Phe Trp Asn Asp Ile Cys Gln Ile Asp Thr
                 85                  90                  95

AAT GCT CCT GTT GCG GCT ACA ATA ACA TCA AGT CAA AAA GAG CCC TTC         576
Asn Ala Pro Val Ala Ala Thr Ile Thr Ser Ser Gln Lys Glu Pro Phe
            100                 105                 110

TTT CTG GTA ACA AAA ATC ACT GAT ATG CTA TTG CAC AAA TAT TAT ATT         624
Phe Leu Val Thr Lys Ile Thr Asp Met Leu Leu His Lys Tyr Tyr Ile
        115                 120                 125

GTT TCC AGC AGC AAA TCA ATG ATA AAT GAC GAG AAC TAC ATC ATC AAT         672
Val Ser Ser Ser Lys Ser Met Ile Asn Asp Glu Asn Tyr Ile Ile Asn
    130                 135                 140

GAT ATA AAG AAA AAC AAC AAG ATA AAG TTG AAT ATT CTC AAA ATA TTA         720
Asp Ile Lys Lys Asn Asn Lys Ile Lys Leu Asn Ile Leu Lys Ile Leu
145                 150                 155                 160

TCC AGT TTA ATT TTG AAA ATT TTT CAA GAA CAA TCT TTA GAG GTG TTT         768
Ser Ser Leu Ile Leu Lys Ile Phe Gln Glu Gln Ser Leu Glu Val Phe
                165                 170                 175

ATA TTT CCC ACA TCT AAC TGG GAA ATT TAC AAG CCC TTA CTT TTT GAA         816
Ile Phe Pro Thr Ser Asn Trp Glu Ile Tyr Lys Pro Leu Leu Phe Glu
            180                 185                 190

ATA GTC TCA AAC GCC GAC ACT AAT CAA AAT TCT GAT ATG AAG AAA AAA         864
Ile Val Ser Asn Ala Asp Thr Asn Gln Asn Ser Asp Met Lys Lys Lys
        195                 200                 205

TTA GAG TTA ATT AGT TAC AGA AAC GAG TCA TTG AAG AAT AAT TCT TCT         912
Leu Glu Leu Ile Ser Tyr Arg Asn Glu Ser Leu Lys Asn Asn Ser Ser
    210                 215                 220
```

```
ATA CGA AAC GTA ATA ATG TCT GCC AGC AAC GCA AAT GAC TTT CAA TTA      960
Ile Arg Asn Val Ile Met Ser Ala Ser Asn Ala Asn Asp Phe Gln Leu
225                 230                 235                 240

ACT ATC GTC ACC TGT AAA CAA TTT CCA AAA CTA TCA TGC ATT CAA TTA     1008
Thr Ile Val Thr Cys Lys Gln Phe Pro Lys Leu Ser Cys Ile Gln Leu
                245                 250                 255

AAT TGT ATA GAT ACT CAG TTC ACC AAG CTA CTG GAC GAT AAC CCT ACA     1056
Asn Cys Ile Asp Thr Gln Phe Thr Lys Leu Leu Asp Asp Asn Pro Thr
                    260                 265                 270

GAA TTC GAT TGG CCC ACT TAC GTT GAC CAA AAT CCC CTT ACA ATG CAT     1104
Glu Phe Asp Trp Pro Thr Tyr Val Asp Gln Asn Pro Leu Thr Met His
                275                 280                 285

AAA ATT ATT CAA TTA ATT CTC TGG TCC ATA CAT CCA TCA AGG CAA TTT     1152
Lys Ile Ile Gln Leu Ile Leu Trp Ser Ile His Pro Ser Arg Gln Phe
290                 295                 300

GAT CAC TAT GAA TCT AAT CAA CTG GTA GCG AAA TTA TTA CTA TTG CGA     1200
Asp His Tyr Glu Ser Asn Gln Leu Val Ala Lys Leu Leu Leu Leu Arg
305                 310                 315                 320

ATA AAT TCA ACA GAT GAG GAT TTG CAC GAA TTC CAG ATA GAA GAT GCC     1248
Ile Asn Ser Thr Asp Glu Asp Leu His Glu Phe Gln Ile Glu Asp Ala
                    325                 330                 335

ATT TGG TCA TTG GTT TTC CAA TTA GCC AAA AAT TTT TCG GCC CAA AAG     1296
Ile Trp Ser Leu Val Phe Gln Leu Ala Lys Asn Phe Ser Ala Gln Lys
                340                 345                 350

AGG GTG GTA TCA TAT ATG ATG CCT TCT TTG TAT CGC CTG CTT AAT ATA     1344
Arg Val Val Ser Tyr Met Met Pro Ser Leu Tyr Arg Leu Leu Asn Ile
            355                 360                 365

CTA ATT ACT TAT GGC ATC ATT AAG GTC CCT ACG TAT ATC AGA AAG CTA     1392
Leu Ile Thr Tyr Gly Ile Ile Lys Val Pro Thr Tyr Ile Arg Lys Leu
370                 375                 380

ATC AGT TCC GGC CTA CTT TAT CTC CAA GAT TCC AAT GAT AAG TTT GTG     1440
Ile Ser Ser Gly Leu Leu Tyr Leu Gln Asp Ser Asn Asp Lys Phe Val
385                 390                 395                 400

CAT GTC CAG CTG TTA ATT AAC TTG AAA ATT TCA CCG TTG ATG AAA AGT     1488
His Val Gln Leu Leu Ile Asn Leu Lys Ile Ser Pro Leu Met Lys Ser
                    405                 410                 415

CAA TAC AAT ATG GTA TTG AGG AAC GTT ATG GAA TAT GAC GTT AAA TTT     1536
Gln Tyr Asn Met Val Leu Arg Asn Val Met Glu Tyr Asp Val Lys Phe
                420                 425                 430

TAT GAA ATT TTT AAT TTC GAC CAA CTC GTG GAA ATC ACA GAA CAA ATC     1584
Tyr Glu Ile Phe Asn Phe Asp Gln Leu Val Glu Ile Thr Glu Gln Ile
            435                 440                 445

AAA ATG CGA ATA CTC TCC AAT GAT ATA ACT AAT TTG CAA CTG TCG AAA     1632
Lys Met Arg Ile Leu Ser Asn Asp Ile Thr Asn Leu Gln Leu Ser Lys
450                 455                 460

ACT CCT CTG AGC ATT AAA ATC ATG GTT GCA GAA TGG TAC TTA TCA CAT     1680
Thr Pro Leu Ser Ile Lys Ile Met Val Ala Glu Trp Tyr Leu Ser His
465                 470                 475                 480

TTA TGT TCC GGT ATT TTA TCT AGT GTT AAC CGC ACA GTG TTG CTA AAA     1728
Leu Cys Ser Gly Ile Leu Ser Ser Val Asn Arg Thr Val Leu Leu Lys
                    485                 490                 495

ATA TTC AAG ATT TTT TGT ATC GAT CTG GAG GTT TTC CAC CAC TTT TTT     1776
Ile Phe Lys Ile Phe Cys Ile Asp Leu Glu Val Phe His His Phe Phe
                500                 505                 510

AAG TGG ATC GAG TTT ATT GTC TAC CAT CAA TTG CTA AGT GAT ATA GAA     1824
Lys Trp Ile Glu Phe Ile Val Tyr His Gln Leu Leu Ser Asp Ile Glu
            515                 520                 525

TCT CTG GAG GCA TTG ATG GAC ATC TTG CTA TGC TAC CAA AAA TTG TTC     1872
Ser Leu Glu Ala Leu Met Asp Ile Leu Leu Cys Tyr Gln Lys Leu Phe
530                 535                 540
```

```
TCA CAA TTC ATT AAT GAC CAT ATT CTT TTT ACG AAG ACG TTC ATA TTC    1920
Ser Gln Phe Ile Asn Asp His Ile Leu Phe Thr Lys Thr Phe Ile Phe
545                 550                 555                 560

ATT TAC AAG AAA GTT TTG AAA GAA AAA GAC GTG CCT GCT TAT AAT GTG    1968
Ile Tyr Lys Lys Val Leu Lys Glu Lys Asp Val Pro Ala Tyr Asn Val
                565                 570                 575

ACT TCA TTT ATG CCA TTC TGG AAA TTT TTT ATG AAA AAC TTC CCT TTT    2016
Thr Ser Phe Met Pro Phe Trp Lys Phe Phe Met Lys Asn Phe Pro Phe
            580                 585                 590

GTT TTA AAG GTG GAT AAC GAT TTA AGG ATT GAG TTA CAA TCT GTT TAC    2064
Val Leu Lys Val Asp Asn Asp Leu Arg Ile Glu Leu Gln Ser Val Tyr
        595                 600                 605

AAT GAT GAG AAA TTG AAA ACT GAG AAG CTG AAG AAT GAT AAA TCA GAA    2112
Asn Asp Glu Lys Leu Lys Thr Glu Lys Leu Lys Asn Asp Lys Ser Glu
    610                 615                 620

GTC TTG AAG GTG TAT TCC ATG ATC AAT AAT TCA AAC CAA GCT GTT GGA    2160
Val Leu Lys Val Tyr Ser Met Ile Asn Asn Ser Asn Gln Ala Val Gly
625                 630                 635                 640

CAG ACT TGG AAT TTT CCC GAG GTG TTT CAA GTA AAC ATC AGG TTT CTA    2208
Gln Thr Trp Asn Phe Pro Glu Val Phe Gln Val Asn Ile Arg Phe Leu
                645                 650                 655

CTA CAC AAC TCC GAG ATC ATT GAT ACA AAT ACA AGC AAA CAG TTC CAG    2256
Leu His Asn Ser Glu Ile Ile Asp Thr Asn Thr Ser Lys Gln Phe Gln
            660                 665                 670

AAA GCA CGA AAC AAT GTC ATG CTT TTG ATT GCC ACT AAC TTG AAG GAG    2304
Lys Ala Arg Asn Asn Val Met Leu Leu Ile Ala Thr Asn Leu Lys Glu
        675                 680                 685

TAC ATT AAA TTT ATG TCC ATT TTC TTG AAA AGG AAA GAC TTT ACT AAC    2352
Tyr Ile Lys Phe Met Ser Ile Phe Leu Lys Arg Lys Asp Phe Thr Asn
    690                 695                 700

AAA AAT TTA ATT CAA TTG ATC TCT CTA AAA CTT CTA ACT TTT GAA GTG    2400
Lys Asn Leu Ile Gln Leu Ile Ser Leu Lys Leu Leu Thr Phe Glu Val
705                 710                 715                 720

ACG CAG AAT GTG TTG GGG CTC GAG TAT ATT ATT CGA TTA TTA CCA ATA    2448
Thr Gln Asn Val Leu Gly Leu Glu Tyr Ile Ile Arg Leu Leu Pro Ile
                725                 730                 735

AAC TTG GAA AAT AAT GAC GGC TCA TAT GGT CTG TTT TTG AAG TAT CAT    2496
Asn Leu Glu Asn Asn Asp Gly Ser Tyr Gly Leu Phe Leu Lys Tyr His
            740                 745                 750

AAA GAA CAA TTC ATA AAG TCA AAT TTT GAG AAA ATT TTA CTT ACA TGT    2544
Lys Glu Gln Phe Ile Lys Ser Asn Phe Glu Lys Ile Leu Leu Thr Cys
        755                 760                 765

TAT GAA TTA GAA AAA AAA TAT CAT GGC AAC GAA TGT GAA ATA AAT TAT    2592
Tyr Glu Leu Glu Lys Lys Tyr His Gly Asn Glu Cys Glu Ile Asn Tyr
    770                 775                 780

TAT GAG ATC CTA TTG AAA ATT TTA ATA ACT TAT GGG TCA TCT CCC AAA    2640
Tyr Glu Ile Leu Leu Lys Ile Leu Ile Thr Tyr Gly Ser Ser Pro Lys
785                 790                 795                 800

TTA CTT GCA ACA TCT ACA AAA ATC ATT ATG TTG TTA TTG AAT GAT AGC    2688
Leu Leu Ala Thr Ser Thr Lys Ile Ile Met Leu Leu Leu Asn Asp Ser
                805                 810                 815

GTG GAA AAC TCA TCT AAT ATT TTG GAG GAT ATT TTG TAC TAC TCA ACT    2736
Val Glu Asn Ser Ser Asn Ile Leu Glu Asp Ile Leu Tyr Tyr Ser Thr
            820                 825                 830

TGT CCG TCG GAA ACC GAT CTT AAC GAT ATT CCA TTG GGT AGT GGA CAA    2784
Cys Pro Ser Glu Thr Asp Leu Asn Asp Ile Pro Leu Gly Ser Gly Gln
        835                 840                 845

CCA GAC AAT GAC ACT GTT GTA ACC AAC GAT GAT AAA AGT GAC GAT GAT    2832
Pro Asp Asn Asp Thr Val Val Thr Asn Asp Asp Lys Ser Asp Asp Asp
```

```
                850                       855                       860
GAT CAC ACA GTC GAC GAA ATT GAT CAT GTA GAA TAT TAC GTT ATG ATG          2880
Asp His Thr Val Asp Glu Ile Asp His Val Glu Tyr Tyr Val Met Met
865                     870                     875                 880

GAC TTT GCC AAT CTT TGG GTT TTC CAA GCG TTT ACC TGT TTC TGC ATC          2928
Asp Phe Ala Asn Leu Trp Val Phe Gln Ala Phe Thr Cys Phe Cys Ile
                    885                     890                 895

AAA AAA ATC ATG GAG AAT AAT GAG CCA GCA ATG GCA ATG GAA GAC TTG          2976
Lys Lys Ile Met Glu Asn Asn Glu Pro Ala Met Ala Met Glu Asp Leu
                900                     905                 910

AAG AAC TTC ATA TTC CAA ATT ATC GAA ATA ACT AAT TCT AAT GAT TTA          3024
Lys Asn Phe Ile Phe Gln Ile Ile Glu Ile Thr Asn Ser Asn Asp Leu
            915                     920                 925

TGT TCA CAA ATA TTT GAC CAA CTG AAG GAT ATG CAG ACC ATT GAG ATG          3072
Cys Ser Gln Ile Phe Asp Gln Leu Lys Asp Met Gln Thr Ile Glu Met
930                     935                     940

ATA ACC CAA ATA GTG GAG AAA GAT TTC TGC ACT TCT TGT TTG CAA AAC          3120
Ile Thr Gln Ile Val Glu Lys Asp Phe Cys Thr Ser Cys Leu Gln Asn
945                     950                     955                 960

AAC AAC CAA AAG ATA GAT GAT AAT TAC ATC GTT GTG GTG ATC GAG ATT          3168
Asn Asn Gln Lys Ile Asp Asp Asn Tyr Ile Val Val Val Ile Glu Ile
                965                     970                 975

ATA ACG TCA TTA TCG ATG AGG TTT CAA AGA GAA ACT TCT GGT ATG ATA          3216
Ile Thr Ser Leu Ser Met Arg Phe Gln Arg Glu Thr Ser Gly Met Ile
            980                     985                 990

GTT ATT TCC ATG GAG AAC TAT CAT TTA CTA ATA AAG ATC ATA AGA CAA          3264
Val Ile Ser Met Glu Asn Tyr His Leu Leu Ile Lys Ile Ile Arg Gln
        995                     1000                    1005

TTA AGT GAA CTG AAC GAA GGA AAT TTA TCT AAG AGA GAA ATC CAA ATA          3312
Leu Ser Glu Leu Asn Glu Gly Asn Leu Ser Lys Arg Glu Ile Gln Ile
    1010                    1015                    1020

GAT GCC GTC TTG AAA ATT TTT AGC TTT CAT CAG GAT TCC ATT TTC CAA          3360
Asp Ala Val Leu Lys Ile Phe Ser Phe His Gln Asp Ser Ile Phe Gln
1025                    1030                    1035                1040

CGC ATC ATC GCT GAT TTA TCA GCT GAT AAA CCC ACA AGT CCA TTC ATT          3408
Arg Ile Ile Ala Asp Leu Ser Ala Asp Lys Pro Thr Ser Pro Phe Ile
                1045                    1050                    1055

GAT AGC ATA TGC AAG CTG TTT GAT AAA ATA TCA TTT AAT TTA AGA TTG          3456
Asp Ser Ile Cys Lys Leu Phe Asp Lys Ile Ser Phe Asn Leu Arg Leu
            1060                    1065                    1070

AAG CTG TTC TTG TAC GAA ATT TTG TCT TCA TTG AAA TCA TTC GCC ATC          3504
Lys Leu Phe Leu Tyr Glu Ile Leu Ser Ser Leu Lys Ser Phe Ala Ile
        1075                    1080                    1085

TAT TCA TCC ACA ATT GAT GCC CCA GCA TTC CAC ACA AGC GGT AAG GTC          3552
Tyr Ser Ser Thr Ile Asp Ala Pro Ala Phe His Thr Ser Gly Lys Val
    1090                    1095                    1100

GAA CTA CCG AAG AAA TTG CTG AAC TTA CCA CCA TTC CAA GTG TCC TCT          3600
Glu Leu Pro Lys Lys Leu Leu Asn Leu Pro Pro Phe Gln Val Ser Ser
1105                    1110                    1115                1120

TTC GTT AAG GAA ACA AAA CTT CAT AGT GGC GAC TAC GGG GAA GAA GAA          3648
Phe Val Lys Glu Thr Lys Leu His Ser Gly Asp Tyr Gly Glu Glu Glu
                1125                    1130                    1135

GAT GCA GAC CAA GAA GAA TCG TTT AGT TTA AAT TTA GGA ATC GGC ATA          3696
Asp Ala Asp Gln Glu Glu Ser Phe Ser Leu Asn Leu Gly Ile Gly Ile
            1140                    1145                    1150

GTT GAA ATA GCG CAC GAA AAC GAA CAG AAA TGG CTC ATT TAT GAC AAG          3744
Val Glu Ile Ala His Glu Asn Glu Gln Lys Trp Leu Ile Tyr Asp Lys
        1155                    1160                    1165

AAA GAT CAT AAA TAT GTC TGC ACA TTT TCC ATG GAG CCG TAC CAC TTC          3792
```

-continued

```
Lys Asp His Lys Tyr Val Cys Thr Phe Ser Met Glu Pro Tyr His Phe
    1170                1175                1180

ATC TCC AAC TAT AAT ACC AAG TAC ACA GAT GAC ATG GCT ACA GGC AGT           3840
Ile Ser Asn Tyr Asn Thr Lys Tyr Thr Asp Asp Met Ala Thr Gly Ser
1185                1190                1195                1200

AAT GAT ACG ACT GCG TTT AAC GAT TCC TGT GTA AAC CTG AGT CTT TTT           3888
Asn Asp Thr Thr Ala Phe Asn Asp Ser Cys Val Asn Leu Ser Leu Phe
                1205                1210                1215

GAT GCT CGG TTT GAG AGG AAA AAT CCA CAT TGATCTCAGA ATATATCCAA             3938
Asp Ala Arg Phe Glu Arg Lys Asn Pro His
                1220                1225

ATGGATAAAT TATAAATTTA CCAATAACAG TAATTATGTG TCAGTTTTAA TACCCAACCA         3998

ATTG                                                                      4002
```

(2) INFORMATION FOR SEQ ID NO:12:

(i) SEQUENCE CHARACTERISTICS:
        (A) LENGTH: 1226 amino acids
        (B) TYPE: amino acid
        (D) TOPOLOGY: linear (ii) MOLECULE TYPE: protein (xi) SEQUENCE DESCRIPTION: SEQ ID NO:12:

```
Met His Leu Leu Lys Asp Trp Thr Asp Thr Phe Val Tyr Ile Leu Glu
 1               5                  10                  15

Lys Leu Ile Phe Asp Met Thr Asn His Tyr Asn Asp Ser Gln Gln Leu
            20                  25                  30

Arg Thr Trp Lys Arg Gln Ile Ser Tyr Phe Leu Lys Leu Leu Gly Asn
        35                  40                  45

Cys Tyr Ser Leu Arg Leu Ile Asn Lys Glu Ile Phe His His Trp Leu
50                  55                  60

Val Glu Phe Ile Asn Lys Met Glu Asn Phe Glu Phe Leu Pro Leu Ser
65                  70                  75                  80

Leu His Ile Leu Met Ile Phe Trp Asn Asp Ile Cys Gln Ile Asp Thr
                85                  90                  95

Asn Ala Pro Val Ala Ala Thr Ile Thr Ser Ser Gln Lys Glu Pro Phe
            100                 105                 110

Phe Leu Val Thr Lys Ile Thr Asp Met Leu Leu His Lys Tyr Tyr Ile
        115                 120                 125

Val Ser Ser Ser Lys Ser Met Ile Asn Asp Glu Asn Tyr Ile Ile Asn
    130                 135                 140

Asp Ile Lys Lys Asn Asn Lys Ile Lys Leu Asn Ile Leu Lys Ile Leu
145                 150                 155                 160

Ser Ser Leu Ile Leu Lys Ile Phe Gln Glu Gln Ser Leu Glu Val Phe
                165                 170                 175

Ile Phe Pro Thr Ser Asn Trp Glu Ile Tyr Lys Pro Leu Leu Phe Glu
            180                 185                 190

Ile Val Ser Asn Ala Asp Thr Asn Gln Asn Ser Asp Met Lys Lys Lys
        195                 200                 205

Leu Glu Leu Ile Ser Tyr Arg Asn Glu Ser Leu Lys Asn Asn Ser Ser
    210                 215                 220

Ile Arg Asn Val Ile Met Ser Ala Ser Asn Ala Asn Asp Phe Gln Leu
225                 230                 235                 240

Thr Ile Val Thr Cys Lys Gln Phe Pro Lys Leu Ser Cys Ile Gln Leu
                245                 250                 255
```

-continued

```
Asn Cys Ile Asp Thr Gln Phe Thr Lys Leu Leu Asp Asp Asn Pro Thr
            260                 265                 270

Glu Phe Asp Trp Pro Thr Tyr Val Asp Gln Asn Pro Leu Thr Met His
            275                 280                 285

Lys Ile Ile Gln Leu Ile Leu Trp Ser Ile His Pro Ser Arg Gln Phe
            290                 295                 300

Asp His Tyr Glu Ser Asn Gln Leu Val Ala Lys Leu Leu Leu Leu Arg
305                 310                 315                 320

Ile Asn Ser Thr Asp Glu Asp Leu His Glu Phe Gln Ile Glu Asp Ala
            325                 330                 335

Ile Trp Ser Leu Val Phe Gln Leu Ala Lys Asn Phe Ser Ala Gln Lys
            340                 345                 350

Arg Val Val Ser Tyr Met Met Pro Ser Leu Tyr Arg Leu Leu Asn Ile
            355                 360                 365

Leu Ile Thr Tyr Gly Ile Ile Lys Val Pro Thr Tyr Ile Arg Lys Leu
            370                 375                 380

Ile Ser Ser Gly Leu Leu Tyr Leu Gln Asp Ser Asn Asp Lys Phe Val
385                 390                 395                 400

His Val Gln Leu Leu Ile Asn Leu Lys Ile Ser Pro Leu Met Lys Ser
            405                 410                 415

Gln Tyr Asn Met Val Leu Arg Asn Val Met Glu Tyr Asp Val Lys Phe
            420                 425                 430

Tyr Glu Ile Phe Asn Phe Asp Gln Leu Val Glu Ile Thr Glu Gln Ile
            435                 440                 445

Lys Met Arg Ile Leu Ser Asn Asp Ile Thr Asn Leu Gln Leu Ser Lys
            450                 455                 460

Thr Pro Leu Ser Ile Lys Ile Met Val Ala Glu Trp Tyr Leu Ser His
465                 470                 475                 480

Leu Cys Ser Gly Ile Leu Ser Ser Val Asn Arg Thr Val Leu Leu Lys
            485                 490                 495

Ile Phe Lys Ile Phe Cys Ile Asp Leu Glu Val Phe His His Phe Phe
            500                 505                 510

Lys Trp Ile Glu Phe Ile Val Tyr His Gln Leu Leu Ser Asp Ile Glu
            515                 520                 525

Ser Leu Glu Ala Leu Met Asp Ile Leu Leu Cys Tyr Gln Lys Leu Phe
            530                 535                 540

Ser Gln Phe Ile Asn Asp His Ile Leu Phe Thr Lys Thr Phe Ile Phe
545                 550                 555                 560

Ile Tyr Lys Lys Val Leu Lys Glu Lys Asp Val Pro Ala Tyr Asn Val
            565                 570                 575

Thr Ser Phe Met Pro Phe Trp Lys Phe Phe Met Lys Asn Phe Pro Phe
            580                 585                 590

Val Leu Lys Val Asp Asn Asp Leu Arg Ile Glu Leu Gln Ser Val Tyr
            595                 600                 605

Asn Asp Glu Lys Leu Lys Thr Glu Lys Leu Lys Asn Asp Lys Ser Glu
            610                 615                 620

Val Leu Lys Val Tyr Ser Met Ile Asn Asn Ser Asn Gln Ala Val Gly
625                 630                 635                 640

Gln Thr Trp Asn Phe Pro Glu Val Phe Gln Val Asn Ile Arg Phe Leu
            645                 650                 655

Leu His Asn Ser Glu Ile Ile Asp Thr Asn Thr Ser Lys Gln Phe Gln
            660                 665                 670

Lys Ala Arg Asn Asn Val Met Leu Leu Ile Ala Thr Asn Leu Lys Glu
```

-continued

```
                675                 680                 685

Tyr Ile Lys Phe Met Ser Ile Phe Leu Lys Arg Lys Asp Phe Thr Asn
            690                 695                 700

Lys Asn Leu Ile Gln Leu Ile Ser Leu Lys Leu Leu Thr Phe Glu Val
705                 710                 715                 720

Thr Gln Asn Val Leu Gly Leu Glu Tyr Ile Ile Arg Leu Leu Pro Ile
                725                 730                 735

Asn Leu Glu Asn Asn Asp Gly Ser Tyr Gly Leu Phe Leu Lys Tyr His
            740                 745                 750

Lys Glu Gln Phe Ile Lys Ser Asn Phe Glu Lys Ile Leu Leu Thr Cys
                755                 760                 765

Tyr Glu Leu Glu Lys Lys Tyr His Gly Asn Glu Cys Glu Ile Asn Tyr
            770                 775                 780

Tyr Glu Ile Leu Leu Lys Ile Leu Ile Thr Tyr Gly Ser Ser Pro Lys
785                 790                 795                 800

Leu Leu Ala Thr Ser Thr Lys Ile Ile Met Leu Leu Leu Asn Asp Ser
                805                 810                 815

Val Glu Asn Ser Ser Asn Ile Leu Glu Asp Ile Leu Tyr Tyr Ser Thr
            820                 825                 830

Cys Pro Ser Glu Thr Asp Leu Asn Asp Ile Pro Leu Gly Ser Gly Gln
                835                 840                 845

Pro Asp Asn Asp Thr Val Val Thr Asn Asp Asp Lys Ser Asp Asp Asp
850                 855                 860

Asp His Thr Val Asp Glu Ile Asp His Val Glu Tyr Tyr Val Met Met
865                 870                 875                 880

Asp Phe Ala Asn Leu Trp Val Phe Gln Ala Phe Thr Cys Phe Cys Ile
            885                 890                 895

Lys Lys Ile Met Glu Asn Asn Glu Pro Ala Met Ala Met Glu Asp Leu
                900                 905                 910

Lys Asn Phe Ile Phe Gln Ile Ile Glu Ile Thr Asn Ser Asn Asp Leu
            915                 920                 925

Cys Ser Gln Ile Phe Asp Gln Leu Lys Asp Met Gln Thr Ile Glu Met
            930                 935                 940

Ile Thr Gln Ile Val Glu Lys Asp Phe Cys Thr Ser Cys Leu Gln Asn
945                 950                 955                 960

Asn Asn Gln Lys Ile Asp Asp Asn Tyr Ile Val Val Ile Glu Ile
                965                 970                 975

Ile Thr Ser Leu Ser Met Arg Phe Gln Arg Glu Thr Ser Gly Met Ile
            980                 985                 990

Val Ile Ser Met Glu Asn Tyr His Leu Leu Ile Lys Ile Ile Arg Gln
            995                 1000                1005

Leu Ser Glu Leu Asn Glu Gly Asn Leu Ser Lys Arg Glu Ile Gln Ile
        1010                1015                1020

Asp Ala Val Leu Lys Ile Phe Ser Phe His Gln Asp Ser Ile Phe Gln
1025                1030                1035                1040

Arg Ile Ile Ala Asp Leu Ser Ala Asp Lys Pro Thr Ser Pro Phe Ile
                1045                1050                1055

Asp Ser Ile Cys Lys Leu Phe Asp Lys Ile Ser Phe Asn Leu Arg Leu
            1060                1065                1070

Lys Leu Phe Leu Tyr Glu Ile Leu Ser Ser Leu Lys Ser Phe Ala Ile
        1075                1080                1085

Tyr Ser Ser Thr Ile Asp Ala Pro Ala Phe His Thr Ser Gly Lys Val
        1090                1095                1100
```

-continued

```
Glu Leu Pro Lys Lys Leu Leu Asn Leu Pro Pro Phe Gln Val Ser Ser
1105                1110                1115                1120

Phe Val Lys Glu Thr Lys Leu His Ser Gly Asp Tyr Gly Glu Glu
                1125                1130                1135

Asp Ala Asp Gln Glu Glu Ser Phe Ser Leu Asn Leu Gly Ile Gly Ile
            1140                1145                1150

Val Glu Ile Ala His Glu Asn Glu Gln Lys Trp Leu Ile Tyr Asp Lys
        1155                1160                1165

Lys Asp His Lys Tyr Val Cys Thr Phe Ser Met Glu Pro Tyr His Phe
    1170                1175                1180

Ile Ser Asn Tyr Asn Thr Lys Tyr Thr Asp Asp Met Ala Thr Gly Ser
1185                1190                1195                1200

Asn Asp Thr Thr Ala Phe Asn Asp Ser Cys Val Asn Leu Ser Leu Phe
                1205                1210                1215

Asp Ala Arg Phe Glu Arg Lys Asn Pro His
            1220                1225
```

(2) INFORMATION FOR SEQ ID NO:13:

(i) SEQUENCE CHARACTERISTICS:
        (A) LENGTH: 4849 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 148..4407

(xi) SEQUENCE DESCRIPTION: SEQ ID NO:13:

```
GATCAAGTAG TGTAGTATTT ATTGTAGTAC ACTCTTACAA CAACCCTTTA AGACGAATGG      60

TGTGAAATCG GAAATTACTT TGTTGAAGTA AGGTGTAACT ATATTTTAAG AACGTTTAAG     120

CTGGATATCA AGATCTGAGG AGGTAGT ATG AGT TCT GAC GCT TCC ACG TAC         171
                              Met Ser Ser Asp Ala Ser Thr Tyr
                                1               5

AGA CTT GAG GAT GTT TTA TCC AGC TTC TAT AGA GTG GAG AAA ATC AAA       219
Arg Leu Glu Asp Val Leu Ser Ser Phe Tyr Arg Val Glu Lys Ile Lys
    10                  15                  20

AAG ATC AAC TAT CAT CAG TAC ATT TCT AAA GCC CAA AAC GAT CAA TGG       267
Lys Ile Asn Tyr His Gln Tyr Ile Ser Lys Ala Gln Asn Asp Gln Trp
 25                  30                  35                  40

TCT ATC CAA ATG GAA TTC ATG CTA CGG AAG CAG GAT CCA AAG ACT CTA       315
Ser Ile Gln Met Glu Phe Met Leu Arg Lys Gln Asp Pro Lys Thr Leu
                45                  50                  55

GTT GCG CTG CTT TCA AGG GAT TTA TGG TGT TTC AGT ATA AAT GAT GAT       363
Val Ala Leu Leu Ser Arg Asp Leu Trp Cys Phe Ser Ile Asn Asp Asp
            60                  65                  70

CCG GTA CCG ACA CCT CCT GCG ATA GAA CAT AAA CCA GTG AGC CCA GAT       411
Pro Val Pro Thr Pro Pro Ala Ile Glu His Lys Pro Val Ser Pro Asp
        75                  80                  85

AAA ATC GGA ACT TTC ACT GCC GAT TAT TCA AAG CCA AAC TTA CCG CCA       459
Lys Ile Gly Thr Phe Thr Ala Asp Tyr Ser Lys Pro Asn Leu Pro Pro
    90                  95                 100

CAC TAT GCT CTT TTT TTA AAA GCT TTA AGA AGG AAA ATT TAC ATT AAT       507
His Tyr Ala Leu Phe Leu Lys Ala Leu Arg Arg Lys Ile Tyr Ile Asn
105                 110                 115                 120

TTG GCA TTA GGT TCA CAC AAT AAG CTA ATA CAA TTT GGG AAT GCC TGC       555
```

```
                                                    -continued

Leu Ala Leu Gly Ser His Asn Lys Leu Ile Gln Phe Gly Asn Ala Cys
            125                 130                 135

ATA TCA TTA AGC GGA GTG CCA AAT TAT CTC GTA CAG CTA GAA CCA CAC      603
Ile Ser Leu Ser Gly Val Pro Asn Tyr Leu Val Gln Leu Glu Pro His
            140                 145                 150

CTT TTT GTA AAC GGA GAT CTC ACA GTG TCG TTA TGT GCC AAG AAC ATG      651
Leu Phe Val Asn Gly Asp Leu Thr Val Ser Leu Cys Ala Lys Asn Met
            155                 160                 165

GGA TTA GTA CCA ATG AAG GAG GAA AAT TTG GAA GAA TCT TTC CTT TCA      699
Gly Leu Val Pro Met Lys Glu Glu Asn Leu Glu Glu Ser Phe Leu Ser
170             175                 180

AAG CAT GCG CTT TAT TTA GCA CCA TCT GGA ATA AGG ATG CAT TTG GCC      747
Lys His Ala Leu Tyr Leu Ala Pro Ser Gly Ile Arg Met His Leu Ala
185             190                 195                 200

CCT GCT TCC AAG CAA GGA TAC TTG ATA ACG CCA CCA AAA CAT ACA GAA      795
Pro Ala Ser Lys Gln Gly Tyr Leu Ile Thr Pro Pro Lys His Thr Glu
                205                 210                 215

CTT CTC TTG ACG ACG TTA AGT GTA TCT CAT GGT ATA AAC TTA CAA AAT      843
Leu Leu Leu Thr Thr Leu Ser Val Ser His Gly Ile Asn Leu Gln Asn
                220                 225                 230

AAA AAA AAT TTG AAA TGG GTT GCT GTT GTT CCT GAC TTA GGA CAT CTC      891
Lys Lys Asn Leu Lys Trp Val Ala Val Val Pro Asp Leu Gly His Leu
                235                 240                 245

AAC GGC CAC ACA CCT ACT ATA GCT TCG TAT TTA ACT CCC TTA CTT GAA      939
Asn Gly His Thr Pro Thr Ile Ala Ser Tyr Leu Thr Pro Leu Leu Glu
250             255                 260

GCA AAG AAG CTA GTA TGG CCG CTG CAT TTA ATC TTC GCC CAA CCA GTA      987
Ala Lys Lys Leu Val Trp Pro Leu His Leu Ile Phe Ala Gln Pro Val
265             270                 275                 280

GCT GAT ATA GAA AAT TCT ACT TCC GGA GAT CCA TCA GAA TTT CAC TGT     1035
Ala Asp Ile Glu Asn Ser Thr Ser Gly Asp Pro Ser Glu Phe His Cys
                285                 290                 295

TTG CAA GAT GCT CTG GAT GCC ATT GAT GAT TTC ATA CAA TTA AAG CAA     1083
Leu Gln Asp Ala Leu Asp Ala Ile Asp Asp Phe Ile Gln Leu Lys Gln
                300                 305                 310

ACA GCT GCC TAT AGG ACT CCA GGA AGT TCC GGC GTA TTG AGC AGT AAT     1131
Thr Ala Ala Tyr Arg Thr Pro Gly Ser Ser Gly Val Leu Ser Ser Asn
                315                 320                 325

ATT GCT GGT ACA AAT CCC TTA AGC TCA GAT GGA GCA TAT ACA GAA CAG     1179
Ile Ala Gly Thr Asn Pro Leu Ser Ser Asp Gly Ala Tyr Thr Glu Gln
            330                 335                 340

TTT CAA CAT TAT AAG AAC AAC TCA ATT AGT TCT CAA CCC GCT TCT TAT     1227
Phe Gln His Tyr Lys Asn Asn Ser Ile Ser Ser Gln Pro Ala Ser Tyr
345             350                 355                 360

CAT TCT GTC CAA GAA ACT AAT AAG ATA TCT CCG AAA GAT TTC TCC CCT     1275
His Ser Val Gln Glu Thr Asn Lys Ile Ser Pro Lys Asp Phe Ser Pro
                365                 370                 375

AAT TTC ACA GGC ATT GAT AAA TTA ATG CTG TCG CCC AGC GAT CAA TTT     1323
Asn Phe Thr Gly Ile Asp Lys Leu Met Leu Ser Pro Ser Asp Gln Phe
            380                 385                 390

GCT CCA GCT TTC TTA AAT ACC CCT AAT AAT AAC ATC AAT GAG AAT GAA     1371
Ala Pro Ala Phe Leu Asn Thr Pro Asn Asn Asn Ile Asn Glu Asn Glu
                395                 400                 405

TTA TTT AAT GAT AGG AAA CAA ACT ACA GTA TCA AAT GAC TTA GAG AAC     1419
Leu Phe Asn Asp Arg Lys Gln Thr Thr Val Ser Asn Asp Leu Glu Asn
            410                 415                 420

AGC CCA CTG AAA ACG GAA CTG GAG GCA AAT GGT AGA TCA CTC GAA AAG     1467
Ser Pro Leu Lys Thr Glu Leu Glu Ala Asn Gly Arg Ser Leu Glu Lys
425             430                 435                 440
```

```
GTA AAT AAT TCC GTG AGC AAG ACA GGA AGC GTA GAC ACA CTT CAT AAT    1515
Val Asn Asn Ser Val Ser Lys Thr Gly Ser Val Asp Thr Leu His Asn
                445                 450                 455

AAA GAG GGA ACA CTG GAA CAA CGA GAA CAG AAC GAA AAT CTG CCA AGT    1563
Lys Glu Gly Thr Leu Glu Gln Arg Glu Gln Asn Glu Asn Leu Pro Ser
                460                 465                 470

GAT AAA AGT GAC TCT ATG GTA GAC AAG GAA TTG TTT GGT GAG GAT GAG    1611
Asp Lys Ser Asp Ser Met Val Asp Lys Glu Leu Phe Gly Glu Asp Glu
                475                 480                 485

GAT GAG GAT TTA TTT GGC GAT AGC AAT AAA TCG AAT TCT ACA AAC GAA    1659
Asp Glu Asp Leu Phe Gly Asp Ser Asn Lys Ser Asn Ser Thr Asn Glu
                490                 495                 500

TCG AAC AAA AGT ATA TCG GAC GAA ATT ACC GAG GAT ATG TTC GAA ATG    1707
Ser Asn Lys Ser Ile Ser Asp Glu Ile Thr Glu Asp Met Phe Glu Met
505                 510                 515                 520

TCT GAT GAA GAA GAA AAT AAT AAC AAT AAA AGC ATT AAT AAA AAT AAC    1755
Ser Asp Glu Glu Glu Asn Asn Asn Asn Lys Ser Ile Asn Lys Asn Asn
                525                 530                 535

AAG GAA ATG CAT ACT GAT CTT GGT AAA GAT ATT CCA TTT TTT CCC TCA    1803
Lys Glu Met His Thr Asp Leu Gly Lys Asp Ile Pro Phe Phe Pro Ser
                540                 545                 550

TCT GAA AAA CCG AAT ATC CGT ACG ATG AGC GGA ACT ACA AAA AGA TTA    1851
Ser Glu Lys Pro Asn Ile Arg Thr Met Ser Gly Thr Thr Lys Arg Leu
                555                 560                 565

AAT GGA AAG AGG AAA TAT TTG GAT ATT CCG ATA GAT GAA ATG ACC TTG    1899
Asn Gly Lys Arg Lys Tyr Leu Asp Ile Pro Ile Asp Glu Met Thr Leu
                570                 575                 580

CCA ACG AGT CCA TTA TAT ATG GAC CCA GGT GCG CCA CTC CCT GTG GAA    1947
Pro Thr Ser Pro Leu Tyr Met Asp Pro Gly Ala Pro Leu Pro Val Glu
585                 590                 595                 600

ACA CCC CGC GAT AGA CGC AAA AGT GTG TTC GCT CCA CTG AAT TTT AAC    1995
Thr Pro Arg Asp Arg Arg Lys Ser Val Phe Ala Pro Leu Asn Phe Asn
                605                 610                 615

CCC ATA ATA GAA AAC AAT GTT GAT AAC AAA TAC AAA TCT GGA GGG AAA    2043
Pro Ile Ile Glu Asn Asn Val Asp Asn Lys Tyr Lys Ser Gly Gly Lys
                620                 625                 630

TTT TCC TTC AGT CCG TTG CAA AAG GAG GAA GCA TTA AAC TTT GAT ATT    2091
Phe Ser Phe Ser Pro Leu Gln Lys Glu Glu Ala Leu Asn Phe Asp Ile
                635                 640                 645

TCT ATG GCG GAT CTT TCT AGC TCT GAA GAG GAA GAG GAT GAA GAA GAG    2139
Ser Met Ala Asp Leu Ser Ser Ser Glu Glu Glu Glu Asp Glu Glu Glu
650                 655                 660

AAC GGT AGC AGC GAT GAG GAT CTA AAG TCA TTG AAC GTA CGC GAC GAC    2187
Asn Gly Ser Ser Asp Glu Asp Leu Lys Ser Leu Asn Val Arg Asp Asp
665                 670                 675                 680

ATG AAA CCT TCT GAT AAC ATC AGT ACT AAT ACT AAT ATT CAT GAG CCT    2235
Met Lys Pro Ser Asp Asn Ile Ser Thr Asn Thr Asn Ile His Glu Pro
                685                 690                 695

CAA TAC ATA AAT TAC TCT TCG ATC CCA AGT CTA CAA GAC TCT ATT ATA    2283
Gln Tyr Ile Asn Tyr Ser Ser Ile Pro Ser Leu Gln Asp Ser Ile Ile
                700                 705                 710

AAG CAA GAA AAT TTC AAT TCA GTA AAC GAT GCT AAT ATC ACT AGC AAT    2331
Lys Gln Glu Asn Phe Asn Ser Val Asn Asp Ala Asn Ile Thr Ser Asn
                715                 720                 725

AAG GAA GGC TTC AAC TCT ATT TGG AAA ATT CCT CAA AAT GAT ATA CCA    2379
Lys Glu Gly Phe Asn Ser Ile Trp Lys Ile Pro Gln Asn Asp Ile Pro
                730                 735                 740

CAG ACC GAG TCA CCA CTG AAG ACC GTT GAT TCA TCT ATT CAA CCC ATA    2427
Gln Thr Glu Ser Pro Leu Lys Thr Val Asp Ser Ser Ile Gln Pro Ile
745                 750                 755                 760
```

```
GAA TCC AAT ATA AAG ATG ACC TTG GAA GAT AAT AAT GTT ACC AGT AAT    2475
Glu Ser Asn Ile Lys Met Thr Leu Glu Asp Asn Asn Val Thr Ser Asn
                765                 770                 775

CCG TCC GAA TTT ACG CCG AAT ATG GTA AAT TCT CAA ATT TCT AAC CTA    2523
Pro Ser Glu Phe Thr Pro Asn Met Val Asn Ser Gln Ile Ser Asn Leu
            780                 785                 790

CCA AAG GAC AAG AGT GGT ATC CCC GAA TTC ACA CCG GCG GAC CCC AAT    2571
Pro Lys Asp Lys Ser Gly Ile Pro Glu Phe Thr Pro Ala Asp Pro Asn
        795                 800                 805

TTA TCT TTT GAA TCA TCA AGT AGT CTA CCG TTT CTA TTG AGA CAC ATG    2619
Leu Ser Phe Glu Ser Ser Ser Ser Leu Pro Phe Leu Leu Arg His Met
    810                 815                 820

CCG CTA GCA TCT ATA CCG GAC ATT TTC ATC ACG CCT ACT CCC GTT GTT    2667
Pro Leu Ala Ser Ile Pro Asp Ile Phe Ile Thr Pro Thr Pro Val Val
825                 830                 835                 840

ACA ATT TCA GAA AAA GAA CAA GAC ATC TTA GAT TTA ATT GCA GAA CAA    2715
Thr Ile Ser Glu Lys Glu Gln Asp Ile Leu Asp Leu Ile Ala Glu Gln
                845                 850                 855

GTC GTC ACT GAT TAT AAT ATC TTA GGA AAC CTC GGT ATT CCA AAG ATC    2763
Val Val Thr Asp Tyr Asn Ile Leu Gly Asn Leu Gly Ile Pro Lys Ile
            860                 865                 870

GCC TAT AGG GGA GTT AAA GAT TGC CAA GAA GGT TTA ATA ACC ACC ACA    2811
Ala Tyr Arg Gly Val Lys Asp Cys Gln Glu Gly Leu Ile Thr Thr Thr
        875                 880                 885

ATG TTA CAG TTA TTT TCC ACT TCG GAT AGA TTA AAT GGC AAT GAT ACG    2859
Met Leu Gln Leu Phe Ser Thr Ser Asp Arg Leu Asn Gly Asn Asp Thr
    890                 895                 900

ATC TCC AAA TTC TAT AAC ATG AAG CAG CCG TAC GTT TTT GTA AAG AAA    2907
Ile Ser Lys Phe Tyr Asn Met Lys Gln Pro Tyr Val Phe Val Lys Lys
905                 910                 915                 920

CAT CAC GAA CTA ATC AAA GTC AAA CAC GAC TCT CAG CCA TTT ATT AAG    2955
His His Glu Leu Ile Lys Val Lys His Asp Ser Gln Pro Phe Ile Lys
                925                 930                 935

TTC CTC AAT TTT CGC CCT CCA AAT GGA ATA AAA AAC TTC AAA TCC TTA    3003
Phe Leu Asn Phe Arg Pro Pro Asn Gly Ile Lys Asn Phe Lys Ser Leu
            940                 945                 950

TTA TTA AGT TCA TCT TTC AAA GAA GAT TGT CTG TCA TTT GCG CCA ACT    3051
Leu Leu Ser Ser Ser Phe Lys Glu Asp Cys Leu Ser Phe Ala Pro Thr
        955                 960                 965

CTA TCT CAA ACA TAT ATT AAT CAA GAG TTA GGG TTT TGT GAG TTG CTT    3099
Leu Ser Gln Thr Tyr Ile Asn Gln Glu Leu Gly Phe Cys Glu Leu Leu
    970                 975                 980

AAA CTA ACT AAT GAA GAC CCG CCC GGA CTG ATG TAC TTG AAG GCA TTT    3147
Lys Leu Thr Asn Glu Asp Pro Pro Gly Leu Met Tyr Leu Lys Ala Phe
985                 990                 995                 1000

GAT AAA AAC AAG TTA CTG TTG TTA GCT GCG CAG ATT GTT TCA TAC TGT    3195
Asp Lys Asn Lys Leu Leu Leu Leu Ala Ala Gln Ile Val Ser Tyr Cys
                1005                1010                1015

TCT AAT AAT AAG AAC TCC ATC AAA AAC GTG CCA CCA ATA TTA ATA ATT    3243
Ser Asn Asn Lys Asn Ser Ile Lys Asn Val Pro Pro Ile Leu Ile Ile
            1020                1025                1030

TTA CCC TTG GAT AAT GCA ACT CTG ACT GAA TTA GTA GAC AAG GCG AAT    3291
Leu Pro Leu Asp Asn Ala Thr Leu Thr Glu Leu Val Asp Lys Ala Asn
        1035                1040                1045

ATT TTT CAG GTG ATC AAG AAC GAA GTT TGT GCC AAG ATG CCT AAC ATT    3339
Ile Phe Gln Val Ile Lys Asn Glu Val Cys Ala Lys Met Pro Asn Ile
    1050                1055                1060

GAA CTA TAT TTG AAA GTT ATT CCT ATG GAT TTC ATT AGA AAC GTA CTG    3387
Glu Leu Tyr Leu Lys Val Ile Pro Met Asp Phe Ile Arg Asn Val Leu
```

```
1065                1070                1075                1080
GTG ACA GTG GAT CAG TAC GTC AAC GTA GCA ATT TCT ATA TAT AAC ATG    3435
Val Thr Val Asp Gln Tyr Val Asn Val Ala Ile Ser Ile Tyr Asn Met
            1085                1090                1095

CTG CCG CCA AAA TCT GTA AAG TTC ACC CAC ATT GCG CAT ACG CTG CCG    3483
Leu Pro Pro Lys Ser Val Lys Phe Thr His Ile Ala His Thr Leu Pro
            1100                1105                1110

GAG AAA GTG AAT TTC AGA ACC ATG CAG CAA CAG CAA ATG CAA CAG CAA    3531
Glu Lys Val Asn Phe Arg Thr Met Gln Gln Gln Gln Met Gln Gln Gln
            1115                1120                1125

CAG CAA CAG CAA CAG CAG CAG AAT AAC AGT ACA GGA TCA TCT TCT        3579
Gln Gln Gln Gln Gln Gln Gln Asn Asn Ser Thr Gly Ser Ser Ser
            1130                1135            1140

ATA ATA TAT TAT GAC TCG TAC ATC CAC CTG GCA TAC TCG CGT AGT GTA    3627
Ile Ile Tyr Tyr Asp Ser Tyr Ile His Leu Ala Tyr Ser Arg Ser Val
1145                1150                1155                1160

GAT AAA GAG TGG GTT TTT GCA GCT CTT TCA GAT AGC TAT GGA CAA GGC    3675
Asp Lys Glu Trp Val Phe Ala Ala Leu Ser Asp Ser Tyr Gly Gln Gly
            1165                1170                1175

AGC ATG ACG AAA ACG TGG TAC GTC GGG AAT TCC AGA GGA AAA TTT GAC    3723
Ser Met Thr Lys Thr Trp Tyr Val Gly Asn Ser Arg Gly Lys Phe Asp
            1180                1185                1190

GAC GCA TGT AAT CAA ATA TGG AAT ATC GCC CTA AAT TTA GCG TCT AAA    3771
Asp Ala Cys Asn Gln Ile Trp Asn Ile Ala Leu Asn Leu Ala Ser Lys
            1195                1200                1205

AAA TTC GGA AAA ATA TGT CTA ATT TTA ACT AGA TTG AAT GGC ATA CTG    3819
Lys Phe Gly Lys Ile Cys Leu Ile Leu Thr Arg Leu Asn Gly Ile Leu
            1210                1215                1220

CCG GAT GAT GAA TTG ATG AAT TGG AGG AGA CTT TCT GGT AGG AAT ATA    3867
Pro Asp Asp Glu Leu Met Asn Trp Arg Arg Leu Ser Gly Arg Asn Ile
1225                1230                1235                1240

CAT CTT GCT GTG GTG TGT GTG GAT GAC AAC TCT AAA ATC TCC TTC ATA    3915
His Leu Ala Val Val Cys Val Asp Asp Asn Ser Lys Ile Ser Phe Ile
            1245                1250                1255

GAT GAG GAC AAA TTG TAC CCT AGT TTC AAG CCG ATC TAC AAA GAC ACT    3963
Asp Glu Asp Lys Leu Tyr Pro Ser Phe Lys Pro Ile Tyr Lys Asp Thr
            1260                1265                1270

AGG TTT GGA GGA CGC ATG GAT ATG ACC AGA TTA TAC GAC TAT GAA ATA    4011
Arg Phe Gly Gly Arg Met Asp Met Thr Arg Leu Tyr Asp Tyr Glu Ile
            1275                1280                1285

AGG GAT ATA GAC CAG GAC ATC CAT GGA ATA GTA TTT CAG CAC CCG TTC    4059
Arg Asp Ile Asp Gln Asp Ile His Gly Ile Val Phe Gln His Pro Phe
            1290                1295                1300

CCA CTG GCA CAC TCA CAG CAT CGC TGT GCT ATT AGG AGT GGT GCT TTG    4107
Pro Leu Ala His Ser Gln His Arg Cys Ala Ile Arg Ser Gly Ala Leu
1305                1310                1315                1320

ATC AAA TTC AAA AAA TGC GAC GGT GAT ACG GTT TGG GAC AAA TTC GCA    4155
Ile Lys Phe Lys Lys Cys Asp Gly Asp Thr Val Trp Asp Lys Phe Ala
            1325                1330                1335

GTC AAC CTT TTA AAC TGT CCA CAT TCT GAT AGT ACA CAA TTG CTG GAA    4203
Val Asn Leu Leu Asn Cys Pro His Ser Asp Ser Thr Gln Leu Leu Glu
            1340                1345                1350

ACC ATC TTA GAA GAG TTT CGC AAC CTG GCT GCT CTA AAC GTG TGG TAC    4251
Thr Ile Leu Glu Glu Phe Arg Asn Leu Ala Ala Leu Asn Val Trp Tyr
            1355                1360                1365

GGT CTC TCT GAT GGC GAA GAT GGC CAT ATT CCA TGG CAT ATC CTA GCC    4299
Gly Leu Ser Asp Gly Glu Asp Gly His Ile Pro Trp His Ile Leu Ala
            1370                1375                1380

GTG AAA AAA ATG ATG AAC ACT CTT GTG CAC ACC AGA GTA AAA ATT GCT    4347
```

```
Val Lys Lys Met Met Asn Thr Leu Val His Thr Arg Val Lys Ile Ala
1385               1390               1395               1400

AAT ACT TCC GCC GCT ACT GTG CAT ACC GCT ACT TCT TCA TCA ATT ATT    4395
Asn Thr Ser Ala Ala Thr Val His Thr Ala Thr Ser Ser Ser Ile Ile
                1405               1410               1415

CTC TCG GAT AAA TAAACTTTTT CCGGCAACGT TTTCCTGCTC ATCTGTAGCC        4447
Leu Ser Asp Lys
            1420

CTATTTACCA GTTTTGGTTT TAGTATTATT CCGGGGTGTA AACCCAGAAG TCTATTTCTC  4507

CAGTCGGATT TATAAAAACA AAACCGGAAG CGGGGCGGTA CGGCATTTTC ACTGGTGATG  4567

CACGCCCAGC GTGTAGTCCG AGACAATTTC CACAGAACGC GAATGAGATT GCGTTTAAGG  4627

CTGTATTTTC AAGGCACACG AAGCGGCCAC GTGGGTCTGC GATGGTGTGT TGATGATGTC  4687

AAGAATGGTA TCATACTCCG TATAAGGTTA TGTAATCGGA AGTCGCGATT CTTTTTCAAT  4747

TTTTTCTTTT TATTTTTTTC CAGTTTTTTC GTCTCTGCGA TGGAAAATTG TTGAAGTTCT  4807

CTTGATTAGC AAGTAGTTCT TACATCGCAG GAATCTTATG TT                    4849

(2) INFORMATION FOR SEQ ID NO:14:

(i) SEQUENCE CHARACTERISTICS:
        (A) LENGTH: 1420 amino acids
        (B) TYPE: amino acid
        (D) TOPOLOGY: linear (ii) MOLECULE TYPE: protein (xi) SEQUENCE DESCRIPTION: SEQ ID NO:14:

Met Ser Ser Asp Ala Ser Thr Tyr Arg Leu Glu Asp Val Leu Ser Ser
1               5                   10                  15

Phe Tyr Arg Val Glu Lys Ile Lys Lys Ile Asn Tyr His Gln Tyr Ile
                20                  25                  30

Ser Lys Ala Gln Asn Asp Gln Trp Ser Ile Gln Met Glu Phe Met Leu
            35                  40                  45

Arg Lys Gln Asp Pro Lys Thr Leu Val Ala Leu Leu Ser Arg Asp Leu
        50                  55                  60

Trp Cys Phe Ser Ile Asn Asp Asp Pro Val Pro Thr Pro Ala Ile
65                  70                  75                  80

Glu His Lys Pro Val Ser Pro Asp Lys Ile Gly Thr Phe Thr Ala Asp
                85                  90                  95

Tyr Ser Lys Pro Asn Leu Pro Pro His Tyr Ala Leu Phe Leu Lys Ala
                100                 105                 110

Leu Arg Arg Lys Ile Tyr Ile Asn Leu Ala Leu Gly Ser His Asn Lys
            115                 120                 125

Leu Ile Gln Phe Gly Asn Ala Cys Ile Ser Leu Ser Gly Val Pro Asn
        130                 135                 140

Tyr Leu Val Gln Leu Glu Pro His Leu Phe Val Asn Gly Asp Leu Thr
145                 150                 155                 160

Val Ser Leu Cys Ala Lys Asn Met Gly Leu Val Pro Met Lys Glu Glu
                165                 170                 175

Asn Leu Glu Glu Ser Phe Leu Ser Lys His Ala Leu Tyr Leu Ala Pro
                180                 185                 190

Ser Gly Ile Arg Met His Leu Ala Pro Ala Ser Lys Gln Gly Tyr Leu
            195                 200                 205

Ile Thr Pro Pro Lys His Thr Glu Leu Leu Leu Thr Thr Leu Ser Val
        210                 215                 220
```

```
Ser His Gly Ile Asn Leu Gln Asn Lys Lys Asn Leu Lys Trp Val Ala
225                 230                 235                 240

Val Val Pro Asp Leu Gly His Leu Asn Gly His Thr Pro Thr Ile Ala
            245                 250                 255

Ser Tyr Leu Thr Pro Leu Leu Glu Ala Lys Lys Leu Val Trp Pro Leu
            260                 265                 270

His Leu Ile Phe Ala Gln Pro Val Ala Asp Ile Glu Asn Ser Thr Ser
            275                 280                 285

Gly Asp Pro Ser Glu Phe His Cys Leu Gln Asp Ala Leu Asp Ala Ile
        290                 295                 300

Asp Asp Phe Ile Gln Leu Lys Gln Thr Ala Ala Tyr Arg Thr Pro Gly
305                 310                 315                 320

Ser Ser Gly Val Leu Ser Ser Asn Ile Ala Gly Thr Asn Pro Leu Ser
                325                 330                 335

Ser Asp Gly Ala Tyr Thr Glu Gln Phe Gln His Tyr Lys Asn Asn Ser
            340                 345                 350

Ile Ser Ser Gln Pro Ala Ser Tyr His Ser Val Gln Glu Thr Asn Lys
        355                 360                 365

Ile Ser Pro Lys Asp Phe Ser Pro Asn Phe Thr Gly Ile Asp Lys Leu
    370                 375                 380

Met Leu Ser Pro Ser Asp Gln Phe Ala Pro Ala Phe Leu Asn Thr Pro
385                 390                 395                 400

Asn Asn Asn Ile Asn Glu Asn Glu Leu Phe Asn Asp Arg Lys Gln Thr
                405                 410                 415

Thr Val Ser Asn Asp Leu Glu Asn Ser Pro Leu Lys Thr Glu Leu Glu
            420                 425                 430

Ala Asn Gly Arg Ser Leu Glu Lys Val Asn Asn Ser Val Ser Lys Thr
        435                 440                 445

Gly Ser Val Asp Thr Leu His Asn Lys Glu Gly Thr Leu Glu Gln Arg
    450                 455                 460

Glu Gln Asn Glu Asn Leu Pro Ser Asp Lys Ser Asp Ser Met Val Asp
465                 470                 475                 480

Lys Glu Leu Phe Gly Glu Asp Glu Asp Leu Phe Gly Asp Ser
                485                 490                 495

Asn Lys Ser Asn Ser Thr Asn Glu Ser Asn Lys Ser Ile Ser Asp Glu
        500                 505                 510

Ile Thr Glu Asp Met Phe Glu Met Ser Asp Glu Glu Asn Asn Asn
    515                 520                 525

Asn Lys Ser Ile Asn Lys Asn Lys Glu Met His Thr Asp Leu Gly
    530                 535                 540

Lys Asp Ile Pro Phe Phe Pro Ser Ser Glu Lys Pro Asn Ile Arg Thr
545                 550                 555                 560

Met Ser Gly Thr Thr Lys Arg Leu Asn Gly Lys Arg Lys Tyr Leu Asp
                565                 570                 575

Ile Pro Ile Asp Glu Met Thr Leu Pro Thr Ser Pro Leu Tyr Met Asp
            580                 585                 590

Pro Gly Ala Pro Leu Pro Val Glu Thr Pro Arg Asp Arg Arg Lys Ser
        595                 600                 605

Val Phe Ala Pro Leu Asn Phe Asn Pro Ile Ile Glu Asn Asn Val Asp
    610                 615                 620

Asn Lys Tyr Lys Ser Gly Gly Lys Phe Ser Phe Ser Pro Leu Gln Lys
625                 630                 635                 640

Glu Glu Ala Leu Asn Phe Asp Ile Ser Met Ala Asp Leu Ser Ser Ser
```

-continued

```
                    645                 650                 655
Glu Glu Glu Glu Asp Glu Glu Asn Gly Ser Ser Asp Glu Asp Leu
                660                 665                 670
Lys Ser Leu Asn Val Arg Asp Met Lys Pro Ser Asp Asn Ile Ser
            675                 680                 685
Thr Asn Thr Asn Ile His Glu Pro Gln Tyr Ile Asn Tyr Ser Ser Ile
        690                 695                 700
Pro Ser Leu Gln Asp Ser Ile Ile Lys Gln Glu Asn Phe Asn Ser Val
705                 710                 715                 720
Asn Asp Ala Asn Ile Thr Ser Asn Lys Glu Gly Phe Asn Ser Ile Trp
                725                 730                 735
Lys Ile Pro Gln Asn Asp Ile Pro Gln Thr Glu Ser Pro Leu Lys Thr
                740                 745                 750
Val Asp Ser Ser Ile Gln Pro Ile Glu Ser Asn Ile Lys Met Thr Leu
            755                 760                 765
Glu Asp Asn Asn Val Thr Ser Asn Pro Ser Glu Phe Thr Pro Asn Met
770                 775                 780
Val Asn Ser Gln Ile Ser Asn Leu Pro Lys Asp Lys Ser Gly Ile Pro
785                 790                 795                 800
Glu Phe Thr Pro Ala Asp Pro Asn Leu Ser Phe Glu Ser Ser Ser Ser
                805                 810                 815
Leu Pro Phe Leu Leu Arg His Met Pro Leu Ala Ser Ile Pro Asp Ile
                820                 825                 830
Phe Ile Thr Pro Thr Pro Val Val Thr Ile Ser Glu Lys Glu Gln Asp
                835                 840                 845
Ile Leu Asp Leu Ile Ala Glu Gln Val Val Thr Asp Tyr Asn Ile Leu
    850                 855                 860
Gly Asn Leu Gly Ile Pro Lys Ile Ala Tyr Arg Gly Val Lys Asp Cys
865                 870                 875                 880
Gln Glu Gly Leu Ile Thr Thr Met Leu Gln Leu Phe Ser Thr Ser
                885                 890                 895
Asp Arg Leu Asn Gly Asn Asp Thr Ile Ser Lys Phe Tyr Asn Met Lys
                900                 905                 910
Gln Pro Tyr Val Phe Val Lys Lys His His Glu Leu Ile Lys Val Lys
            915                 920                 925
His Asp Ser Gln Pro Phe Ile Lys Phe Leu Asn Phe Arg Pro Pro Asn
    930                 935                 940
Gly Ile Lys Asn Phe Lys Ser Leu Leu Leu Ser Ser Phe Lys Glu
945                 950                 955                 960
Asp Cys Leu Ser Phe Ala Pro Thr Leu Ser Gln Thr Tyr Ile Asn Gln
                965                 970                 975
Glu Leu Gly Phe Cys Glu Leu Leu Lys Leu Thr Asn Glu Asp Pro Pro
            980                 985                 990
Gly Leu Met Tyr Leu Lys Ala Phe Asp Lys Asn Lys Leu Leu Leu Leu
            995                 1000                1005
Ala Ala Gln Ile Val Ser Tyr Cys Ser Asn Asn Lys Asn Ser Ile Lys
        1010                1015                1020
Asn Val Pro Pro Ile Leu Ile Ile Leu Pro Leu Asp Asn Ala Thr Leu
1025                1030                1035                1040
Thr Glu Leu Val Asp Lys Ala Asn Ile Phe Gln Val Ile Lys Asn Glu
                1045                1050                1055
Val Cys Ala Lys Met Pro Asn Ile Glu Leu Tyr Leu Lys Val Ile Pro
                1060                1065                1070
```

```
Met Asp Phe Ile Arg Asn Val Leu Val Thr Val Asp Gln Tyr Val Asn
            1075                1080                1085
Val Ala Ile Ser Ile Tyr Asn Met Leu Pro Pro Lys Ser Val Lys Phe
    1090                1095                1100
Thr His Ile Ala His Thr Leu Pro Glu Lys Val Asn Phe Arg Thr Met
1105                1110                1115                1120
Gln Gln Gln Gln Met Gln Gln Gln Gln Gln Gln Gln Gln Gln Gln Gln
                1125                1130                1135
Asn Asn Ser Thr Gly Ser Ser Ile Ile Tyr Tyr Asp Ser Tyr Ile
            1140                1145                1150
His Leu Ala Tyr Ser Arg Ser Val Asp Lys Glu Trp Val Phe Ala Ala
            1155                1160                1165
Leu Ser Asp Ser Tyr Gly Gln Gly Ser Met Thr Lys Thr Trp Tyr Val
    1170                1175                1180
Gly Asn Ser Arg Gly Lys Phe Asp Asp Ala Cys Asn Gln Ile Trp Asn
1185                1190                1195                1200
Ile Ala Leu Asn Leu Ala Ser Lys Lys Phe Gly Lys Ile Cys Leu Ile
            1205                1210                1215
Leu Thr Arg Leu Asn Gly Ile Leu Pro Asp Asp Glu Leu Met Asn Trp
            1220                1225                1230
Arg Arg Leu Ser Gly Arg Asn Ile His Leu Ala Val Val Cys Val Asp
            1235                1240                1245
Asp Asn Ser Lys Ile Ser Phe Ile Asp Glu Asp Lys Leu Tyr Pro Ser
            1250                1255                1260
Phe Lys Pro Ile Tyr Lys Asp Thr Arg Phe Gly Gly Arg Met Asp Met
1265                1270                1275                1280
Thr Arg Leu Tyr Asp Tyr Glu Ile Arg Asp Ile Asp Gln Asp Ile His
            1285                1290                1295
Gly Ile Val Phe Gln His Pro Phe Pro Leu Ala His Ser Gln His Arg
            1300                1305                1310
Cys Ala Ile Arg Ser Gly Ala Leu Ile Lys Phe Lys Lys Cys Asp Gly
            1315                1320                1325
Asp Thr Val Trp Asp Lys Phe Ala Val Asn Leu Leu Asn Cys Pro His
            1330                1335                1340
Ser Asp Ser Thr Gln Leu Leu Glu Thr Ile Leu Glu Glu Phe Arg Asn
1345                1350                1355                1360
Leu Ala Ala Leu Asn Val Trp Tyr Gly Leu Ser Asp Gly Glu Asp Gly
            1365                1370                1375
His Ile Pro Trp His Ile Leu Ala Val Lys Lys Met Met Asn Thr Leu
            1380                1385                1390
Val His Thr Arg Val Lys Ile Ala Asn Thr Ser Ala Ala Thr Val His
            1395                1400                1405
Thr Ala Thr Ser Ser Ser Ile Ile Leu Ser Asp Lys
            1410                1415                1420

(2) INFORMATION FOR SEQ ID NO:15:

(i) SEQUENCE CHARACTERISTICS:
        (A) LENGTH: 2434 base pairs
        (B) TYPE: nucleic acid
        (C) STRANDEDNESS: double
        (D) TOPOLOGY: linear (ii) MOLECULE TYPE: DNA (genomic)

(ix) FEATURE:
```

(A) NAME/KEY: CDS
        (B) LOCATION: 421..2043

(xi) SEQUENCE DESCRIPTION: SEQ ID NO:15:

```
AGACGGATTA TTGTTTTCAG TTGAAGTTGC GCACTCGGCA TATGATTTAT AGATTCCCAA      60

TATATTGTAC TTCGTTATAT ATGTGTTACG AATATTTTTG ATTTCGTTTT AGAGAGTTTT     120

GATTAGAGGA AATTATAGCT TTTTTTAACA GTGAAATAAA TATCATACAT CAAAAGTCTT     180

CAAGAATTAC GTGGTGTGGC TTAAGTTGCG TTTCATTTTC CCGCTTCAAT ACTTGAAAGT     240

TATCCCACAA TCACTGCTGA CAAAAAGGAT ACAAGAAAGG TTTATAGGAA AGAAAAAAGG     300

CGGAAGGGTA TACTGAAGTT AGTAATTTTG CTTCCCAATT GAATTAAGGC CGCCTAGTTT     360

TGACGGGAGG AGAGAGAAAT GTATAATGGC AAGGATAGAG CACAAAACTC CTATCAGCCA     420
```

```
ATG TAC CAA AGG CCT ATG CAG GTA CAA GGA CAA CAG CAA GCT CAA TCG      468
Met Tyr Gln Arg Pro Met Gln Val Gln Gly Gln Gln Gln Ala Gln Ser
 1               5                  10                  15

TTC GTT GGA AAG AAA AAC ACA ATC GGA AGT GTG CAT GGA AAA GCC CCG      516
Phe Val Gly Lys Lys Asn Thr Ile Gly Ser Val His Gly Lys Ala Pro
             20                  25                  30

ATG CTA ATG GCC AAT AAT GAT GTT TTT ACT ATT GGA CCT TAT AGG GCA      564
Met Leu Met Ala Asn Asn Asp Val Phe Thr Ile Gly Pro Tyr Arg Ala
         35                  40                  45

AGA AAA GAT AGA ATG CGG GTA TCT GTC TTA GAA AAG TAC GAA GTT ATT      612
Arg Lys Asp Arg Met Arg Val Ser Val Leu Glu Lys Tyr Glu Val Ile
     50                  55                  60

GGC TAC ATT GCT GCG GGC ACA TAT GGT AAA GTT TAC AAA GCG AAA AGA      660
Gly Tyr Ile Ala Ala Gly Thr Tyr Gly Lys Val Tyr Lys Ala Lys Arg
 65                  70                  75                  80

CAA ATC AAC TCC GGT ACC AAT TCC GCT AAT GGT TCT AGT CTG AAT GGT      708
Gln Ile Asn Ser Gly Thr Asn Ser Ala Asn Gly Ser Ser Leu Asn Gly
                 85                  90                  95

ACC AAT GCG AAA ATT CCG CAG TTT GAC AGC ACG CAA CCA AAA TCA AGC      756
Thr Asn Ala Lys Ile Pro Gln Phe Asp Ser Thr Gln Pro Lys Ser Ser
            100                 105                 110

TCT TCA ATG GAC ATG CAG GCA AAT ACA AAC GCA TTA AGA AGA AAC TTG      804
Ser Ser Met Asp Met Gln Ala Asn Thr Asn Ala Leu Arg Arg Asn Leu
        115                 120                 125

TTA AAG GAT GAA GGA GTG ACC CCC GGA AGA ATA CGA ACT ACG AGG GAA      852
Leu Lys Asp Glu Gly Val Thr Pro Gly Arg Ile Arg Thr Thr Arg Glu
    130                 135                 140

GAT GTA TCC CCG CAC TAT AAT TCC CAA AAA CAA ACC CTC ATT AAA AAA      900
Asp Val Ser Pro His Tyr Asn Ser Gln Lys Gln Thr Leu Ile Lys Lys
145                 150                 155                 160

CCG CTG ACG GTA TTT TAT GCC ATT AAA AAG TTC AAG ACA GAG AAG GAT      948
Pro Leu Thr Val Phe Tyr Ala Ile Lys Lys Phe Lys Thr Glu Lys Asp
                165                 170                 175

GGC GTC GAA CAA TTG CAT TAT ACG GGA ATA TCT CAG AGT GCC TGT AGA      996
Gly Val Glu Gln Leu His Tyr Thr Gly Ile Ser Gln Ser Ala Cys Arg
            180                 185                 190

GAA ATG GCA TTA TGT CGA GAA TTG CAC AAC AAG CAT TTA ACC ACA TTA     1044
Glu Met Ala Leu Cys Arg Glu Leu His Asn Lys His Leu Thr Thr Leu
        195                 200                 205

GTG GAA ATT TTT TTG GAA AGG AAA TGT GTC CAT ATG GTA TAC GAA TAT     1092
Val Glu Ile Phe Leu Glu Arg Lys Cys Val His Met Val Tyr Glu Tyr
    210                 215                 220

GCG GAG CAT GAT CTG CTA CAA ATT ATC CAC TTC CAT TCC CAT CCC GAA     1140
Ala Glu His Asp Leu Leu Gln Ile Ile His Phe His Ser His Pro Glu
225                 230                 235                 240
```

```
AAA AGG ATG ATA CCA CCA AGA ATG GTT CGG TCT ATT ATG TGG CAG CTT      1188
Lys Arg Met Ile Pro Pro Arg Met Val Arg Ser Ile Met Trp Gln Leu
            245                 250                 255

TTA GAC GGC GTA TCG TAT CTT CAT CAA AAT TGG GTG CTT CAT CGA GAT      1236
Leu Asp Gly Val Ser Tyr Leu His Gln Asn Trp Val Leu His Arg Asp
            260                 265                 270

TTG AAA CCC GCA AAT ATA ATG GTG ACC ATA GAT GGA TGT GTT AAA ATT      1284
Leu Lys Pro Ala Asn Ile Met Val Thr Ile Asp Gly Cys Val Lys Ile
            275                 280                 285

GGT GAT TTA GGT TTG GCC AGA AAA TTT CAT AAT ATG CTG CAA ACC CTC      1332
Gly Asp Leu Gly Leu Ala Arg Lys Phe His Asn Met Leu Gln Thr Leu
            290                 295                 300

TAT ACT GGG GAT AAA GTG GTT GTC ACT ATA TGG TAC CGT GCA CCT GAG      1380
Tyr Thr Gly Asp Lys Val Val Val Thr Ile Trp Tyr Arg Ala Pro Glu
305             310                 315                 320

TTG CTA TTG GGA GCA CGG CAC TAT ACC CCT GCG GTT GAT TTA TGG TCC      1428
Leu Leu Leu Gly Ala Arg His Tyr Thr Pro Ala Val Asp Leu Trp Ser
                325                 330                 335

GTT GGC TGC ATT TTT GCA GAA CTG ATA GGA TTA CAG CCC ATA TTT AAA      1476
Val Gly Cys Ile Phe Ala Glu Leu Ile Gly Leu Gln Pro Ile Phe Lys
            340                 345                 350

GGT GAA GAA GCT AAA CTA GAC TCT AAA AAG ACT GTT CCA TTT CAA GTG      1524
Gly Glu Glu Ala Lys Leu Asp Ser Lys Lys Thr Val Pro Phe Gln Val
            355                 360                 365

AAT CAA CTA CAG AGA ATT TTG GAA GTT CTT GGC ACT CCC GAT CAA AAA      1572
Asn Gln Leu Gln Arg Ile Leu Glu Val Leu Gly Thr Pro Asp Gln Lys
370             375                 380

ATT TGG CCT TAT TTG GAG AAG TAT CCA GAA TAT GAT CAA ATT ACG AAG      1620
Ile Trp Pro Tyr Leu Glu Lys Tyr Pro Glu Tyr Asp Gln Ile Thr Lys
385             390                 395                 400

TTT CCA AAG TAT AGG GAT AAC CTT GCT ACA TGG TAT CAT TCC GCG GGA      1668
Phe Pro Lys Tyr Arg Asp Asn Leu Ala Thr Trp Tyr His Ser Ala Gly
                405                 410                 415

GGA AGG GAC AAG CAT GCT TTA AGC TTA CTT TAC CAC TTG TTA AAT TAT      1716
Gly Arg Asp Lys His Ala Leu Ser Leu Leu Tyr His Leu Leu Asn Tyr
            420                 425                 430

GAT CCA ATT AAA AGA ATA GAT GCA TTT AAT GCG TTG GAA CAT AAG TAC      1764
Asp Pro Ile Lys Arg Ile Asp Ala Phe Asn Ala Leu Glu His Lys Tyr
            435                 440                 445

TTC ACA GAA AGT GAT ATT CCT GTT AGT GAA AAT GTA TTT GAA GGT CTA      1812
Phe Thr Glu Ser Asp Ile Pro Val Ser Glu Asn Val Phe Glu Gly Leu
450             455                 460

ACT TAC AAA TAC CCG GCA AGA AGA ATT CAC ACG AAC GAT AAT GAC ATC      1860
Thr Tyr Lys Tyr Pro Ala Arg Arg Ile His Thr Asn Asp Asn Asp Ile
465             470                 475                 480

ATG AAT CTT GGA TCA AGA ACG AAA AAC AAT ACA CAA GCT TCA GGA ATC      1908
Met Asn Leu Gly Ser Arg Thr Lys Asn Asn Thr Gln Ala Ser Gly Ile
                485                 490                 495

ACC GCA GGT GCC GCT GCA AAT GCG TTA GGT GGG CTT GGT GTT AAC CGT      1956
Thr Ala Gly Ala Ala Ala Asn Ala Leu Gly Gly Leu Gly Val Asn Arg
            500                 505                 510

AGA ATT CTG GCC GCG GCA GCA GCA GCC GCT GCT GCG GTG TCA GGA AAC      2004
Arg Ile Leu Ala Ala Ala Ala Ala Ala Ala Ala Val Ser Gly Asn
            515                 520                 525

AAT GCA TCA GAT GAG CCA TCT CGA AAG AAA AAC AGA AGA TAGGCTTCTA      2053
Asn Ala Ser Asp Glu Pro Ser Arg Lys Lys Asn Arg Arg
            530                 535                 540

TTTTTATATA TATTTGGAAT TTTTCATTCC ACAGCACTGT CACTATTATA TTCATTAAAC    2113

TTTTTTTTAT CTTTATAGTA TTTAAATCGG CATACAGTTT CAATTTTTCG CTTTAGAGGC    2173
```

```
ACTAAGAATG CAAGTCTGCA ACATTCAGGT AAAATAATGG GTTGATTTTA GGTCGAGCTA      2233

AAACCCTGTT CTCCGCAGAT GTATGCGAAT TCGTCATAA TTCATCTCAA CTAATGGGGC       2293

TTTAAAACAT ATGAATATCT CATGCAAACC CAAAAAAGAA GAAAGAAAAG ACTTCAAGTC      2353

CCCCCCTTAA TTTTTATATA ATGGTAGTAG TAGGTTTGTT CGTAACTTAT CGGCAATAGT      2413

AATATGTTCC CATTATCAAC A                                                2434
```

(2) INFORMATION FOR SEQ ID NO:16:

(i) SEQUENCE CHARACTERISTICS:
        (A) LENGTH: 541 amino acids
        (B) TYPE: amino acid
        (D) TOPOLOGY: linear (ii) MOLECULE TYPE: protein (xi) SEQUENCE DESCRIPTION: SEQ ID NO:16:

```
Met Tyr Gln Arg Pro Met Gln Val Gln Gly Gln Gln Ala Gln Ser
 1               5                  10                  15

Phe Val Gly Lys Lys Asn Thr Ile Gly Ser Val His Gly Lys Ala Pro
                20                  25                  30

Met Leu Met Ala Asn Asn Asp Val Phe Thr Ile Gly Pro Tyr Arg Ala
            35                  40                  45

Arg Lys Asp Arg Met Arg Val Ser Val Leu Glu Lys Tyr Glu Val Ile
 50                  55                  60

Gly Tyr Ile Ala Ala Gly Thr Tyr Gly Lys Val Tyr Lys Ala Lys Arg
 65                  70                  75                  80

Gln Ile Asn Ser Gly Thr Asn Ser Ala Asn Gly Ser Ser Leu Asn Gly
                85                  90                  95

Thr Asn Ala Lys Ile Pro Gln Phe Asp Ser Thr Gln Pro Lys Ser Ser
            100                 105                 110

Ser Ser Met Asp Met Gln Ala Asn Thr Asn Ala Leu Arg Arg Asn Leu
        115                 120                 125

Leu Lys Asp Glu Gly Val Thr Pro Gly Arg Ile Arg Thr Thr Arg Glu
130                 135                 140

Asp Val Ser Pro His Tyr Asn Ser Gln Lys Gln Thr Leu Ile Lys Lys
145                 150                 155                 160

Pro Leu Thr Val Phe Tyr Ala Ile Lys Lys Phe Lys Thr Glu Lys Asp
                165                 170                 175

Gly Val Glu Gln Leu His Tyr Thr Gly Ile Ser Gln Ser Ala Cys Arg
            180                 185                 190

Glu Met Ala Leu Cys Arg Glu Leu His Asn Lys His Leu Thr Thr Leu
        195                 200                 205

Val Glu Ile Phe Leu Glu Arg Lys Cys Val His Met Val Tyr Glu Tyr
210                 215                 220

Ala Glu His Asp Leu Leu Gln Ile Ile His Phe His Ser His Pro Glu
225                 230                 235                 240

Lys Arg Met Ile Pro Pro Arg Met Val Arg Ser Ile Met Trp Gln Leu
                245                 250                 255

Leu Asp Gly Val Ser Tyr Leu His Gln Asn Trp Val Leu His Arg Asp
            260                 265                 270

Leu Lys Pro Ala Asn Ile Met Val Thr Ile Asp Gly Cys Val Lys Ile
        275                 280                 285

Gly Asp Leu Gly Leu Ala Arg Lys Phe His Asn Met Leu Gln Thr Leu
290                 295                 300
```

-continued

```
Tyr Thr Gly Asp Lys Val Val Thr Ile Trp Tyr Arg Ala Pro Glu
305                 310                 315                 320

Leu Leu Leu Gly Ala Arg His Tyr Thr Pro Ala Val Asp Leu Trp Ser
            325                 330                 335

Val Gly Cys Ile Phe Ala Glu Leu Ile Gly Leu Gln Pro Ile Phe Lys
            340                 345                 350

Gly Glu Glu Ala Lys Leu Asp Ser Lys Lys Thr Val Pro Phe Gln Val
            355                 360                 365

Asn Gln Leu Gln Arg Ile Leu Glu Val Leu Gly Thr Pro Asp Gln Lys
370                 375                 380

Ile Trp Pro Tyr Leu Glu Lys Tyr Pro Glu Tyr Asp Gln Ile Thr Lys
385                 390                 395                 400

Phe Pro Lys Tyr Arg Asp Asn Leu Ala Thr Trp Tyr His Ser Ala Gly
                405                 410                 415

Gly Arg Asp Lys His Ala Leu Ser Leu Leu Tyr His Leu Leu Asn Tyr
            420                 425                 430

Asp Pro Ile Lys Arg Ile Asp Ala Phe Asn Ala Leu Glu His Lys Tyr
            435                 440                 445

Phe Thr Glu Ser Asp Ile Pro Val Ser Glu Asn Val Phe Glu Gly Leu
450                 455                 460

Thr Tyr Lys Tyr Pro Ala Arg Arg Ile His Thr Asn Asp Asn Asp Ile
465                 470                 475                 480

Met Asn Leu Gly Ser Arg Thr Lys Asn Thr Gln Ala Ser Gly Ile
                485                 490                 495

Thr Ala Gly Ala Ala Ala Asn Ala Leu Gly Gly Leu Gly Val Asn Arg
            500                 505                 510

Arg Ile Leu Ala Ala Ala Ala Ala Ala Ala Val Ser Gly Asn
            515                 520                 525

Asn Ala Ser Asp Glu Pro Ser Arg Lys Lys Asn Arg Arg
530                 535                 540
```

(2) INFORMATION FOR SEQ ID NO:17:

(i) SEQUENCE CHARACTERISTICS:
        (A) LENGTH: 1610 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 495..1463

(xi) SEQUENCE DESCRIPTION: SEQ ID NO:17:

```
GGTACCAGGT CAAGAAGCAG AATACCCAAG GGCATCCTCC TTAATGAGTT GATTTAAACA      60

ATTTAAAATT TTTAAATCTC ATTACGTTTT CCGCATACGA ATTGGTGGGA GACTTTCAAC     120

CCAAAGCATA TTACTGAGTA AAAAAATTT TACTCCATTT TGTAAGCTTC GATTTGTGAC      180

GATTCTTTGG TCATGGATTG AAGAACTTTA AACGAGAAGA AATTAGAAAA CAGGTGAAGA     240

CCACTATTTA GTTCTTTACC GCAACATAGG ATAAACAAAG TTATTTTCTT ACTCCTTTAT     300

ATATTTGAAA AAATATAAAA TCCACGGAAA AACATCGAAA ATTCATTTTT CATGAAGGAA     360

AATTAGGGTT CATACAGGAG TAGAGTTCAT TGATGTGGTA GCAACCTTGT TAGCACTCAT     420

ATTGTTCGAA CAAAAAATGC CCTCTCAAAC TTTAGTTGAA GAGCGATAAG GCATCTGAAT     480
```

```
CTCAAAAGTT AGAC ATG TCG GGG AGC TTC TGG ACA TCT ACA CAA AGG CAT              530
          Met Ser Gly Ser Phe Trp Thr Ser Thr Gln Arg His
           1           5                  10

CAT TGG CAA TAT ACC AAG GCA TCA TTG GCT AAA GAG AGG CAG AAG TTA              578
His Trp Gln Tyr Thr Lys Ala Ser Leu Ala Lys Glu Arg Gln Lys Leu
         15                  20                  25

TGG CTA TTG GAG TGC CAG CTG TTT CCT CAA GGT TTG AAT ATT GTA ATG              626
Trp Leu Leu Glu Cys Gln Leu Phe Pro Gln Gly Leu Asn Ile Val Met
     30                  35                  40

GAT TCG AAG CAA AAC GGC ATC GAA CAA TCC ATC ACA AAG AAT ATA CCA              674
Asp Ser Lys Gln Asn Gly Ile Glu Gln Ser Ile Thr Lys Asn Ile Pro
 45                  50                  55                  60

ATA ACT CAC CGA GAC TTA CAC TAT GAT AAA GAT TAT AAT CTA AGG ATC              722
Ile Thr His Arg Asp Leu His Tyr Asp Lys Asp Tyr Asn Leu Arg Ile
                 65                  70                  75

TAC TGC TAT TTC CTG ATA ATG AAG CTT GGA AGG AGA CTA AAT ATA AGA              770
Tyr Cys Tyr Phe Leu Ile Met Lys Leu Gly Arg Arg Leu Asn Ile Arg
             80                  85                  90

CAG TAT GCA CTG GCT ACA GCA CAT ATT TAT CTA TCA AGG TTT TTA ATA              818
Gln Tyr Ala Leu Ala Thr Ala His Ile Tyr Leu Ser Arg Phe Leu Ile
         95                 100                 105

AAG GCT TCA GTT AGA GAA ATA AAC CTA TAT ATG CTG GTT ACT ACG TGT              866
Lys Ala Ser Val Arg Glu Ile Asn Leu Tyr Met Leu Val Thr Thr Cys
    110                 115                 120

GTA TAT TTA GCA TGC AAA GTT GAA GAA TGC CCG CAA TAT ATC AGA ACT              914
Val Tyr Leu Ala Cys Lys Val Glu Glu Cys Pro Gln Tyr Ile Arg Thr
125                 130                 135                 140

TTG GTA AGT GAA GCC CGT ACC TTA TGG CCC GAA TTT ATT CCT CCT GAC              962
Leu Val Ser Glu Ala Arg Thr Leu Trp Pro Glu Phe Ile Pro Pro Asp
                145                 150                 155

CCT ACT AAA GTT ACT GAG TTT GAG TTC TAC TTA CTA GAA GAA TTG GAA             1010
Pro Thr Lys Val Thr Glu Phe Glu Phe Tyr Leu Leu Glu Glu Leu Glu
            160                 165                 170

AGT TAC TTA ATT GTC CAC CAC CCT TAT CAA TCC TTA AAG CAA ATT GTT             1058
Ser Tyr Leu Ile Val His His Pro Tyr Gln Ser Leu Lys Gln Ile Val
        175                 180                 185

CAA GTC TTA AAG CAA CCG CCA TTT CAA ATA ACA CTA TCG TCA GAT GAT             1106
Gln Val Leu Lys Gln Pro Pro Phe Gln Ile Thr Leu Ser Ser Asp Asp
    190                 195                 200

CTA CAA AAC TGT TGG TCC TTA ATC AAC GAC AGT TAT ATA AAT GAT GTT             1154
Leu Gln Asn Cys Trp Ser Leu Ile Asn Asp Ser Tyr Ile Asn Asp Val
205                 210                 215                 220

CAT TTG CTT TAC CCT CCT CAT ATT ATC GCT GTT GCA TGT TTA TTC ATT             1202
His Leu Leu Tyr Pro Pro His Ile Ile Ala Val Ala Cys Leu Phe Ile
                225                 230                 235

ACG ATT TCC ATT CAT GGG AAA CCA ACC AAA GGA TCA TCG TTA GCA TCT             1250
Thr Ile Ser Ile His Gly Lys Pro Thr Lys Gly Ser Ser Leu Ala Ser
            240                 245                 250

GCG GCT TCT GAA GCC ATC AGA GAT CCT AAA AAT TCT AGT TCT CCT GTT             1298
Ala Ala Ser Glu Ala Ile Arg Asp Pro Lys Asn Ser Ser Ser Pro Val
        255                 260                 265

CAA ATA GCT TTT AAT CGT TTT ATG GCA GAA TCT CTT GTA GAT CTT GAG             1346
Gln Ile Ala Phe Asn Arg Phe Met Ala Glu Ser Leu Val Asp Leu Glu
    270                 275                 280

GAG GTT ATG GAT ACG ATT CAA GAG CAA ATT ACA TTA TAC GAT CAT TGG             1394
Glu Val Met Asp Thr Ile Gln Glu Gln Ile Thr Leu Tyr Asp His Trp
285                 290                 295                 300

GAC AAG TAC CAC GAA CAA TGG ATA AAG TTT CTG CTA CAT ACT TTG TAT             1442
Asp Lys Tyr His Glu Gln Trp Ile Lys Phe Leu Leu His Thr Leu Tyr
                305                 310                 315
```

-continued

```
CTT AGA CCA GCA TCT GCA ATT TAATCATGCG AAGAATAAAT TTAAAAACCG    1493
Leu Arg Pro Ala Ser Ala Ile
            320

TTAAGCCTGT AAATTCAATC ATTATGGTGG TGATGATCCG TTTTGGAAAT GTTTCGTCCT    1553

TGACTACCTT TGTTTAACAT GATATTGGAA CGTCAAGACA TATTGAGAAT AGGTACC       1610
```

(2) INFORMATION FOR SEQ ID NO:18:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO:18:

```
Met Ser Gly Ser Phe Trp Thr Ser Thr Gln Arg His His Trp Gln Tyr
 1               5                  10                  15

Thr Lys Ala Ser Leu Ala Lys Glu Arg Gln Lys Leu Trp Leu Leu Glu
            20                  25                  30

Cys Gln Leu Phe Pro Gln Gly Leu Asn Ile Val Met Asp Ser Lys Gln
        35                  40                  45

Asn Gly Ile Glu Gln Ser Ile Thr Lys Asn Ile Pro Ile Thr His Arg
 50                  55                  60

Asp Leu His Tyr Asp Lys Asp Tyr Asn Leu Arg Ile Tyr Cys Tyr Phe
 65                  70                  75                  80

Leu Ile Met Lys Leu Gly Arg Arg Leu Asn Ile Arg Gln Tyr Ala Leu
                85                  90                  95

Ala Thr Ala His Ile Tyr Leu Ser Arg Phe Leu Ile Lys Ala Ser Val
            100                 105                 110

Arg Glu Ile Asn Leu Tyr Met Leu Val Thr Thr Cys Val Tyr Leu Ala
            115                 120                 125

Cys Lys Val Glu Glu Cys Pro Gln Tyr Ile Arg Thr Leu Val Ser Glu
        130                 135                 140

Ala Arg Thr Leu Trp Pro Glu Phe Ile Pro Asp Pro Thr Lys Val
145                 150                 155                 160

Thr Glu Phe Glu Phe Tyr Leu Leu Glu Glu Leu Glu Ser Tyr Leu Ile
                165                 170                 175

Val His His Pro Tyr Gln Ser Leu Lys Gln Ile Val Gln Val Leu Lys
            180                 185                 190

Gln Pro Pro Phe Gln Ile Thr Leu Ser Ser Asp Leu Gln Asn Cys
        195                 200                 205

Trp Ser Leu Ile Asn Asp Ser Tyr Ile Asn Asp Val His Leu Leu Tyr
210                 215                 220

Pro Pro His Ile Ile Ala Val Ala Cys Leu Phe Ile Thr Ile Ser Ile
225                 230                 235                 240

His Gly Lys Pro Thr Lys Gly Ser Ser Leu Ala Ser Ala Ser Glu
            245                 250                 255

Ala Ile Arg Asp Pro Lys Asn Ser Ser Ser Pro Val Gln Ile Ala Phe
            260                 265                 270

Asn Arg Phe Met Ala Glu Ser Leu Val Asp Leu Glu Val Met Asp
        275                 280                 285

Thr Ile Gln Glu Gln Ile Thr Leu Tyr Asp His Trp Asp Lys Tyr His
        290                 295                 300

Glu Gln Trp Ile Lys Phe Leu Leu His Thr Leu Tyr Leu Arg Pro Ala
```

```
            305                 310                 315                 320
Ser Ala Ile (2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

ACTACAATCC GGGCTTATCC                                                   20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TCTTGGTCTC AAACTCGCCC                                                   20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GTTGTCCTTG ATTAGCACGG                                                   20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

CCAAAGTGAA ATTTTACTGG                                                   20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

TAGACTTTCG GACGTACCGG                                                   20
```

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

```
CGGTGAGACG TTGATCTTGG                                           20
```

(2) INFORMATION FOR SEQ ID NO:25:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

```
GAAGGAAGGG GCAGGTGGTT ACGCGGTGTA TACGTATAG                      39
```

(2) INFORMATION FOR SEQ ID NO:26:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

```
AGCATTCGTA AGAACTCAAG CGTAGTCTGG GACGTCGTAT GGGTACAGCT CCAGAGCACG  60

AAC                                                              63
```

(2) INFORMATION FOR SEQ ID NO:27:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
TCCACGAATA TAACAGCCTG ATTTTCCCAT G                              31
```

(2) INFORMATION FOR SEQ ID NO:28:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

```
TCGGCATATG GGAAAATCAG CTGTTAT                                   27
```

(2) INFORMATION FOR SEQ ID NO:29:

(i) SEQUENCE CHARACTERISTICS:
    (A) LENGTH: 30 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:29:

CCGTGGATCC TCACAGCTCC AGAGCACGAA                          30

(2) INFORMATION FOR SEQ ID NO:30:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

GGAAGAGTAC AAGGACAAAA CGGCTTGGAT GGAAACGTAG AAGGCATTCC A      51

(2) INFORMATION FOR SEQ ID NO:31:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

GGGGCTACTC TCGAAGATCC CGTCATTATG TACAGCAGGT TGAGCATGCC T      51

(2) INFORMATION FOR SEQ ID NO:32:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

GCCTTACCGG CACGCATCAT GATGGGGACG CCCTCCCAAC GCTCGACACT T      51

(2) INFORMATION FOR SEQ ID NO:33:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

GCAGTGGCTG CAGGAGCTGC AGAAGCATCG GTACTGGGGG ATGCAATCCA        50

(2) INFORMATION FOR SEQ ID NO:34:

(i) SEQUENCE CHARACTERISTICS:
        (A) LENGTH: 54 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:34:

GTCGACGGGT TCAACTTCTC CCTCTTTGTA ACTTGCATCA GCAAACGGAT GACA                54

(2) INFORMATION FOR SEQ ID NO:35:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

GGATGTCAAC AACGGTGACA GCTTCGACAA CTTCACGCTT GTGGTGAGCT                     50

(2) INFORMATION FOR SEQ ID NO:36:

(i) SEQUENCE CHARACTERISTICS:
        (A) LENGTH: 780 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 10..441

(xi) SEQUENCE DESCRIPTION: SEQ ID NO:36:

```
GGTAGGAAC ATG GCG GAT CGG CTC ACG CAG CTT CAG GAC GCT GTG AAT             48
          Met Ala Asp Arg Leu Thr Gln Leu Gln Asp Ala Val Asn
            1               5                  10

TCG CTT GCA GAT CAG TTT TGT AAT GCC ATT GGA GTA TTG CAG CAA TGT           96
Ser Leu Ala Asp Gln Phe Cys Asn Ala Ile Gly Val Leu Gln Gln Cys
 15                  20                  25

GGT CCT CCT GCC TCT TTC AAT AAT ATT CAG ACA GCA ATT AAC AAA GAC          144
Gly Pro Pro Ala Ser Phe Asn Asn Ile Gln Thr Ala Ile Asn Lys Asp
 30                  35                  40                  45

CAG CCA GCT AAC CCT ACA GAA GAG TAT GCC CAG CTT TTT GCA GCA CTG          192
Gln Pro Ala Asn Pro Thr Glu Glu Tyr Ala Gln Leu Phe Ala Ala Leu
                 50                  55                  60

ATT GCA CGA ACA GCA AAA GAC ATT GAT GTT TTG ATA GAT TCC TTA CCC          240
Ile Ala Arg Thr Ala Lys Asp Ile Asp Val Leu Ile Asp Ser Leu Pro
 65                  70                  75

AGT GAA GAA TCT ACA GCT GCT TTA CAG GCT GCT AGC TTG TAT AAG CTA          288
Ser Glu Glu Ser Thr Ala Ala Leu Gln Ala Ala Ser Leu Tyr Lys Leu
 80                  85                  90

GAA GAA GAA AAC CAT GAA GCT GCT ACA TGT CTG GAG GAT GTT GTT TAT          336
Glu Glu Glu Asn His Glu Ala Ala Thr Cys Leu Glu Asp Val Val Tyr
 95                 100                 105

CGA GGA GAC ATG CTT CTG GAG AAG ATA CAA AGC GCA CTT GCT GAT ATT          384
Arg Gly Asp Met Leu Leu Glu Lys Ile Gln Ser Ala Leu Ala Asp Ile
110                 115                 120                 125

GCA CAG TCA CAG CTG AAG ACA AGA AGT GGT ACC CAT AGC CAG TCT CTT          432
Ala Gln Ser Gln Leu Lys Thr Arg Ser Gly Thr His Ser Gln Ser Leu
                130                 135                 140

CCA GAC TCA TAGCATCAGT GGATACCATG TGGCTGAGAA AAGAACTGTT                  481
Pro Asp Ser
```

```
TGAGTGCCAT TAAGAATTCT GCATCAGACT TAGATACAAG CCTTACCAAC AATTACAGAA      541

ACATTAAACA ATATGACACA TTACCTTTTT AGCTATTTTT AATAGTCTTC TATTTTCACT      601

CTTGATAAGC TTATAAAATC ATGATCGAAT CAGCTTTAAA GCATCATACC ATCATTTTTT      661

AACTGAGTGA AATTATTAAG GCATGTAATA CATTAATGAA CATAATATAA GGAAACATAT      721

GTAAAATTCA AAAAAAAAAA AAAAAAAAAA AAAAAAAAAA AAAAAAAAAA AAAAAAAA        780
```

(2) INFORMATION FOR SEQ ID NO:37:

(i) SEQUENCE CHARACTERISTICS:
        (A) LENGTH: 144 amino acids
        (B) TYPE: amino acid
        (D) TOPOLOGY: linear (ii) MOLECULE TYPE: protein (xi) SEQUENCE DESCRIPTION: SEQ ID NO:37:

```
Met Ala Asp Arg Leu Thr Gln Leu Gln Asp Ala Val Asn Ser Leu Ala
 1               5                  10                  15

Asp Gln Phe Cys Asn Ala Ile Gly Val Leu Gln Cys Gly Pro Pro
            20                  25                  30

Ala Ser Phe Asn Asn Ile Gln Thr Ala Ile Asn Lys Asp Gln Pro Ala
        35                  40                  45

Asn Pro Thr Glu Glu Tyr Ala Gln Leu Phe Ala Ala Leu Ile Ala Arg
    50                  55                  60

Thr Ala Lys Asp Ile Asp Val Leu Ile Asp Ser Leu Pro Ser Glu Glu
65                  70                  75                  80

Ser Thr Ala Ala Leu Gln Ala Ala Ser Leu Tyr Lys Leu Glu Glu Glu
                85                  90                  95

Asn His Glu Ala Ala Thr Cys Leu Glu Asp Val Val Tyr Arg Gly Asp
            100                 105                 110

Met Leu Leu Glu Lys Ile Gln Ser Ala Leu Ala Asp Ile Ala Gln Ser
        115                 120                 125

Gln Leu Lys Thr Arg Ser Gly Thr His Ser Gln Ser Leu Pro Asp Ser
    130                 135                 140
```

(2) INFORMATION FOR SEQ ID NO:38:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:38:

```
Met Xaa Asp Arg Leu Thr Leu Gln
 1               5
```

(2) INFORMATION FOR SEQ ID NO:39:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:39:

```
Leu Ile Asp Ser Leu Pro
 1               5
```